US009073895B2

(12) United States Patent
Berry et al.

(10) Patent No.: US 9,073,895 B2
(45) Date of Patent: Jul. 7, 2015

(54) BIARYLAMIDE INHIBITORS OF LEUKOTRIENE PRODUCTION

(75) Inventors: Angela Berry, Gaylordsville, CT (US); Zhidong Chen, New Milford, CT (US); Stephane De Lombaert, Branford, CT (US); Michel Jose Emmanuel, New Fairfield, CT (US); Pui Leng Loke, Abingdon (GB); Chuk Chui Man, Ridgefield, CT (US); Tina Marie Morwick, Carmel, IN (US); Hidenori Takahashi, LaGrangeville, NY (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 71 days.

(21) Appl. No.: 13/325,564

(22) Filed: Dec. 14, 2011

(65) Prior Publication Data

US 2012/0322795 A1  Dec. 20, 2012

Related U.S. Application Data

(60) Provisional application No. 61/423,667, filed on Dec. 16, 2010.

(51) Int. Cl.
| | |
|---|---|
| C07D 213/72 | (2006.01) |
| A61K 31/345 | (2006.01) |
| C07D 405/10 | (2006.01) |
| C07D 239/42 | (2006.01) |
| C07D 403/04 | (2006.01) |
| C07D 403/12 | (2006.01) |
| C07D 403/14 | (2006.01) |
| C07D 405/12 | (2006.01) |
| C07D 405/14 | (2006.01) |
| C07D 409/14 | (2006.01) |
| C07D 413/12 | (2006.01) |
| C07D 413/14 | (2006.01) |
| C07D 417/12 | (2006.01) |
| C07D 417/14 | (2006.01) |

(52) U.S. Cl.
CPC ............ *C07D 405/10* (2013.01); *C07D 239/42* (2013.01); *C07D 403/04* (2013.01); *C07D 403/12* (2013.01); *C07D 403/14* (2013.01); *C07D 405/12* (2013.01); *C07D 405/14* (2013.01); *C07D 409/14* (2013.01); *C07D 413/12* (2013.01); *C07D 413/14* (2013.01); *C07D 417/12* (2013.01); *C07D 417/14* (2013.01)

(58) Field of Classification Search
None
See application file for complete search history.

(56) References Cited

U.S. PATENT DOCUMENTS

| 6,911,444 B2 | 6/2005 | Lacrampe et al. |
|---|---|---|
| 7,319,108 B2 | 1/2008 | Schwink et al. |

FOREIGN PATENT DOCUMENTS

| WO | 2005075435 A1 | 8/2005 |
|---|---|---|
| WO | 2006044602 A2 | 4/2006 |
| WO | 2006136829 A2 | 12/2006 |
| WO | 2007120570 A2 | 10/2007 |
| WO | 2007120574 A2 | 10/2007 |
| WO | 2008030369 A1 | 3/2008 |
| WO | 2008128335 A1 | 10/2008 |
| WO | 2008156721 A1 | 12/2008 |
| WO | 2009048547 A1 | 4/2009 |
| WO | 2009075874 A1 | 6/2009 |
| WO | 2011022473 A1 | 2/2011 |
| WO | 2011143466 A1 | 11/2011 |

OTHER PUBLICATIONS

Evans. Trends in Pharmacological Science, 2008, 29(2), 72-78.*
Zhu. Tetrahedron Letters, 2006, 47, 7267-70.*
International Search Report for PCT/US2011/064770 mailed Mar. 6, 2012.

* cited by examiner

*Primary Examiner* — Noble Jarrell
(74) *Attorney, Agent, or Firm* — Michael P. Morris; Usha R. Patel

(57) ABSTRACT

The present invention relates to compounds of formula (I):

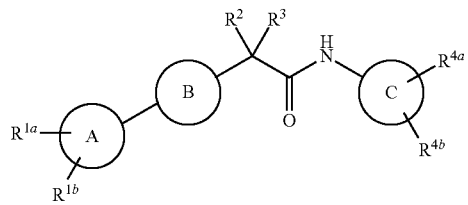

and pharmaceutically acceptable salts thereof, wherein A, B, C, $R^{1a}$, $R^{1b}$, $R^2$, $R^3$, $R^{4a}$ and $R^{4b}$ are as defined herein. The invention also relates to pharmaceutical compositions comprising these compounds, methods of using these compounds in the treatment of various diseases and disorders, processes for preparing these compounds and intermediates useful in these processes.

13 Claims, No Drawings

BIARYLAMIDE INHIBITORS OF LEUKOTRIENE PRODUCTION

FIELD OF THE INVENTION

This invention relates to biaryl compounds that are useful as inhibitors of five lipoxygenase activating protein (FLAP) and are thus useful for treating a variety of diseases and disorders that are mediated or sustained through the activity of leukotrienes including asthma, allergy, rheumatoid arthritis, multiple sclerosis, inflammatory pain, acute chest syndrome and cardiovascular diseases including atherosclerosis, myocardial infarction and stroke. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Leukotrienes (LTs) and the biosynthetic pathway from arachidonic acid leading to their production have been the targets of drug discovery efforts for over twenty years. LTs are produced by several cell types including neutrophils, mast cells, eosinophils, basophils monocytes and macrophages. The first committed step in the intracellular synthesis of LTs involves oxidation of arachidonic acid by 5-lipoxygenase (5-LO) to LTA4, a process requiring the presence of the 18 kD integral membrane protein 5-lipoxygenase-activating protein (FLAP) (D. K. Miller et al., Nature, 1990, 343, 278-281; R. A. F. Dixon et al., Nature, 1990, 343, 282-284). Subsequent metabolism of $LTA_4$ leads to $LTB_4$, and the cysteinyl LTs-$LTC_4$, $LTD_4$ and $LTE_4$ (B. Samuelsson, Science, 1983, 220, 568-575). The cysteinyl LTs have potent smooth muscle constricting and bronchoconstricting effects and they stimulate mucous secretion and vascular leakage. $LTB_4$ is a potent chemotactic agent for leukocytes, and stimulates adhesion, aggregation and enzyme release.

Much of the early drug discovery effort in the LT area was directed towards the treatment of allergy, asthma and other inflammatory conditions. Research efforts have been directed towards numerous targets in the pathway including antagonists of $LTB_4$ and the cysteinyl leukotrienes $LTC_4$, $LTD_4$ and $LTE_4$, as well as inhibitors of 5-lipoxygenase (5-LO), $LTA_4$ hydrolase and inhibitors of 5-lipoxygenase activating protein (FLAP) (R. W. Friesen and D. Riendeau, Leukotriene Biosynthesis Inhibitors, Ann. Rep. Med. Chem., 2005, 40, 199-214). Years of effort in the above areas have yielded a few marketed products for the treatment of asthma including a 5-LO inhibitor, zileuton, and LT antagonists, montelukast, pranlukast and zafirlukast.

More recent work has implicated LTs in cardiovascular disease, including myocardial infarction, stroke and atherosclerosis (G. Riccioni et al., J. Leukoc. Biol., 2008, 1374-1378). FLAP and 5-LO were among the components of the 5-LO and LT cascade found in atherosclerotic lesions, suggesting their involvement in atherogenesis (R. Spanbroek et al., Proc. Natl. Acad. Sci. U.S.A., 2003, 100, 1238-1243). Pharmacological inhibition of FLAP has been reported to decrease atherosclerotic lesion size in animal models. In one study, oral dosing of the FLAP inhibitor MK-886 to apoE/LDL-R double knockout mice fed a high-fat diet from 2 months of age to 6 months led to a 56% decrease in plaque coverage in the aorta and a 43% decrease in the aortic root (J. Jawien et al., Eur. J. Clin. Invest., 2006, 36, 141-146). This plaque effect was coupled with a decrease in plaque-macrophage content and a concomitant increase in collagen and smooth muscle content which suggests a conversion to a more stable plaque phenotype. In another study, it was reported that administration of MK-886 via infusion to ApoExCD4dnT RII mice (apoE KO mice expressing a dominant-negative TGF-beta receptor which effectively removes all TGF-beta from the system) resulted in about a 40% decrease in plaque area in the aortic root (M. Back et al., Circ. Res., 2007, 100, 946-949). The mice were only treated for four weeks after plaque growth was already somewhat mature (12 weeks) thus raising the possibility of therapeutically treating atherosclerosis via this mechanism. In a study examining human atherosclerotic lesions, it was found that the expression of FLAP, 5-LO and $LTA_4$ hydrolase was significantly increased compared to healthy controls (H. Qiu et al., Proc. Natl. Acad. Sci. U.S.A., 103, 21, 8161-8166). Similar studies suggest that inhibition of the LT pathway, for example by inhibition of FLAP, would be useful for the treatment of atherosclerosis (for reviews, see M. Back Curr. Athero. Reports, 2008 10, 244-251 and Curr. Pharm. Des., 2009, 15, 3116-3132).

In addition to the work cited above, many other studies have been directed towards understanding the biological actions of LTs and the role of LTs in disease. These studies have implicated LTs as having a possible role in numerous diseases or conditions (for a review, see M. Peters-Golden and W.R. Henderson, Jr., M.D., N. Engl. J. Med., 2007, 357, 1841-1854). In addition to the specific diseases cited above, LTs have been implicated as having a possible role in numerous allergic, pulmonary, fibrotic, inflammatory and cardiovascular diseases, as well as cancer. Inhibition of FLAP is also reported to be useful for treating renal diseases such as diabetes-induced proteinuria (see for example J. M. Valdivieso et al., Journal of Nephrology, 2003, 16, 85-94 and A Montero et al., Journal of Nephrology, 2003, 16, 682-690).

A number of FLAP inhibitors have been reported in the scientific literature (see for example J. F. Evans et al., Trends in Pharmacological Sciences, 2008, 72-78) and in U.S. patents. Some have been evaluated in clinical trials for asthma, including MK-886, MK-591, and BAY X1005, also known as DG-031. More recently, the FLAP inhibitor AM-103 (J. H. Hutchinson et al., J. Med. Chem. 52, 5803-5815) has been evaluated in clinical trials, based on its anti-inflammatory properties (D. S. Lorrain et al., J. Pharm. Exp. Ther., 2009, DOI:10.1124/jpet.109.158089). Subsequently, it was replaced by the back-up compound AM-803 (GSK-2190915) for the treatment of respiratory diseases. DG-031 has also been in clinical trials to evaluate its effect on biomarkers for myocardial infarction risk and showed a dose-dependent suppression of several biomarkers for the disease (H. Hakonarson et al., JAMA, 2005, 293, 2245-2256). MK-591 was shown in a clinical trial to reduce proteinuria in human glomerulonephritis (see for example A. Guash et al., Kidney International, 1999, 56, 291-267).

However, to date, no FLAP inhibitor has been approved as a marketed drug.

BRIEF SUMMARY OF THE INVENTION

The present invention provides novel compounds which inhibit 5-lipoxygenase activating protein (FLAP) and are thus useful for treating a variety of diseases and disorders that are mediated or sustained through the activity of leukotrienes, including allergic, pulmonary, fibrotic, inflammatory and cardiovascular diseases and cancer. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In its first broadest embodiment, the present invention relates to a compound of formula

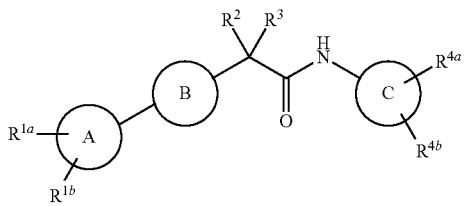

or a pharmaceutically acceptable salt thereof, wherein:
A is a 5-10 membered heteroaryl ring containing 1-3 heteroatoms selected from nitrogen, sulfur and oxygen;
B is a 6-10 membered aryl ring or a 5-6 membered heteroaryl ring containing 1-3 heteroatoms selected from nitrogen, sulfur and oxygen;
C is a 6-10 membered aryl ring or a 5-10 membered heteroaryl ring containing 1-3 heteroatoms selected from nitrogen, sulfur and oxygen;
$R^{1a}$ and $R^{1b}$ are each independently selected from —H, $C_{1-6}$ alkyl, $C_{1-6}$ alkoxyl, —$C_{1-6}$ alkyl —OH, hydroxy, —C(O)—$C_{1-6}$ alkyl and —$NR^5R^6$;
$R^2$ and $R^3$ are each independently —$C_{1-6}$ alkyl or —H, with the proviso that both $R^2$ and $R^3$ cannot be hydrogen; or
$R^2$ and $R^3$ together with the carbon atom to which they are attached form a $C_{3-8}$ cycloalkyl or $C_{3-8}$ heterocyclic ring;
$R^{4a}$ and $R^{4b}$ are each independently selected from —H, $C_{1-6}$ alkyl, $C_{1-6}$ alkoxyl, —$C_{1-6}$ alkyl-OH, aryl, —O-aryl, 5-6 membered heteroaryl, $C_{3-8}$ cycloalkyl, $C_{3-8}$ heterocyclyl, —$C_{1-3}$alkyl-aryl, —$C_{1-3}$ alkyl-heteroaryl, —$C_{1-3}$ alkyl-heterocyclyl, —O—$C_{1-3}$ alkyl-aryl, —O—$C_{1-3}$ alkyl-heteroaryl, —$OC_{1-6}$ alkyl, $CF_3$, O—$CF_3$, —$COOR^5$, —C(O)$C_{1-3}$ alkyl —$S(O)_2$—$NR^5R^6$, —$S(O)_2CF_3$, —$S(O)_2C_{1-3}$ alkyl, —$C(O)NR^7R^8$, hydroxy, halogen, and cyano, wherein each group is optionally independently substituted with 1-3 substituents chosen from $C_{1-6}$ alkyl, $C_{1-6}$ alkoxyl, hydroxy and halogen;
$R^5$ and $R^6$ are each independently chosen from H, $C_{1-6}$ alkyl, —$C_{1-6}$alkylhydroxy and $C_{1-6}$ alkyl-O—$C_{1-6}$ alkyl;
Or, $R^5$ and $R^6$ together with the nitrogen atom to which they are attached form a 5-6 membered heterocyclic ring;
$R^7$ and $R^8$ are each independently chosen from H, $C_{1-6}$ alkyl, —$S(O)_2C_{1-3}$ alkyl, and —C(NH)—$NH_2$.

In a second embodiment, the present invention relates to a compound as described in the broadest embodiment above, or a pharmaceutically acceptable salt thereof, wherein:
A is selected from pyrazolyl, imidazolyl, pyrrolyl, thienyl, thiazolyl, triazolyl, pyridinyl, pyrimidinyl, pyrazinyl, pyridazinyl, indolyl, pyrrolopyridinyl, dihydropyrrolopyridinyl, imidazopyridinyl, pyrazolopyridinyl and quinolinyl;
B is selected from phenyl, pyridinyl, pyrimidinyl, pyrazinyl and pyridazinyl;
C is selected from phenyl, indanyl, pyrazolyl, imidazolyl, pyrrolyl, thienyl, thiazolyl, triazolyl, thiadiazolyl, oxazolyl, isoxazolyl, oxadiazolyl, pyridinyl, pyrimidinyl, pyrazinyl, pyridazinyl, indolyl, pyrrolopyridinyl, dihydropyrrolopyridinyl, imidazopyridinyl, pyrazolopyridinyl, quinolinyl, isoquinolinyl, benzothiazolyl, benzofuranyl, dihydrobenzofuranyl, benzodioxolanyl, benzodioxolinyl, dihydroindolyl, naphthyridinyl, pyrimidinopyridinyl, thiazolopyridinyl, tetrahydrothiazolopyridinyl and benzothienyl;
$R^{1a}R^{1b}$ are each independently selected from —H, $C_{1-6}$ alkyl, $C_{1-3}$ alkoxyl, —$C_{1-3}$ alkyl —OH, hydroxy, —C(O)—$C_{1-3}$ alkyl and —$NR^5R^6$;
$R^2$ and $R^3$ are each independently —$C_{1-6}$ alkyl or —H, with the proviso that both $R^2$ and $R^3$ cannot be hydrogen; or
$R^2$ and $R^3$ together with the carbon atom to which they are attached form a cyclopropyl, cyclobutyl, cyclopentyl, cyclohexyl, tetrahydrofuranyl or a tetrahydropyranyl ring;
$R^{4a}$ and $R^{4b}$ are each independently selected from —H, $C_{1-3}$ alkyl, $C_{1-3}$ alkoxyl, —$C_{1-3}$ alkyl-OH, phenyl, —O-phenyl, thiazolyl, oxazolyl, isoxazolyl, furanyl, thienyl, pyrrolyl, thiadiazolyl, tetrazolyl, pyridinyl, pyrimidinyl, pyridazinyl, pyrazinyl, cyclopropyl, cyclopbutyl, cyclophenyl, cyclohexyl, pyrrolidinyl, tetrahydrothienyl, piperidinyl, piperazinyl, morpholinyl, —$C_{1-3}$alkyl-phenyl, —$C_{1-3}$ alkyl-pyridinyl, —$C_{1-3}$ alkyl-pyrimidinyl, —$C_{1-3}$ alkyl-pyridazinyl, —$C_{1-3}$ alkyl-pyrazinyl, —$C_{1-3}$ alkyl-heterocyclyl, —O—$C_{1-3}$ alkyl-phenyl, —O—$C_{1-3}$ alkyl-pyridinyl, —$OC_{1-3}$ alkyl, $CF_3$, O—$CF_3$, —$COOR^5$, —C(O)$C_{1-3}$ alkyl-$S(O)_2$—$NR^5R^6$, —$S(O)_2CF_3$, —$S(O)_2C_{1-3}$ alkyl, —$C(O)NR^7R^8$, hydroxy, halogen, and cyano, wherein each group is optionally independently substituted with 1-3 substituents chosen from $C_{1-6}$ alkyl, $C_{1-6}$ alkoxyl, hydroxy and halogen;
$R^5$ and $R^6$ are each independently chosen from H, $C_{1-5}$ alkyl, —$C_{1-3}$ alkylhydroxy and $C_{1-3}$ alkyl-O—$C_{1-3}$ alkyl;
Or, $R^5$ and $R^6$ together with the nitrogen atom to which they are attached form a piperidinyl, morpholinyl or thiomorpholinyl ring;
$R^7$ and $R^8$ are each independently chosen from H, $C_{1-6}$ alkyl, —$S(O)_2C_{1-3}$ alkyl, and —C(NH)—$NH_2$.

In a third embodiment, the present invention relates to a compound as described in any of the embodiments above, or a pharmaceutically acceptable salt thereof, wherein:
A is selected from pyrazolyl, pyridinyl, pyrimidinyl, pyrazinyl, pyrrolopyridinyl, dihydropyrrolopyridinyl and imidazopyridinyl.

In a fourth embodiment there is provided a compound of formula (I) as described in any of the embodiments above, or a pharmaceutically acceptable salt thereof, wherein:
B is selected from phenyl and pyridinyl.

In a fifth embodiment there is provided a compound as described in any of the embodiments above, or a pharmaceutically acceptable salt thereof, wherein:
C is selected from phenyl, indanyl, pyrazolyl, imidazolyl, thienyl, thiazolyl, triazolyl, thiadiazolyl, oxazolyl, isoxazolyl, oxadiazolyl, pyridinyl, pyrimidinyl, pyrazinyl, pyridazinyl, indolyl, pyrrolopyridinyl, dihydropyrrolopyridinyl, imidazopyridinyl, pyrazolopyridinyl, quinolinyl, isoquinolinyl, benzothiazolyl, benzofuranyl, dihydrobenzofuranyl, benzodioxolanyl, benzodioxolinyl, dihydroindolyl, naphthyridinyl, pyrimidinopyridinyl, thiazolopyridinyl, tetrahydrothiazolopyridinyl and benzothienyl.

In a sixth embodiment there is provided a compound of formula (I) as described in any of the embodiments above, or a pharmaceutically acceptable salt thereof, wherein:
$R^2$ and $R^3$ are each independently H, methyl, ethyl, propyl, isopropyl or tert. butyl, with the proviso that both $R^2$ and $R^3$ cannot be hydrogen; or
$R^2$ and $R^3$ together with the carbon atom to which they are attached form a cyclopropyl, cyclobutyl, cyclopentyl, cyclohexyl or a tetrahydropyranyl ring.

In a seventh embodiment there is provided a compound as described in the first or second embodiment, or a pharmaceutically acceptable salt thereof, wherein:

A is selected from pyrazolyl, pyridinyl, pyrimidinyl, pyrazinyl, pyrrolopyridinyl, dihydropyrrolopyridinyl and imidazopyridinyl;

B is selected from phenyl and pyridinyl;

C is selected from phenyl, indanyl, pyrazolyl, imidazolyl, thienyl, thiazolyl, triazolyl, thiadiazolyl, oxazolyl, isoxazolyl, oxadiazolyl, pyridinyl, pyrimidinyl, pyrazinyl, pyridazinyl, indolyl, pyrrolopyridinyl, dihydropyrrolopyridinyl, imidazopyridinyl, pyrazolopyridinyl, quinolinyl, isoquinolinyl, benzothiazolyl, benzofuranyl, dihydrobenzofuranyl, benzodioxolanyl, benzodioxolinyl, dihydroindolyl, naphthyridinyl, pyrimidinopyridinyl, thiazolopyridinyl, tetrahydrothiazolopyridinyl and benzothienyl;

$R^2$ and $R^3$ are each independently H, methyl, ethyl, isopropyl or tert. butyl, with the proviso that both $R^2$ and $R^3$ cannot be hydrogen; or $R^2$ and $R^3$ together with the carbon atom to which they are attached form a cyclopropyl, cyclobutyl, cyclopentyl, cyclohexyl or a tetrahydropyranyl ring;

$R^{1a}R^{1b}$ are each independently selected from —H, $C_{1-6}$ alkyl, methoxy, —CH$_2$—OH, hydroxy, —C(O)—CH$_3$ and —NR$^5$R$^6$;

$R^{4a}$ and $R^{4b}$ are each independently selected from —H, $C_{1-3}$ alkyl, $C_{1-3}$alkoxyl, —$C_{1-3}$ alkyl-OH, phenyl, —O-phenyl, thiazolyl, oxazolyl, isoxazolyl, furanyl, thienyl, pyrrolyl, thiadiazolyl, tetrazolyl, pyridinyl, pyrimidinyl, pyridazinyl, pyrazinyl, cyclopropyl, cyclopbutyl, cyclophenyl, cyclohexyl, pyrrolidinyl, tetrahydrothienyl, piperidinyl, piperazinyl, morpholinyl, —$C_{1-3}$alkyl-phenyl, —$C_{1-3}$ alkyl-pyridinyl, —$C_{1-3}$ alkyl-pyrimidinyl, —$C_{1-3}$ alkyl-pyridazinyl, —$C_{1-3}$ alkyl-pyrazinyl, —$C_{1-3}$ alkyl-heterocyclyl, —O—$C_{1-3}$ alkyl-phenyl, —O—$C_{1-3}$ alkyl-pyridinyl, —OC$_{1-3}$ alkyl, CF$_3$, O—CF$_3$, —COOR$^5$, —C(O)C$_{1-3}$ alkyl-S(O)$_2$—NR$^5$R$^6$, —S(O)$_2$CF$_3$, —S(O)$_2$ $C_{1-3}$ alkyl, —C(O)NR$^7$R$^8$, hydroxy, halogen, and cyano, wherein each group is optionally independently substituted with 1-3 substituents chosen from $C_{1-6}$ alkyl, $C_{1-6}$ alkoxyl, hydroxy and halogen;

$R^5$ and $R^6$ are each independently chosen from H, $C_{1-5}$ alkyl, —$C_{1-3}$alkylhydroxy and $C_{1-3}$ alkyl-O—$C_{1-3}$ alkyl;

Or, $R^5$ and $R^6$ together with the nitrogen atom to which they are attached form a piperidinyl, morpholinyl or thiomorpholinyl ring;

$R^7$ and $R^8$ are each independently chosen from H, $C_{1-6}$ alkyl, —S(O)$_2$C$_{1-3}$ alkyl, and —C(NH)—NH$_2$.

In an eighth embodiment there is provided a compound as described in the seventh embodiment above, or a pharmaceutically acceptable salt thereof, wherein:

$R^2$ and $R^3$ are each independently H, methyl, ethyl, isopropyl or tert. butyl, with the proviso that both $R^2$ and $R^3$ cannot be hydrogen.

In a ninth embodiment there is provided a compound as described in the seventh embodiment, or a pharmaceutically acceptable salt thereof, wherein:

$R^2$ and $R^3$ together with the carbon atom to which they are attached form a cyclopropyl, cyclobutyl, cyclopentyl, cyclohexyl or a tetrahydropyranyl ring.

In a tenth embodiment there is provided a compound as described in the seventh embodiment, or a pharmaceutically acceptable salt thereof, wherein:

B is phenyl.

In an eleventh embodiment there is provided a compound as described in the seventh embodiment, or a pharmaceutically acceptable salt thereof, wherein:

B is pyridyl.

The following are representative compounds of the invention which can be made by the general synthetic schemes, the examples, and known methods in the art.

TABLE 1

| Example | Structure | Names |
|---|---|---|
| 1 | 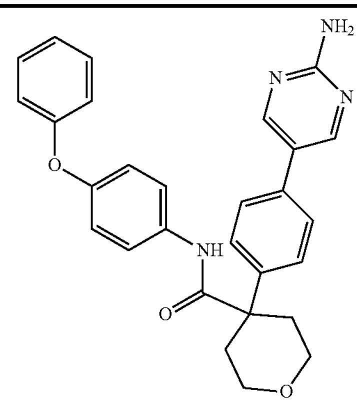 | 4-[4-(2-aminopyrimidin-5-yl)phenyl]-N-(4-phenoxyphenyl)tetrahydro-2H-pyran-4-carboxamide |
| 2 | 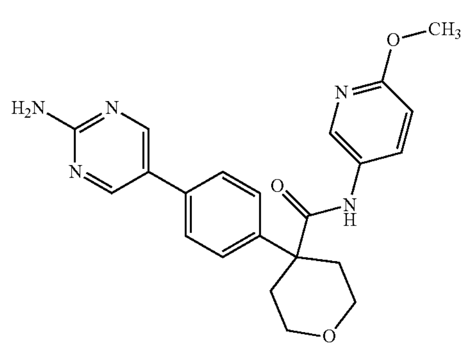 [SMILES: COc1ccc(NC(=O)C2(c3ccc(-c4cnc(N)nc4)cc3)CCOCC2)cn1] | 4-[4-(2-aminopyrimidin-5-yl)phenyl]-N-(6-methoxypyridin-3-yl)tetrahydro-2H-pyran-4-carboxamide |

TABLE 1-continued

| Example | Structure | Names |
|---|---|---|
| 3 | 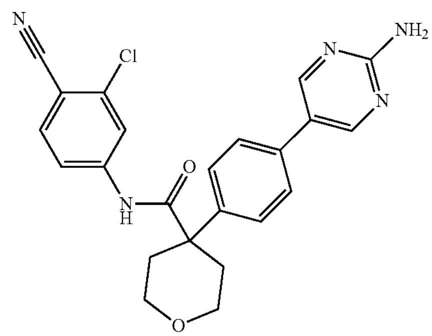 [SMILES: N#Cc1ccc(NC(=O)C2(c3ccc(-c4cnc(N)nc4)cc3)CCOCC2)cc1Cl] | 4-[4-(2-aminopyrimidin-5-yl)phenyl]-N-(3-chloro-4-cyanophenyl)tetrahydro-2H-pyran-4-carboxamide |
| 4 | 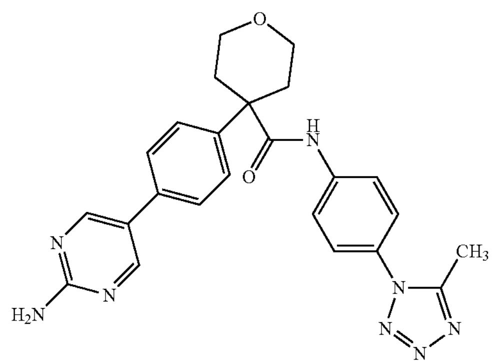 [SMILES: Cc1nnnn1-c1ccc(NC(=O)C2(c3ccc(-c4cnc(N)nc4)cc3)CCOCC2)cc1] | 4-[4-(2-aminopyrimidin-5-yl)phenyl]-N-[4-(5-methyl-1H-tetrazol-1-yl)phenyl]tetrahydro-2H-pyran-4-carboxamide |
| 5 | 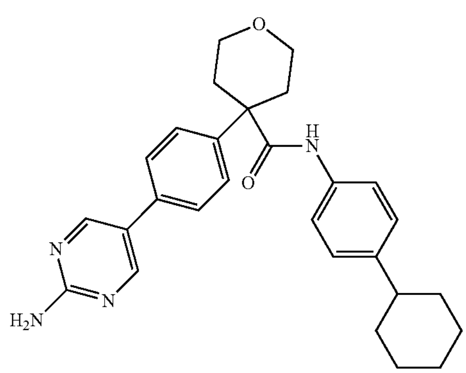 [SMILES: Nc1ncc(-c2ccc(C3(C(=O)Nc4ccc(C5CCCCC5)cc4)CCOCC3)cc2)cn1] | 4-[4-(2-aminopyrimidin-5-yl)phenyl]-N-(4-cyclohexylphenyl)tetrahydro-2H-pyran-4-carboxamide |
| 6 | 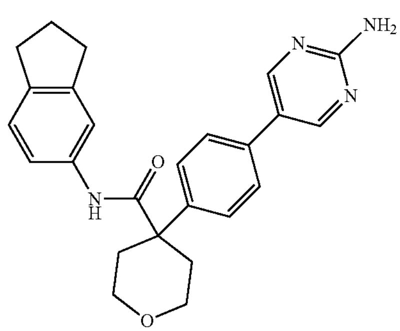 [SMILES: Nc1ncc(-c2ccc(C3(C(=O)Nc4ccc5c(c4)CCC5)CCOCC3)cc2)cn1] | 4-[4-(2-aminopyrimidin-5-yl)phenyl]-N-(2,3-dihydro-1H-inden-5-yl)tetrahydro-2H-pyran-4-carboxamide |

TABLE 1-continued

| Example | Structure | Names |
|---|---|---|
| 7 | 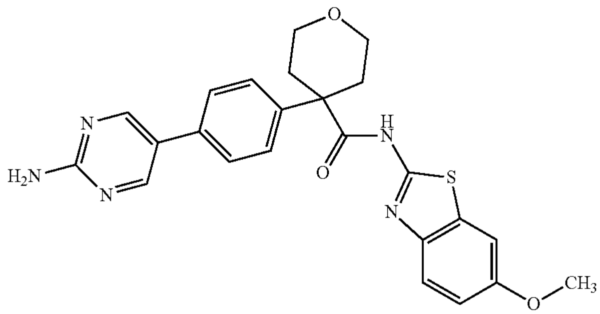 [SMILES: COc1ccc2nc(NC(=O)C3(c4ccc(-c5cnc(N)nc5)cc4)CCOCC3)sc2c1] | 4-[4-(2-aminopyrimidin-5-yl)phenyl]-N-(6-methoxy-1,3-benzothiazol-2-yl)tetrahydro-2H-pyran-4-carboxamide |
| 8 | 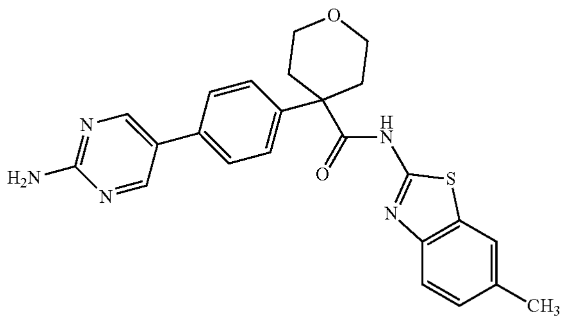 [SMILES: Cc1ccc2nc(NC(=O)C3(c4ccc(-c5cnc(N)nc5)cc4)CCOCC3)sc2c1] | 4-[4-(2-aminopyrimidin-5-yl)phenyl]-N-(6-methyl-1,3-benzothiazol-2-yl)tetrahydro-2H-pyran-4-carboxamide |
| 9 | 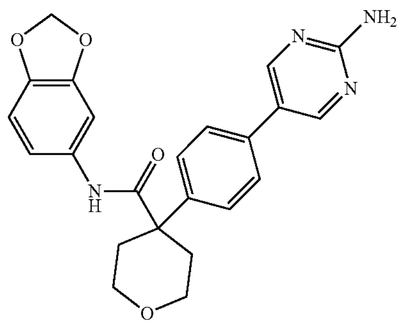 [SMILES: Nc1ncc(-c2ccc(C3(C(=O)Nc4ccc5c(c4)OCO5)CCOCC3)cc2)cn1] | 4-[4-(2-aminopyrimidin-5-yl)phenyl]-N-(1,3-benzodioxol-5-yl)tetrahydro-2H-pyran-4-carboxamide |
| 10 | 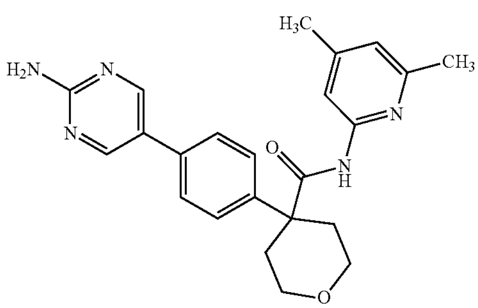 [SMILES: Cc1cc(C)nc(NC(=O)C2(c3ccc(-c4cnc(N)nc4)cc3)CCOCC2)c1] | 4-[4-(2-aminopyrimidin-5-yl)phenyl]-N-(4,6-dimethylpyridin-2-yl)tetrahydro-2H-pyran-4-carboxamide |
| 11 | 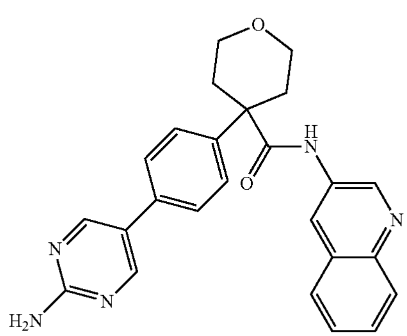 [SMILES: Nc1ncc(-c2ccc(C3(C(=O)Nc4cnc5ccccc5c4)CCOCC3)cc2)cn1] | 4-[4-(2-aminopyrimidin-5-yl)phenyl]-N-(quinolin-3-yl)tetrahydro-2H-pyran-4-carboxamide |

TABLE 1-continued

| Example | Structure | Names |
|---|---|---|
| 12 | 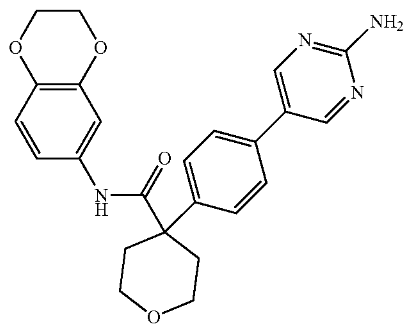 [SMILES: Nc1ncc(-c2ccc(C3(C(=O)Nc4ccc5c(c4)OCCO5)CCOCC3)cc2)cn1] | 4-[4-(2-aminopyrimidin-5-yl)phenyl]-N-(2,3-dihydro-1,4-benzodioxin-6-yl)tetrahydro-2H-pyran-4-carboxamide |
| 13 | 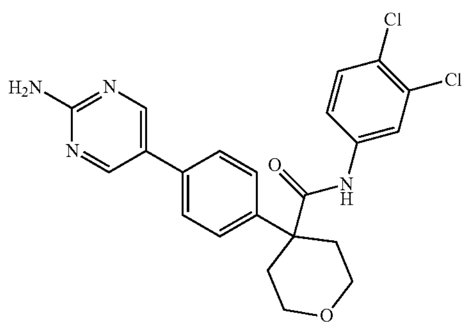 [SMILES: Nc1ncc(-c2ccc(C3(C(=O)Nc4ccc(Cl)c(Cl)c4)CCOCC3)cc2)cn1] | 4-[4-(2-aminopyrimidin-5-yl)phenyl]-N-(3,4-dichlorophenyl)tetrahydro-2H-pyran-4-carboxamide |
| 14 | 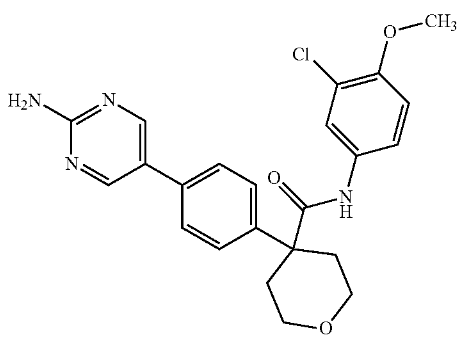 [SMILES: COc1ccc(NC(=O)C2(c3ccc(-c4cnc(N)nc4)cc3)CCOCC2)cc1Cl] | 4-[4-(2-aminopyrimidin-5-yl)phenyl]-N-(3-chloro-4-methoxyphenyl)tetrahydro-2H-pyran-4-carboxamide |
| 15 | 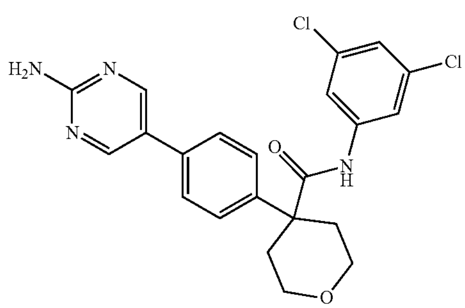 [SMILES: Nc1ncc(-c2ccc(C3(C(=O)Nc4cc(Cl)cc(Cl)c4)CCOCC3)cc2)cn1] | 4-[4-(2-aminopyrimidin-5-yl)phenyl]-N-(3,5-dichlorophenyl)tetrahydro-2H-pyran-4-carboxamide |

TABLE 1-continued

| Example | Structure | Names |
|---|---|---|
| 16 | 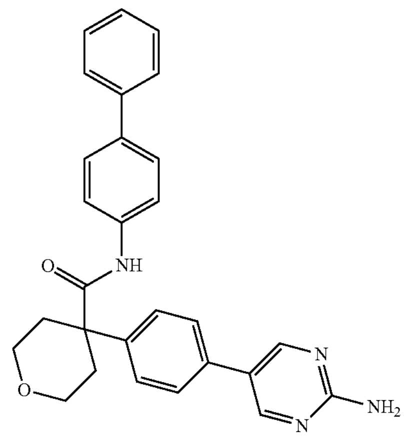 [SMILES: Nc1ncc(-c2ccc(C3(C(=O)Nc4ccc(-c5ccccc5)cc4)CCOCC3)cc2)cn1] | 4-[4-(2-aminopyrimidin-5-yl)phenyl]-N-(biphenyl-4-yl)tetrahydro-2H-pyran-4-carboxamide |
| 17 | 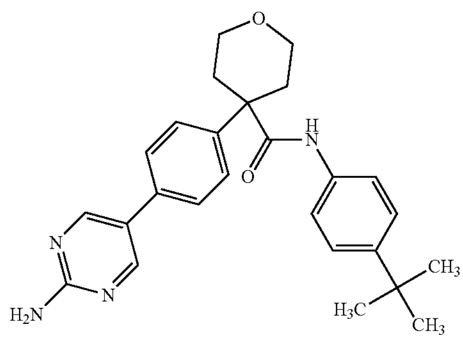 [SMILES: CC(C)(C)c1ccc(NC(=O)C2(c3ccc(-c4cnc(N)nc4)cc3)CCOCC2)cc1] | 4-[4-(2-aminopyrimidin-5-yl)phenyl]-N-(4-tert-butylphenyl)tetrahydro-2H-pyran-4-carboxamide |
| 18 | 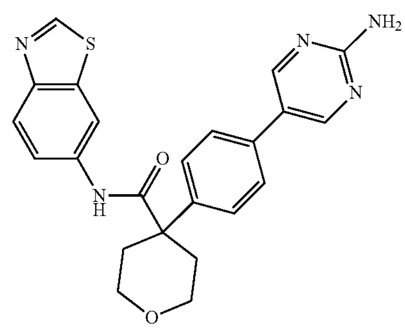 [SMILES: Nc1ncc(-c2ccc(C3(C(=O)Nc4ccc5ncsc5c4)CCOCC3)cc2)cn1] | 4-[4-(2-aminopyrimidin-5-yl)phenyl]-N-(1,3-benzothiazol-6-yl)tetrahydro-2H-pyran-4-carboxamide |
| 19 | 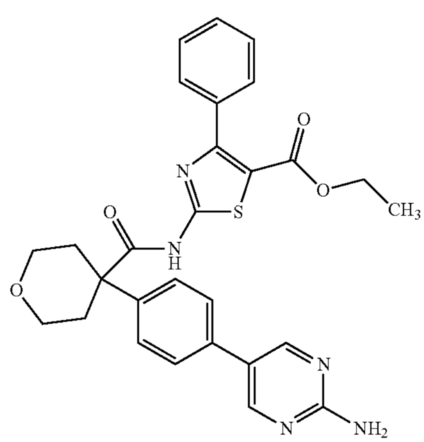 [SMILES: CCOC(=O)c1sc(NC(=O)C2(c3ccc(-c4cnc(N)nc4)cc3)CCOCC2)nc1-c1ccccc1] | ethyl 2-[({4-[4-(2-aminopyrimidin-5-yl)phenyl]tetrahydro-2H-pyran-4-yl}carbonyl)amino]-4-phenyl-1,3-thiazole-5-carboxylate |

TABLE 1-continued

| Example | Structure | Names |
|---|---|---|
| 20 | 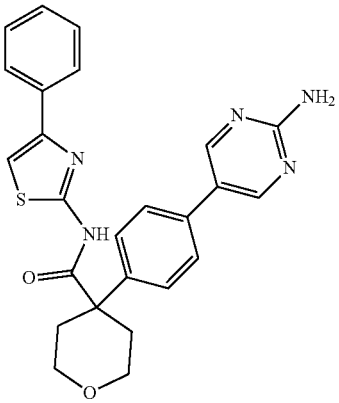 [SMILES: Nc1ncc(-c2ccc(C3(C(=O)Nc4nc(-c5ccccc5)cs4)CCOCC3)cc2)cn1] | 4-[4-(2-aminopyrimidin-5-yl)phenyl]-N-(4-phenyl-1,3-thiazol-2-yl)tetrahydro-2H-pyran-4-carboxamide |
| 21 | 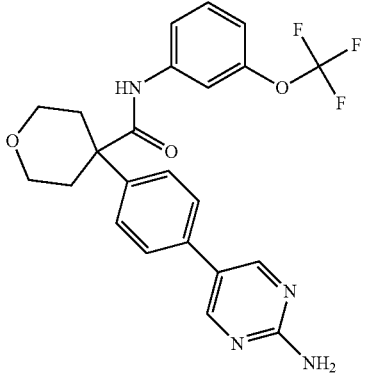 [SMILES: Nc1ncc(-c2ccc(C3(C(=O)Nc4cccc(OC(F)(F)F)c4)CCOCC3)cc2)cn1] | 4-[4-(2-aminopyrimidin-5-yl)phenyl-N-[3-(trifluoromethoxy)phenyl]tetrahydro-2H-pyran-4-carboxamide |
| 22 | 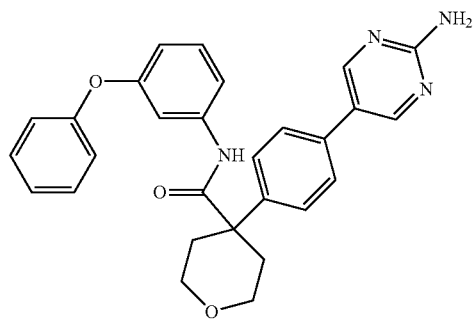 [SMILES: Nc1ncc(-c2ccc(C3(C(=O)Nc4cccc(Oc5ccccc5)c4)CCOCC3)cc2)cn1] | 4-[4-(2-aminopyrimidin-5-yl)phenyl]-N-(3-phenoxyphenyl)tetrahydro-2H-pyran-4-carboxamide |
| 23 | 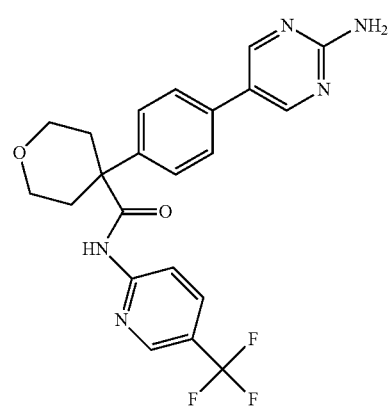 [SMILES: Nc1ncc(-c2ccc(C3(C(=O)Nc4ccc(C(F)(F)F)cn4)CCOCC3)cc2)cn1] | 4-[4-(2-aminopyrimidin-5-yl)phenyl]-N-[5-(trifluoromethyl)pyridin-2-yl]tetrahydro-2H-pyran-4-carboxamide |

TABLE 1-continued

| Example | Structure | Names |
|---|---|---|
| 24 | 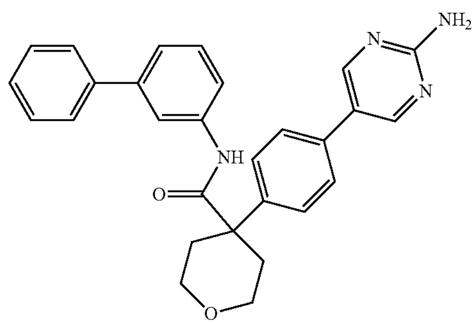 [SMILES: Nc1ncc(-c2ccc(C3(C(=O)Nc4cccc(-c5ccccc5)c4)CCOCC3)cc2)cn1] | 4-[4-(2-aminopyrimidin-5-yl)phenyl]-N-(biphenyl-3-yl)tetrahydro-2H-pyran-4-carboxamide |
| 25 | 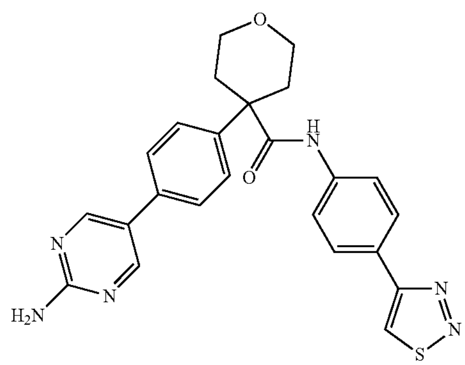 [SMILES: Nc1ncc(-c2ccc(C3(C(=O)Nc4ccc(-c5csnn5)cc4)CCOCC3)cc2)cn1] | 4-[4-(2-aminopyrimidin-5-yl)phenyl]-N-[4-(1,2,3-thiadiazol-4-yl)phenyl]tetrahydro-2H-pyran-4-carboxamide |
| 26 | 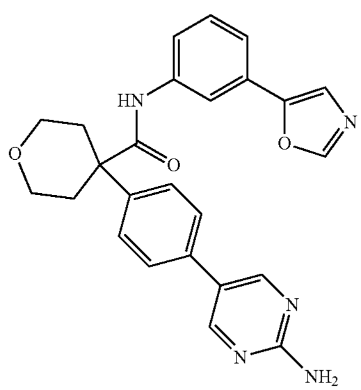 [SMILES: Nc1ncc(-c2ccc(C3(C(=O)Nc4cccc(-c5cnco5)c4)CCOCC3)cc2)cn1] | 4-[4-(2-aminopyrimidin-5-yl)phenyl]-N-[3-(1,3-oxazol-5-yl)phenyl]tetrahydro-2H-pyran-4-carboxamide |
| 27 | 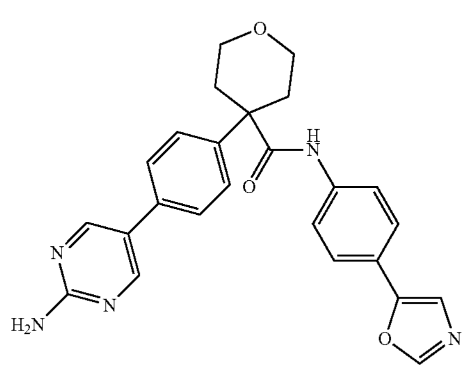 [SMILES: Nc1ncc(-c2ccc(C3(C(=O)Nc4ccc(-c5cnco5)cc4)CCOCC3)cc2)cn1] | 4-[4-(2-aminopyrimidin-5-yl)phenyl]-N-[4-(1,3-oxazol-5-yl)phenyl]tetrahydro-2H-pyran-4-carboxamide |

TABLE 1-continued

| Example | Structure | Names |
|---|---|---|
| 28 | 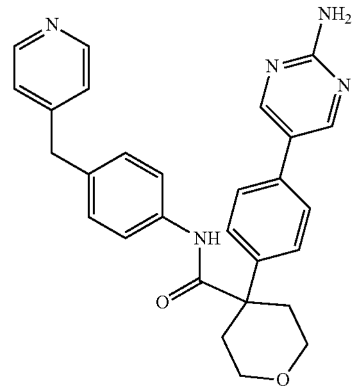 [SMILES: Nc1ncc(-c2ccc(C3(C(=O)Nc4ccc(Cc5ccncc5)cc4)CCOCC3)cc2)cn1] | 4-[4-(2-aminopyrimidin-5-yl)phenyl]-N-[4-(pyridin-4-ylmethyl)phenyl]tetrahydro-2H-pyran-4-carboxamide |
| 29 | 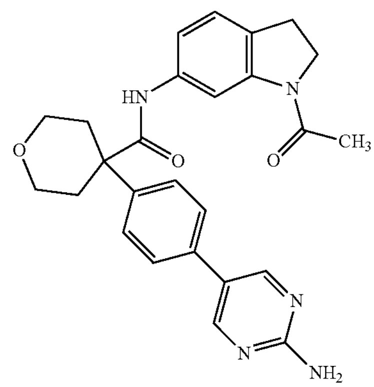 [SMILES: CC(=O)N1CCc2ccc(NC(=O)C3(c4ccc(-c5cnc(N)nc5)cc4)CCOCC3)cc21] | N-(1-acetyl-2,3-dihydro-1H-indol-6-yl)-4-[4-(2-aminopyrimidin-5-yl)phenyl]tetrahydro-2H-pyran-4-carboxamide |
| 30 | 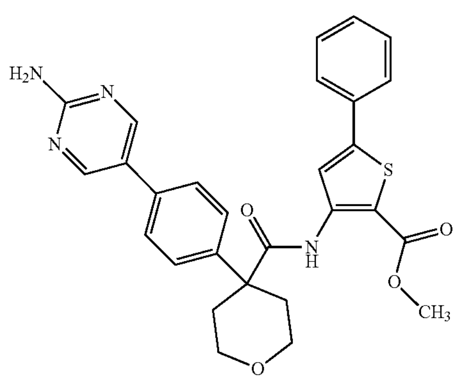 [SMILES: COC(=O)c1sc(-c2ccccc2)cc1NC(=O)C1(c2ccc(-c3cnc(N)nc3)cc2)CCOCC1] | methyl 3-[({4-[4-(2-aminopyrimidin-5-yl)phenyl]tetrahydro-2H-pyran-4-yl}carbonyl)amino]-5-phenylthiophene-2-carboxylate |
| 31 | 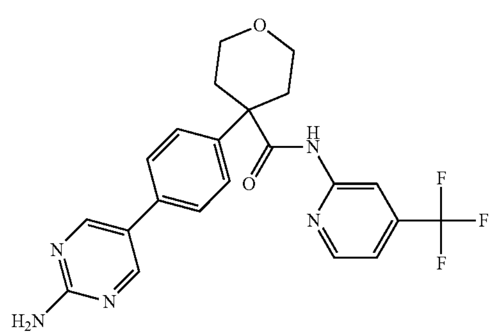 [SMILES: Nc1ncc(-c2ccc(C3(C(=O)Nc4cc(C(F)(F)F)ccn4)CCOCC3)cc2)cn1] | 4-[4-(2-aminopyrimidin-5-yl)phenyl]-N-[4-(trifluoromethyl)pyridin-2-yl]tetrahydro-2H-pyran-4-carboxamide |

TABLE 1-continued

| Example | Structure | Names |
|---|---|---|
| 32 | 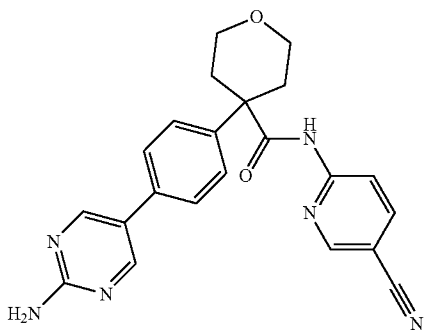 [SMILES: N#Cc1ccc(NC(=O)C2(c3ccc(-c4cnc(N)nc4)cc3)CCOCC2)nc1] | 4-[4-(2-aminopyrimidin-5-yl)phenyl]-N-(5-cyanopyridin-2-yl)tetrahydro-2H-pyran-4-carboxamide |
| 33 | 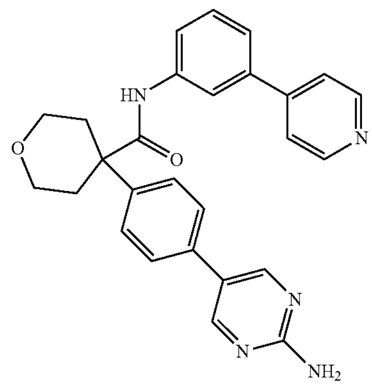 [SMILES: Nc1ncc(-c2ccc(C3(C(=O)Nc4cccc(-c5ccncc5)c4)CCOCC3)cc2)cn1] | 4-[4-(2-aminopyrimidin-5-yl)phenyl]-N-[3-(pyridin-4-yl)phenyl]tetrahydro-2H-pyran-4-carboxamide |
| 34 | 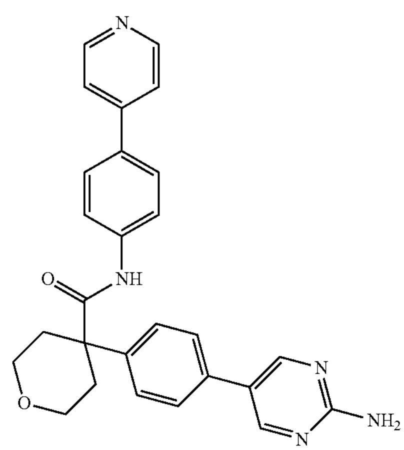 [SMILES: Nc1ncc(-c2ccc(C3(C(=O)Nc4ccc(-c5ccncc5)cc4)CCOCC3)cc2)cn1] | 4-[4-(2-aminopyrimidin-5-yl)phenyl]-N-[4-(pyridin-4-yl)phenyl]tetrahydro-2H-pyran-4-carboxamide |
| 35 | 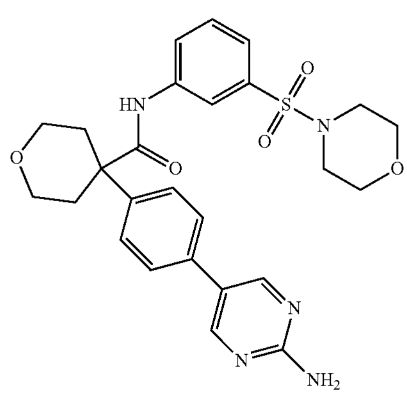 [SMILES: Nc1ncc(-c2ccc(C3(C(=O)Nc4cccc(S(=O)(=O)N5CCOCC5)c4)CCOCC3)cc2)cn1] | 4-[4-(2-aminopyrimidin-5-yl)phenyl]-N-[3-(mopholin-4-ylsulfonyl)phenyl]tetrahydro-2H-pyran-4-carboxamide |

TABLE 1-continued

| Example | Structure | Names |
|---|---|---|
| 36 | 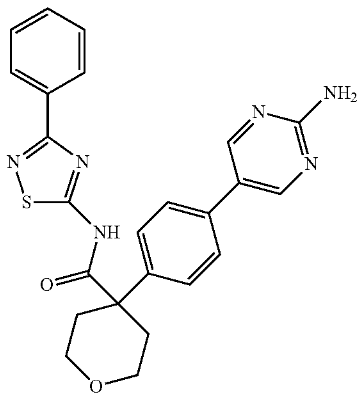 [SMILES: Nc1ncc(-c2ccc(C3(C(=O)Nc4nc(-c5ccccc5)ns4)CCOCC3)cc2)cn1] | 4-[4-(2-aminopyrimidin-5-yl)phenyl]-N-(3-phenyl-1,2,4-thiadiazol-5-yl)tetrahydro-2H-pyran-4-carboxamide |
| 37 | 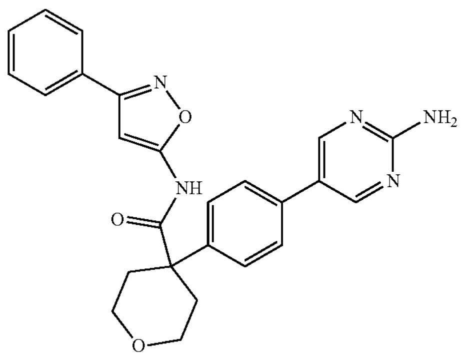 [SMILES: Nc1ncc(-c2ccc(C3(C(=O)Nc4cc(-c5ccccc5)no4)CCOCC3)cc2)cn1] | 4-[4-(2-aminopyrimidin-5-yl)phenyl]-N-(3-phenyl-1,2-oxazol-5-yl)tetrahydro-2H-pyran-4-carboxamide |
| 38 | 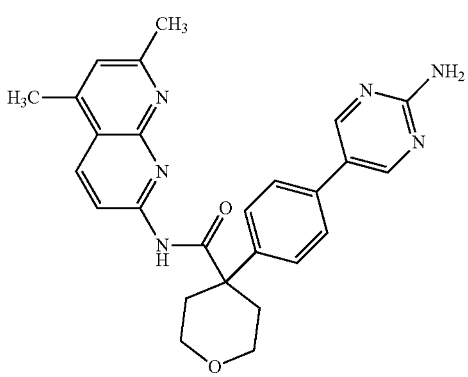 [SMILES: Cc1cc(C)c2ccc(NC(=O)C3(c4ccc(-c5cnc(N)nc5)cc4)CCOCC3)nc2n1] | 4-[4-(2-aminopyrimidin-5-yl)phenyl]-N-(5,7-dimethyl-1,8-naphthyridin-2-yl)tetrahydro-2H-pyran-4-carboxamide |
| 39 | 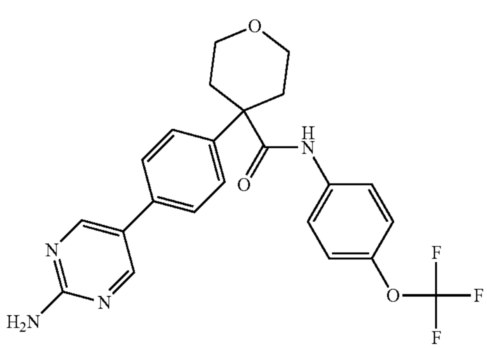 [SMILES: Nc1ncc(-c2ccc(C3(C(=O)Nc4ccc(OC(F)(F)F)cc4)CCOCC3)cc2)cn1] | 4-[4-(2-aminopyrimidin-5-yl)phenyl]-N-[4-(trifluoromethoxy)phenyl]tetrahydro-2H-pyran-4-carboxamide |

TABLE 1-continued

| Example | Structure | Names |
|---|---|---|
| 40 | 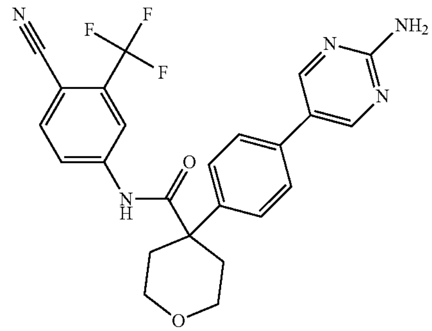 [SMILES: N#Cc1ccc(NC(=O)C2(c3ccc(-c4cnc(N)nc4)cc3)CCOCC2)cc1C(F)(F)F] | 4-[4-(2-aminopyrimidin-5-yl)phenyl]-N-[4-cyano-3-(trifluoromethyl)phenyl]tetrahydro-2H-pyran-4-carboxamide |
| 41 | 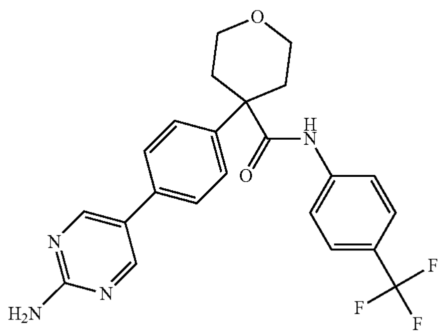 [SMILES: Nc1ncc(-c2ccc(C3(C(=O)Nc4ccc(C(F)(F)F)cc4)CCOCC3)cc2)cn1] | 4-[4-(2-aminopyrimidin-5-yl)phenyl]-N-[4-(trifluoromethyl)phenyl]tetrahydro-2H-pyran-4-carboxamide |
| 42 | 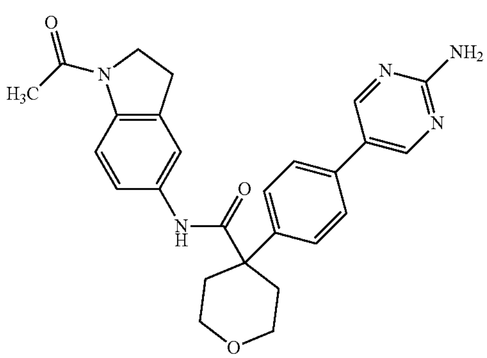 [SMILES: CC(=O)N1CCc2cc(NC(=O)C3(c4ccc(-c5cnc(N)nc5)cc4)CCOCC3)ccc21] | N-(1-acetyl-2,3-dihydro-1H-indol-5-yl)-4-[4-(2-aminopyrimidin-5-yl)phenyl]tetrahydro-2H-pyran-4-carboxamide |
| 43 | 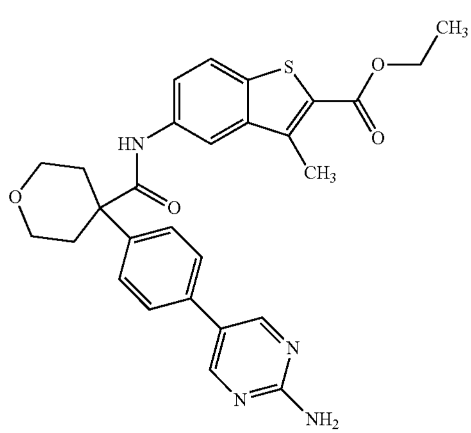 [SMILES: CCOC(=O)c1sc2ccc(NC(=O)C3(c4ccc(-c5cnc(N)nc5)cc4)CCOCC3)cc2c1C] | ethyl 5-[({4-[4-(2-aminopyrimidin-5-yl)phenyl]tetrahydro-2H-pyran-4-yl}carbonyl)amino]-3-methyl-1-benzothiophene-2-carboxylate |

TABLE 1-continued

| Example | Structure | Names |
|---|---|---|
| 44 | 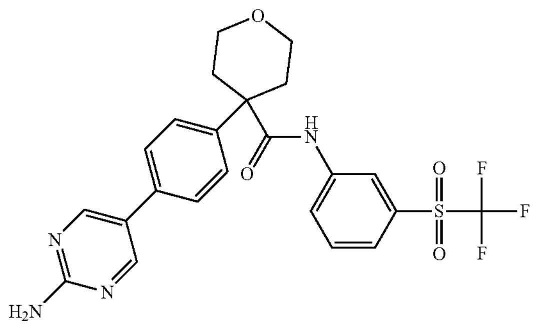 [SMILES: Nc1ncc(-c2ccc(C3(C(=O)Nc4cccc(S(=O)(=O)C(F)(F)F)c4)CCOCC3)cc2)cn1] | 4-[4-(2-aminopyrimidin-5-yl)phenyl]-N-{3-[(trifluoromethyl)sulfonyl]phenyl}tetrahydro-2H-pyran-4-carboxamide |
| 45 | 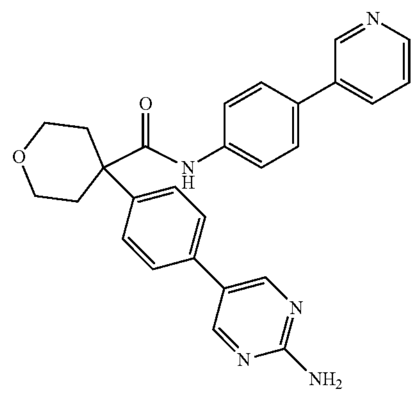 [SMILES: Nc1ncc(-c2ccc(C3(C(=O)Nc4ccc(-c5cccnc5)cc4)CCOCC3)cc2)cn1] | 4-[4-(2-aminopyrimidin-5-yl)phenyl]-N-[4-(pyridin-3-yl)phenyl]tetrahydro-2H-pyran-4-carboxamide |
| 46 | 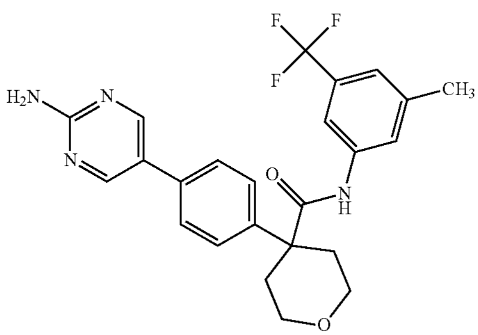 [SMILES: Cc1cc(NC(=O)C2(c3ccc(-c4cnc(N)nc4)cc3)CCOCC2)cc(C(F)(F)F)c1] | 4-[4-(2-aminopyrimidin-5-yl)phenyl]-N-[3-methyl-5-(trifluoromethyl)phenyl]tetrahydro-2H-pyran-4-carboxamide |
| 47 | 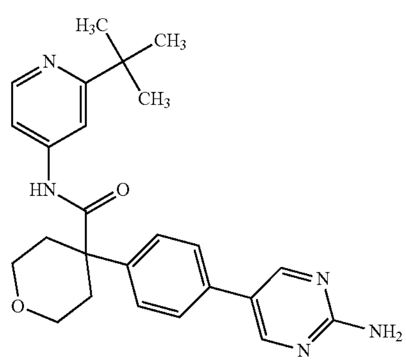 [SMILES: CC(C)(C)c1cc(NC(=O)C2(c3ccc(-c4cnc(N)nc4)cc3)CCOCC2)ccn1] | 4-[4-(2-aminopyrimidin-5-yl)phenyl]-N-(2-tert-butylpyridin-4-yl)tetrahydro-2H-pyran-4-carboxamide |

TABLE 1-continued

| Example | Structure | Names |
|---|---|---|
| 48 | 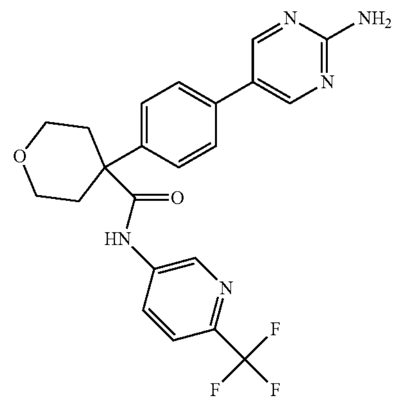 [SMILES: Nc1ncc(-c2ccc(C3(C(=O)Nc4ccc(C(F)(F)F)nc4)CCOCC3)cc2)cn1] | 4-[4-(2-aminopyrimidin-5-yl)phenyl]-N-[6-(trifluoromethyl)pyridin-3-yl]tetrahydro-2H-pyran-4-carboxamide |
| 49 | 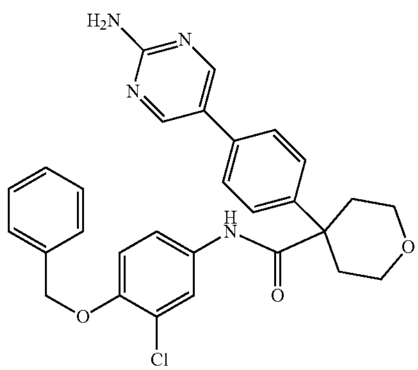 [SMILES: Nc1ncc(-c2ccc(C3(C(=O)Nc4ccc(OCc5ccccc5)c(Cl)c4)CCOCC3)cc2)cn1] | 4-[4-(2-aminopyrimidin-5-yl)phenyl]-N-[4-(benzyloxy)-3-chlorophenyl]tetrahydro-2H-pyran-4-carboxamide |
| 50 | 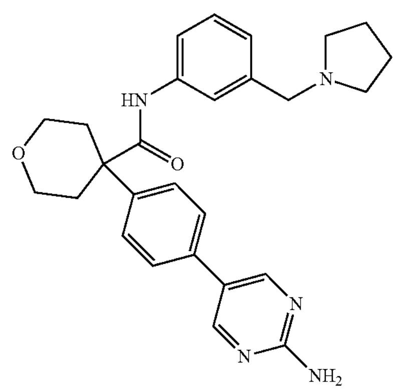 [SMILES: Nc1ncc(-c2ccc(C3(C(=O)Nc4cccc(CN5CCCC5)c4)CCOCC3)cc2)cn1] | 4-[4-(2-aminopyrimidin-5-yl)phenyl]-N-[3-(pyrrolidin-1-ylmethyl)phenyl]tetrahydro-2H-pyran-4-carboxamide |
| 51 | 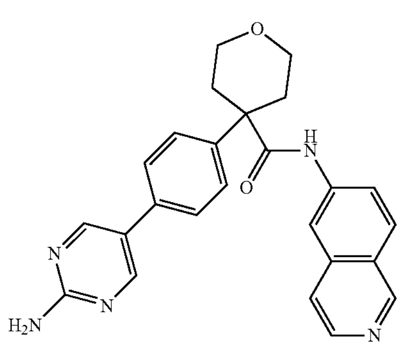 [SMILES: Nc1ncc(-c2ccc(C3(C(=O)Nc4ccc5cnccc5c4)CCOCC3)cc2)cn1] | 4-[4-(2-aminopyrimidin-5-yl)phenyl]-N-(isoquinolin-6-yl)tetrahydro-2H-pyran-4-carboxamide |

TABLE 1-continued

| Example | Structure | Names |
|---|---|---|
| 52 | 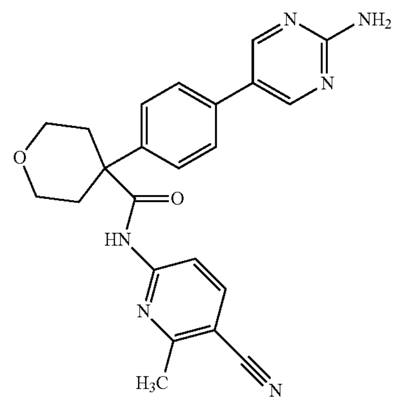 [SMILES: Cc1nc(NC(=O)C2(c3ccc(-c4cnc(N)nc4)cc3)CCOCC2)ccc1C#N] | 4-[4-(2-aminopyrimidin-5-yl)phenyl]-N-(5-cyano-6-methylpyridin-2-yl)tetrahydro-2H-pyran-4-carboxamide |
| 53 | 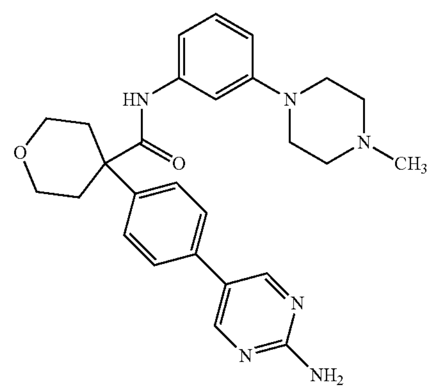 [SMILES: CN1CCN(c2cccc(NC(=O)C3(c4ccc(-c5cnc(N)nc5)cc4)CCOCC3)c2)CC1] | 4-[4-(2-aminopyrimidin-5-yl)phenyl]-N-[3-(4-methylpiperazin-1-yl)phenyl]tetrahydro-2H-pyran-4-carboxamide |
| 54 | 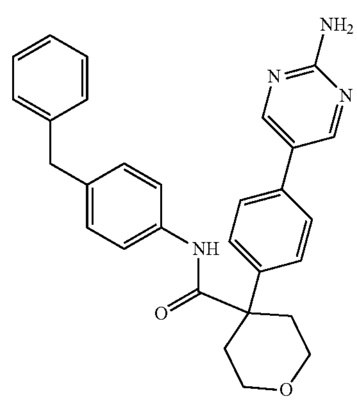 [SMILES: Nc1ncc(-c2ccc(C3(C(=O)Nc4ccc(Cc5ccccc5)cc4)CCOCC3)cc2)cn1] | 4-[4-(2-aminopyrimidin-5-yl)phenyl]-N-(4-benzylphenyl)tetrahydro-2H-pyran-4-carboxamide |
| 55 | 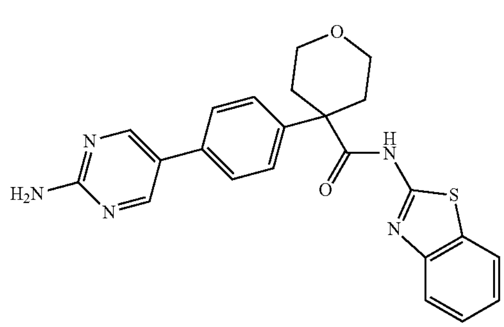 [SMILES: Nc1ncc(-c2ccc(C3(C(=O)Nc4nc5ccccc5s4)CCOCC3)cc2)cn1] | 4-[4-(2-aminopyrimidin-5-yl)phenyl]-N-(1,3-benzothiazol-2-yl)tetrahydro-2H-pyran-4-carboxamide |

TABLE 1-continued

| Example | Structure | Names |
|---|---|---|
| 56 | 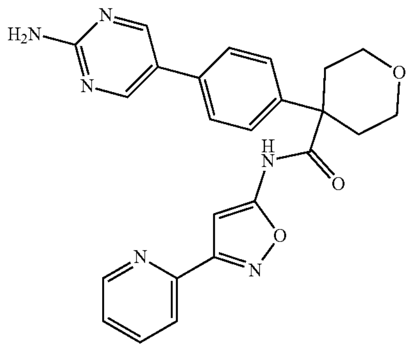 [SMILES: Nc1ncc(-c2ccc(C3(C(=O)Nc4cc(-c5ccccn5)no4)CCOCC3)cc2)cn1] | 4-[4-(2-aminopyrimidin-5-yl)phenyl]-N-[3-(pyridin-2-yl)-1,2-oxazol-5-yl]tetrahydro-2H-pyran-4-carboxamide |
| 57 | 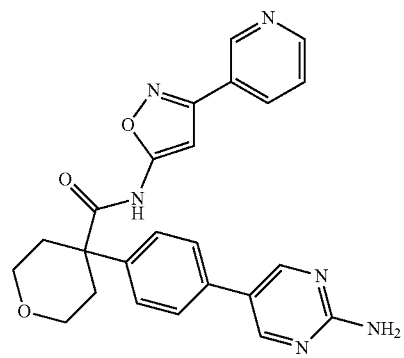 [SMILES: Nc1ncc(-c2ccc(C3(C(=O)Nc4cc(-c5cccnc5)no4)CCOCC3)cc2)cn1] | 4-[4-(2-aminopyrimidin-5-yl)phenyl]-N-[3-(pyridin-3-yl)-1,2-oxazol-5-yl]tetrahydro-2H-pyran-4-carboxamide |
| 58 | 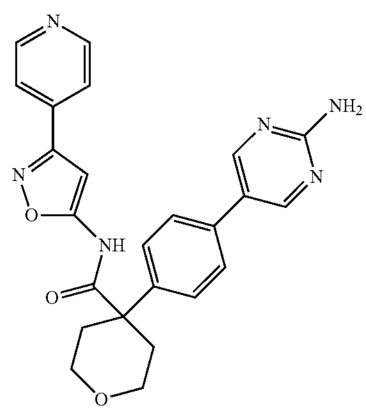 [SMILES: Nc1ncc(-c2ccc(C3(C(=O)Nc4cc(-c5ccncc5)no4)CCOCC3)cc2)cn1] | 4-[4-(2-aminopyrimidin-5-yl)phenyl]-N-[3-(pyridin-4-yl)-1,2-oxazol-5-yl]tetrahydro-2H-pyran-4-carboxamide |
| 59 | 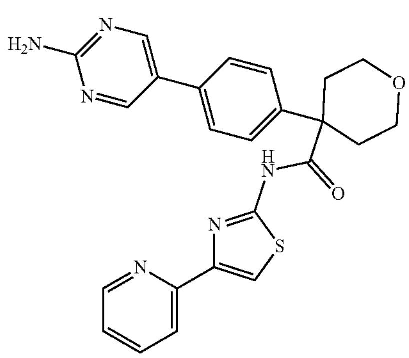 [SMILES: Nc1ncc(-c2ccc(C3(C(=O)Nc4nc(-c5ccccn5)cs4)CCOCC3)cc2)cn1] | 4-[4-(2-aminopyrimidin-5-yl)phenyl]-N-[4-(pyridin-2-yl)-1,3-thiazol-2-yl]tetrahydro-2H-pyran-4-carboxamide |

TABLE 1-continued

| Example | Structure | Names |
|---|---|---|
| 60 | 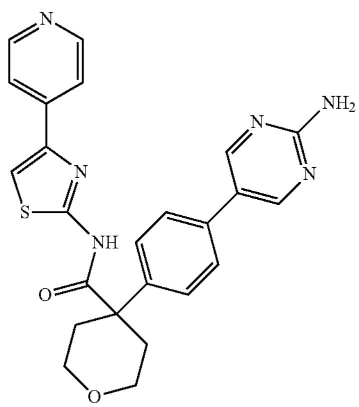 [SMILES: Nc1ncc(-c2ccc(C3(C(=O)Nc4nc(-c5ccncc5)cs4)CCOCC3)cc2)cn1] | 4-[4-(2-aminopyrimidin-5-yl)phenyl]-N-[4-(pyridin-4-yl)-1,3-thiazol-2-yl]tetrahydro-2H-pyran-4-carboxamide |
| 61 | 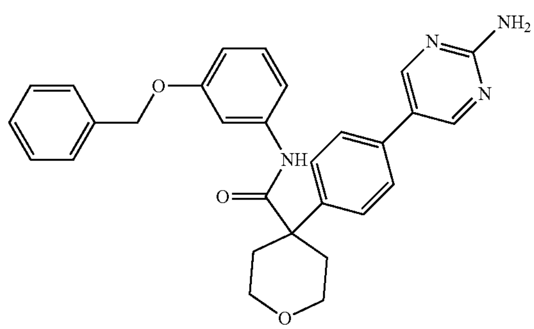 [SMILES: Nc1ncc(-c2ccc(C3(C(=O)Nc4cccc(OCc5ccccc5)c4)CCOCC3)cc2)cn1] | 4-[4-(2-aminopyrimidin-5-yl)phenyl]-N-[3-(benzyloxy)phenyl]tetrahydro-2H-pyran-4-carboxamide |
| 62 | 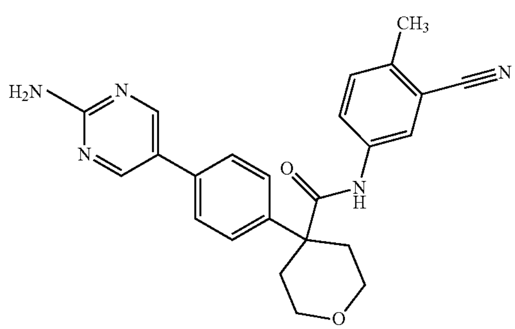 | 4-[4-(2-aminopyrimidin-5-yl)phenyl]-N-(3-cyano-4-methylphenyl)tetrahydro-2H-pyran-4-carboxamide |
| 63 | 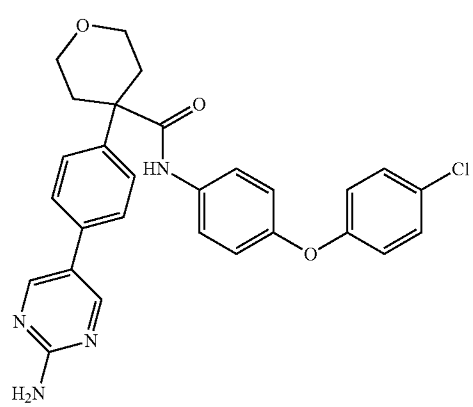 [SMILES: Nc1ncc(-c2ccc(C3(C(=O)Nc4ccc(Oc5ccc(Cl)cc5)cc4)CCOCC3)cc2)cn1] | 4-[4-(2-aminopyrimidin-5-yl)phenyl]-N-[4-(4-chlorophenoxy)phenyl]tetrahydro-2H-pyran-4-carboxamide |

TABLE 1-continued

| Example | Structure | Names |
|---|---|---|
| 64 | 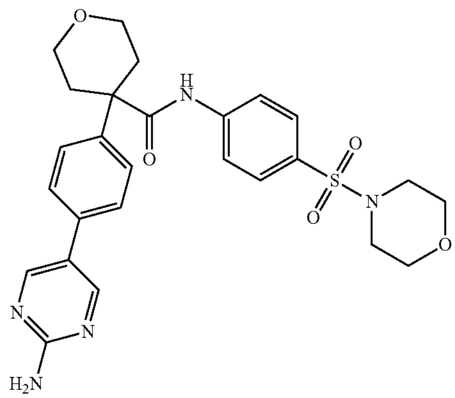 [SMILES: Nc1ncc(-c2ccc(C3(C(=O)Nc4ccc(S(=O)(=O)N5CCOCC5)cc4)CCOCC3)cc2)cn1] | 4-[4-(2-aminopyrimidin-5-yl)phenyl]-N-[4-(morpholin-4-ylsulfonyl)phenyl]tetrahydro-2H-pyran-4-carboxamide |
| 65 | 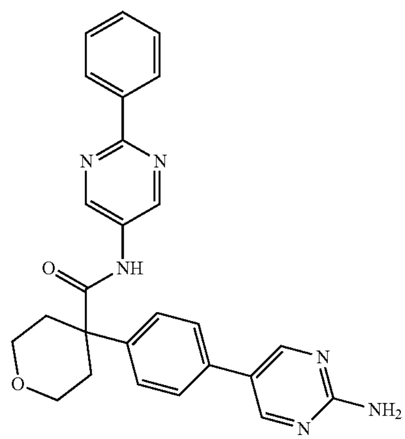 [SMILES: Nc1ncc(-c2ccc(C3(C(=O)Nc4cnc(-c5ccccc5)nc4)CCOCC3)cc2)cn1] | 4-[4-(2-aminopyrimidin-5-yl)phenyl]-N-(2-phenylpyrimidin-5-yl)tetrahydro-2H-pyran-4-carboxamide |
| 66 | 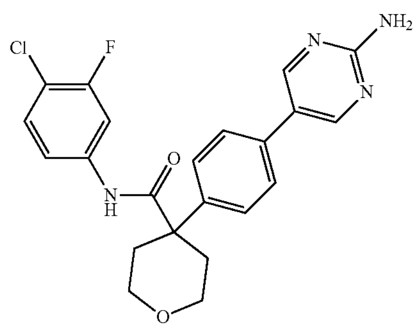 [SMILES: Nc1ncc(-c2ccc(C3(C(=O)Nc4ccc(Cl)c(F)c4)CCOCC3)cc2)cn1] | 4-[4-(2-aminopyrimidin-5-yl)phenyl]-N-(4-chloro-3-fluorophenyl)tetrahydro-2H-pyran-4-carboxamide |
| 67 | 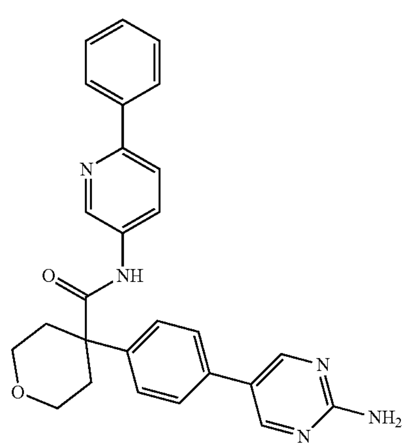 [SMILES: Nc1ncc(-c2ccc(C3(C(=O)Nc4ccc(-c5ccccc5)nc4)CCOCC3)cc2)cn1] | 4-[4-(2-aminopyrimidin-5-yl)phenyl]-N-(6-phenylpyridin-3-yl)tetrahydro-2H-pyran-4-carboxamide |

TABLE 1-continued

| Example | Structure | Names |
|---|---|---|
| 68 | 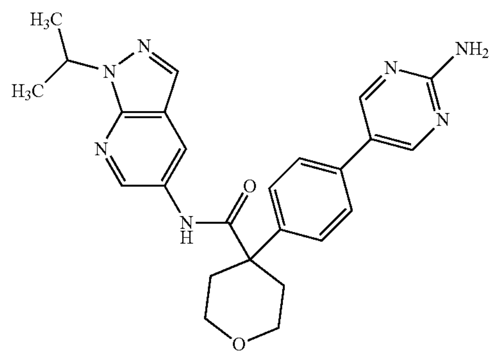 [SMILES: CC(C)n1ncc2cc(NC(=O)C3(c4ccc(-c5cnc(N)nc5)cc4)CCOCC3)cnc21] | 4-[4-(2-aminopyrimidin-5-yl)phenyl]-N-[1-(propan-2-yl)-1H-pyrazolo[3,4-b]pyridin-5-yl)tetrahydro-2H-pyran-4-carboxamide |
| 69 | 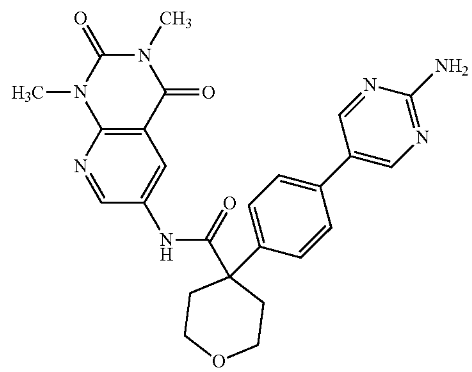 [SMILES: Cn1c(=O)c2cc(NC(=O)C3(c4ccc(-c5cnc(N)nc5)cc4)CCOCC3)cnc2n(C)c1=O] | 4-[4-(2-aminopyrimidin-5-yl)phenyl]-N-(1,3-dimethyl-2,4-dioxo-1,2,3,4-tetrahydropyrido[2,3-d]pyrimidin-6-yl)tetrahydro-2H-pyran-4-carboxamide |
| 70 | 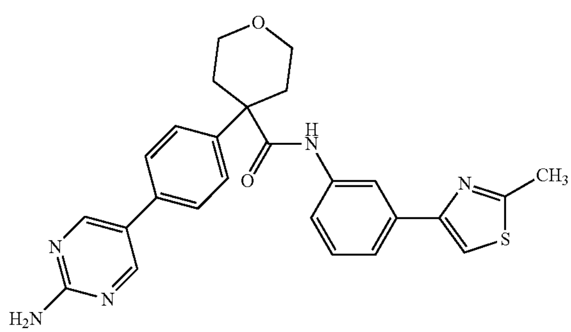 [SMILES: Cc1nc(-c2cccc(NC(=O)C3(c4ccc(-c5cnc(N)nc5)cc4)CCOCC3)c2)cs1] | 4-[4-(2-aminopyrimidin-5-yl)phenyl]-N-[3-(2-methyl-1,3-thiazol-4-yl)phenyl]tetrahydro-2H-pyran-4-carboxamide |
| 71 | 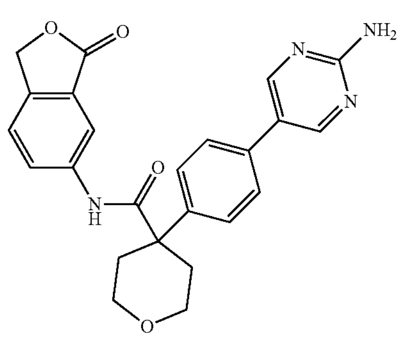 [SMILES: Nc1ncc(-c2ccc(C3(C(=O)Nc4ccc5c(c4)C(=O)OC5)CCOCC3)cc2)cn1] | 4-[4-(2-aminopyrimidin-5-yl)phenyl]-N-(3-oxo-1,3-dihydro-2-benzofuran-5-yl)tetrahydro-2H-pyran-4-carboxamide |

TABLE 1-continued

| Example | Structure | Names |
|---|---|---|
| 72 | 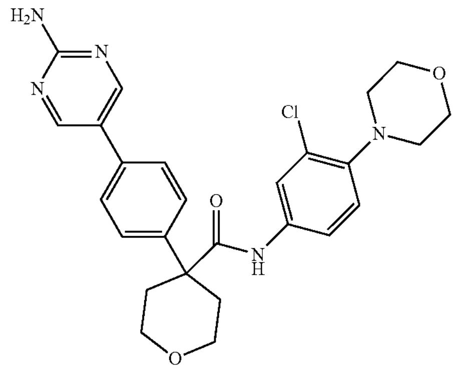 [SMILES: Nc1ncc(-c2ccc(C3(C(=O)Nc4ccc(N5CCOCC5)c(Cl)c4)CCOCC3)cc2)cn1] | 4-[4-(2-aminopyrimidin-5-yl)phenyl]-N-[3-chloro-4-(mopholin-4-yl)phenyl]tetrahydro-2H-pyran-4-carboxamide |
| 73 | 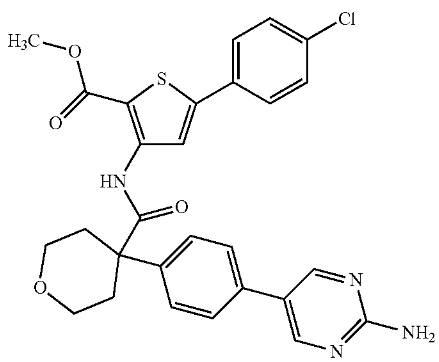 [SMILES: COC(=O)c1sc(-c2ccc(Cl)cc2)cc1NC(=O)C1(c2ccc(-c3cnc(N)nc3)cc2)CCOCC1] | methyl 3-[({4-[4-(2-aminopyrimidin-5-yl)phenyl]tetrahydro-2H-pyran-4-yl}carbonyl)amino]-5-(4-chlorophenyl)thiophene-2-carboxylate |
| 74 | 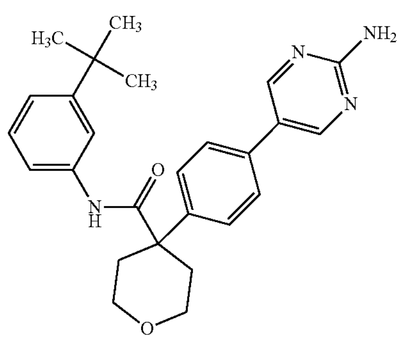 [SMILES: CC(C)(C)c1cccc(NC(=O)C2(c3ccc(-c4cnc(N)nc4)cc3)CCOCC2)c1] | 4-[4-(2-aminopyrimidin-5-yl)phenyl]-N-(3-tert-butylphenyl)tetrahydro-2H-pyran-4-carboxamide |
| 75 | 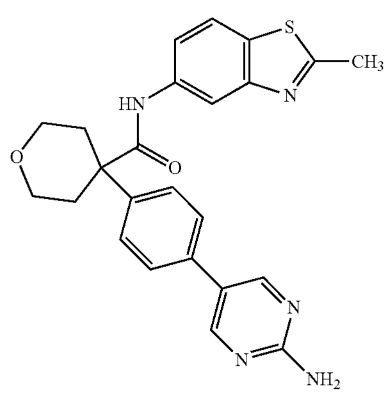 [SMILES: Cc1nc2cc(NC(=O)C3(c4ccc(-c5cnc(N)nc5)cc4)CCOCC3)ccc2s1] | 4-[4-(2-aminopyrimidin-5-yl)phenyl]-N-(2-methyl-1,3-benzothiazol-5-yl)tetrahydro-2H-pyran-4-carboxamide |

TABLE 1-continued

| Example | Structure | Names |
|---------|-----------|-------|
| 76 | 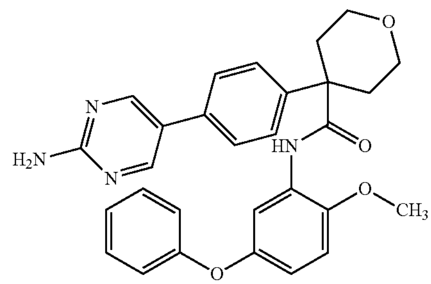 [SMILES: COc1ccc(Oc2ccccc2)cc1NC(=O)C1(c2ccc(-c3cnc(N)nc3)cc2)CCOCC1] | 4-[4-(2-aminopyrimidin-5-yl)phenyl]-N-(2-methoxy-5-phenoxyphenyl)tetrahydro-2H-pyran-4-carboxamide |
| 77 | 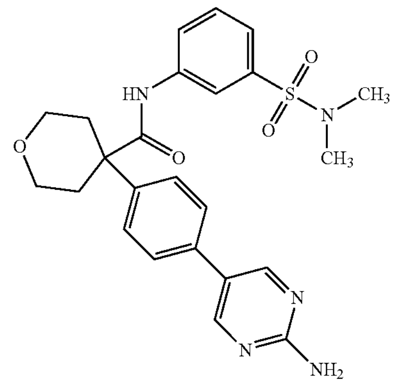 [SMILES: CN(C)S(=O)(=O)c1cccc(NC(=O)C2(c3ccc(-c4cnc(N)nc4)cc3)CCOCC2)c1] | 4-[4-(2-aminopyrimidin-5-yl)phenyl]-N-[3-(dimethylsulfamoyl)phenyl]tetrahydro-2H-pyran-4-carboxamide |
| 78 | 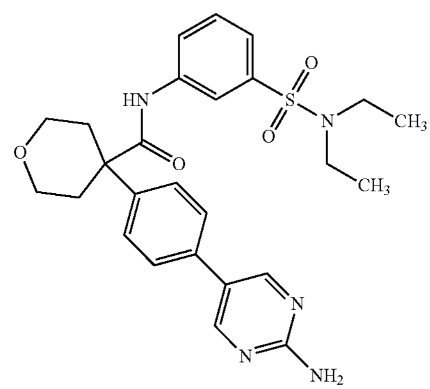 [SMILES: CCN(CC)S(=O)(=O)c1cccc(NC(=O)C2(c3ccc(-c4cnc(N)nc4)cc3)CCOCC2)c1] | 4-[4-(2-aminopyrimidin-5-yl)phenyl]-N-[3-(diethylsulfamoyl)phenyl]tetrahydro-2H-pyran-4-carboxamide |
| 79 | 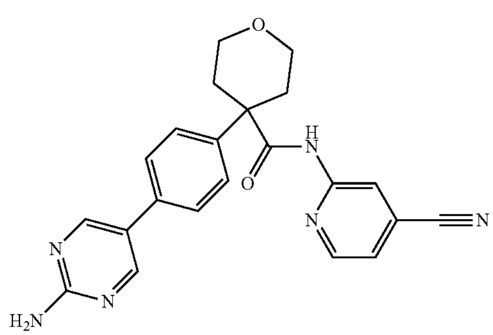 [SMILES: N#Cc1ccnc(NC(=O)C2(c3ccc(-c4cnc(N)nc4)cc3)CCOCC2)c1] | 4-[4-(2-aminopyrimidin-5-yl)phenyl]-N-(4-cyanopyridin-2-yl)tetrahydro-2H-pyran-4-carboxamide |

TABLE 1-continued

| Example | Structure | Names |
|---|---|---|
| 80 | 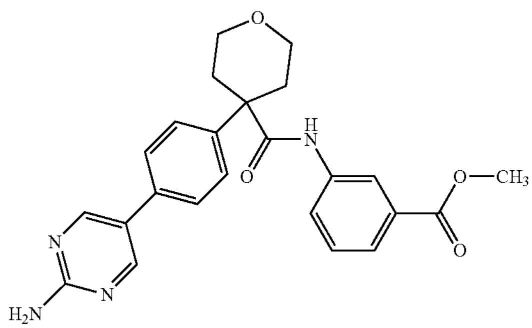 [SMILES: COC(=O)c1cccc(NC(=O)C2(c3ccc(-c4cnc(N)nc4)cc3)CCOCC2)c1] | methyl 3-[({4-[4-(2-aminopyrimidin-5-yl)phenyl]tetrahydro-2H-pyran-4-yl}carbonyl)amino]benzoate |
| 81 | 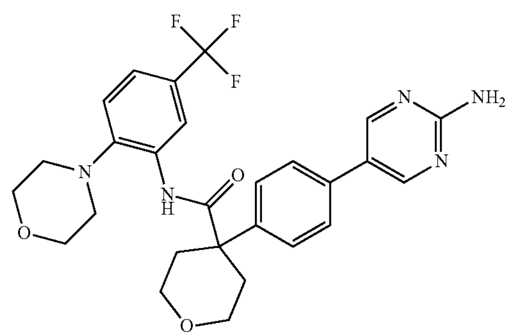 [SMILES: Nc1ncc(-c2ccc(C3(C(=O)Nc4cc(C(F)(F)F)ccc4N4CCOCC4)CCOCC3)cc2)cn1] | 4-[4-(2-aminopyrimidin-5-yl)phenyl]-N-[2-(morpholin-4-yl)-5-(trifluoromethyl)phenyl]tetrahydro-2H-pyran-4-carboxamide |
| 82 | 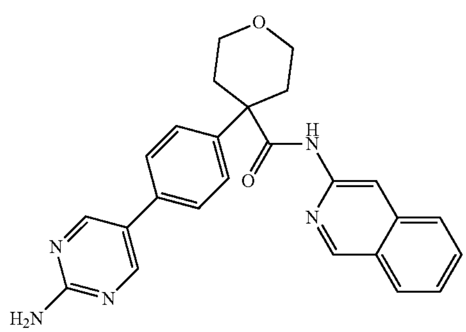 [SMILES: Nc1ncc(-c2ccc(C3(C(=O)Nc4cc5ccccc5cn4)CCOCC3)cc2)cn1] | 4-[4-(2-aminopyrimidin-5-yl)phenyl]-N-(isoquinolin-3-yl)tetrahydro-2H-pyran-4-carboxamide |
| 83 | 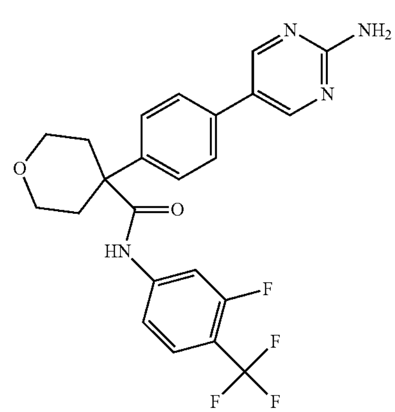 [SMILES: Nc1ncc(-c2ccc(C3(C(=O)Nc4ccc(C(F)(F)F)c(F)c4)CCOCC3)cc2)cn1] | 4-[4-(2-aminopyrimidin-5-yl)phenyl]-N-[3-fluoro-4-(trifluoromethyl)phenyl]tetrahydro-2H-pyran-4-carboxamide |

TABLE 1-continued

| Example | Structure | Names |
|---|---|---|
| 84 | 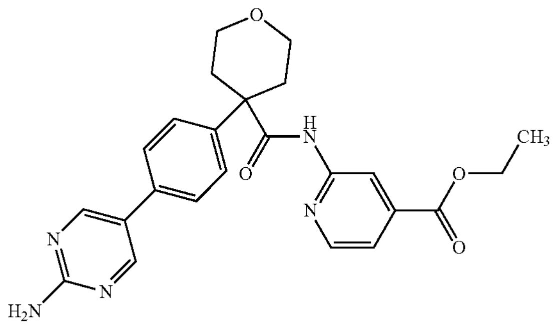 [SMILES: CCOC(=O)c1ccnc(NC(=O)C2(c3ccc(-c4cnc(N)nc4)cc3)CCOCC2)c1] | ethyl 2-[({4-[4-(2-aminopyrimidin-5-yl)phenyl]tetrahydro-2H-pyran-4-yl}carbonyl)amino]pyridine-4-carboxylate |
| 85 | 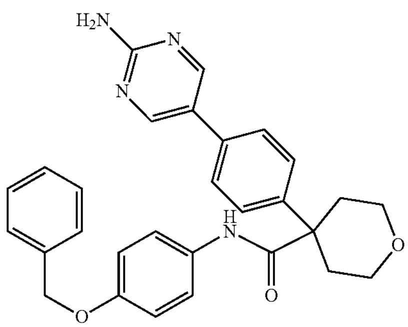 [SMILES: Nc1ncc(-c2ccc(C3(C(=O)Nc4ccc(OCc5ccccc5)cc4)CCOCC3)cc2)cn1] | 4-[4-(2-aminopyrimidin-5-yl)phenyl]-N-[4-(benzyloxy)phenyl]tetrahydro-2H-pyran-4-carboxamide |
| 86 | 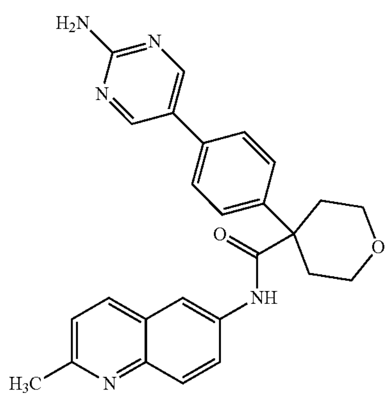 [SMILES: Cc1ccc2cc(NC(=O)C3(c4ccc(-c5cnc(N)nc5)cc4)CCOCC3)ccc2n1] | 4-[4-(2-aminopyrimidin-5-yl)phenyl]-N-(2-methylquinolin-6-yl)tetrahydro-2H-pyran-4-carboxamide |
| 87 | 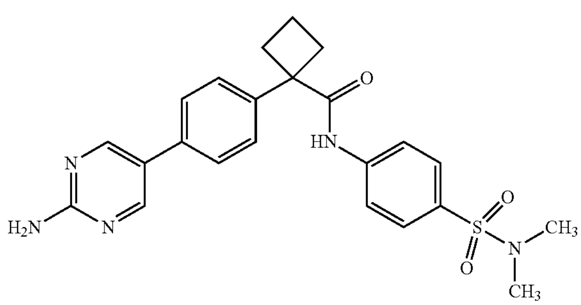 [SMILES: CN(C)S(=O)(=O)c1ccc(NC(=O)C2(c3ccc(-c4cnc(N)nc4)cc3)CCC2)cc1] | 1-[4-(2-aminopyrimidin-5-yl)phenyl]-N-[4-(dimethylsulfamoyl)phenyl]cyclobutanecarboxamide |

TABLE 1-continued

| Example | Structure | Names |
|---|---|---|
| 88 | 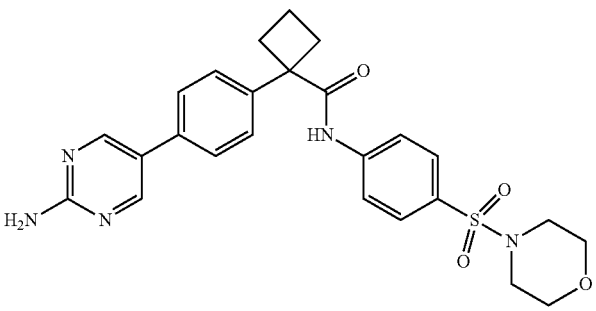 [SMILES: Nc1ncc(-c2ccc(C3(C(=O)Nc4ccc(S(=O)(=O)N5CCOCC5)cc4)CCC3)cc2)cn1] | 1-[4-(2-aminopyrimidin-5-yl)phenyl]-N-[4-(mopholin-4-ylsulfonyl)phenyl]cyclobutane-carboxamide |
| 89 | 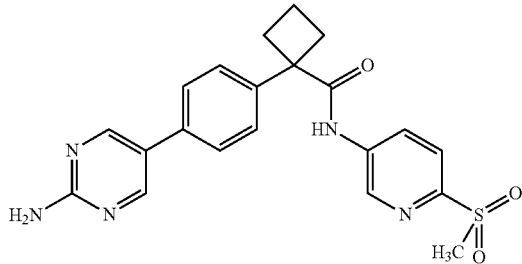 [SMILES: CS(=O)(=O)c1ccc(NC(=O)C2(c3ccc(-c4cnc(N)nc4)cc3)CCC2)cn1] | 1-[4-(2-aminopyrimidin-5-yl)phenyl]-N-[6-(methylsulfonyl)pyridin-3-yl]cyclobutanecarboxamide |
| 90 | 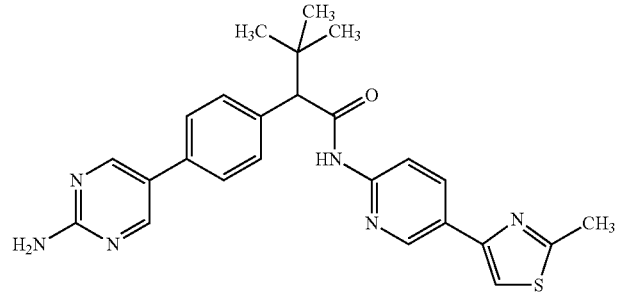 [SMILES: Cc1nc(-c2ccc(NC(=O)C(c3ccc(-c4cnc(N)nc4)cc3)C(C)(C)C)nc2)cs1] | 2-[4-(2-aminopyrimidin-5-yl)phenyl]-3,3-dimethyl-N-[5-(2-methyl-1,3-thiazol-4-yl)pyridin-2-yl]butanamide |
| 91 | 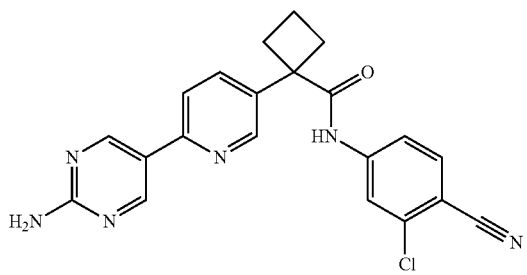 [SMILES: N#Cc1ccc(NC(=O)C2(c3ccc(-c4cnc(N)nc4)nc3)CCC2)cc1Cl] | 1-[6-(2-aminopyrimidin-5-yl)pyridin-3-yl]-N-(3-chloro-4-cyanophenyl)cyclobutane-carboxamide |
| 92 | 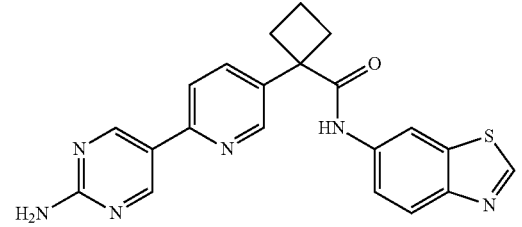 | 1-[6-(2-aminopyrimidin-5-yl)pyridin-3-yl]-N-(1,3-benzothiazol-6-yl)cyclobutanecarboxamide |

TABLE 1-continued

| Example | Structure | Names |
|---|---|---|
| 93 | 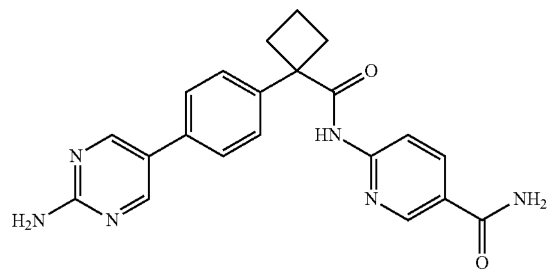 [SMILES: NC(=O)c1ccc(NC(=O)C2(c3ccc(-c4cnc(N)nc4)cc3)CCC2)nc1] | 6-[({1-[4-(2-aminopyrimidin-5-yl)phenyl]cyclobutyl}carbonyl)amino]pyridine-3-carboxamide |
| 94 | 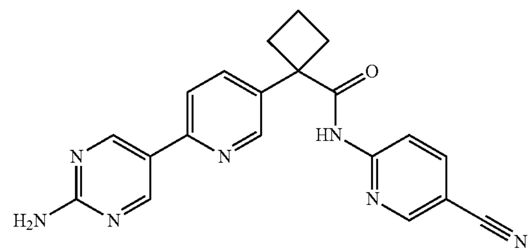 [SMILES: N#Cc1ccc(NC(=O)C2(c3ccc(-c4cnc(N)nc4)nc3)CCC2)nc1] | 1-[6-(2-aminopyrimidin-5-yl)pyridin-3-yl]-N-(5-cyanopyridin-2-yl)cyclobutanecarboxamide |
| 95 | 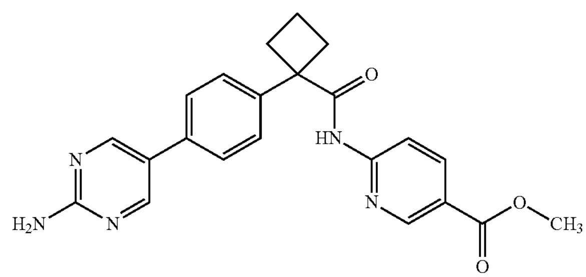 [SMILES: COC(=O)c1ccc(NC(=O)C2(c3ccc(-c4cnc(N)nc4)cc3)CCC2)nc1] | methyl 6-[({1-[4-(2-aminopyrimidin-5-yl)phenyl]cyclobuyl}carbonyl)amino]pyridine-3-carboxylate |
| 96 | 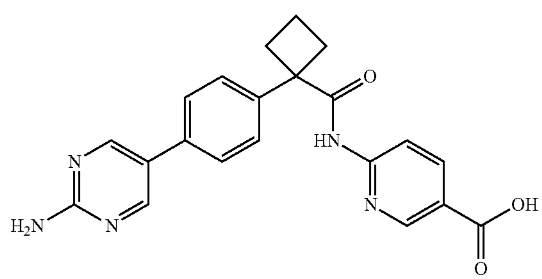 [SMILES: Nc1ncc(-c2ccc(C3(C(=O)Nc4ccc(C(=O)O)cn4)CCC3)cc2)cn1] | 6-[({1-[4-(2-aminopyrimidin-5-yl)phenyl]cyclobutyl}carbonyl)amino]pyridine-3-carboxylic acid |
| 97 | 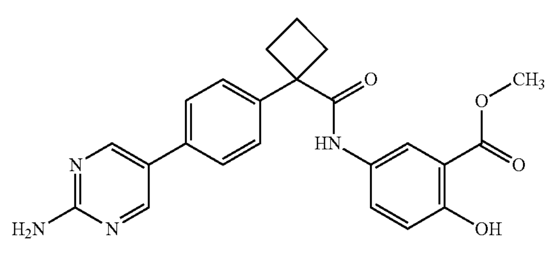 [SMILES: COC(=O)c1cc(NC(=O)C2(c3ccc(-c4cnc(N)nc4)cc3)CCC2)ccc1O] | methyl 5-[({1-[4-(2-aminopyrimidin-5-yl)phenyl]cyclobutyl}carbonyl)amino]-2-hydroxybenzoate |
| 98 | 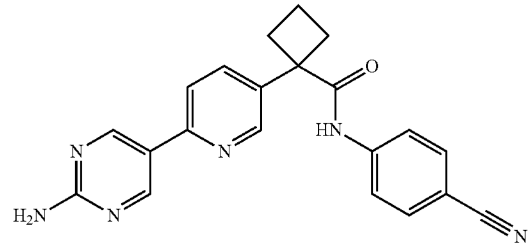 | 1-[6-(2-aminopyrimidin-5-yl)pyridin-3-yl]-N-(4-cyanophenyl)cyclobutane-carboxamide |

TABLE 1-continued

| Example | Structure | Names |
|---|---|---|
| 99 | 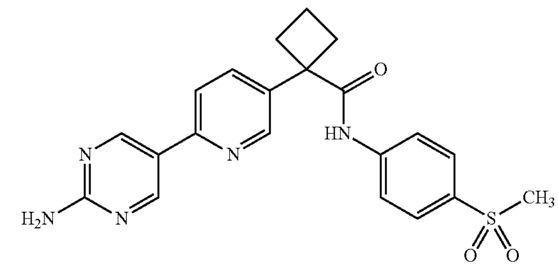 [SMILES: CS(=O)(=O)c1ccc(NC(=O)C2(c3ccc(-c4cnc(N)nc4)nc3)CCC2)cc1] | 1-[6-(2-aminopyrimidin-5-yl)pyridin-3-yl]-N-[4-(methylsulfonyl)phenyl]cyclobutane-carboxamide |
| 100 | 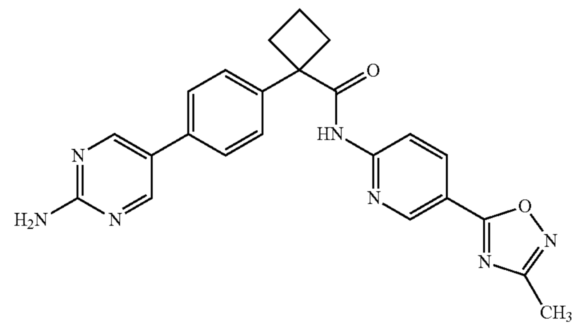 [SMILES: Cc1noc(-c2ccc(NC(=O)C3(c4ccc(-c5cnc(N)nc5)cc4)CCC3)nc2)n1] | 1-[4-(2-aminopyrimidin-5-yl)phenyl]-N-[5-(3-methyl-1,2,4-oxadiazol-5-yl)pyridin-2-yl]cyclobutanecarboxamide |
| 101 | 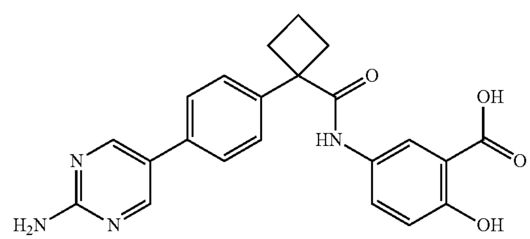 [SMILES: Nc1ncc(-c2ccc(C3(C(=O)Nc4ccc(O)c(C(=O)O)c4)CCC3)cc2)cn1] | 5-[({1-[4-(2-aminopyrimidin-5-yl)phenyl]cyclobutyl}carbonyl)amino]-2-hydroxybenzoic acid |
| 102 | 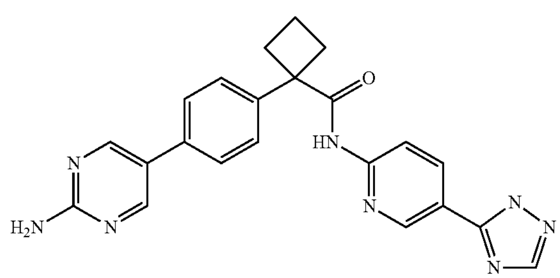 [SMILES: Nc1ncc(-c2ccc(C3(C(=O)Nc4ccc(-c5ncn[nH]5)cn4)CCC3)cc2)cn1] | 1-[4-(2-aminopyrimidin-5-yl)phenyl]-N-[5-(1H-1,2,4-triazol-5-yl)pyridin-2-yl]cyclobutanecarboxamide |
| 103 | 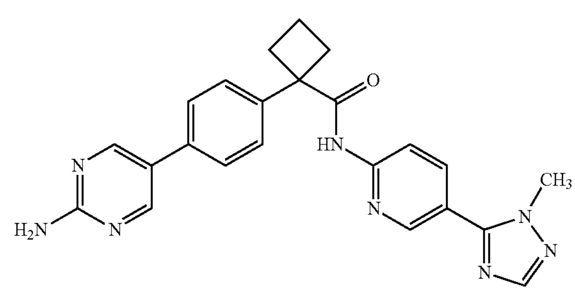 [SMILES: Cn1ncnc1-c1ccc(NC(=O)C2(c3ccc(-c4cnc(N)nc4)cc3)CCC2)nc1] | 1-[4-(2-aminopyrimidin-5-yl)phenyl]-N-[5-(1-methyl-1H-1,2,4-triazol-5-yl)pyridin-2-yl]cyclobutanecarboxamide |

TABLE 1-continued

| Example | Structure | Names |
|---|---|---|
| 104 | 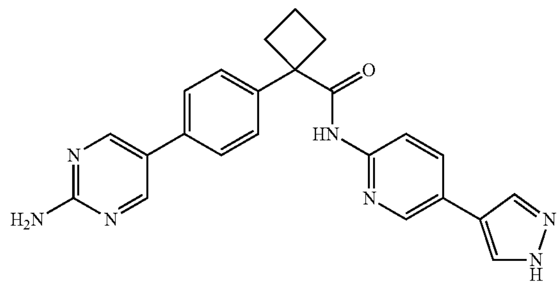 [SMILES: Nc1ncc(-c2ccc(C3(C(=O)Nc4ccc(-c5cn[nH]c5)cn4)CCC3)cc2)cn1] | 1-[4-(2-aminopyrimidin-5-yl)phenyl]-N-[5-(1H-pyrazol-4-yl)pyridin-2-yl]cyclobutanecarboxamide |
| 105 | 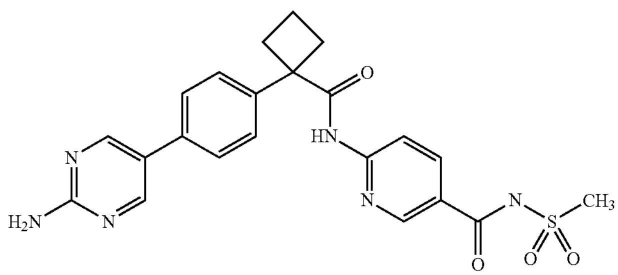 [SMILES: CS(=O)(=O)NC(=O)c1ccc(NC(=O)C2(c3ccc(-c4cnc(N)nc4)cc3)CCC2)nc1] | 6-[({1-[4-(2-aminopyrimidin-5-yl)phenyl]cyclobutyl}carbonyl)amino]-N-(methylsulfonyl)pyridine-3-carboxamide |
| 106 | 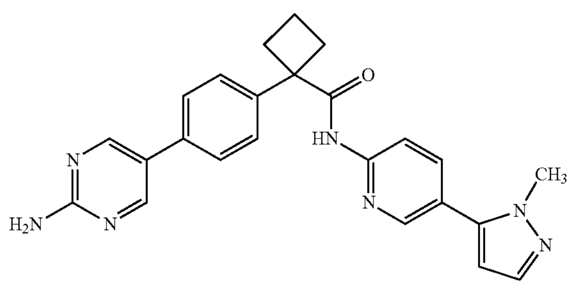 [SMILES: Cn1nccc1-c1ccc(NC(=O)C2(c3ccc(-c4cnc(N)nc4)cc3)CCC2)nc1] | 1-[4-(2-aminopyrimidin-5-yl)phenyl]-N-[5-(1-methyl-1H-pyrazol-5-yl)pyridin-2-yl]cyclobutanecarboxamide |
| 107 | 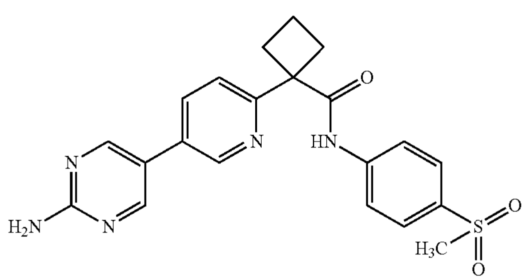 | 1-[5-(2-aminopyrimidin-5-yl)pyridin-2-yl]-N-[4-(methylsulfonyl)phenyl]cyclobutanecarboxamide |
| 108 | 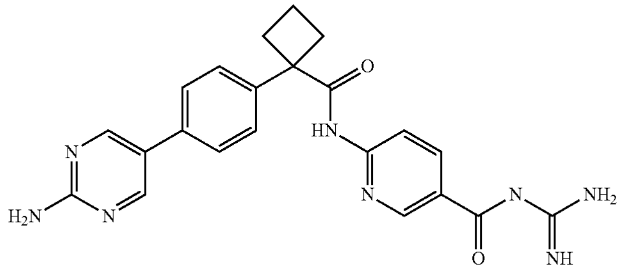 [SMILES: N=C(N)NC(=O)c1ccc(NC(=O)C2(c3ccc(-c4cnc(N)nc4)cc3)CCC2)nc1] | 6-[({1-[4-(2-aminopyrimidin-5-yl)phenyl]cyclobutyl}carbonyl)amino]-N-carbamimidoylpyridine-3-carboxamide |

TABLE 1-continued

| Example | Structure | Names |
| --- | --- | --- |
| 109 | 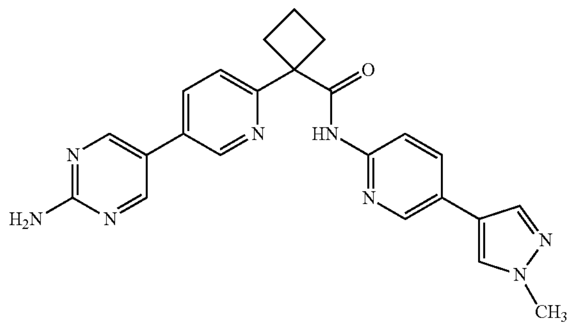 | 1-[5-(2-aminopyrimidin-5-yl)pyridin-2-yl]-N-[5-(1-methyl-1H-pyrazol-4-yl)pyridin-2-yl]cyclobutanecarboxamide |
| 110 | 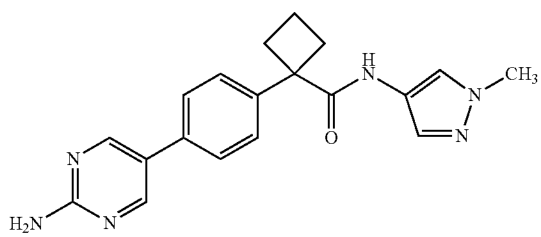 [SMILES: Cn1cc(NC(=O)C2(c3ccc(-c4cnc(N)nc4)cc3)CCC2)cn1] | 1-[4-(2-aminopyrimidin-5-yl)phenyl]-N-(1-methyl-1H-pyrazol-4-yl)cyclobutanecarboxamide |
| 111 | 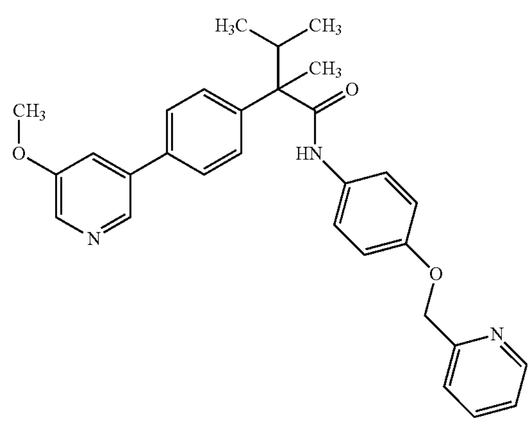 [SMILES: COc1cncc(-c2ccc(C(C)(C(=O)Nc3ccc(OCc4ccccn4)cc3)C(C)C)cc2)c1] | 2-[4-(5-methoxypyrimidin-3-yl)phenyl]-2,3-dimethyl-N-[4-(pyridin-2-ylmethoxy)phenyl]butanamide |
| 112 | 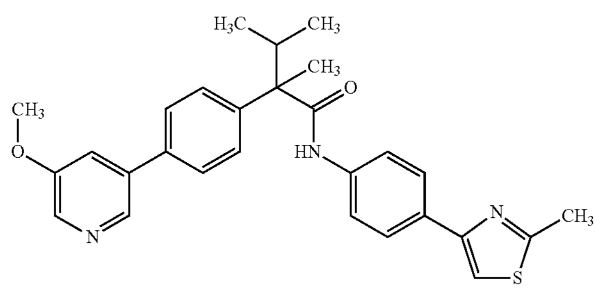 [SMILES: COc1cncc(-c2ccc(C(C)(C(=O)Nc3ccc(-c4csc(C)n4)cc3)C(C)C)cc2)c1] | 2-[4-(5-methoxypyridin-3-yl)phenyl]-2,3-dimethyl-N-[4-(2-methyl-1,3-thiazol-4-yl)phenyl]butanamide |

TABLE 1-continued

| Example | Structure | Names |
|---|---|---|
| 113 | 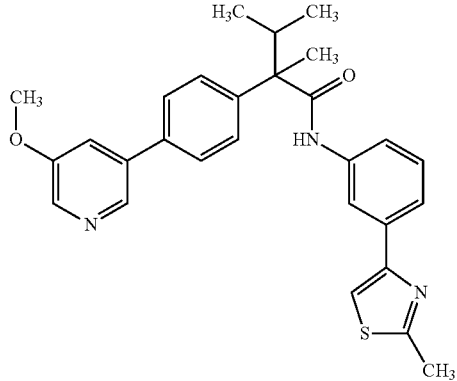 [SMILES: COc1cncc(-c2ccc(C(C)(C(=O)Nc3cccc(-c4csc(C)n4)c3)C(C)C)cc2)c1] | 2-[4-(5-methoxypyridin-3-yl)phenyl]-2,3-dimethyl-N-[3-(2-methyl-1,3-thiazol-4-yl)phenyl]butanamide |
| 114 | 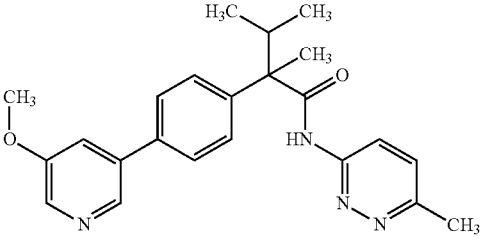 [SMILES: COc1cncc(-c2ccc(C(C)(C(=O)Nc3ccc(C)nn3)C(C)C)cc2)c1] | 2-[4-(5-methoxypyrimidin-3-yl)phenyl]-2,3-dimethyl-N-(6-methylpyridazin-3-yl)butanamide |
| 115 | 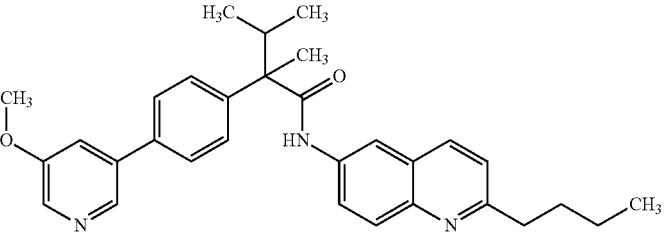 [SMILES: CCCCc1ccc2cc(NC(=O)C(C)(c3ccc(-c4cncc(OC)c4)cc3)C(C)C)ccc2n1] | N-(2-butylquinolin-6-yl)-2-[4-(5-methoxypyridin-3-yl)phenyl]-2,3-dimethylbutanamide |
| 116 | 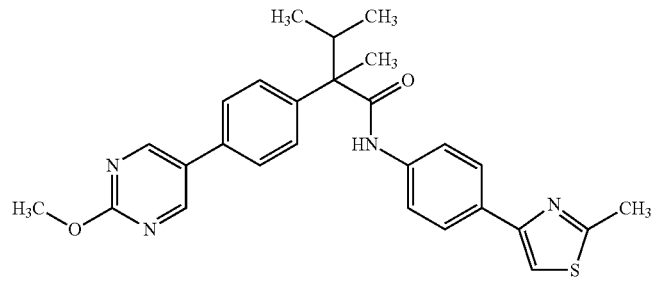 | 2-[4-(2-methoxypyrimidin-5-yl)phenyl]-2,3-dimethyl-N-[4-(2-methyl-1,3-thiazol-4-yl)phenyl]butanamide |
| 117 | 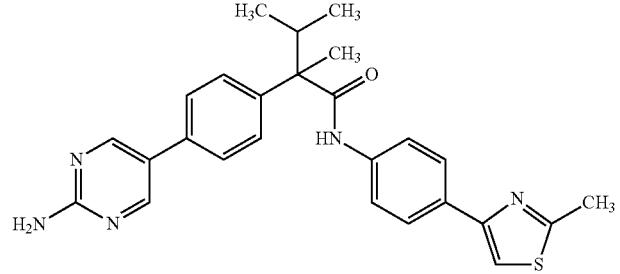 [SMILES: Cc1nc(-c2ccc(NC(=O)C(C)(c3ccc(-c4cnc(N)nc4)cc3)C(C)C)cc2)cs1] | 2-[4-(2-aminopyrimidin-5-yl)phenyl]-2,3-dimethyl-N-[4-(2-methyl-1,3-thiazol-4-yl)phenyl]butanamide |

TABLE 1-continued

| Example | Structure | Names |
|---|---|---|
| 118 | 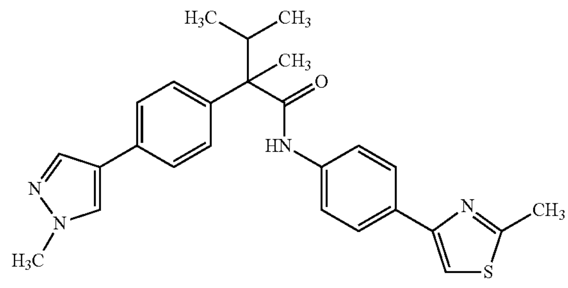 [SMILES: Cc1nc(-c2ccc(NC(=O)C(C)(c3ccc(-c4cnn(C)c4)cc3)C(C)C)cc2)cs1] | 2,3-dimethyl-2-[4-(1-methyl-1H-pyrazol-4-yl)phenyl]-N-[4-(2-methyl-1,3-thiazol-4-yl)phenyl]butanamide |
| 119 | 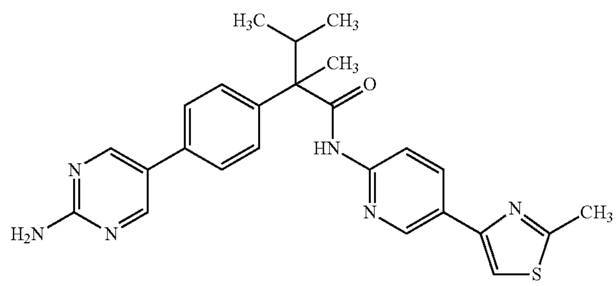 [SMILES: Cc1nc(-c2ccc(NC(=O)C(C)(c3ccc(-c4cnc(N)nc4)cc3)C(C)C)nc2)cs1] | 2-[4-(2-aminopyrimidin-5-yl)phenyl]-2,3-dimethyl-N-[5-(2-methyl-1,3-thiazol-4-yl)pyridin-2-yl]butanamide |
| 120 | 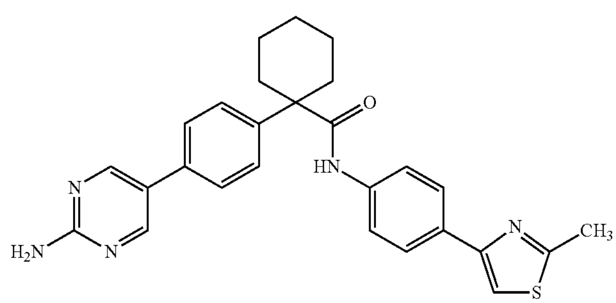 [SMILES: Cc1nc(-c2ccc(NC(=O)C3(c4ccc(-c5cnc(N)nc5)cc4)CCCCC3)cc2)cs1] | 1-[4-(2-aminopyrimidin-5-yl)phenyl]-N-[4-(2-methyl-1,3-thiazol-4-yl)phenyl]cyclohexane-carboxamide |
| 121 | 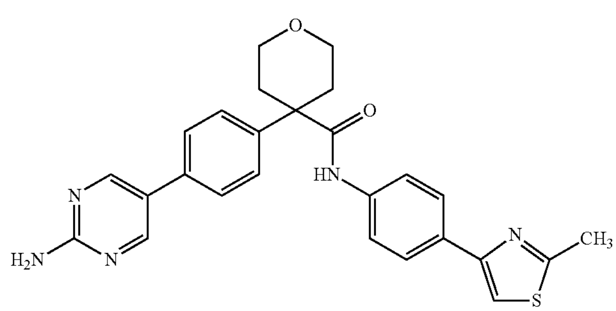 [SMILES: Cc1nc(-c2ccc(NC(=O)C3(c4ccc(-c5cnc(N)nc5)cc4)CCOCC3)cc2)cs1] | 4-[4-(2-aminopyrimidin-5-yl)phenyl]-N-[4-(2-methyl-1,3-thiazol-4-yl)phenyl]tetrahydro-2H-pyran-4-carboxamide |
| 122 | 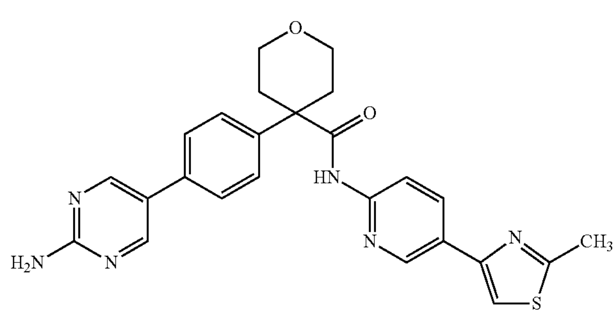 [SMILES: Cc1nc(-c2ccc(NC(=O)C3(c4ccc(-c5cnc(N)nc5)cc4)CCOCC3)nc2)cs1] | 4-[4-(2-aminopyrimidin-5-yl)phenyl]-N-[5-(2-methyl-1,3-thiazol-4-yl)pyridin-2-yl]tetrahydro-2H-pyran-4-carboxamide |

TABLE 1-continued

| Example | Structure | Names |
|---|---|---|
| 123 | 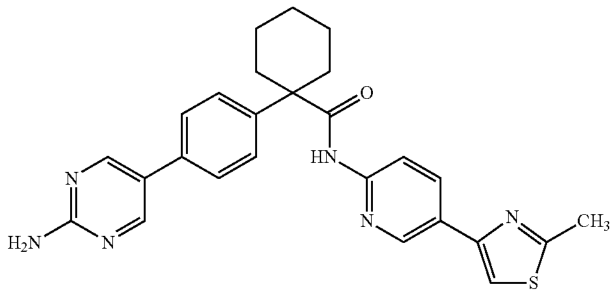 [SMILES: Cc1nc(-c2ccc(NC(=O)C3(c4ccc(-c5cnc(N)nc5)cc4)CCCCC3)nc2)cs1] | 1-[4-(2-aminopyrimidin-5-yl)phenyl]-N-[5-(2-methyl-1,3-thiazol-4-yl)pyridin-2-yl]cyclohexanecarboxamide |
| 124 | 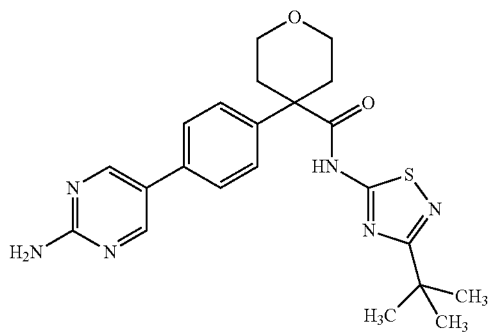 [SMILES: CC(C)(C)c1nsc(NC(=O)C2(c3ccc(-c4cnc(N)nc4)cc3)CCOCC2)n1] | 4-[4-(2-aminopyrimidin-5-yl)phenyl]-N-(3-tert-butyl-1,2,4-thiadiazol-5-yl)tetrahydro-2H-pyran-4-carboxamide |
| 125 | 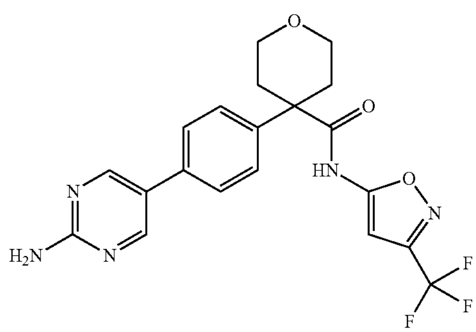 [SMILES: Nc1ncc(-c2ccc(C3(C(=O)Nc4cc(C(F)(F)F)no4)CCOCC3)cc2)cn1] | 4-[4-(2-aminopyrimidin-5-yl)phenyl]-N-[3-(trifluoromethyl)-1,2-oxazol-5-yl]tetrahydro-2H-pyran-4-carboxamide |
| 126 | 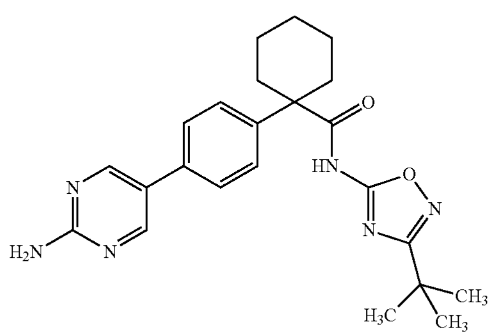 [SMILES: CC(C)(C)c1noc(NC(=O)C2(c3ccc(-c4cnc(N)nc4)cc3)CCCCC2)n1] | 1-[4-(2-aminopyrimidin-5-yl)phenyl]-N-(3-tert-butyl-1,2,4-oxadiazol-5-yl)cyclohexanecarboxamide |
| 127 | 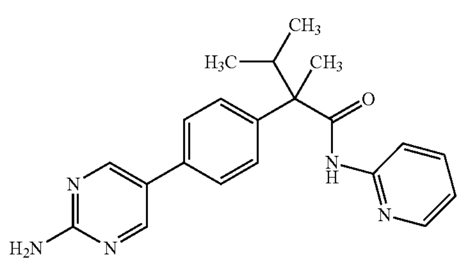 [SMILES: CC(C)C(C)(C(=O)Nc1ccccn1)c1ccc(-c2cnc(N)nc2)cc1] | 2-[4-(2-aminopyrimidin-5-yl)phenyl]-2,3-dimethyl-N-(pyridin-2-yl)butanamide |

TABLE 1-continued

| Example | Structure | Names |
|---|---|---|
| 128 | 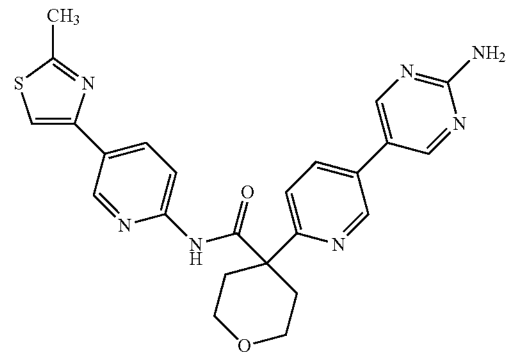 [SMILES: Cc1nc(-c2ccc(NC(=O)C3(c4ccc(-c5cnc(N)nc5)cn4)CCOCC3)nc2)cs1] | 4-[5-(2-aminopyrimidin-5-yl)pyridin-2-yl]-N-[5-(2-methyl-1,3-thiazol-4-yl)pyridin-2-yl]tetrahydro-2H-pyran-4-carboxamide |
| 129 | 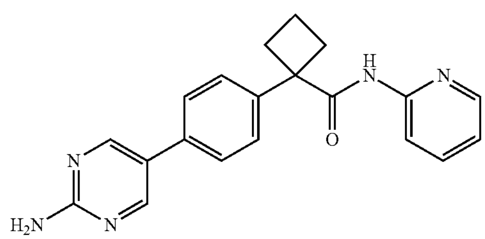 [SMILES: Nc1ncc(-c2ccc(C3(C(=O)Nc4ccccn4)CCC3)cc2)cn1] | 1-[4-(2-aminopyrimidin-5-yl)phenyl]-N-(pyridin-2-yl)cyclobutanecarboxamide |
| 130 | 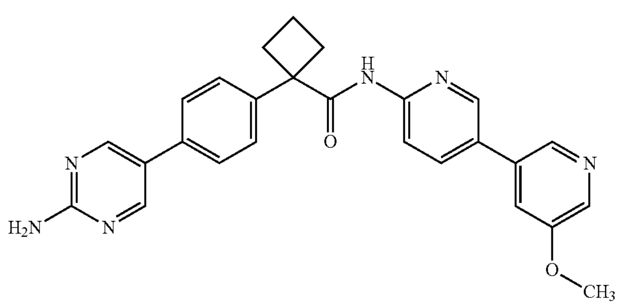 [SMILES: COc1cncc(-c2ccc(NC(=O)C3(c4ccc(-c5cnc(N)nc5)cc4)CCC3)nc2)c1] | 1-[4-(2-aminopyrimidin-5-yl)phenyl]-N-(5'-methoxy-3,3'-bipyridin-6-yl)cyclobutanecarboxamide |
| 131 | 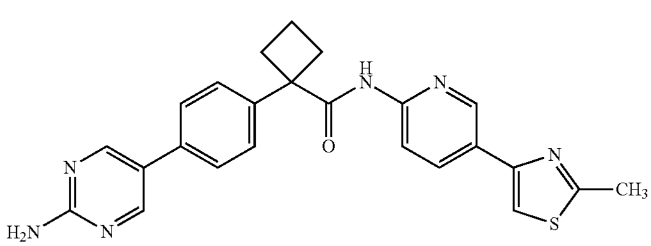 [SMILES: Cc1nc(-c2ccc(NC(=O)C3(c4ccc(-c5cnc(N)nc5)cc4)CCC3)nc2)cs1] | 1-[4-(2-aminopyrimidin-5-yl)phenyl]-N-[5-(2-methyl-1,3-thiazol-4-yl)pyridin-2-yl]cyclobutanecarboxamide |
| 132 | 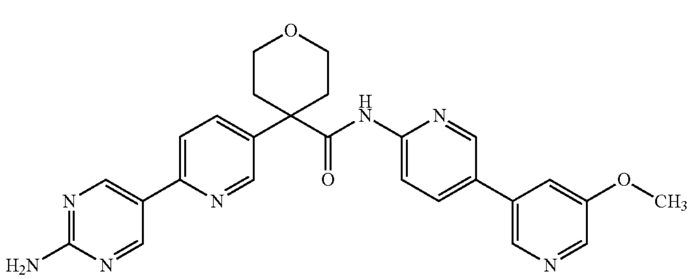 [SMILES: COc1cncc(-c2ccc(NC(=O)C3(c4ccc(-c5cnc(N)nc5)nc4)CCOCC3)nc2)c1] | 4-[6-(2-aminopyrimidin-5-yl)pyridin-3-yl]-N-(5'-methoxy-3,3'-bipyridin-6-yl)tetrahydro-2H-pyran-4-carboxamide |

TABLE 1-continued

| Example | Structure | Names |
|---|---|---|
| 133 | 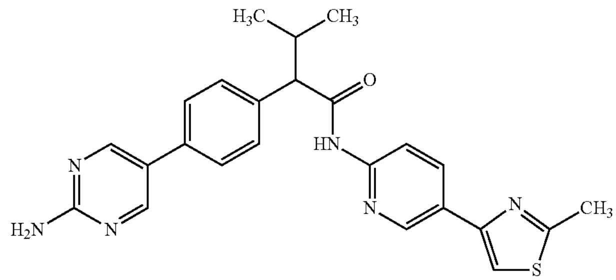 [SMILES: Cc1nc(-c2ccc(NC(=O)C(c3ccc(-c4cnc(N)nc4)cc3)C(C)C)nc2)cs1] | 2-[4-(2-aminopyrimidin-5-yl)phenyl]-3-methyl-N-[5-(2-methyl-1,3-thiazol-4-yl)pyridin-2-yl]butanamide |
| 134 | 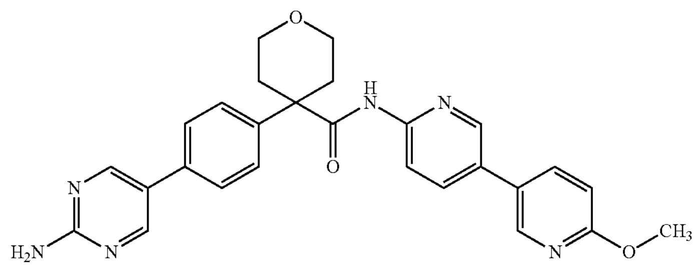 [SMILES: COc1ccc(-c2ccc(NC(=O)C3(c4ccc(-c5cnc(N)nc5)cc4)CCOCC3)nc2)cn1] | 4-[4-(2-aminopyrimidin-5-yl)phenyl]-N-(6'-methoxy-3,3'-bipyridin-6-yl)tetrahydro-2H-pyran-4-carboxamide |
| 135 | 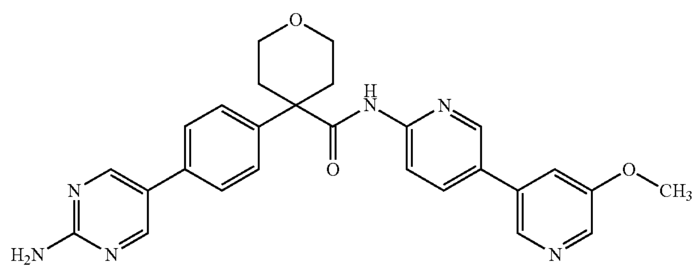 [SMILES: COc1cncc(-c2ccc(NC(=O)C3(c4ccc(-c5cnc(N)nc5)cc4)CCOCC3)nc2)c1] | 4-[4-(2-aminopyrimidin-5-yl)phenyl]-N-(5'-methoxy-3,3'-bipyridin-6-yl)tetrahydro-2H-pyran-4-carboxamide |
| 136 | 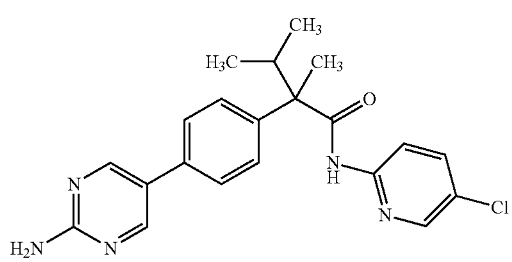 [SMILES: CC(C)C(C)(C(=O)Nc1ccc(Cl)cn1)c1ccc(-c2cnc(N)nc2)cc1] | 2-[4-(2-aminopyrimidin-5-yl)phenyl]-N-(5-chloropyridin-2-yl)-2,3-dimethylbutanamide |
| 138 | 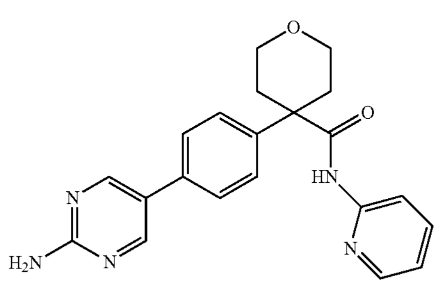 [SMILES: Nc1ncc(-c2ccc(C3(C(=O)Nc4ccccn4)CCOCC3)cc2)cn1] | 4-[4-(2-aminopyrimidin-5-yl)phenyl]-N-(pyridin-2-yl)tetrahydro-2H-pyran-4-carboxamide |

| Example | Structure | Names |
|---|---|---|
| 139 | 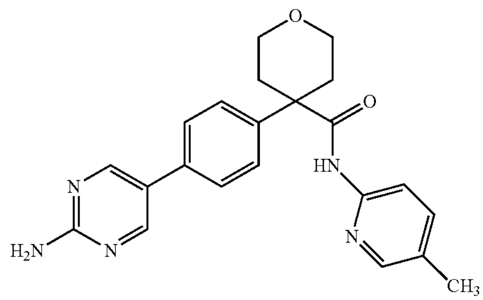 [SMILES: Cc1ccc(NC(=O)C2(c3ccc(-c4cnc(N)nc4)cc3)CCOCC2)nc1] | 4-[4-(2-aminopyrimidin-5-yl)phenyl]-N-(5-methylpyridin-2-yl)tetrahydro-2H-pyran-4-carboxamide |
| 140 | 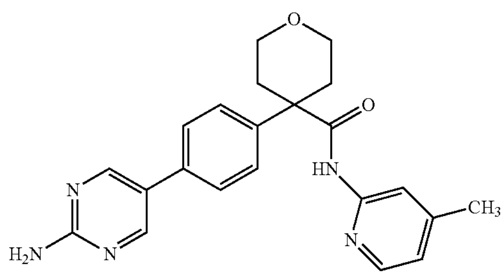 [SMILES: Cc1ccnc(NC(=O)C2(c3ccc(-c4cnc(N)nc4)cc3)CCOCC2)c1] | 4-[4-(2-aminopyrimidin-5-yl)phenyl]-N-(4-methylpyridin-2-yl)tetrahydro-2H-pyran-4-carboxamide |
| 141 | 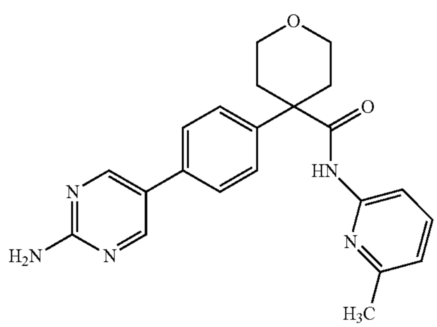 [SMILES: Cc1cccc(NC(=O)C2(c3ccc(-c4cnc(N)nc4)cc3)CCOCC2)n1] | 4-[4-(2-aminopyrimidin-5-yl)phenyl]-N-(6-methylpyridin-2-yl)tetrahydro-2H-pyran-4-carboxamide |
| 142 | 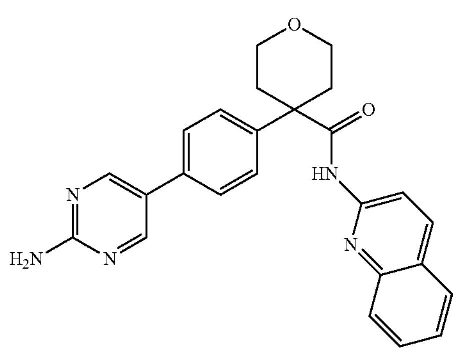 [SMILES: Nc1ncc(-c2ccc(C3(C(=O)Nc4ccc5ccccc5n4)CCOCC3)cc2)cn1] | 4-[4-(2-aminopyrimidin-5-yl)phenyl]-N-(quinolin-2-yl)tetrahydro-2H-pyran-4-carboxamide |
| 143 | 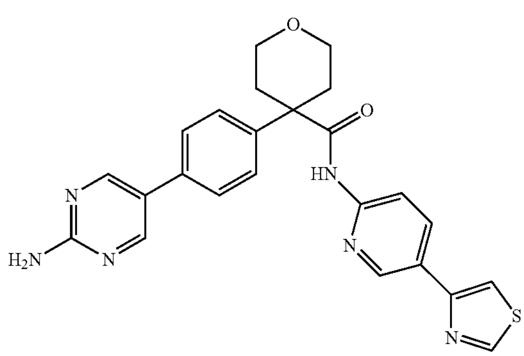 [SMILES: Nc1ncc(-c2ccc(C3(C(=O)Nc4ccc(-c5cscn5)cn4)CCOCC3)cc2)cn1] | 4-[4-(2-aminopyrimidin-5-yl)phenyl]-N-[5-(1,3-thiazol-4-yl)pyridin-2-yl]tetrahydro-2H-pyran-4-carboxamide |

| Example | Structure | Names |
|---|---|---|
| 144 | 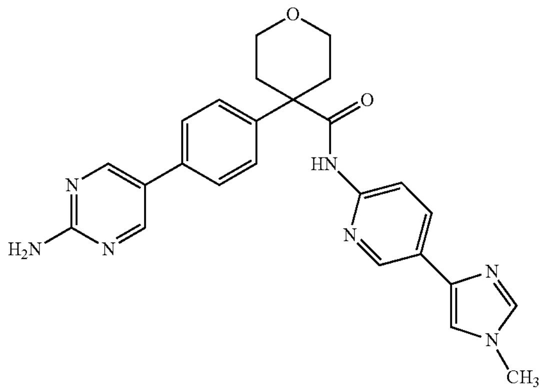 [SMILES: Cn1cnc(-c2ccc(NC(=O)C3(c4ccc(-c5cnc(N)nc5)cc4)CCOCC3)nc2)c1] | 4-[4-(2-aminopyrimidin-5-yl)phenyl]-N-[5-(1-methyl-1H-imidazol-4-yl)pyridin-2-yl]tetrahydro-2H-pyran-4-carboxamide |
| 145 | 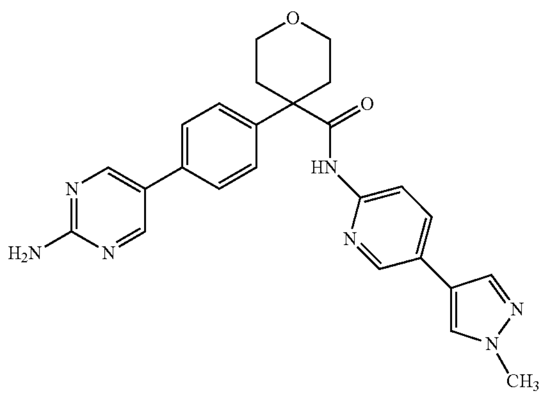 [SMILES: Cn1cc(-c2ccc(NC(=O)C3(c4ccc(-c5cnc(N)nc5)cc4)CCOCC3)nc2)cn1] | 4-[4-(2-aminopyrimidin-5-yl)phenyl]-N-[5-(1-methyl-1H-imidazol-4-yl)pyridin-2-yl]tetrahydro-2H-pyran-4-carboxamide |
| 146 | 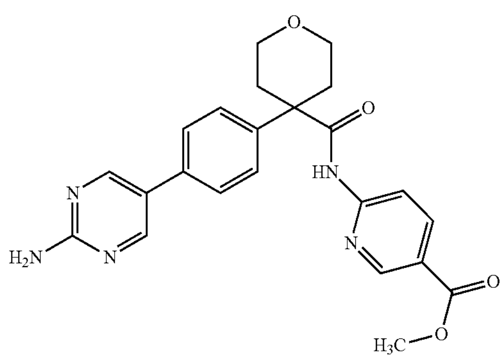 [SMILES: COC(=O)c1ccc(NC(=O)C2(c3ccc(-c4cnc(N)nc4)cc3)CCOCC2)nc1] | methyl 6-[({4-[4-(2-aminopyrimidin-5-yl)phenyl]tetrahydro-2H-pyran-4-yl}carbonyl)amino]pyridine-3-carboxylate |
| 147 | 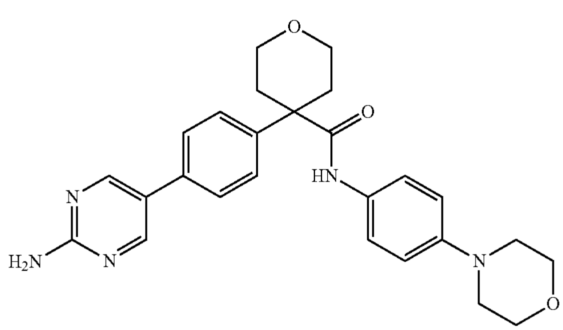 [SMILES: Nc1ncc(-c2ccc(C3(C(=O)Nc4ccc(N5CCOCC5)cc4)CCOCC3)cc2)cn1] | 4-[4-(2-aminopyrimidin-5-yl)phenyl]-N-[4-(mopholin-4-yl)phenyl]tetrahydro-2H-pyran-4-carboxamide |

TABLE 1-continued

| Example | Structure | Names |
|---|---|---|
| 148 | 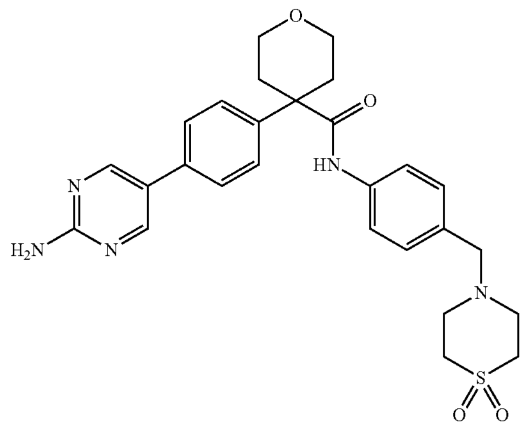 [SMILES: Nc1ncc(-c2ccc(C3(C(=O)Nc4ccc(CN5CCS(=O)(=O)CC5)cc4)CCOCC3)cc2)cn1] | 4-[4-(2-aminopyrimidin-5-yl)phenyl]-N-{4-[(1,1-dioxidothiomorpholin-4-yl)methyl]phenyl}tetrahydro-2H-pyran-4-carboxamide |
| 149 | 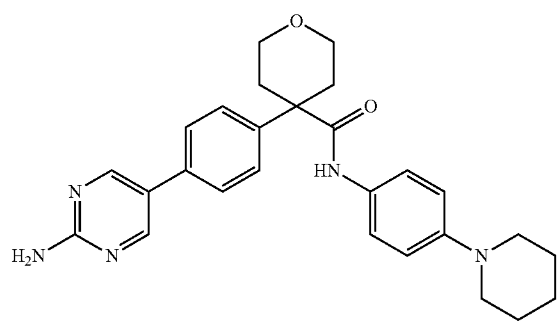 [SMILES: Nc1ncc(-c2ccc(C3(C(=O)Nc4ccc(N5CCCCC5)cc4)CCOCC3)cc2)cn1] | 4-[4-(2-aminopyrimidin-5-yl)phenyl]-N-[4-(piperidin-1-yl)phenyl]tetrahydro-2H-pyran-4-carboxamide |
| 150 | 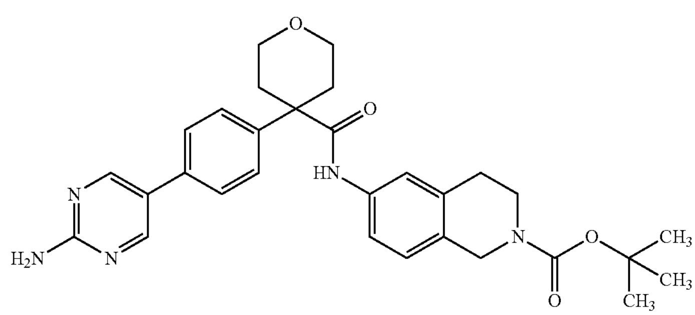 [SMILES: CC(C)(C)OC(=O)N1CCc2cc(NC(=O)C3(c4ccc(-c5cnc(N)nc5)cc4)CCOCC3)ccc2C1] | tert-butyl 6-[({4-[4-(2-aminopyrimidin-5-yl)phenyl]tetrahydro-2H-pyran-4-yl}carbonyl)amino]-3,4-dihydroisoquinolin-2(1H)-carboxylate |
| 151 | 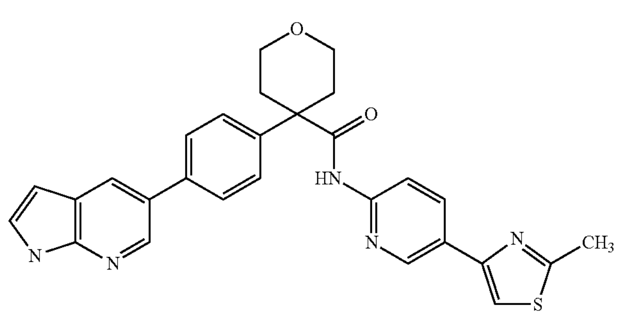 [SMILES: Cc1nc(-c2ccc(NC(=O)C3(c4ccc(-c5cnc6[nH]ccc6c5)cc4)CCOCC3)nc2)cs1] | N-[5-(2-methyl-1,3-thiazol-4-yl)pyridin-2-yl]-4-[4-(1H-pyrrolo[2,3-b]pyridin-5-yl)phenyl]tetrahydro-2H-pyran-4-carboxamide |

TABLE 1-continued

| Example | Structure | Names |
|---|---|---|
| 152 | 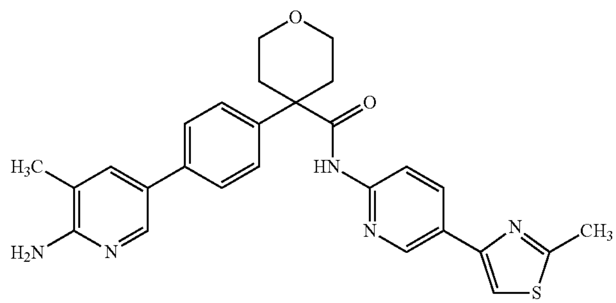 [SMILES: Cc1nc(-c2ccc(NC(=O)C3(c4ccc(-c5cnc(N)c(C)c5)cc4)CCOCC3)nc2)cs1] | 4-[4-(6-amino-5-methylpyridin-3-yl)phenyl]-N-[5-(2-methyl-1,3-thiazol-4-yl)pyridin-2-yl]tetrahydro-2H-pyran-4-carboxamide |
| 153 | 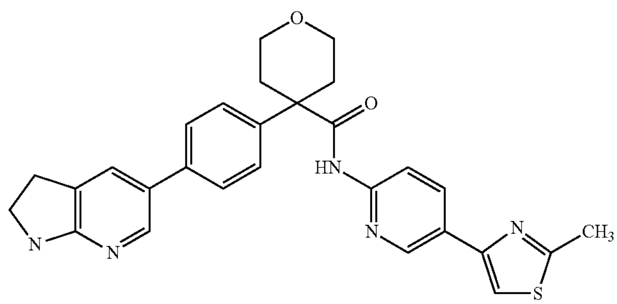 [SMILES: Cc1nc(-c2ccc(NC(=O)C3(c4ccc(-c5cnc6c(c5)CCN6)cc4)CCOCC3)nc2)cs1] | 4-[4-(2,3-dihydro-1H-pyrrolo[2,3-b]pyridin-5-yl)phenyl]-N-[5-(2-methyl-1,3-thiazol-4-yl)pyridin-2-yl]tetrahydro-2H-pyran-4-carboxamide |
| 154 | 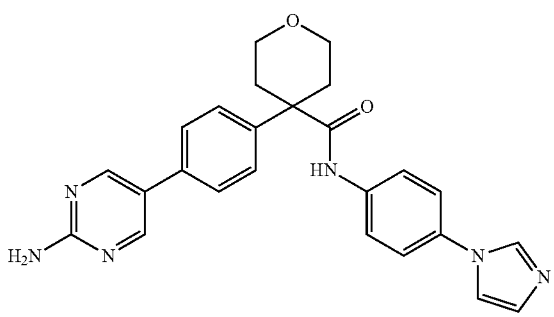 [SMILES: Nc1ncc(-c2ccc(C3(C(=O)Nc4ccc(-n5ccnc5)cc4)CCOCC3)cc2)cn1] | 4-[4-(2-aminopyrimidin-5-yl)phenyl]-N-[4-(1H-imidazol-1-yl)phenyl]tetrahydro-2H-pyran-4-carboxamide |
| 155 | 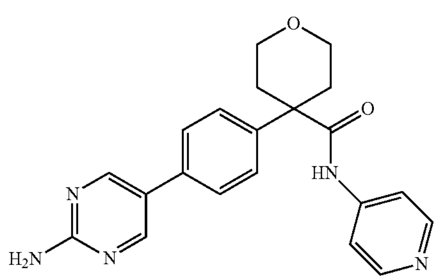 [SMILES: Nc1ncc(-c2ccc(C3(C(=O)Nc4ccncc4)CCOCC3)cc2)cn1] | 4-[4-(2-aminopyrimidin-5-yl)phenyl]-N-(pyridin-4-yl)tetrahydro-2H-pyran-4-carboxamide |
| 156 | 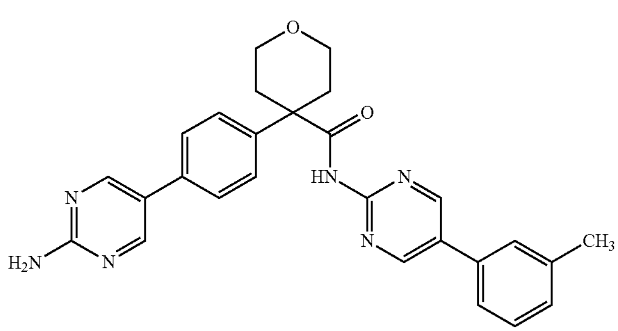 [SMILES: Cc1cccc(-c2cnc(NC(=O)C3(c4ccc(-c5cnc(N)nc5)cc4)CCOCC3)nc2)c1] | 4-[4-(2-aminopyrimidin-5-yl)phenyl]-N-[5-(3-methylphenyl)pyrimidin-2-yl]tetrahydro-2H-pyran-4-carboxamide |

TABLE 1-continued

| Example | Structure | Names |
|---|---|---|
| 157 | 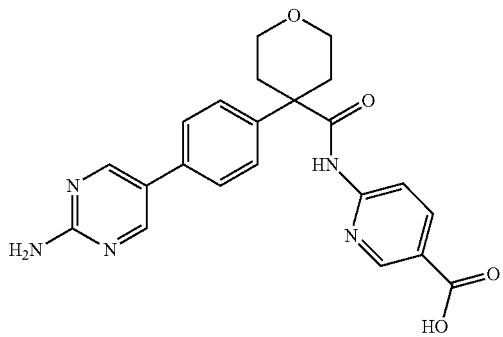 [SMILES: Nc1ncc(-c2ccc(C3(C(=O)Nc4ccc(C(=O)O)cn4)CCOCC3)cc2)cn1] | 6-[({4-[4-(2-aminopyrimidin-5-yl)phenyl]tetrahydro-2H-pyran-4-yl}carbonyl)amino]pyridine-3-carboxylic acid |
| 158 | 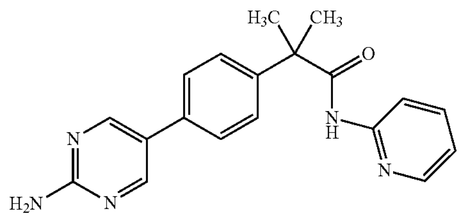 [SMILES: CC(C)(C(=O)Nc1ccccn1)c1ccc(-c2cnc(N)nc2)cc1] | 2-[4-(2-aminopyrimidin-5-yl)phenyl]-2-methyl-N-(pyridin-2-yl)propanamide |
| 159 | 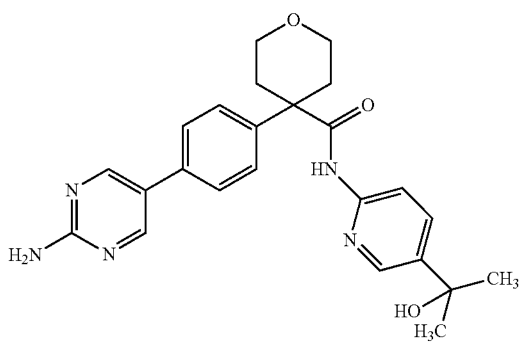 [SMILES: CC(C)(O)c1ccc(NC(=O)C2(c3ccc(-c4cnc(N)nc4)cc3)CCOCC2)nc1] | 4-[4-(2-aminopyrimidin-5-yl)phenyl]-N-[5-(2-hydroxypropan-2-yl)pyridin-2-yl]tetrahydro-2H-pyran-4-carboxamide |
| 160 | 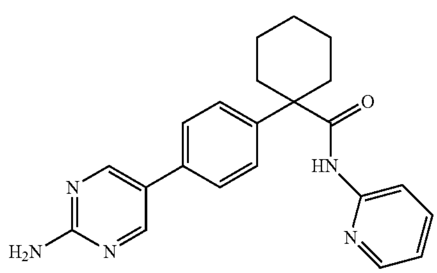 [SMILES: Nc1ncc(-c2ccc(C3(C(=O)Nc4ccccn4)CCCCC3)cc2)cn1] | 1-[4-(2-aminopyrimidin-5-yl)phenyl]-N-(pyridin-2-yl)cyclohexanecarboxamide |
| 161 | 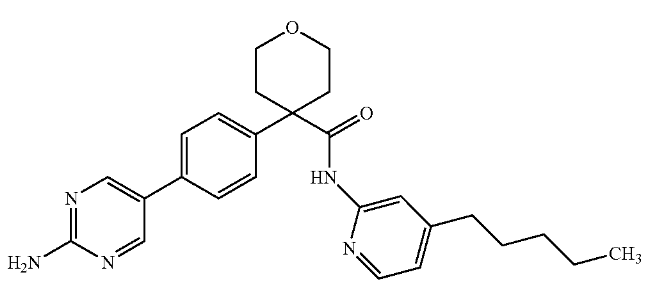 [SMILES: CCCCCc1ccnc(NC(=O)C2(c3ccc(-c4cnc(N)nc4)cc3)CCOCC2)c1] | 4-[4-(2-aminopyrimidin-5-yl)phenyl]-N-(4-pentylpyridin-2-yl)tetrahydro-2H-pyran-4-carboxamide |

TABLE 1-continued

| Example | Structure | Names |
|---|---|---|
| 162 | 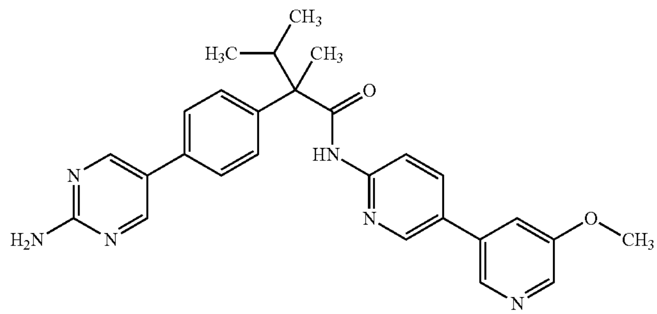 [SMILES: COc1cncc(-c2ccc(NC(=O)C(C)(c3ccc(-c4cnc(N)nc4)cc3)C(C)C)nc2)c1] | 2-[4-(2-aminopyrimidin-5-yl)phenyl]-N-(5'-methoxy-3,3'-bipyridin-6-yl)-2,3-dimethylbutanamide |
| 163 | 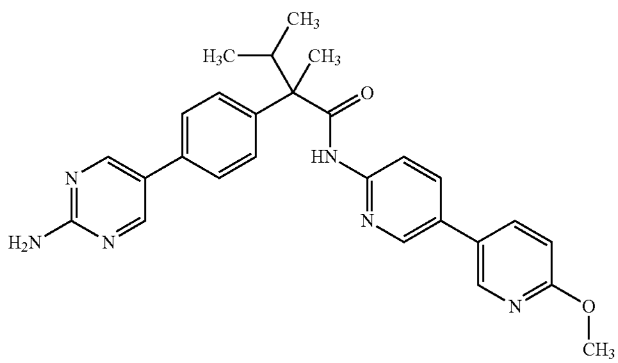 [SMILES: COc1ccc(-c2ccc(NC(=O)C(C)(c3ccc(-c4cnc(N)nc4)cc3)C(C)C)nc2)cn1] | 2-[4-(2-aminopyrimidin-5-yl)phenyl]-N-(6'-methoxy-3,3'-bipyridin-6-yl)-2,3-dimethylbutanamide |
| 164 | 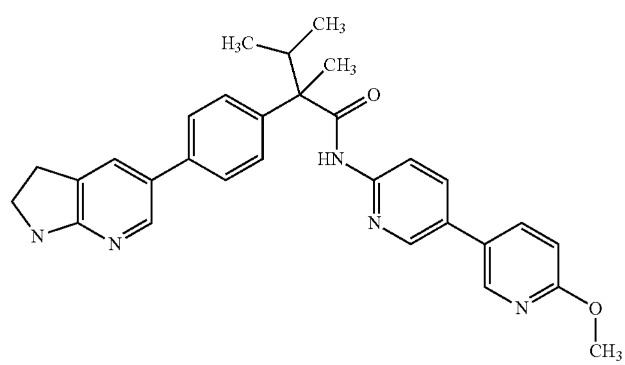 [SMILES: COc1ccc(-c2ccc(NC(=O)C(C)(c3ccc(-c4cnc5c(c4)CCN5)cc3)C(C)C)nc2)cn1] | 2-[4-(2,3-dihydro-1H-pyrrolo[2,3-b]pyridin-5-yl)phenyl]-N-(6'-methoxy-3,3'-bipyridin-6-yl)-2,3-dimethylbutanamide |
| 165 | 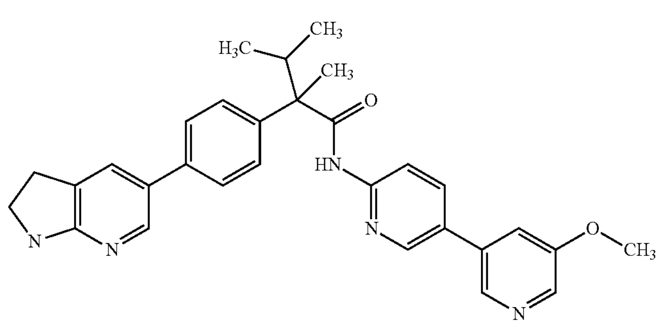 [SMILES: COc1cncc(-c2ccc(NC(=O)C(C)(c3ccc(-c4cnc5c(c4)CCN5)cc3)C(C)C)nc2)c1] | 2-[4-(2,3-dihydro-1H-pyrolo[2,3-b]pyridin-5-yl)phenyl]-N-(5'-methoxy-3,3'-bipyridin-6-yl)-2,3-dimethylbutanamide |

TABLE 1-continued

| Example | Structure | Names |
|---------|-----------|-------|
| 166 | 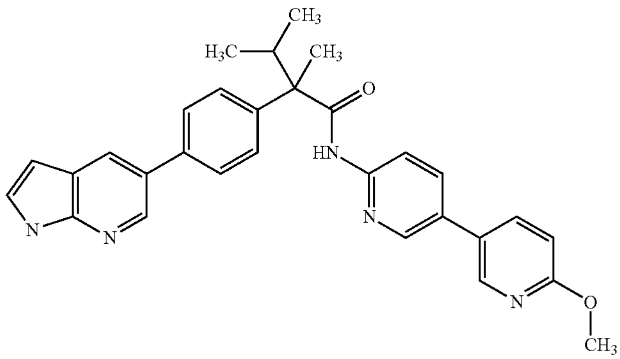 [SMILES: COc1ccc(-c2ccc(NC(=O)C(C)(c3ccc(-c4cnc5[nH]ccc5c4)cc3)C(C)C)nc2)cn1] | N-(6'-methoxy-3,3'-bipyridin-6-yl)-2,3-dimethyl-2-[4-(1H-pyrrolo[2,3-b]pyridin-5-yl)phenyl]butanamide |
| 167 | 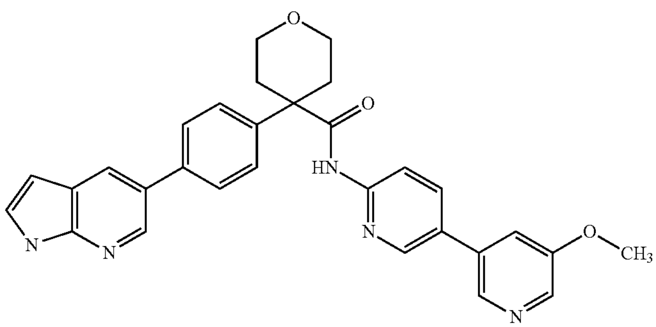 [SMILES: COc1cncc(-c2ccc(NC(=O)C3(c4ccc(-c5cnc6[nH]ccc6c5)cc4)CCOCC3)nc2)c1] | N-(5'-methoxy-3,3'-bipyridin-6-yl)-4-[4-(1H-pyrrolo[2,3-b]pyridin-5-yl)phenyl]tetrahydro-2H-pyran-4-carboxamide |
| 168 | 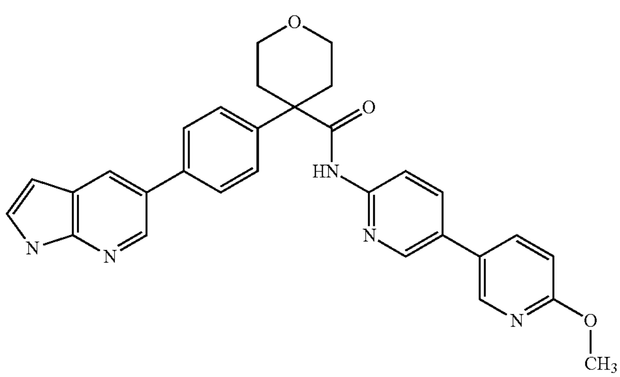 [SMILES: COc1ccc(-c2ccc(NC(=O)C3(c4ccc(-c5cnc6[nH]ccc6c5)cc4)CCOCC3)nc2)cn1] | N-(6'-methoxy-3,3'-bipyridin-6-yl)-4-[4-(1H-pyrrolo[2,3-b]pyridin-5-yl)phenyl]tetrahydro-2H-pyran-4-carboxamide |
| 169 | 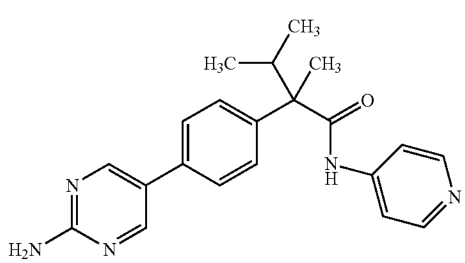 [SMILES: CC(C)C(C)(C(=O)Nc1ccncc1)c1ccc(-c2cnc(N)nc2)cc1] | 2-[4-(2-aminopyrimidin-5-yl)phenyl]-2,3-dimethyl-N-(pyridin-4-yl)butanamide |

TABLE 1-continued

| Example | Structure | Names |
|---|---|---|
| 170 | 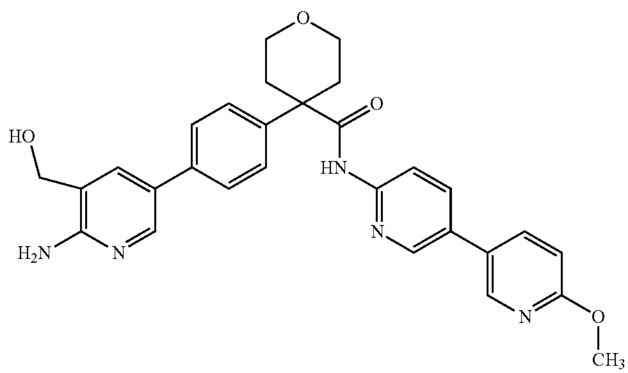 [SMILES: COc1ccc(-c2ccc(NC(=O)C3(c4ccc(-c5cnc(N)c(CO)c5)cc4)CCOCC3)nc2)cn1] | 4-{4-6-amino-5-(hydroxymethyl)pyridin-3-yl]phenyl}-N-(6'-methoxy-3,3'-bipyridin-6-yl)tetrahydro-2H-pyran-4-carboxamide |
| 171 | 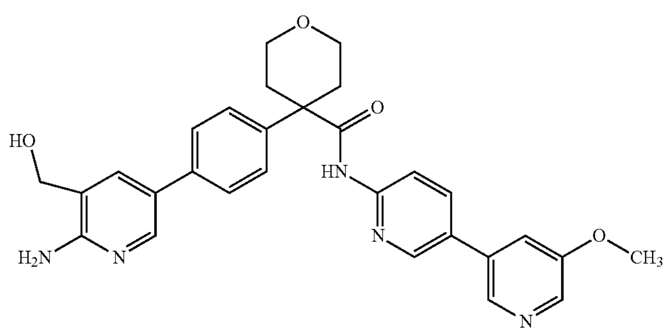 [SMILES: COc1cncc(-c2ccc(NC(=O)C3(c4ccc(-c5cnc(N)c(CO)c5)cc4)CCOCC3)nc2)c1] | 4-{4-[6-amino-5-(hydroxymethyl)pyridin-3-yl]phenyl}-N-(5'-methoxy-3,3'-bipyridin-6-yl)tetrahydro-2H-pyran-4-carboxamide |
| 173 | 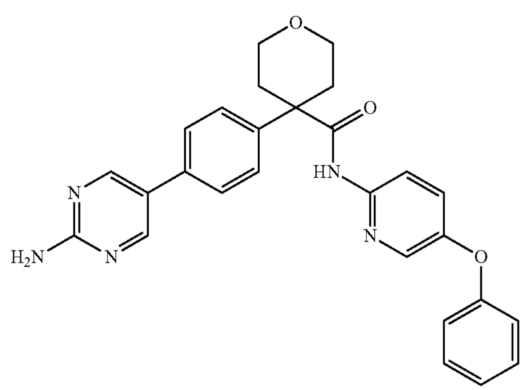 [SMILES: Nc1ncc(-c2ccc(C3(C(=O)Nc4ccc(Oc5ccccc5)cn4)CCOCC3)cc2)cn1] | 4-[4-(2-aminopyrimidin-5-yl)phenyl]-N-(5-phenoxypyridin-2-yl)tetrahydro-2H-pyran-4-carboxamide |
| 174 | 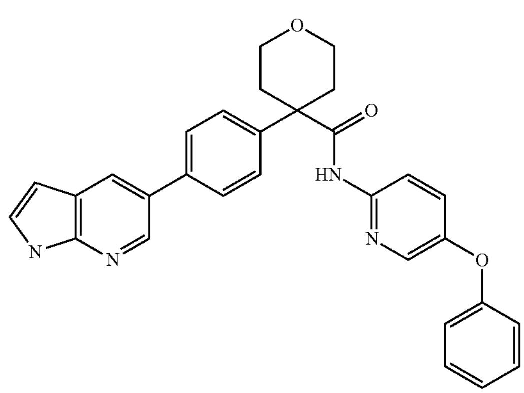 [SMILES: O=C(Nc1ccc(Oc2ccccc2)cn1)C1(c2ccc(-c3cnc4[nH]ccc4c3)cc2)CCOCC1] | N-(5-phenoxypyridin-2-yl)-4-[4-(1H-pyrrolo[2,3-b]pyridin-5-yl)phenyl]tetrahydro-2H-pyran-4-carboxamide |

TABLE 1-continued

| Example | Structure | Names |
|---|---|---|
| 175 | 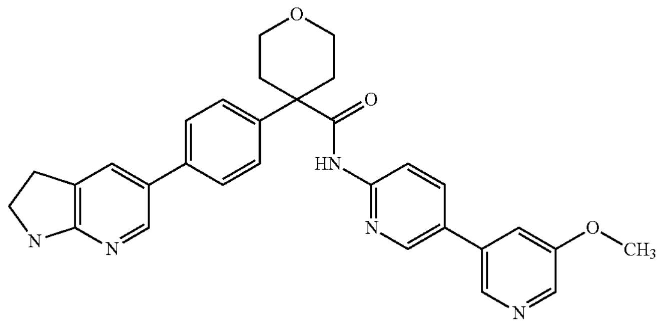 [SMILES: COc1cncc(-c2ccc(NC(=O)C3(c4ccc(-c5cnc6c(c5)CCN6)cc4)CCOCC3)nc2)c1] | 4-[4-(2,3-dihydro-1H-pyrolo[2,3-b]pyridin-5-yl)phenyl]-N-(5'-methoy-3,3'-bipyridin-6-yl)tetrahydro-2H-pyran-4-carboxamide |
| 176 | 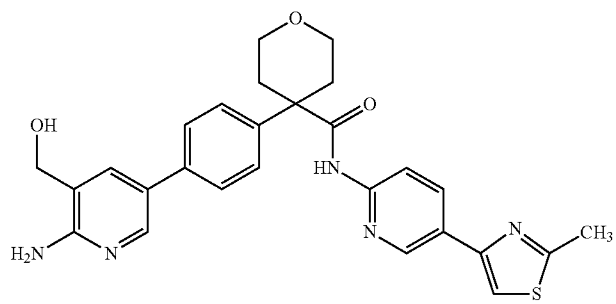 [SMILES: Cc1nc(-c2ccc(NC(=O)C3(c4ccc(-c5cnc(N)c(CO)c5)cc4)CCOCC3)nc2)cs1] | 4-{4-[6-amino-5-(hydroxymethyl)pyridin-3-yl]phenyl}-N-[5-(2-methyl-1,3-thiazol-4-yl)pyridin-2-yl]tetrahydro-2H-pyran-4-carboxamide |
| 177 | 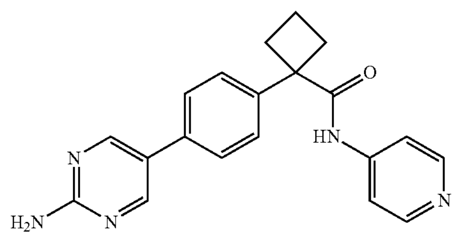 | 1-[4-(2-aminopyrimidin-5-yl)phenyl]-N-(pyridin-4-yl)cyclobutanecarboxamide |
| 178 | 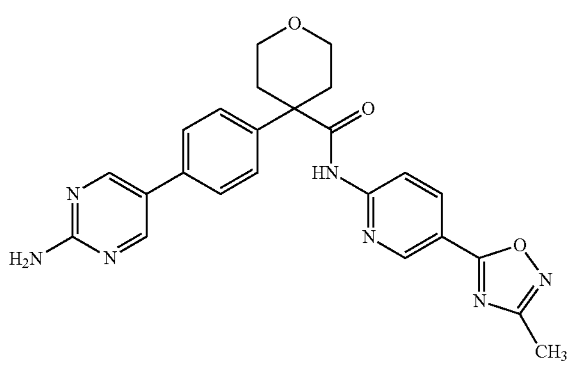 [SMILES: Cc1noc(-c2ccc(NC(=O)C3(c4ccc(-c5cnc(N)nc5)cc4)CCOCC3)nc2)n1] | 4-[4-(2-aminopyrimidin-5-yl)phenyl]-N-[5-(3-methyl-1,2,4-oxadiazol-5-yl)pyridin-2-yl]tetrahydro-2H-pyran-4-carboxamide |
| 179 | 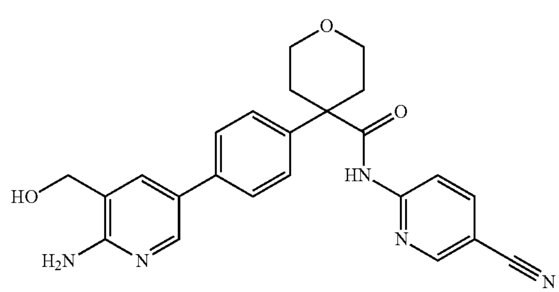 [SMILES: N#Cc1ccc(NC(=O)C2(c3ccc(-c4cnc(N)c(CO)c4)cc3)CCOCC2)nc1] | 4-{4-[6-amino-5-(hydroxymethyl)pyridin-3-yl]phenyl}-N-(5-cyanopyridin-2-yl)tetrahydro-2H-pyran-4-carboxamide |

TABLE 1-continued

| Example | Structure | Names |
|---|---|---|
| 180 | 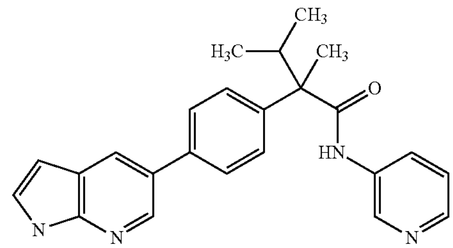 [SMILES: CC(C)C(C)(C(=O)Nc1cccnc1)c1ccc(-c2cnc3[nH]ccc3c2)cc1] | 2,3-dimethyl-N-(pyridin-3-yl)-2-[4-(1H-pyrrolo[2,3-b]pyridin-5-yl)phenyl]butanamide |
| 181 | 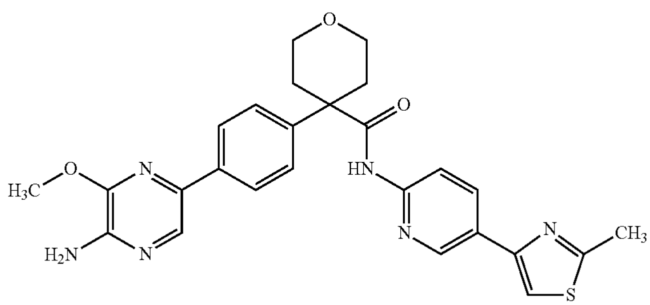 | 4-[4-(5-amino-6-methoypyrazin-2-yl)phenyl]-N-[5-(2-methyl-1,3-thiazol-4-yl)pyridin-2-yl]tetrahydro-2H-pyran-4-carboxamide |
| 182 | 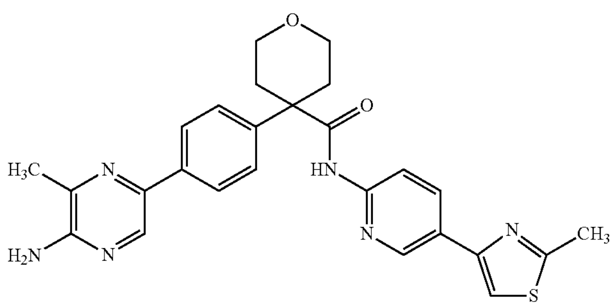 | 4-[4-(5-amino-6-methylpyrazin-2-yl)phenyl]-N-[5-(2-methyl-1,3-thiazol-4-yl)pyridin-2-yl]tetrahydro-2H-pyran-4-carboxamide |
| 183 | 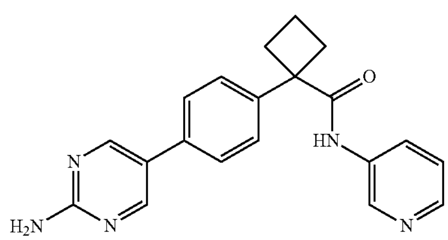 [SMILES: Nc1ncc(-c2ccc(C3(C(=O)Nc4cccnc4)CCC3)cc2)cn1] | 1-[4-(2-aminopyrimidin-5-yl)phenyl]-N-(pyridin-3-yl)cyclobutanecarboxamide |
| 184 | 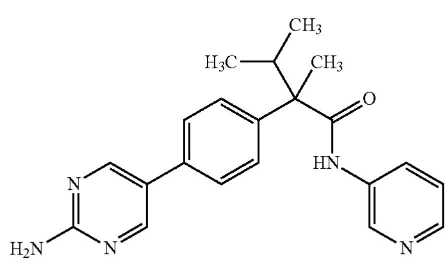 [SMILES: CC(C)C(C)(C(=O)Nc1cccnc1)c1ccc(-c2cnc(N)nc2)cc1] | 2-[4-(2-aminopyrimidin-5-yl)phenyl]-2,3-dimethyl-N-(pyridin-3-yl)butanamide |
| 185 | 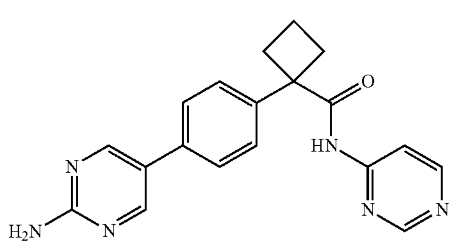 [SMILES: Nc1ncc(-c2ccc(C3(C(=O)Nc4ccncn4)CCC3)cc2)cn1] | 1-[4-(2-aminopyrimidin-5-yl)phenyl]-N-(pyrimidin-4-yl)cyclobutanecarboxamide |

TABLE 1-continued

| Example | Structure | Names |
|---|---|---|
| 186 | 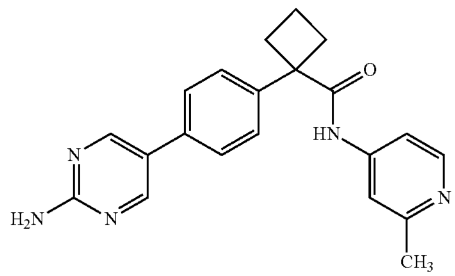 [SMILES: Cc1cc(NC(=O)C2(c3ccc(-c4cnc(N)nc4)cc3)CCC2)ccn1] | 1-[4-(2-aminopyrimidin-5-yl)phenyl]-N-(2-methylpyridin-4-yl)cyclobutanecarboxamide |
| 187 | 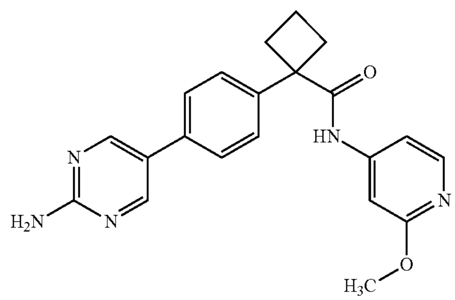 [SMILES: COc1cc(NC(=O)C2(c3ccc(-c4cnc(N)nc4)cc3)CCC2)ccn1] | 1-[4-(2-aminopyrimidin-5-yl)phenyl]-N-(2-methoxypyridin-4-yl)cyclobutanecarboxamide |
| 188 | 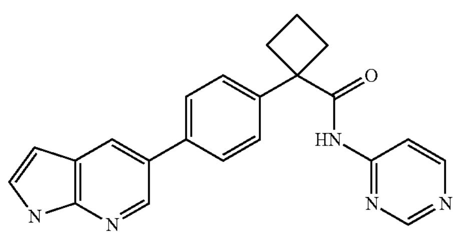 [SMILES: O=C(Nc1ccncn1)C1(c2ccc(-c3cnc4[nH]ccc4c3)cc2)CCC1] | N-(pyrimidin-4-yl)-1-[4-(1H-pyrrolo[2,3-b]pyridin-5-yl)phenyl]cyclobutanecarboxamide |
| 189 | 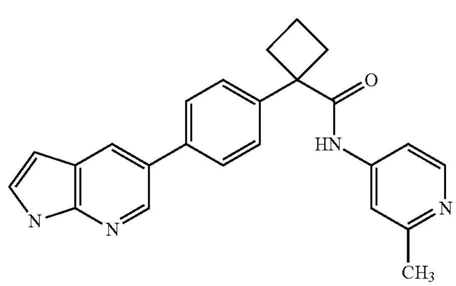 [SMILES: Cc1cc(NC(=O)C2(c3ccc(-c4cnc5[nH]ccc5c4)cc3)CCC2)ccn1] | N-(2-methylpyridin-4-yl)-1-[4-(1H-pyrrolo[2,3-b]pyridin-5-yl)phenyl]cyclobutanecarboxamide |
| 190 | 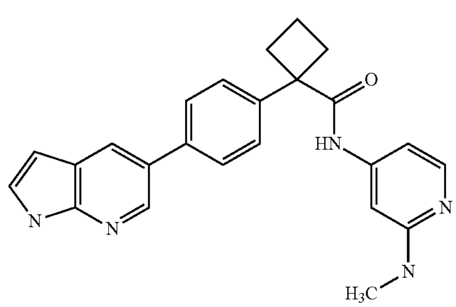 [SMILES: CNc1cc(NC(=O)C2(c3ccc(-c4cnc5[nH]ccc5c4)cc3)CCC2)ccn1] | N-(2-methoxypyridin-4-yl)-1-[4-(1H-pyrrolo[2,3-b]pyridin-5-yl)phenyl]cyclobutanecarboxamide |

TABLE 1-continued

| Example | Structure | Names |
|---|---|---|
| 191 | 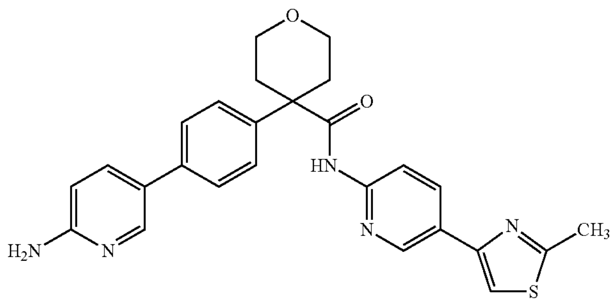 [SMILES: Cc1nc(-c2ccc(NC(=O)C3(c4ccc(-c5ccc(N)nc5)cc4)CCOCC3)nc2)cs1] | 4-[4-(6-aminopyridin-3-yl)phenyl]-N-[5-(2-methyl-1,3-thiazol-4-yl)pyridin-2-yl]tetrahydro-2H-pyran-4-carboxamide |
| 192 | 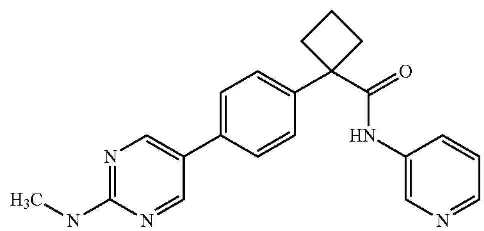 [SMILES: CNc1ncc(-c2ccc(C3(C(=O)Nc4cccnc4)CCC3)cc2)cn1] | 1-{4-[2-(methylamino)pyrimidin-5-yl]phenyl}-N-(pyridin-3-yl)cyclobutanecarboxamide |
| 193 | 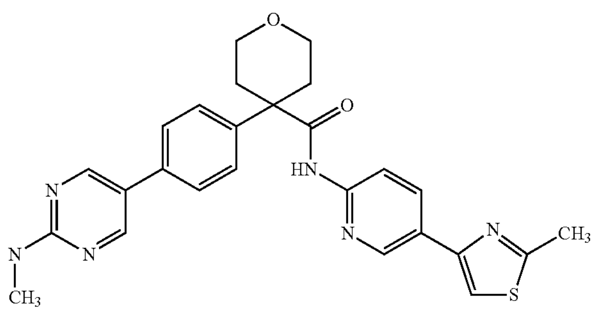 [SMILES: CNc1ncc(-c2ccc(C3(C(=O)Nc4ccc(-c5csc(C)n5)cn4)CCOCC3)cc2)cn1] | 4-{4-[2-(methylamino)pyrimidin-5-yl]phenyl}-N-[5-(2-methyl-1,3-thiazol-4-yl)pyridin-2-yl]tetrahydro-2H-pyran-4-carboxamide |
| 194 | 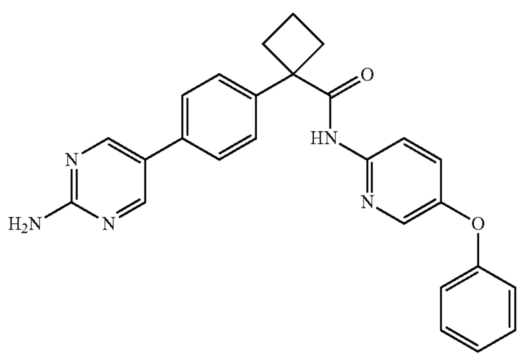 [SMILES: Nc1ncc(-c2ccc(C3(C(=O)Nc4ccc(Oc5ccccc5)cn4)CCC3)cc2)cn1] | 1-[4-(2-aminopyrimidin-5-yl)phenyl]-N-(5-phenoxypyridin-2-yl)cyclobutanecarboxamide |
| 195 | 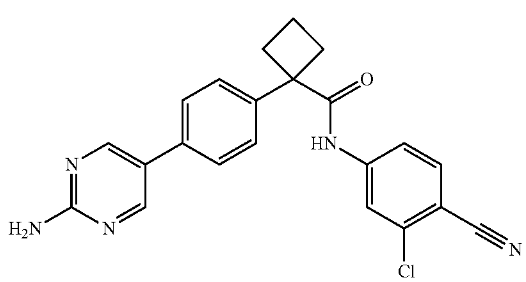 [SMILES: N#Cc1ccc(NC(=O)C2(c3ccc(-c4cnc(N)nc4)cc3)CCC2)cc1Cl] | 1-[4-(2-aminopyrimidin-5-yl)phenyl]-N-(3-chloro-4-cyanophenyl)cyclobutanecarboxamide |

TABLE 1-continued

| Example | Structure | Names |
|---|---|---|
| 196 | 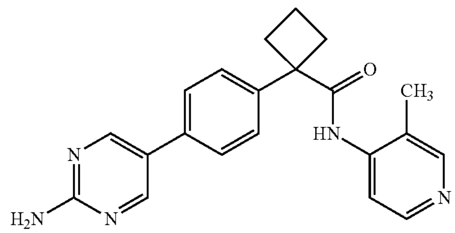 [SMILES: Cc1cnccc1NC(=O)C1(c2ccc(-c3cnc(N)nc3)cc2)CCC1] | 1-[4-(2-aminopyrimidin-5-yl)phenyl]-N-(3-methylpyridin-4-yl)cyclobutanecarboxamide |
| 197 | 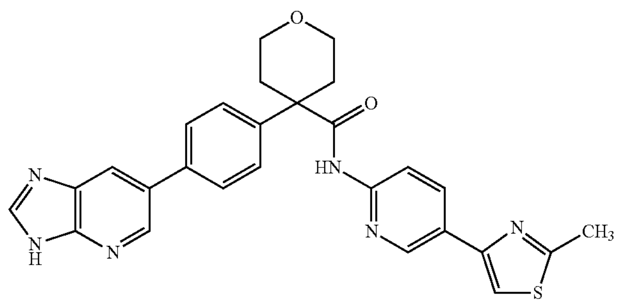 [SMILES: Cc1nc(-c2ccc(NC(=O)C3(c4ccc(-c5cnc6[nH]cnc6c5)cc4)CCOCC3)nc2)cs1] | 4-[4-(3H-imidazo[4,5-b]pyridin-6-yl)phenyl]-N-[5-(2-methyl-1,3-thiazol-4-yl)pyridin-2-yl]tetrahydro-2H-pyran-4-carboxamide |
| 198 | 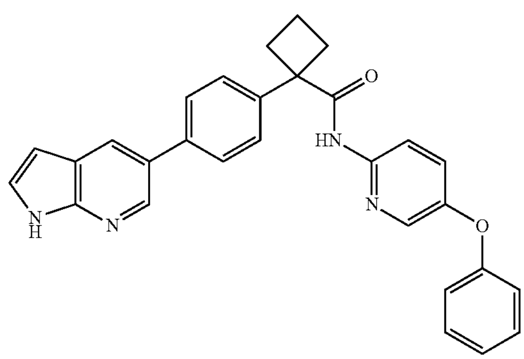 [SMILES: O=C(Nc1ccc(Oc2ccccc2)cn1)C1(c2ccc(-c3cnc4[nH]ccc4c3)cc2)CCC1] | N-(5-phenoxypyridin-2-yl)-1-[4-(1H-pyrrolo[2,3-b]pyridin-5-yl)phenyl]cyclobutane-carboxamide |
| 199 | 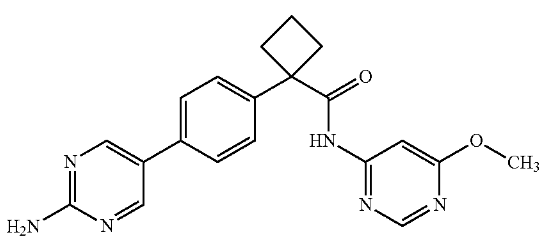 [SMILES: COc1cc(NC(=O)C2(c3ccc(-c4cnc(N)nc4)cc3)CCC2)ncn1] | 1-[4-(2-aminopyrimidin-5-yl)phenyl]-N-(6-methoxypyrimidin-4-yl)cyclobutanecarboxamide |
| 200 | 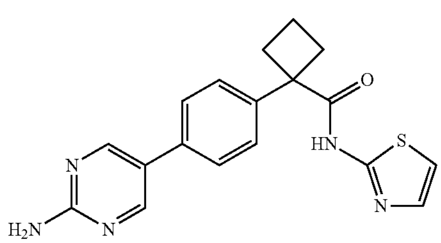 [SMILES: Nc1ncc(-c2ccc(C3(C(=O)Nc4nccs4)CCC3)cc2)cn1] | 1-[4-(2-aminopyrimidin-5-yl)phenyl]-N-(1,3-thiazol-2-yl)cyclobutanaecarboxamide |

TABLE 1-continued

| Example | Structure | Names |
|---|---|---|
| 201 | 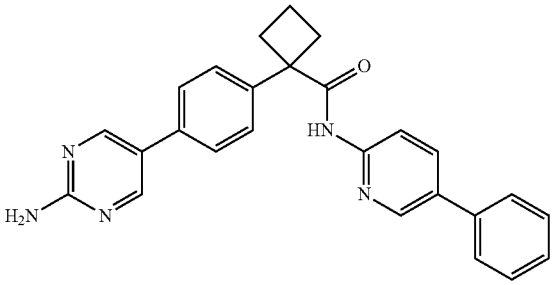 [SMILES: Nc1ncc(-c2ccc(C3(C(=O)Nc4ccc(-c5ccccc5)cn4)CCC3)cc2)cn1] | 1-[4-(2-aminopyrimidin-5-yl)phenyl]-N-(5-phenylpyridin-2-yl)cyclobutanecarboxamide |
| 202 | 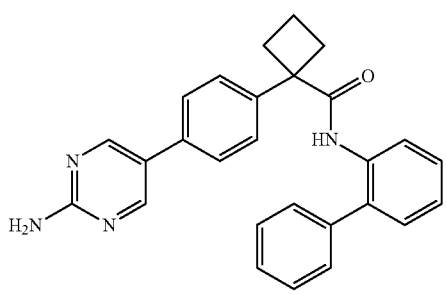 [SMILES: Nc1ncc(-c2ccc(C3(C(=O)Nc4ccccc4-c4ccccc4)CCC3)cc2)cn1] | 1-[4-(2-aminopyrimidin-5-yl)phenyl]-N-(biphenyl-2-yl)cyclobutanecarboxamide |
| 203 | 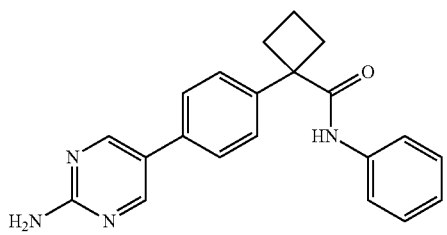 | 1-[4-(2-aminopyrimidin-5-yl)phenyl]-N-phenylcyclobutanecarboxamide |
| 204 | 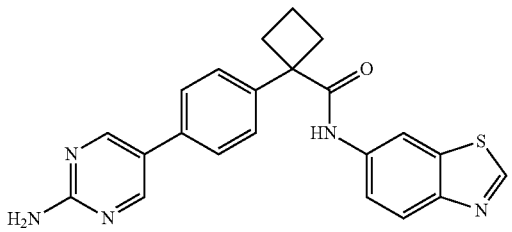 [SMILES: Nc1ncc(-c2ccc(C3(C(=O)Nc4ccc5ncsc5c4)CCC3)cc2)cn1] | 1-[4-(2-aminopyrimidin-5-yl)phenyl]-N-(1,3-benzothiazol-6-yl)cyclobutanecarboxamide |
| 205 | 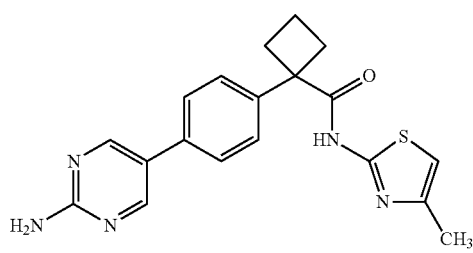 [SMILES: Cc1csc(NC(=O)C2(c3ccc(-c4cnc(N)nc4)cc3)CCC2)n1] | 1-[4-(2-aminopyrimidin-5-yl)phenyl]-N-(4-methyl-1,3-thiazol-2-yl)cyclobutanecarboxamide |

TABLE 1-continued

| Example | Structure | Names |
|---|---|---|
| 206 | 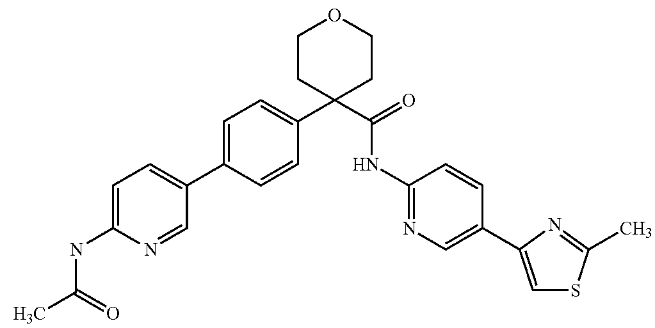 [SMILES: CC(=O)Nc1ccc(-c2ccc(C3(C(=O)Nc4ccc(-c5csc(C)n5)cn4)CCOCC3)cc2)cn1] | 4-{4-[6-(acetylamino)pyridin-3-yl]phenyl}-N-[5-(2-methyl-1,3-thiazol-4-yl)pyridin-2-yl]tetrahydro-2H-pyran-4-carboxamide |
| 207 | 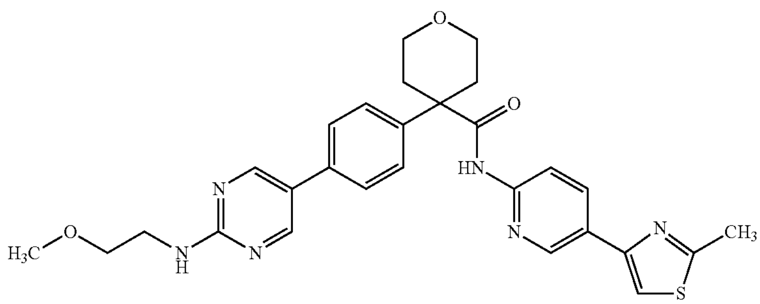 | 4-(4-{2-[(2-methoxyethyl)amino]pyrimidin-5-yl}phenyl)-N-[5-(2-methyl-1,3-thiazol-4-yl)pyridin-2-yl]tetrahydro-2H-pyran-4-carboxamide |
| 208 | 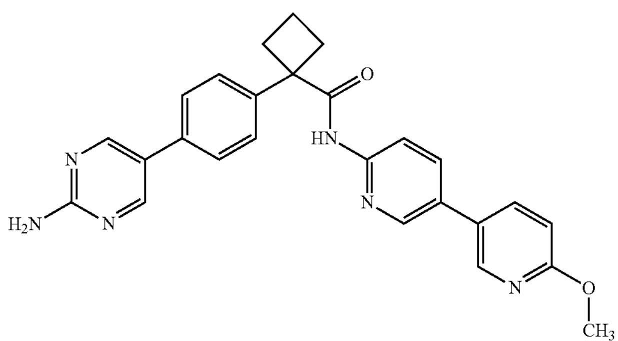 [SMILES: COc1ccc(-c2ccc(NC(=O)C3(c4ccc(-c5cnc(N)nc5)cc4)CCC3)nc2)cn1] | 1-[4-(2-aminopyrimidin-5-yl)phenyl]-N-(6'-methoxy-3,3'-bipyridin-6-yl)cyclobutanecarboxamide |
| 209 | 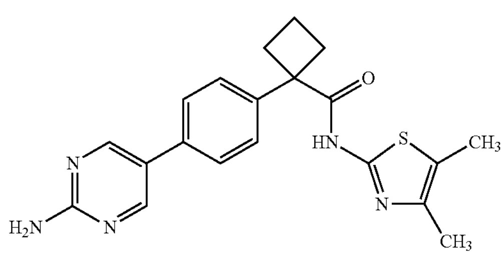 [SMILES: Cc1nc(NC(=O)C2(c3ccc(-c4cnc(N)nc4)cc3)CCC2)sc1C] | 1-[4-(2-aminopyrimidin-5-yl)phenyl]-N-(4,5-dimethyl-1,3-thiazol-2-yl)cyclobutanecarboxamide |
| 210 | 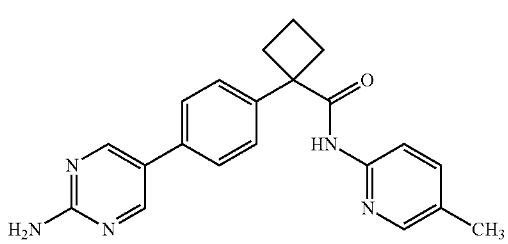 [SMILES: Cc1ccc(NC(=O)C2(c3ccc(-c4cnc(N)nc4)cc3)CCC2)nc1] | 1-[4-(2-aminopyrimidin-5-yl)phenyl]-N-(5-methylpyridin-2-yl)cyclobutanecarboxamide |

TABLE 1-continued

| Example | Structure | Names |
|---|---|---|
| 211 | 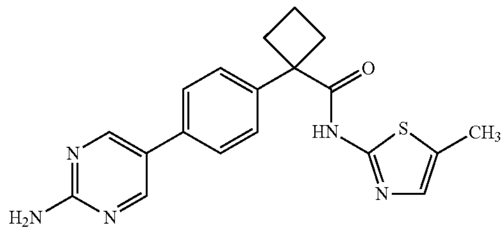 [SMILES: Cc1cnc(NC(=O)C2(c3ccc(-c4cnc(N)nc4)cc3)CCC2)s1] | 1-[4-(2-aminopyrimidin-5-yl)phenyl]-N-(5-methyl-1,3-thiazol-2-yl)cyclobutanecarboxamide |
| 212 | 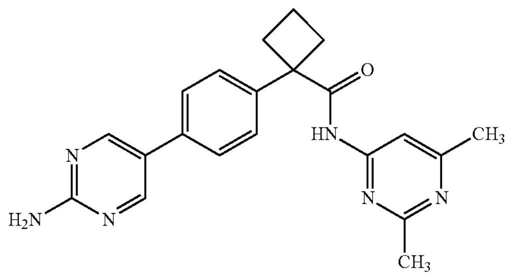 [SMILES: Cc1cc(NC(=O)C2(c3ccc(-c4cnc(N)nc4)cc3)CCC2)nc(C)n1] | 1-[4-(2-aminopyrimidin-5-yl)phenyl]-N-(2,6-dimethylpyrimidin-4-yl)cyclobutanecarboxamide |
| 213 | 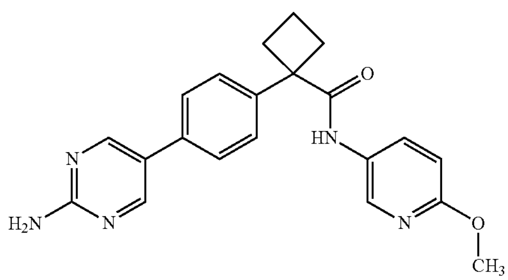 [SMILES: COc1ccc(NC(=O)C2(c3ccc(-c4cnc(N)nc4)cc3)CCC2)cn1] | 1-[4-(2-aminopyrimidin-5-yl)phenyl]-N-(6-methoxypyridin-3-yl)cyclobutanecarboxamide |
| 214 | 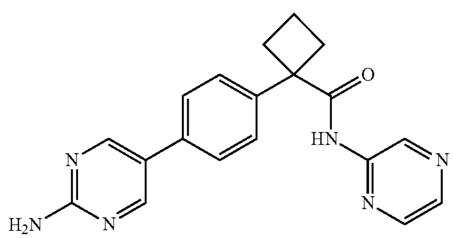 [SMILES: Nc1ncc(-c2ccc(C3(C(=O)Nc4cnccn4)CCC3)cc2)cn1] | 1-[4-(2-aminopyrimidin-5-yl)phenyl]-N-(pyrazin-2-yl)cyclobutanecarboxamide |
| 215 | 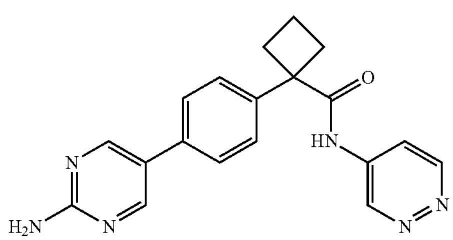 [SMILES: Nc1ncc(-c2ccc(C3(C(=O)Nc4ccnnc4)CCC3)cc2)cn1] | 1-[4-(2-aminopyrimidin-5-yl)phenyl]-N-(pyridazin-4-yl)cyclobutanecarboxamide |
| 216 | 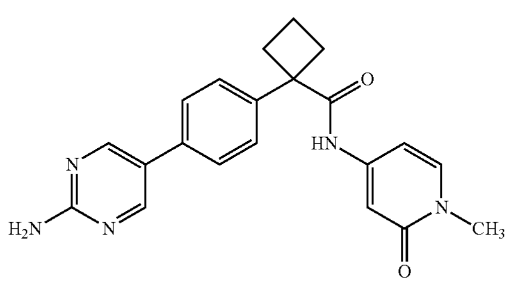 [SMILES: Cn1ccc(NC(=O)C2(c3ccc(-c4cnc(N)nc4)cc3)CCC2)cc1=O] | 1-[4-(2-aminopyrimidin-5-yl)phenyl]-N-(1-methyl-2-oxo-1,2-dihydropyridin-4-yl)cyclobutanecarboxamide |

TABLE 1-continued

| Example | Structure | Names |
|---|---|---|
| 217 | 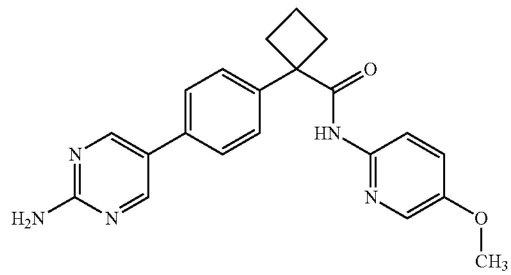 [SMILES: COc1ccc(NC(=O)C2(c3ccc(-c4cnc(N)nc4)cc3)CCC2)nc1] | 1-[4-(2-aminopyrimidin-5-yl)phenyl]-N-(5-methoxypyridin-2-yl)cyclobutanecarboxamide |
| 218 | 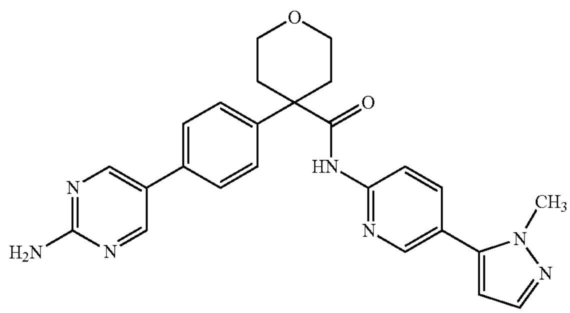 [SMILES: Cn1nccc1-c1ccc(NC(=O)C2(c3ccc(-c4cnc(N)nc4)cc3)CCOCC2)nc1] | 4-[4-(2-aminopyrimidin-5-yl)phenyl]-N-[5-(1-methyl-1H-pyrazol-5-yl)pyridin-2-yl]tetrahydro-2H-pyran-4-carboxamide |
| 219 | 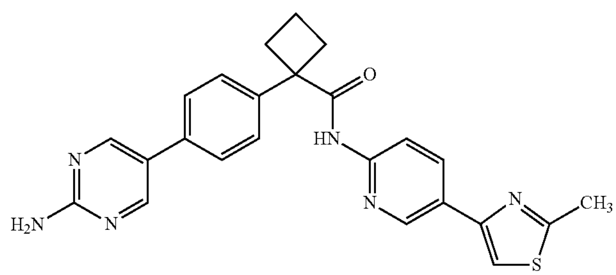 [SMILES: Cc1nc(-c2ccc(NC(=O)C3(c4ccc(-c5cnc(N)nc5)cc4)CCC3)nc2)cs1] | 1-[6-(2-aminopyrimidin-5-yl)pyridin-3-yl]-N-[5-(2-methyl-1,3-thiazol-4-yl)pyridin-2-yl]cyclobutancarboxamide |
| 220 | 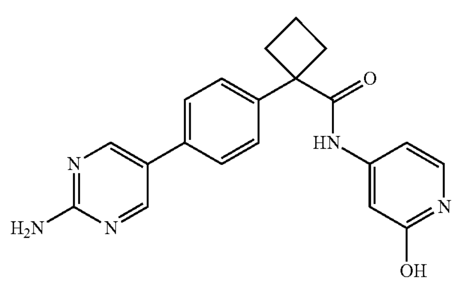 [SMILES: Nc1ncc(-c2ccc(C3(C(=O)Nc4ccnc(O)c4)CCC3)cc2)cn1] | 1-[4-(2-aminopyrimidin-5-yl)phenyl]-N-(2-hydroxypyridin-4-yl)cyclobutanecarboxamide |
| 221 | 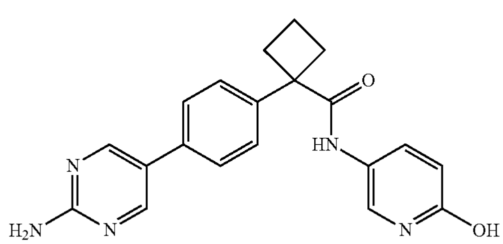 [SMILES: Nc1ncc(-c2ccc(C3(C(=O)Nc4ccc(O)nc4)CCC3)cc2)cn1] | 1-[4-(2-aminopyrimidin-5-yl)phenyl]-N-(6-hydroxypyridin-3-yl)cyclobutanecarboxamide |

TABLE 1-continued

| Example | Structure | Names |
|---|---|---|
| 222 | 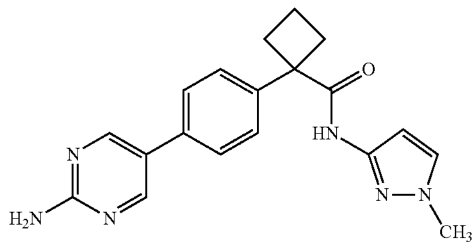 [SMILES: Cn1ccc(NC(=O)C2(c3ccc(-c4cnc(N)nc4)cc3)CCC2)n1] | 1-[4-(2-aminopyrimidin-5-yl)phenyl]-N-(1-methyl-1H-pyrazol-3-yl)cyclobutanecarboxamide |
| 223 | 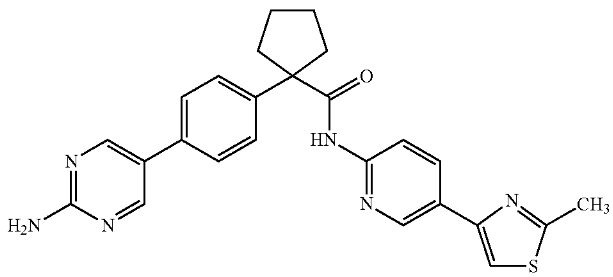 [SMILES: Cc1nc(-c2ccc(NC(=O)C3(c4ccc(-c5cnc(N)nc5)cc4)CCCC3)nc2)cs1] | 1-[4-(2-aminopyrimidin-5-yl)phenyl]-N-[5-(2-methyl-1,3-thiazol-4-yl)pyridin-2-yl]cyclobutanecarboxamide |
| 224 | 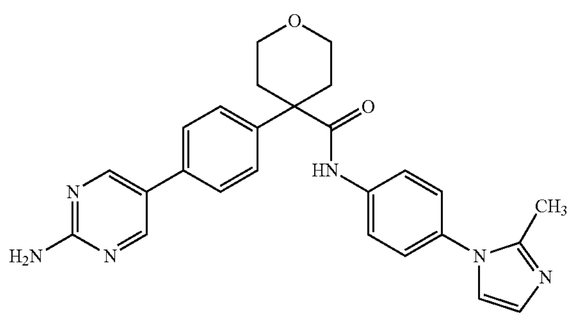 [SMILES: Cc1nccn1-c1ccc(NC(=O)C2(c3ccc(-c4cnc(N)nc4)cc3)CCOCC2)cc1] | 4-[4-(2-aminopyrimidin-5-yl)phenyl]-N-[4-(2-methyl-1H-imidazol-1-yl)phenyl]tetrahydro-2H-pyran-4-carboxamide |
| 225 | 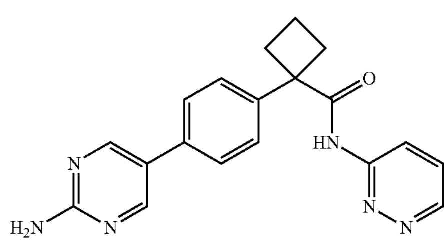 [SMILES: Nc1ncc(-c2ccc(C3(C(=O)Nc4cccnn4)CCC3)cc2)cn1] | 1-[4-(2-aminopyrimidin-5-yl)phenyl]-N-(pyridazin-3-yl)cyclobutanecarboxamide |
| 226 | 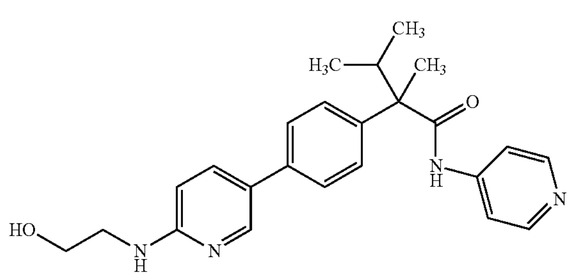 [SMILES: CC(C)C(C)(C(=O)Nc1ccncc1)c1ccc(-c2ccc(NCCO)nc2)cc1] | 2-(4-{6-[(2-hydroxyethyl)amino]pyridin-3-yl}phenyl)-2,3-dimethyl-N-(pyridin-4-yl)butanamide |

TABLE 1-continued

| Example | Structure | Names |
|---|---|---|
| 227 | 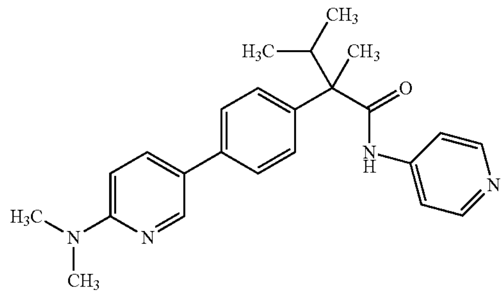 [SMILES: CC(C)C(C)(C(=O)Nc1ccncc1)c1ccc(-c2ccc(N(C)C)nc2)cc1] | 2-{4-[6-(dimethylamino)pyridin-3-yl]phenyl}-2,3-dimethyl-N-(pyridin-4-yl)butanamide |
| 228 | 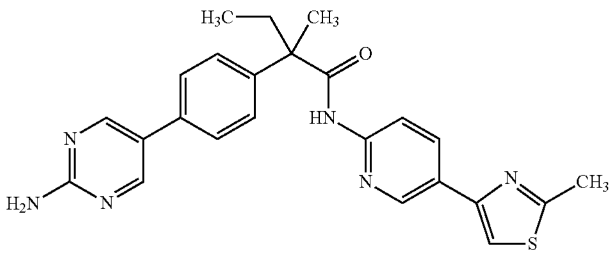 [SMILES: CCC(C)(C(=O)Nc1ccc(-c2csc(C)n2)cn1)c1ccc(-c2cnc(N)nc2)cc1] | 2-[4-(2-aminopyrimidin-5-yl)phenyl]-2-methyl-N-[5-(2-methyl-1,3-thiazol-4-yl)pyridin-2-yl]butanamide |
| 229 | 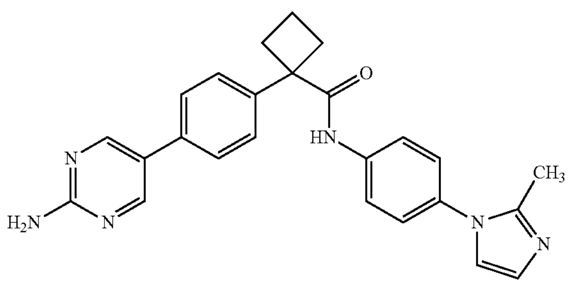 [SMILES: Cc1nccn1-c1ccc(NC(=O)C2(c3ccc(-c4cnc(N)nc4)cc3)CCC2)cc1] | 1-[4-(2-aminopyrimidin-5-yl)phenyl]-N-[4-(2-methyl-1H-imidazol-1-yl)phenyl]cyclobutanecarboxamide |
| 230 | 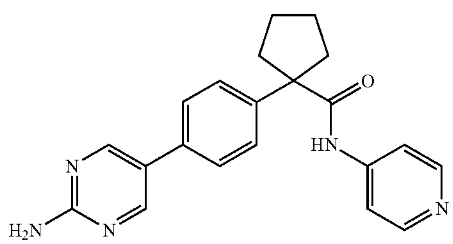 [SMILES: Nc1ncc(-c2ccc(C3(C(=O)Nc4ccncc4)CCCC3)cc2)cn1] | 1-[4-(2-aminopyrimidin-5-yl)phenyl]-N-(pyridin-4-yl)cyclopentanecarboxamide |
| 231 | 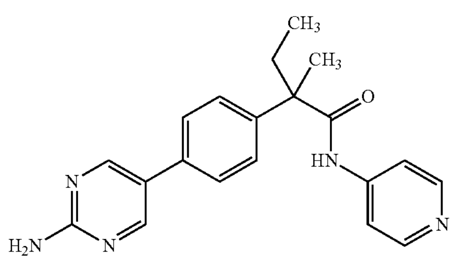 [SMILES: CCC(C)(C(=O)Nc1ccncc1)c1ccc(-c2cnc(N)nc2)cc1] | 2-[4-(2-aminopyrimidin-5-yl)phenyl]-2-methyl-N-(pyridin-4-yl)butanamide |
| 232 | 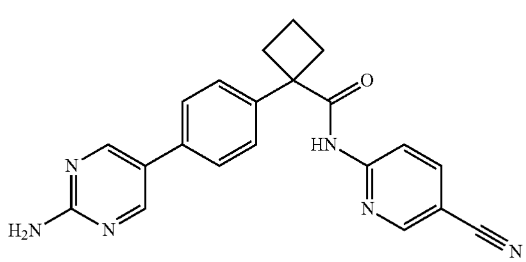 [SMILES: N#Cc1ccc(NC(=O)C2(c3ccc(-c4cnc(N)nc4)cc3)CCC2)nc1] | 1-[4-(2-aminopyrimidin-5-yl)phenyl]-N-(5-cyanopyridin-2-yl)cyclobutanecarboxamide |

| Example | Structure | Names |
|---|---|---|
| 233 | 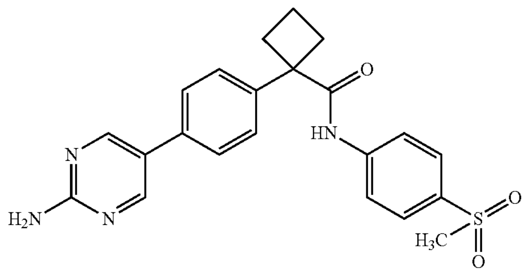 [SMILES: CS(=O)(=O)c1ccc(NC(=O)C2(c3ccc(-c4cnc(N)nc4)cc3)CCC2)cc1] | 1-[4-(2-aminopyrimidin-5-yl)phenyl]-N-[4-(methylsulfonyl)phenyl]cyclobutanecarboxamide |
| 234 | 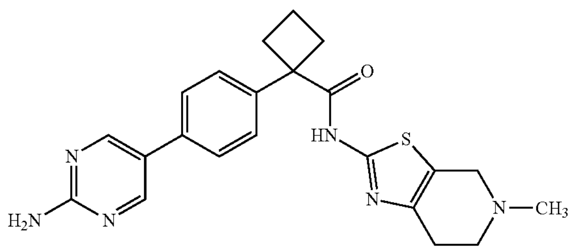 [SMILES: CN1CCc2nc(NC(=O)C3(c4ccc(-c5cnc(N)nc5)cc4)CCC3)sc2C1] | 1-[4-(2-aminopyrimidin-5-yl)phenyl]-N-(5-methyl-4,5,6,7-tetrahydro[1,3]thiazolo[5,4-c]pyridin-2-yl)cyclobutanecarboxamide |
| 235 | 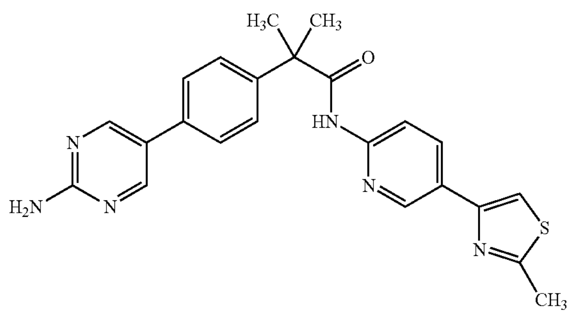 [SMILES: Cc1nc(-c2ccc(NC(=O)C(C)(C)c3ccc(-c4cnc(N)nc4)cc3)nc2)cs1] | 2-[4-(2-aminopyrimidin-5-yl)phenyl]-2-methyl-N-[5-(2-methyl-1,3-thiazol-4-yl)pyridin-2-yl]propanamide |
| 236 | 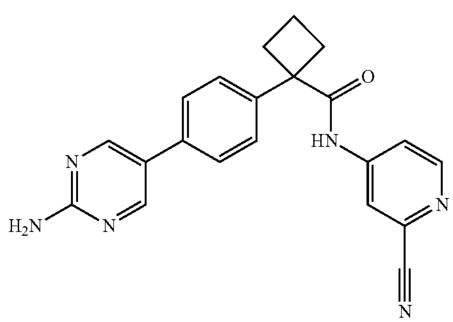 [SMILES: N#Cc1cc(NC(=O)C2(c3ccc(-c4cnc(N)nc4)cc3)CCC2)ccn1] | 1-[4-(2-aminopyrimidin-5-yl)phenyl]-N-(2-cyanopyridin-4-yl)cyclobutanecarboxamide |
| 237 | 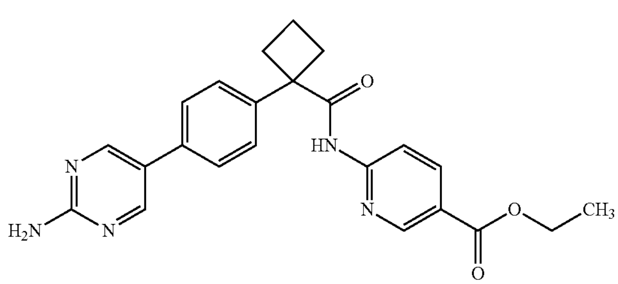 [SMILES: CCOC(=O)c1ccc(NC(=O)C2(c3ccc(-c4cnc(N)nc4)cc3)CCC2)nc1] | ethyl 6-[({1-[4-(2-aminopyrimidin-5-yl)phenyl]cyclobutyl}carbonyl)amino]pyridine-3-carboxylate |

TABLE 1-continued

| Example | Structure | Names |
|---|---|---|
| 238 | 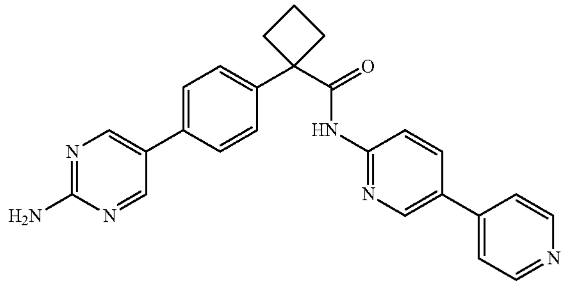 [SMILES: Nc1ncc(-c2ccc(C3(C(=O)Nc4ccc(-c5ccncc5)cn4)CCC3)cc2)cn1] | 1-[4-(2-aminopyrimidin-5-yl)phenyl-N-(3,4'-bipyridin-6-yl)cyclobutanecarboxamide |
| 239 | 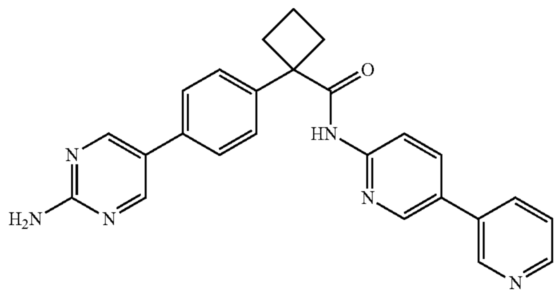 [SMILES: Nc1ncc(-c2ccc(C3(C(=O)Nc4ccc(-c5cccnc5)cn4)CCC3)cc2)cn1] | 1-[4-(2-aminopyrimidin-5-yl)phenyl]-N-(3,3'-bipyridin-6-yl)cyclobutanecarboxamide |
| 240 | 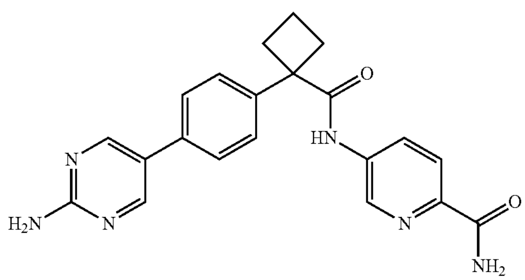 [SMILES: NC(=O)c1ccc(NC(=O)C2(c3ccc(-c4cnc(N)nc4)cc3)CCC2)cn1] | 5-[({1-[4-(2-aminopyrimidin-5-yl)phenyl]cyclobutyl}carbonyl)amino]pyridine-2-carboxamide |
| 241 | 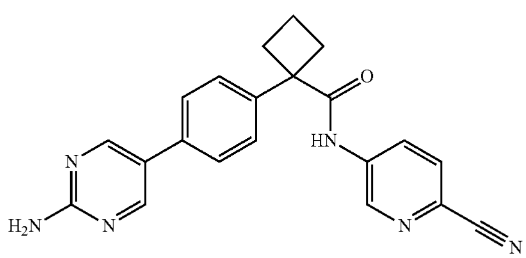 [SMILES: N#Cc1ccc(NC(=O)C2(c3ccc(-c4cnc(N)nc4)cc3)CCC2)cn1] | 1-[4-(2-aminopyrimidin-5-yl)phenyl]-N-(6-cyanopyridin-3-yl)cyclobutanecarboxamide |
| 242 | 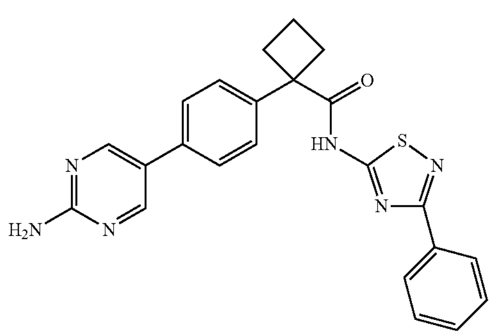 [SMILES: Nc1ncc(-c2ccc(C3(C(=O)Nc4nc(-c5ccccc5)ns4)CCC3)cc2)cn1] | 1-[4-(2-aminopyrimidin-5-yl)phenyl]-N-(3-phenyl-1,2,4-thiadiazol-5-yl)cyclobutanecarboxamide |

TABLE 1-continued

| Example | Structure | Names |
|---|---|---|
| 243 | 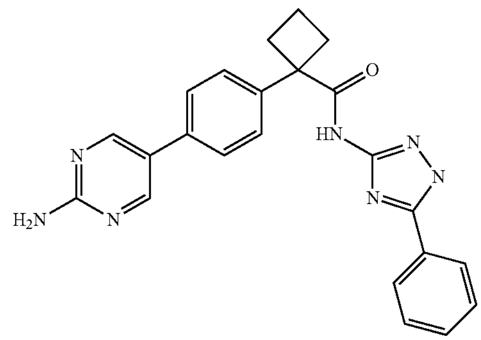 [SMILES: Nc1ncc(-c2ccc(C3(C(=O)Nc4n[nH]c(-c5ccccc5)n4)CCC3)cc2)cn1] | 1-[4-(2-aminopyrimidin-5-yl)phenyl]-N-(5-phenyl-1H-1,2,4-triazol-3-yl)cyclobutanecarboxamide |
| 244 | 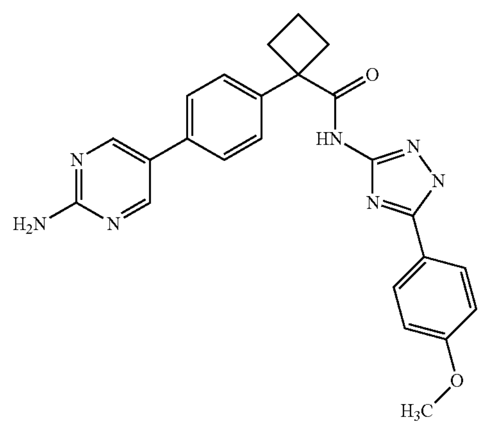 [SMILES: COc1ccc(-c2nc(NC(=O)C3(c4ccc(-c5cnc(N)nc5)cc4)CCC3)n[nH]2)cc1] | 1-[4-(2-aminopyrimidin-5-yl)phenyl]-N-[5-(4-methoxyphenyl)-1H-1,2,4-triazol-3-yl]cyclobutanecarboxamide |
| 245 | 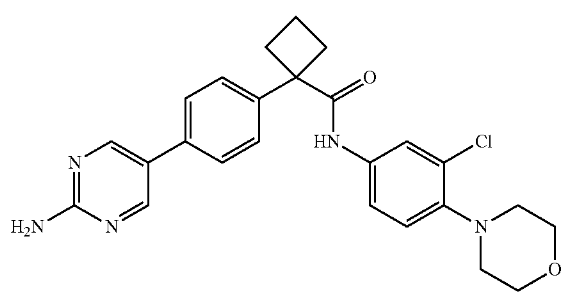 [SMILES: Nc1ncc(-c2ccc(C3(C(=O)Nc4ccc(N5CCOCC5)c(Cl)c4)CCC3)cc2)cn1] | 1-[4-(2-aminopyrimidin-5-yl)phenyl]-N-[3-chloro-4-(morpholin-4-yl)phenyl]cyclobutanecarboxamide |
| 246 | 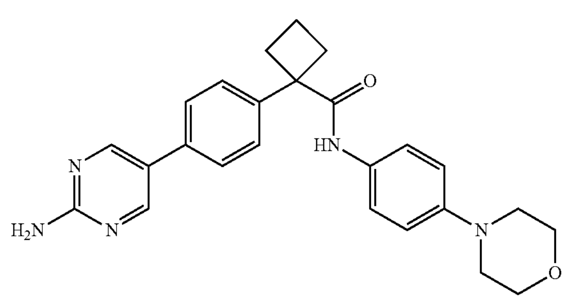 [SMILES: Nc1ncc(-c2ccc(C3(C(=O)Nc4ccc(N5CCOCC5)cc4)CCC3)cc2)cn1] | 1-[4-(2-aminopyrimidin-5-yl)phenyl]-N-[4-(morpholin-4-yl)phenyl]cyclobutanecarboxamide |

TABLE 1-continued

| Example | Structure | Names |
|---|---|---|
| 247 | 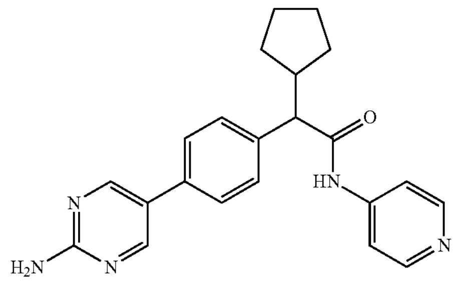 [SMILES: Nc1ncc(-c2ccc(C(C(=O)Nc3ccncc3)C3CCCC3)cc2)cn1] | 2-[4-(2-aminopyrimidin-5-yl)phenyl]-N-cyclopentyl-N-(pyridin-4-yl)acetamide |
| 248 | 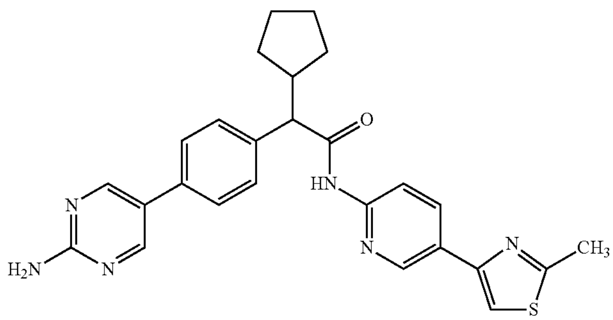 [SMILES: Cc1nc(-c2ccc(NC(=O)C(c3ccc(-c4cnc(N)nc4)cc3)C3CCCC3)nc2)cs1] | 2-[4-(2-aminopyrimidin-5-yl)phenyl]-2-cyclopentyl-N-[5-(2-methyl-1,3-thiazol-4-yl)pyridin-2-yl]acetamide |
| 249 | 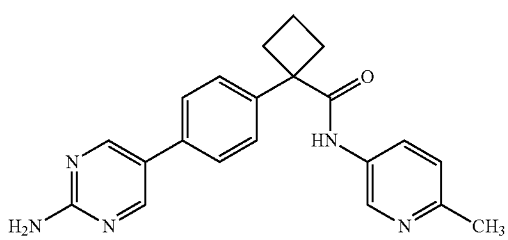 [SMILES: Cc1ccc(NC(=O)C2(c3ccc(-c4cnc(N)nc4)cc3)CCC2)cn1] | 1-[4-(2-aminopyrimidin-5-yl)phenyl]-N-(6-methylpyridin-3-yl)cyclobutanecarboxamide |
| 250 | 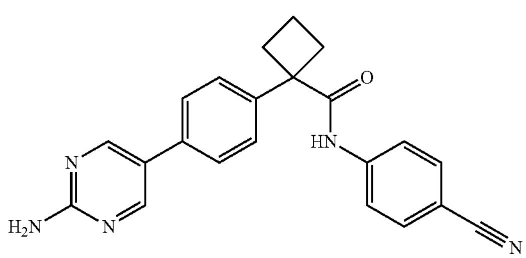 | 1-[4-(2-aminopyrimidin-5-yl)phenyl]-N-(4-cyanophenyl)cyclobutanecarboxamide |
| 251 | 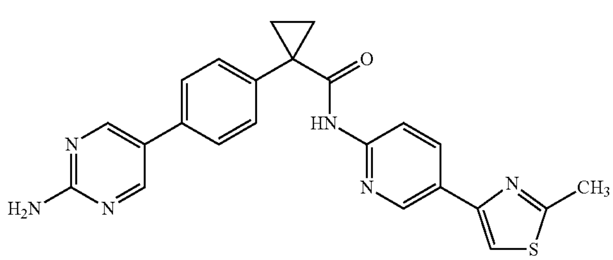 [SMILES: Cc1nc(-c2ccc(NC(=O)C3(c4ccc(-c5cnc(N)nc5)cc4)CC3)nc2)cs1] | 1-[4-(2-aminopyrimidin-5-yl)phenyl]-N-[5-(2-methyl-1,3-thiazol-4-yl)pyridin-2-yl]cyclopropanecarboxamide |

TABLE 1-continued

| Example | Structure | Names |
|---|---|---|
| 252 | 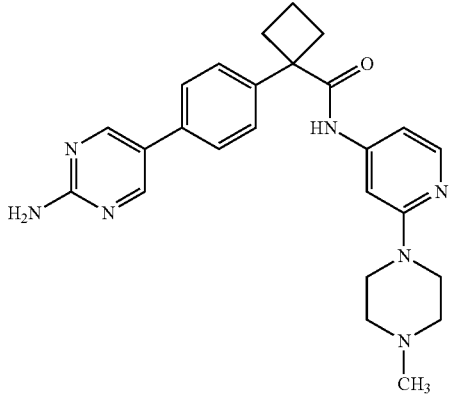 [SMILES: CN1CCN(c2cc(NC(=O)C3(c4ccc(-c5cnc(N)nc5)cc4)CCC3)ccn2)CC1] | 1-[4-(2-aminopyrimidin-5-yl)phenyl]-N-[2-(4-methylpiperazin-1-yl)pyridin-4-yl]cyclobutanecarboxamide |
| 253 | 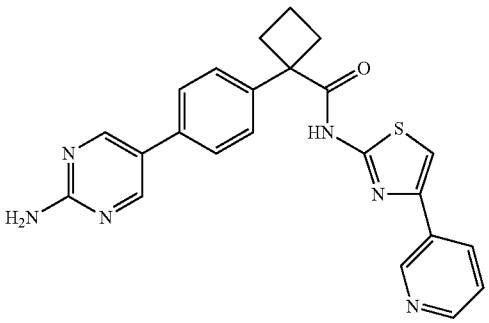 [SMILES: Nc1ncc(-c2ccc(C3(C(=O)Nc4nc(-c5cccnc5)cs4)CCC3)cc2)cn1] | 1-[4-(2-aminopyrimidin-5-yl)phenyl]-N-[4-(pyridin-3-yl)-1,3-thiazol-2-yl]cyclobutanecarboxamide |
| 254 | 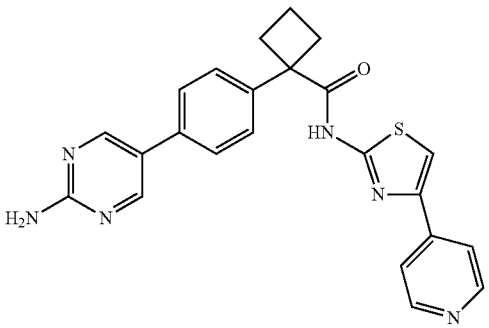 [SMILES: Nc1ncc(-c2ccc(C3(C(=O)Nc4nc(-c5ccncc5)cs4)CCC3)cc2)cn1] | 1-[4-(2-aminopyrimidin-5-yl)phenyl]-N-[4-(pyridin-4-yl)-1,3-thiazol-2-yl]cyclobutanecarboxamide |
| 255 | 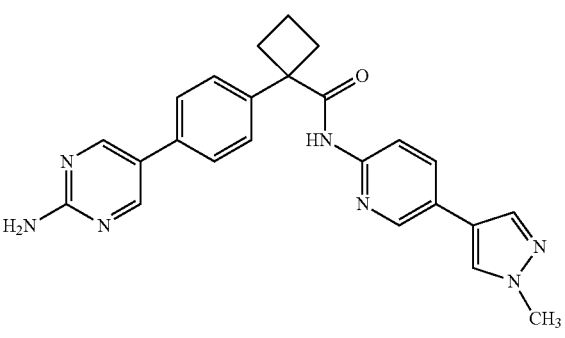 [SMILES: Cn1cc(-c2ccc(NC(=O)C3(c4ccc(-c5cnc(N)nc5)cc4)CCC3)nc2)cn1] | 1-[4-(2-aminopyrimidin-5-yl)phenyl]-N-[5-(1-methyl-1H-pyrazol-4-yl)pyridin-2-yl]cyclobutanecarboxamide |

In one embodiment, the invention relates to any of the compounds depicted in Table 1 above and the pharmaceutically acceptable salts thereof.

Representative compounds of the invention show activity in the FLAP binding assay and in the human whole blood $LTB_4$ production inhibition assay, described in the assessment of biological properties section, as shown in Table 2.

TABLE 2

| Example | hFLAP binding IC50 (nM) | HuWB IC50 (nM) |
|---|---|---|
| 1 | 16 | 461 |
| 2 | 210 | 1372 |

TABLE 2-continued

| Example | hFLAP binding IC50 (nM) | HuWB IC50 (nM) |
| --- | --- | --- |
| 3 | 11.25 | 328 |
| 4 | 38.5 | 808.25 |
| 5 | 101 | 2967 |
| 6 | 150 | |
| 7 | 10.7 | 2658 |
| 8 | 25 | 3564 |
| 9 | 200 | |
| 10 | 240 | |
| 11 | 21.87 | >3000 |
| 12 | 68 | 2225 |
| 13 | 16.75 | 3000 |
| 14 | 8.95 | 2252 |
| 15 | 23.5 | >3000 |
| 16 | 10.7 | 635.75 |
| 17 | 330 | |
| 18 | 16 | 1705 |
| 19 | 120 | |
| 20 | 16 | 1335 |
| 21 | 12 | >3000 |
| 22 | 60.5 | >3000 |
| 23 | 59.67 | >3000 |
| 24 | 95 | >3000 |
| 25 | 8.65 | 501 |
| 26 | 26 | >3000 |
| 27 | 5.5 | 207 |
| 28 | 121.5 | |
| 29 | 190 | |
| 30 | 18 | 2240.5 |
| 31 | 140 | |
| 32 | 46.5 | 1117.5 |
| 33 | 42.5 | >3000 |
| 34 | 11.65 | 160.5 |
| 35 | 390 | |
| 36 | 13.33 | >3000 |
| 37 | 35 | >3000 |
| 38 | 59.5 | >3000 |
| 39 | 55 | 1922 |
| 40 | 29 | 1219 |
| 41 | 120 | >3000 |
| 42 | 310 | |
| 43 | 12.25 | >3000 |
| 44 | 270 | |
| 45 | 6.2 | 459 |
| 46 | 180 | >3000 |
| 47 | 65 | 3202 |
| 48 | 84 | 1628 |
| 49 | 27 | 534.5 |
| 50 | 440 | |
| 51 | 18 | 1694 |
| 52 | 63.5 | 1810 |
| 53 | 280 | |
| 54 | 44.5 | 1123.5 |
| 55 | 29 | >3000 |
| 56 | 380 | |
| 57 | 260 | |
| 58 | 170 | >3000 |
| 59 | 12.65 | >3000 |
| 60 | 3.5 | 310 |
| 61 | 94 | >3000 |
| 62 | 33.5 | >3000 |
| 63 | 30.5 | 811.5 |
| 64 | 48 | 849.5 |
| 65 | 14 | 905 |
| 66 | 11.9 | 1778 |
| 67 | 14.5 | 1214.5 |
| 68 | 68.5 | 1213.5 |
| 69 | 260 | |
| 70 | 42 | >3000 |
| 71 | 190 | >3000 |
| 72 | 28.33 | 244.25 |
| 73 | 53.5 | 1498 |
| 74 | 97 | >3000 |
| 75 | 68 | >3000 |
| 76 | 52.5 | >3000 |
| 77 | 110 | |
| 78 | 112.5 | >3000 |
| 79 | 53.5 | >3000 |
| 80 | 60 | >3000 |
| 81 | 54 | >3000 |
| 82 | 10.5 | 2776.5 |
| 83 | 14.5 | 1059.5 |
| 84 | 180 | |
| 85 | 12.5 | 849 |
| 86 | 18.67 | 412 |
| 87 | 4 | 192 |
| 88 | 5.65 | 277.5 |
| 89 | 8.13 | 202.5 |
| 90 | 31.5 | 2075 |
| 91 | 5.45 | 240 |
| 92 | 15.5 | 717.5 |
| 93 | 2.05 | 311.67 |
| 94 | 65 | 856.67 |
| 95 | 2.35 | 202.5 |
| 96 | 26 | |
| 97 | 4.85 | 4100 |
| 98 | 12.15 | 235.5 |
| 99 | 45.5 | 570 |
| 100 | 1.85 | 184.5 |
| 101 | 47 | |
| 102 | 2.05 | 330 |
| 103 | 4.1 | 101.5 |
| 104 | 1.95 | 155 |
| 105 | 17.5 | |
| 106 | 3 | 195 |
| 107 | 87 | 1100 |
| 108 | 2 | 1900 |
| 109 | 9.4 | 2100 |
| 110 | 120 | 1100 |
| 111 | 180 | 2376.5 |
| 112 | 230 | 2058.5 |
| 113 | 390 | 10397 |
| 114 | 290 | >20000 |
| 115 | 190 | 17108.5 |
| 116 | 430 | 10847 |
| 117 | 9.3 | 1531.25 |
| 118 | 260 | 10665 |
| 119 | 3.95 | 985.75 |
| 120 | 11.5 | 1266 |
| 121 | 19 | 1884.5 |
| 122 | 9.53 | 1036.33 |
| 123 | 4 | 918.75 |
| 124 | 77.5 | 2171.5 |
| 125 | 173.5 | 5556.25 |
| 126 | 180 | 11991.5 |
| 127 | 9 | 3220.17 |
| 128 | 140 | 815 |
| 129 | 10.4 | 8617 |
| 130 | 1.52 | 224.5 |
| 131 | 2.2 | 414 |
| 132 | 220 | 1512.5 |
| 133 | 9.4 | 4402 |
| 134 | 17.5 | 650.75 |
| 135 | 11.15 | 737.5 |
| 136 | 10.25 | 4688.5 |
| 138 | 300 | 11803 |
| 139 | 110 | |
| 140 | 230 | |
| 141 | 190 | |
| 142 | 39 | 11336 |
| 143 | 17.07 | 646 |
| 144 | 66 | 1593.25 |
| 145 | 11.3 | 866.25 |
| 146 | 11.1 | 752 |
| 147 | 490 | 2897 |
| 148 | 360 | 3978.5 |
| 149 | 260 | 1458.5 |
| 150 | 48 | 3594 |
| 151 | 2.1 | 200.25 |
| 152 | 34.5 | 895.83 |
| 153 | 7.8 | 508.67 |
| 154 | 63.33 | 1371.5 |
| 155 | 136 | 857.25 |
| 156 | 490 | |
| 157 | 410 | |

TABLE 2-continued

| Example | hFLAP binding IC50 (nM) | HuWB IC50 (nM) |
|---|---|---|
| 158 | 36 | 5267.5 |
| 159 | 420 | |
| 160 | 12.95 | |
| 161 | 31 | |
| 162 | 4.1 | 896 |
| 163 | 6.75 | 403.5 |
| 164 | 1.9 | 315 |
| 165 | 1.4 | 354 |
| 166 | 3 | 332.5 |
| 167 | 4.7 | 353.5 |
| 168 | 7.95 | 616.25 |
| 169 | 5.25 | 329.75 |
| 170 | 9.8 | 894 |
| 171 | 2.05 | 565.5 |
| 173 | 18 | 929.5 |
| 174 | 18.1 | 685.75 |
| 175 | 22 | 1275.5 |
| 176 | 6.65 | 712 |
| 177 | 5.1 | 216.75 |
| 178 | 35.5 | 557 |
| 179 | 24.67 | 388 |
| 180 | 6.3 | 401.67 |
| 181 | 110 | |
| 182 | 32.5 | 1056 |
| 183 | 51.6 | 480.25 |
| 184 | 39 | 1470.5 |
| 185 | 17.5 | 955 |
| 186 | 3.2 | 334.5 |
| 187 | 5.1 | 517.25 |
| 188 | 1.65 | 129.75 |
| 189 | 1.45 | 190.5 |
| 190 | 2.25 | 148.75 |
| 191 | 27.5 | 1947 |
| 192 | 32 | 861 |
| 193 | 10.1 | 1649 |
| 194 | 19.15 | 577.25 |
| 195 | 2.7 | 174.5 |
| 196 | 50.67 | 2914 |
| 197 | 27 | 2442.5 |
| 198 | 3.75 | 180.25 |
| 199 | 5.7 | 1382 |
| 200 | 19 | 2006 |
| 201 | 3.75 | 224.5 |
| 202 | 56.5 | |
| 203 | 13.7 | 3250 |
| 204 | 2.8 | 415 |
| 205 | 8.4 | 922 |
| 206 | 270 | |
| 207 | 230 | |
| 208 | 3.35 | 459 |
| 209 | 13 | |
| 210 | 5.1 | 791.5 |
| 211 | 23.5 | |
| 212 | 15 | |
| 213 | 12.63 | 333.25 |
| 214 | 24 | 1070 |
| 215 | 17.67 | 705.5 |
| 216 | 91.5 | 3044 |
| 217 | 8.25 | 389 |
| 218 | 32.5 | 958.5 |
| 219 | 5.3 | 348.5 |
| 220 | 470 | |
| 221 | 290 | >3000 |
| 222 | 43.5 | 1229.5 |
| 223 | 7.15 | 1666.25 |
| 224 | 30 | 718 |
| 225 | 78 | 1367.5 |
| 226 | 250 | |
| 227 | 40.5 | >3000 |
| 228 | 12 | 1095.5 |
| 229 | 6.65 | 152.75 |
| 230 | 21.5 | 696.5 |
| 231 | 84 | 1211.5 |
| 232 | 7.45 | 151.5 |
| 233 | 6.5 | 159.5 |
| 234 | 32.5 | 857.75 |
| 235 | 5.4 | 627 |
| 236 | 3.45 | 289.75 |
| 237 | 1.9 | 43 |
| 238 | 2.35 | 74.5 |
| 239 | 2.15 | 144.5 |
| 240 | 4.4 | |
| 241 | 5.6 | 406.5 |
| 242 | 3.95 | |
| 243 | 22 | |
| 244 | 10.85 | |
| 245 | 3.3 | 46 |
| 246 | 34 | |
| 247 | 130 | |
| 248 | 240 | |
| 249 | 22.5 | |
| 250 | 3.2 | 60.75 |
| 251 | 16 | |
| 252 | 7.4 | 227.5 |
| 253 | 1.8 | 270.5 |
| 254 | 1.6 | 111 |
| 255 | 2.5 | 143.5 |

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g. $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-6}$ alkoxy" is a $C_{1-6}$ alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom. "Alkanoyl" refers to an alkyl group linked to a carbonyl group (C=O).

In all alkyl groups or carbon chains, one or more carbon atoms can be optionally replaced by heteroatoms such as O, S or N. It shall be understood that if N is not substituted then it is NH. It shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

As used herein, "nitrogen" and "sulfur" include any oxidized form of nitrogen and sulfur and the quaternized form of any basic nitrogen. For example, for a —S—$C_{1-6}$ alkyl radical, unless otherwise specified, shall be understood to include —S(O)—$C_{1-6}$ alkyl and —S(O)$_2$—$C_{1-6}$ alkyl.

The term "$C_{3-10}$ carbocycle" or "cycloalkyl" refers to a nonaromatic 3 to 10-membered (but preferably, 3 to 6-membered) monocyclic carbocyclic radical or a nonaromatic 6 to 10-membered fused bicyclic, bridged bicyclic, or spirocyclic carbocyclic radical. The $C_{3-10}$ carbocycle may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[3.3.0]octane, bicyclo[4.3.0]nonane, and bicyclo[4.4.0]decanyl (decahydronaphthalenyl). Non-limiting examples of 6 to 10-membered bridged bicyclic carbocyclic radicals include bicyclo[2.2.2]heptanyl, bicyclo[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

The term "$C_{6-10}$ aryl" refers to aromatic hydrocarbon rings containing from six to ten carbon ring atoms. The term $C_{6-10}$ aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

The term "5 to 11-membered heterocycle" refers to a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

The term "5 to 11-membered heteroaryl" shall be understood to mean an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S, Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl, benzothiazolyl, benzodioxolanyl, benzodioxolinyl, dihydroindolyl, naphthyridinyl, pyrimidopyridinyl, thiazolopyridinyl, tetrahydrothiazolopyridinyl, pyrrolopyridinyl, dihydropyrrolopyridinyl, imidazopyridinyl, pyrazolopyridinyl, and pyrimidopyridinyl.

It will be understood that one to three carbon ring moieties in the each of the $C_{3-10}$ carbocyclic rings, the 5 to 11-membered heterocyclic rings, the nonaromatic portion of the bicyclic aryl rings, and the nonaromatic portion of the bicyclic heteroaryl rings can independently be replaced with a carbonyl, thiocarbonyl, or iminyl moiety, i.e., —C(=O)—, —C(=S)— and —C(=NR$^8$)—, respectively, where R$^8$ is as defined above.

The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH$_2$CHF$_2$, —CF$_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1$-$C_4$ alkyl$)_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The compounds of the invention may be prepared by the methods described below. In each of the schemes below, the groups A, B, C, $R^{1a}$, $R^{1b}$, $R^2$, $R^3$, and $R^{4b}$ are as defined above for general formula I unless noted. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Typically, reaction progress may be monitored by thin layer chromatography (TLC) or HPLC-MS if desired. Intermediates and products may be purified by chromatography on silica gel, recrystallization, HPLC and/or reverse phase HPLC.

Starting materials and reagents are either commercially available or may be prepared by one skilled in the art using methods described in the chemical literature and in the Synthetic Examples section below.

Compounds of formula I may be prepared as shown in Scheme 1.

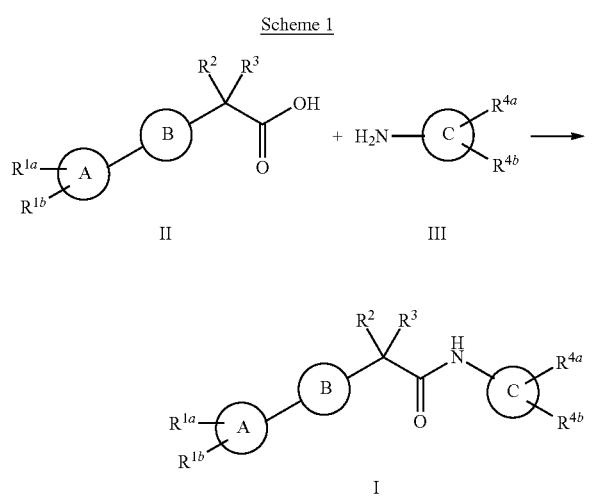

As illustrated in Scheme 1, reaction of an acid of formula II with an amine of formula III, in a suitable solvent, under standard coupling conditions, provides a compound of formula (I). Standard peptide coupling reactions known in the art (see for example M. Bodanszky, 1984, The Practice of Peptide Synthesis, Springer-Verlag) may be employed in these syntheses. An example of suitable coupling conditions is treatment of a solution of the carboxylic acid in a suitable solvent such as DMF with EDC, HOBT, and a base such as diisopropylethylamine, followed by the desired amine.

Alternatively, reaction of the acid of formula II with a reagent such as thionyl chloride or oxalyl chloride, provides the corresponding acid chloride which is then reacted with an amine of formula III, in a suitable solvent, in the presence of a suitable base, to provide a compound of formula (I).

Compounds of formula I may also be made by the sequence outlined in Scheme 2.

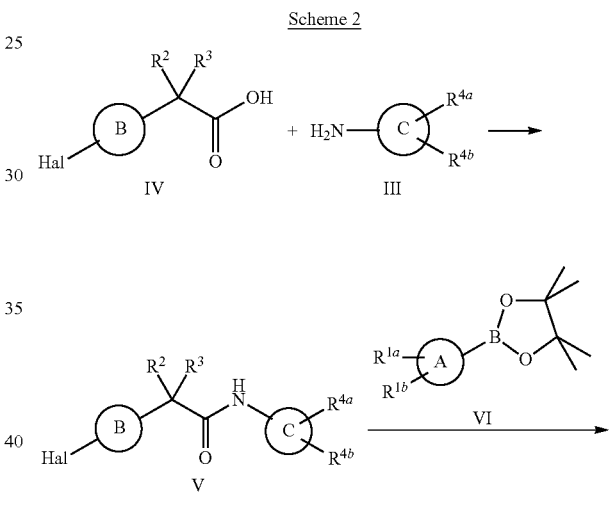

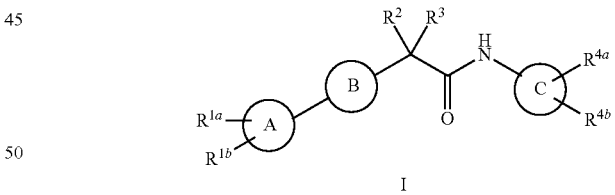

As shown in Scheme 2, reaction of an acid of formula IV, wherein Hal=Cl, Br or I, with an amine of formula III, as in Scheme 1, provides an intermediate amide of formula V. Coupling of intermediate of formula V with a boronic acid ester of formula VI or the corresponding boronic acid, in the presence of a suitable base and catalyst, in a suitable solvent, provides a compound of formula I.

Intermediate acid of formula II, wherein $R^2$ and $R^3$ together with the carbon atom to which they are attached form a heterocyclic or cycloalkyl ring, may be prepared according to the method shown in Scheme 3.

Scheme 3

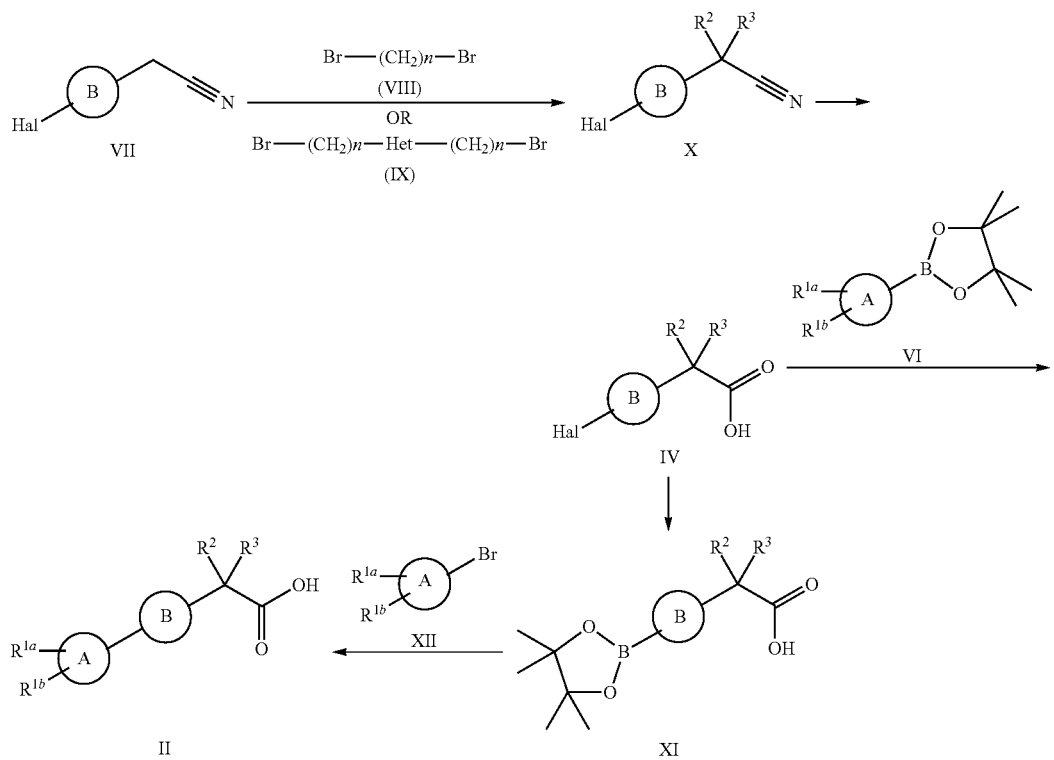

As outlined in Scheme 3, reaction of a nitrile of formula VII with a dibromo or dihalo compound of formula VIII or IX, wherein Het=O, S or N, in a suitable solvent, in the presence of a suitable base, provides the corresponding alkylated nitrile of formula X. Hydrolysis of the nitrile, in a suitable solvent, in the presence of a suitable base, provides the acid of formula IV which may be converted to the corresponding boronic acid of formula XI, under standard reaction conditions. Reaction of the boronic acid of formula XI, under standard coupling conditions, with the halide of formula XII, provides a compound of formula II.

Alternatively, reaction of the acid of formula IV with a boronic acid of formula VI, under standard coupling conditions, provides a compound of formula I.

Intermediate acid of formula IV wherein $R^2$ and $R^3$ are acyclic, may be prepared according to Scheme 4.

Scheme 4

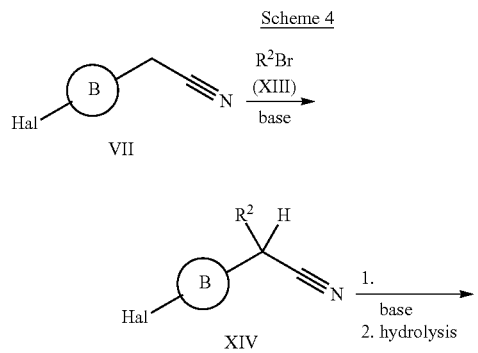

-continued

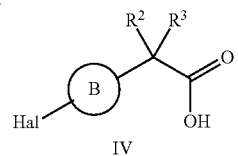

As outlined in Scheme 4, reaction of a nitrile of formula VII with $R^2Br$ (XIII), in a suitable solvent, in the presence of a suitable base, provides a monoalkylated nitrile of formula XIV. Further alkylation with $R^3Br$ provides a dialkylated nitrile which is then hydrolysed to provide an acid of formula IV. The acid of formula IV may be further converted to an acid of formula II by the sequence of steps shown in Scheme 3.

Another method of preparing intermediate acid of formula II is as shown in Scheme 5

Scheme 5

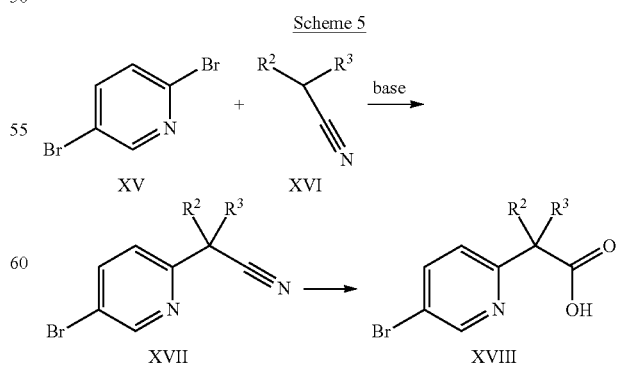

Reaction of 2,5 dibromo pyridine XV, with a nitrile of formula XVI in a suitable solvent, in the presence of a suitable base, provides a nitrile of formula XVII which may be hydrolysed under standard conditions, to provide an acid of formula XVIII. Acid of formula XVIII may be converted to an acid of formula II, via the sequence in Scheme 3

Intermediate acid of formula II, wherein R² or R³ is H, may be prepared starting from a carbonyl compound as shown in Scheme 6 below.

Scheme 6

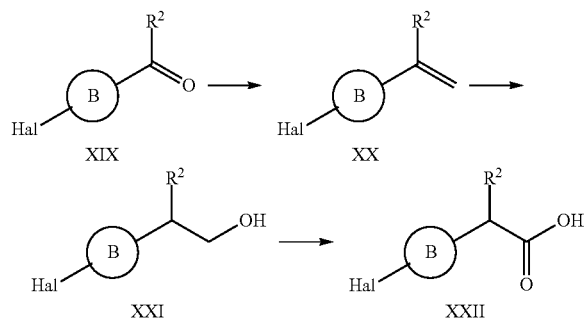

Reaction of a carbonyl compound of formula XIX with triphenylphosphonium bromide, in a suitable solvent, in the presence of a suitable base, provides an alkene of formula XX. Reaction of alkene XX with a reagent such as BH3 and hydrogen peroxide provides an a hydroxy compound of formula XXI. The hydroxyl group in compound XXI may be oxidized, under standard conditions, to provide an acid of formula XXII which may then be converted to an acid of formula II according to Scheme 3.

Intermediate amine of formula III may be prepared as shown in Scheme 7 below.

Scheme 7

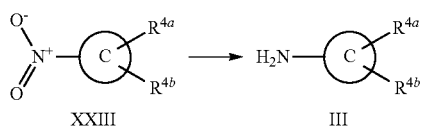

Reduction of a nitro compound of formula XXIII, under standard conditions, provides the corresponding amino compound of formula III.

Syntheses of specific amines are exemplified in the synthetic examples.

Compounds of formula I as well as intermediates prepared by the above methods may be further converted to additional intermediates or compounds of formula I by methods known in the art and exemplified in the Synthetic Examples section below.

SYNTHETIC EXAMPLES

Synthesis of Nitrile Intermediates

Synthesis of
1-(4-bromo-phenyl)-cyclobutanecarbonitrile

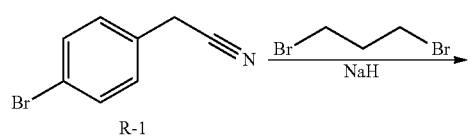

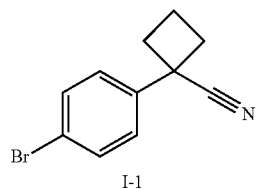

To a solution of R-1 (5.0 g, 26.0 mmol) in DMF (25 mL) at 0° C. is added NaH (60% dispersion in mineral oil, 2.25 g, 56.0 mmol) slowly. The mixture is stirred for 15 minutes, and 1,3-dibromopropane (2.85 mL, 29.0 mmol) is added. The reaction mixture is allowed to warm to room temperature, stirred for 16 hours, and partitioned between EtOAc and H₂O. The combined organics are dried with Na₂SO₄, filtered, and concentrated in vacuo. The residue is purified by flash chromatography (SiO₂, 0-30% EtOAc in heptane) to give the title intermediate I-1 (2.7 g).

The following intermediates were synthesized in similar fashion from the appropriate reagents:

| Intermediate | Structure |
| --- | --- |
| I-2 | 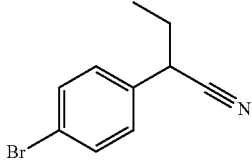 |
| I-3 | 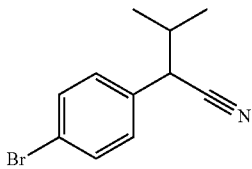 |
| I-4 | 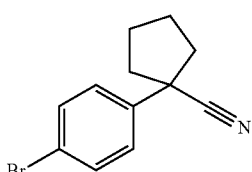 |
| I-5 | 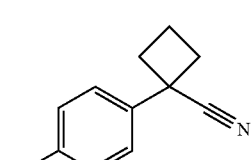 |
| I-6 | 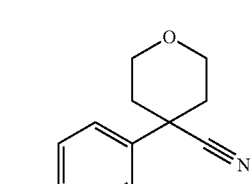 |

Synthesis of 4-(4-bromo-phenyl)-tetrahydro-pyran-4-carbonitrile

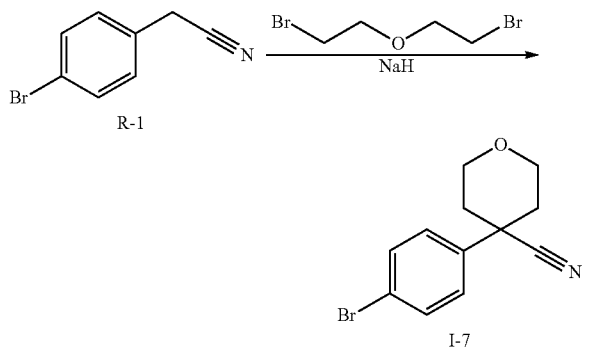

To a solution of NaH (60% dispersion in mineral oil, 2.24 g, 56.0 mmol) in DMSO (10 mL) and THF (10 mL) at −50° C. is added a mixture of R-1 (5.0 g, 25.0 mmol) and 2-bromo-ethylether (6.5 g, 28.0 mmol) in THF (30 mL). The reaction mixture is allowed to warm to room temperature, stirred for 16 hours, and partitioned between EtOAc and H$_2$O. The combined organics are washed with brine, dried with Na$_2$SO$_4$, filtered, and concentrated in vacuo. The residue is purified by flash chromatography (SiO$_2$, 0-20% EtOAc in heptane) to give the title intermediate I-7 (25.0 g).

The following intermediates were synthesized in similar fashion from the appropriate reagents:

| Intermediate | Structure |
|---|---|
| I-8 | 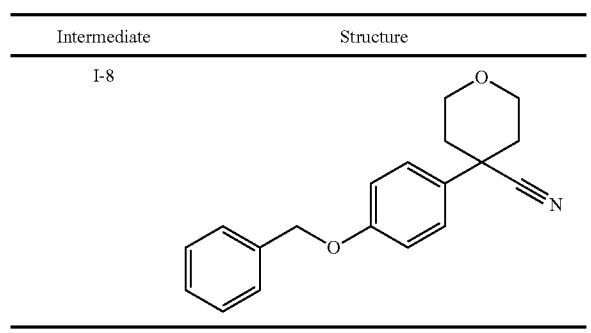 |

Synthesis of 1-(4-bromo-phenyl)-cyclohexanecarbonitrile

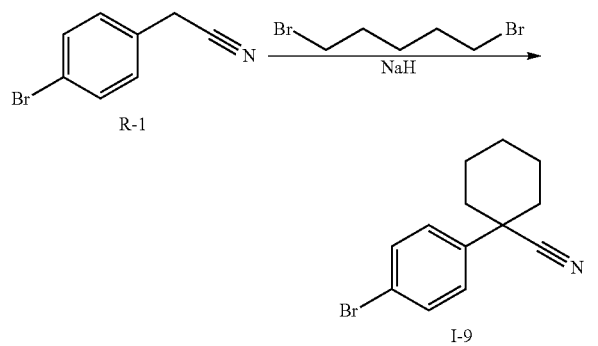

To a solution of NaH (60% dispersion in mineral oil, 808 mg, 34.0 mmol) in DMSO (10 mL) and THF (10 mL) at −50° C. is added a mixture of R-1 (3.0 g, 15.0 mmol) and 1,5-dibromopentane (3.9 g, 17.0 mmol) in THF (10 mL). The reaction mixture is allowed to warm to room temperature, stirred for 16 hours, and heated at 70° C. for 40 minutes. The reaction mixture is allowed to cool to room temperature, and partitioned between EtOAc and H$_2$O. The combined organics are washed with brine, dried with MgSO$_4$, filtered, and concentrated in vacuo to give the title intermediate I-9 (3.7 g).

Synthesis of 2-(4-bromo-phenyl)-2,3-dimethyl-butyronitrile

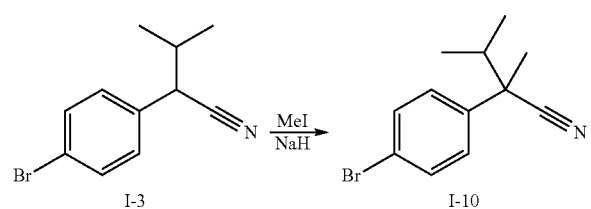

To a solution of NaH (60% dispersion in mineral oil, 1.42 g, 59.0 mmol) in DMF (20 mL) and THF (10 mL) at −50° C. is added a mixture of 1-3 (14.0 g, 58.0 mmol). The reaction mixture is stirred at −78° C. for 20 minutes, followed by the addition of MeI (8.4 g, 59.0 mmol). The reaction mixture is allowed to warm to room temperature slowly, stirred for 2 hours, and heated at 70° C. for 2 hours. The reaction mixture is allowed to cool to room temperature, and partitioned between EtOAc and H$_2$O. The combined organics are dried with Mg$_2$SO$_4$, filtered, and concentrated in vacuo to give the title intermediate I-10 (14.0 g).

The following intermediates were synthesized in similar fashion from the appropriate reagents:

| Intermediate | Structure |
|---|---|
| I-11 | 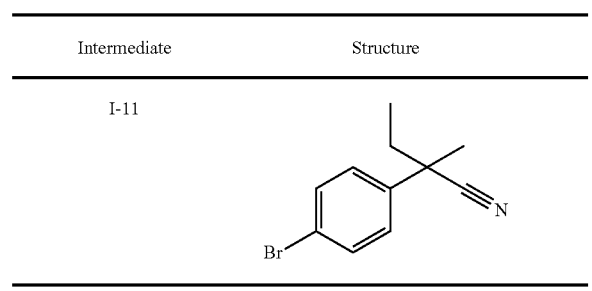 |

Synthesis of 2-[4-(5-methoxy-pyridin-3-yl)-phenyl]-2,3-dimethyl-butyronitrile

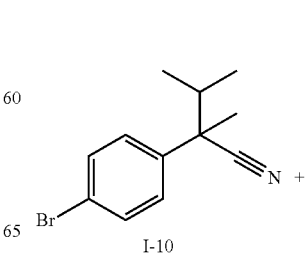

I-10

-continued

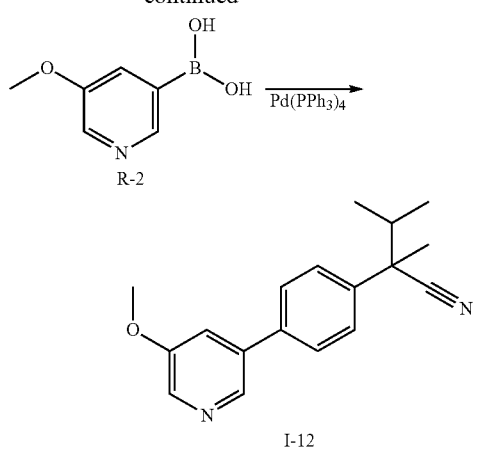

| Intermediate | Structure |
|---|---|
| I-14 | 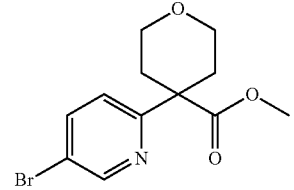 [SMILES: COC(=O)C1(c2ccc(Br)cn2)CCOCC1] |

To a mixture of I-10 (4.0 g, 15.8 mmol) in THF (50 mL) is added R-2 (3.64 g, 23.8 mmol), tetrakis(triphenylphosphine) palladium(0) (1.85 g, 1.6 mmol), and 2M Na$_2$CO$_3$ solution (50 mL). The mixture is refluxed for 16 hours, allowed to cool to room temperature, and partitioned between EtOAc and H$_2$O. The combined organics are dried with Na$_2$SO$_4$, filtered, and concentrated in vacuo. The residue is purified by flash chromatography (SiO$_2$, 25-100% EtOAc in heptane) to give the title intermediate I-12 (3.1 g).

Synthesis of
1-(5-bromo-pyridin-2-yl)-cyclobutanecarbonitrile

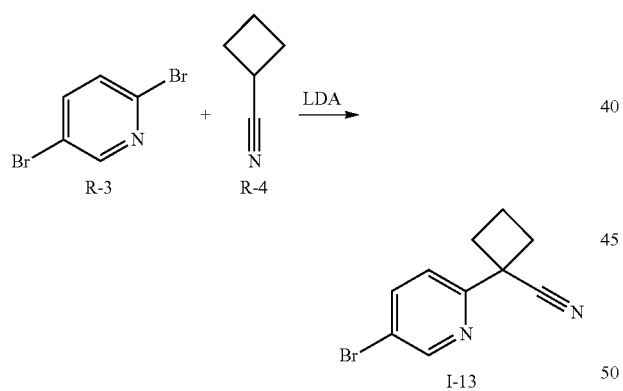

To a solution of lithium diisopropylamine (2.0 M in heptane/THF/ethylbenzene, 10 mL, 20.0 mmol) at −78° C. is added R-4 (811 mg, 10.0 mmol). The reaction mixture is stirred at −78° C. for 45 minutes, followed by the addition of R-3 (1.9 g, 8.0 mmol). The reaction mixture is allowed to warm to room temperature slowly, stirred for 16 hours, and heated at 70° C. for 2 hours. The reaction mixture is allowed to cool to room temperature, and partitioned between EtOAc and H$_2$O. The combined organics are washed with brine, dried with Mg$_2$SO$_4$, filtered, and concentrated in vacuo. The residue is purified by flash chromatography (SiO$_2$, 0-100% EtOAc in heptane) to give the title intermediate I-13 (1.1 g).

The following intermediate (methyl ester) was synthesized in similar fashion from the appropriate reagents:

Synthesis of 4-[4-(pyridin-2-ylmethoxy)-phenyl]-tetrahydro-pyran-4-carbonitrile

A mixture of I-8 (1.5 g, 5.1 mmol), 10% Pd/C in THF (30 mL) is stirred at room temperature under H$_2$ for 16 hours. The reaction mixture is filtered through celite, and concentrated in vacuo to give I-15 (1.0 g).

To a solution of I-15 (1.0 g, 4.9 mmol), triphenylphosphine (2.6 g, 10.0 mmol) in THF (30 mL) is added R-5 (1.1 g, 10.0 mmol). The reaction mixture is cooled to 0° C., followed by the addition of diisopropyl azodicarboxylate (2.0 g, 10.0 mmol). The reaction mixture is allowed to warm to room temperature, stirred for 2 hours, and partitioned between EtOAc and H$_2$O. The combined organics are washed with brine, dried with Mg$_2$SO$_4$, filtered, and concentrated in vacuo. The residue is purified by flash chromatography (SiO$_2$, 20-90% EtOAc in heptane) to give the title intermediate I-16 (760 mg).

Synthesis of Carboxylic Acid Intermediates

Synthesis of 1-(4-bromo-phenyl)-cyclobutanecarboxylic acid

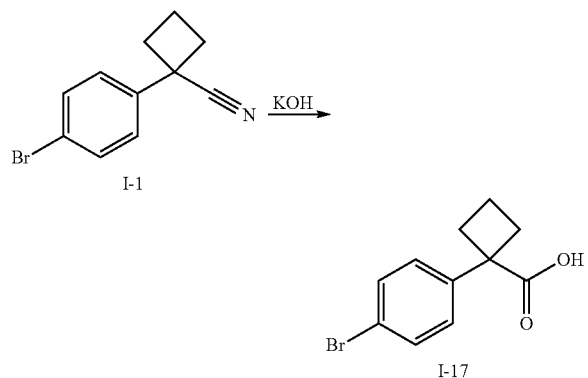

To a solution of I-1 (2.7 g, 11.0 mmol) in EtOH (25 mL) at room temperature is added KOH (1.9 g, 34.0 mmol). The mixture is heated at 110° C. for 48 hours, allowed to cool to room temperature, and concentrated in vacuo. The residue is slurried with 1H HCl solution, and the resulting solid is filtered, collected, and dried to give the title intermediate I-17 (2.74 g).

The following intermediates were synthesized in similar fashion from the appropriate reagents:

| Intermediate | Structure |
|---|---|
| I-18 | 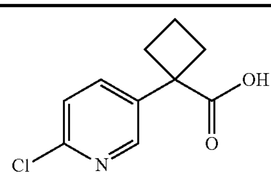 |
| I-19 | 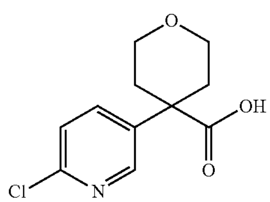 [SMILES: O=C(O)C1(c2ccc(Cl)nc2)CCOCC1] |

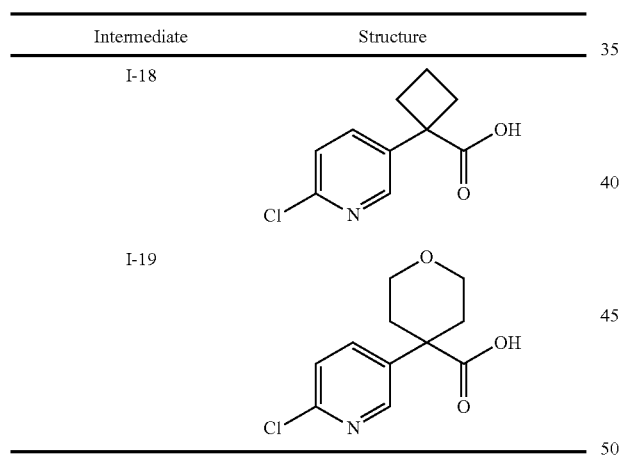

Synthesis of 4-(4-bromo-phenyl)-tetrahydro-pyran-4-carboxylic acid

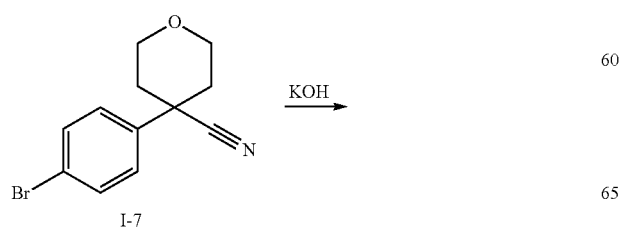

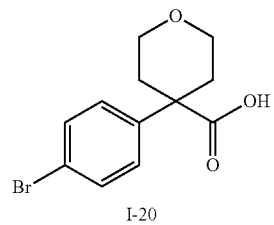

To a solution of I-7 (2.8 g, 11.0 mmol) in ethylene glycol (30 mL) and H$_2$O (15 mL) in a pressure tube at room temperature is added KOH (1.9 g, 56 mmol). The mixture is heated in a pressure tube at 140° C. for 48 hours, allowed to cool to room temperature, decanted to ice, acidified with 1H HCl solution, and partitioned between EtOAc and H$_2$O. The combined organics are dried with Na$_2$SO$_4$, filtered, and concentrated in vacuo to give the title intermediate I-20 (3.0 g).

The following intermediates were synthesized in similar fashion from the appropriate reagents:

| Intermediate | Structure |
|---|---|
| I-21 | 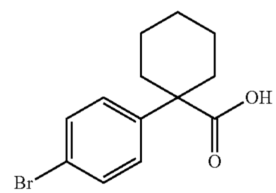 [SMILES: O=C(O)C1(c2ccc(Br)cc2)CCCCC1] |
| I-22 | 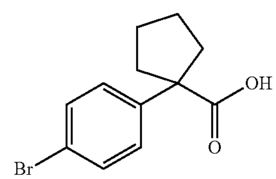 [SMILES: O=C(O)C1(c2ccc(Br)cc2)CCCC1] |
| I-23 | 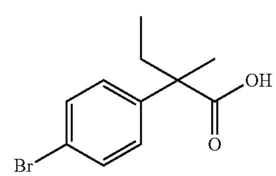 |
| I-24 | 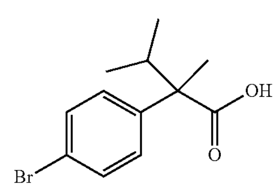 |
| I-25 | 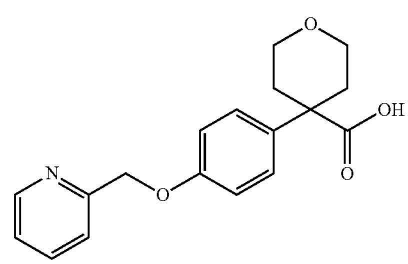 [SMILES: O=C(O)C1(c2ccc(OCc3ccccn3)cc2)CCOCC1] |

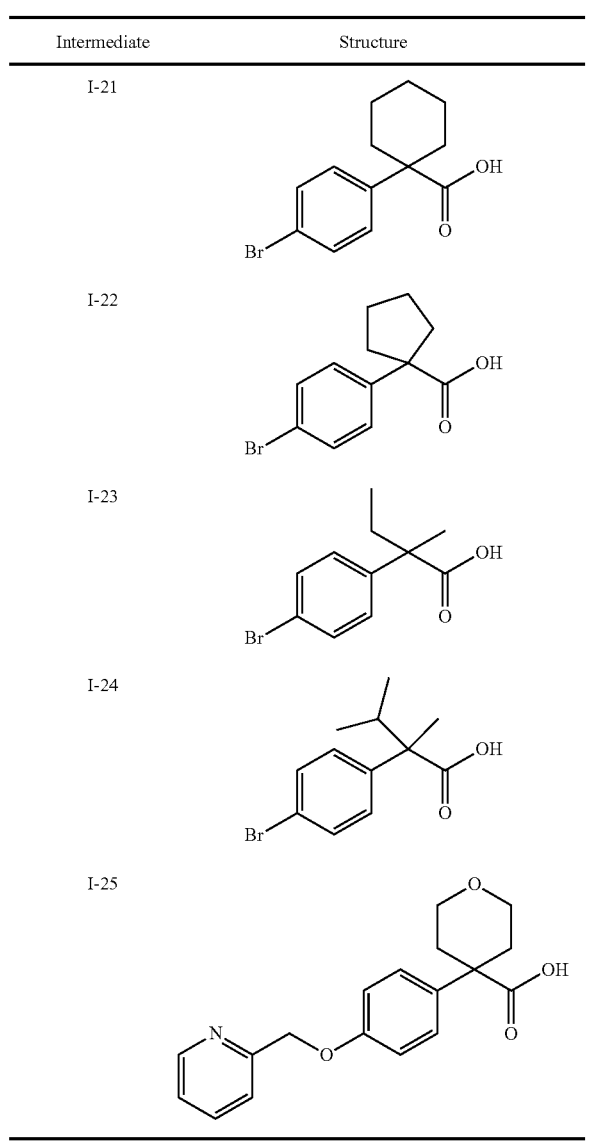

Synthesis of 2-(4-bromo-phenyl)-3-methyl-butyric acid

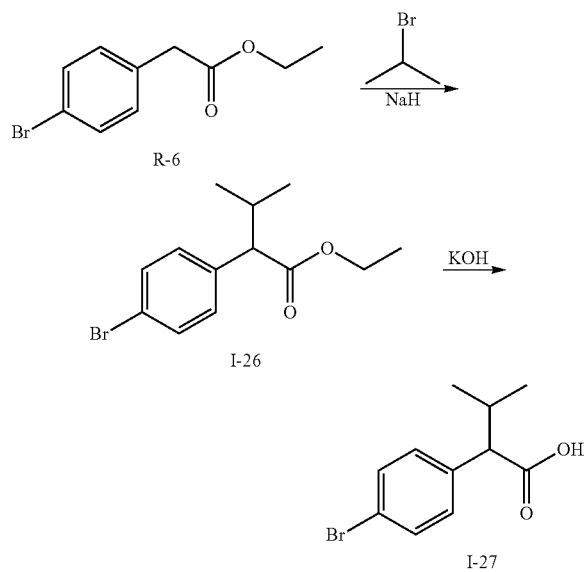

To a solution of ethyl 4-bromophenyl acetate R-6 (2.0 g, 8.23 mmol) in DMF (25 mL) at −78° C. is added NaH (60% dispersion in mineral oil, 217 mg, 9.05 mmol) slowly. The mixture is stirred for 15 minutes, and 2-bromopropane (1.11 g, 9.05 mmol) is added. The reaction mixture is allowed to warm to room temperature, stirred for 16 hours, and partitioned between EtOAc and $H_2O$. The combined organics are dried with $MgSO_4$, filtered, and concentrated in vacuo to give I-26 (2.0 g).

To a solution of I-26 (1.5 g, 5.26 mmol) in ethylene glycol (20 mL) and $H_2O$ (20 mL) in a pressure tube at room temperature is added KOH (0.9 g, 16.0 mmol). The mixture is heated in a pressure tube at 150° C. for 16 hours, allowed to cool to room temperature, decanted to ice, acidified with 1H HCl solution, and partitioned between EtOAc and $H_2O$. The combined organics are dried with $Na_2SO_4$, filtered, and concentrated in vacuo to give the title intermediate I-27 (1.4 g).

Synthesis of (4-bromo-phenyl)-cyclopentyl-acetic acid

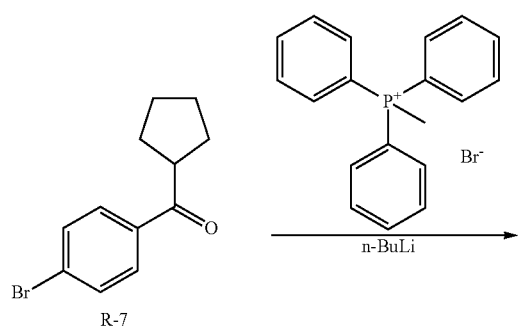

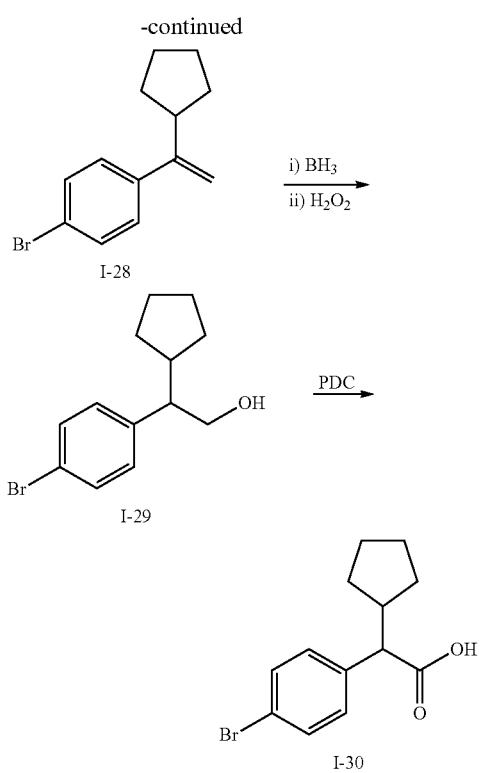

To a solution of methyl triphenylphosphonium bromide (1.46 g, 4.1 mmol) in THF (25 mL) at −78° C. is added n-BuLi (2.5M in hexanes, 1.64 mL, 4.1 mmol) slowly. The mixture is stirred at 0° C. for 30 minutes, and then cooled to −78° C. To the reaction mixture is added R-7 (1.0 g, 3.95 mmol) in THF (8.0 mL). The reaction mixture is allowed to warm to room temperature, stirred for 16 hours, and partitioned between $Et_2O$ and saturated $NH_4Cl$ solution. The combined organics are dried with $Na_2SO_4$, filtered, and concentrated in vacuo. The residue is purified by flash chromatography ($SiO_2$, 100% heptane) to give I-28 (900 mg).

To a solution of I-28 (900 mg, 3.58 mmol) in THF (15 mL) at 0° C. is added $BH_3$ (1.0M in THF, 7.2 mL, 7.2 mmol). The reaction mixture is allowed to warm to room temperature, and stirred for 1 hour. To the reaction mixture is added 1M NaOH solution (8.4 mL), $H_2O_2$ (30% wt. in $H_2O$, 1.0 g, 30 mmol). The reaction mixture is stirred at room temperature for 1 hour, and partitioned between $Et_2O$ and $H_2O$. The combined organics are dried with $Na_2SO_4$, filtered, and concentrated in vacuo to give I-29 (900 mg).

To a solution of I-29 (790 mg, 2.93 mmol) in DMF (10 mL) at room temperature is added pyridinium dichromate (3.4 g, 9.0 mmol). The mixture is stirred at room temperature for 16 hours, diluted with EtOAc, filtered through celite, and partitioned between EtOAc and $H_2O$. The combined organics are dried with $MgSO_4$, filtered, and concentrated in vacuo. The residue is purified by flash chromatography ($SiO_2$, 0-60% EtOAc in heptane) to give the title intermediate I-30 (265 mg).

The following intermediates were synthesized in similar fashion from the appropriate reagents:

| Intermediate | Structure |
|---|---|
| I-31 | 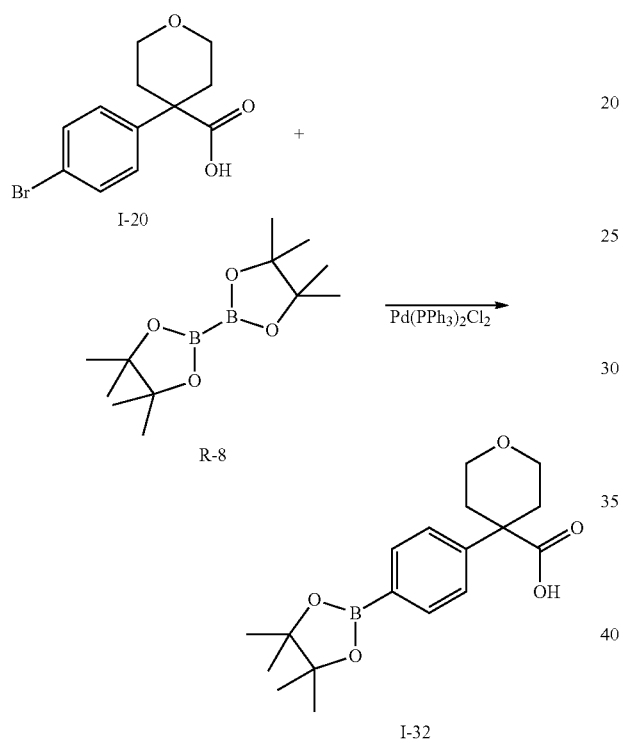 |

Synthesis of 4-[4-(4,4,5,5-tetramethyl-[1,3,2]dioxaborolan-2-yl)-phenyl]-tetrahydro-pyran-4-carboxylic acid

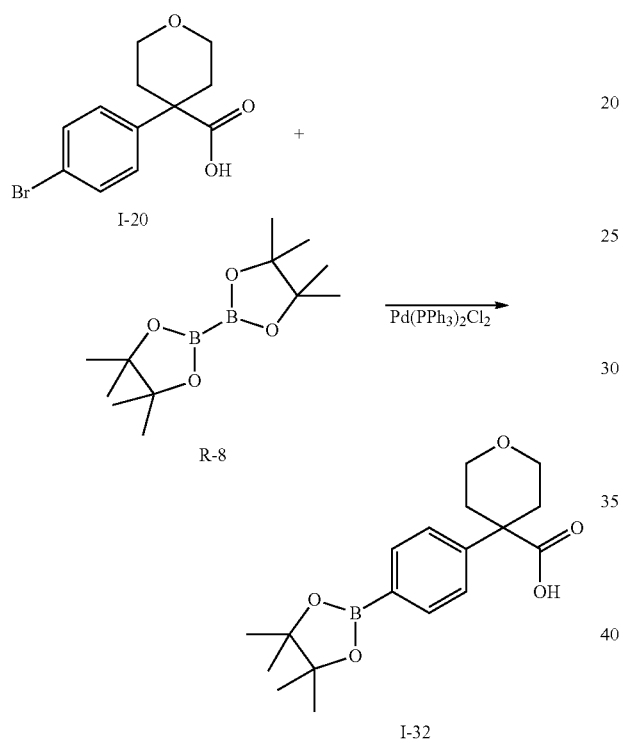

To a mixture of I-20 (91 mg, 0.32 mmol), R-8 (95 mg, 0.38 mmol), bis(triphenylphosphine)palladium(II)dichloride (27 mg, 0.03 mmol) in THF (2.0 mL) at room temperature is added $KCO_3$ (128 mg, 1.3 mmol), and $H_2O$ (0.3 mL). The mixture is heated in the microwave at 120° C. for 30 minutes, allowed to cool to room temperature, and concentrated in vacuo. The residue is purified by flash chromatography ($SiO_2$, 0-10% MeOH in $CH_2Cl_2$) to give the title intermediate I-32 (83 mg).

Synthesis of 1-(5-bromo-pyridin-2-yl)-cyclobutanecarboxylic acid

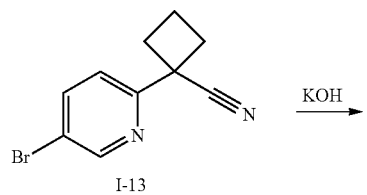

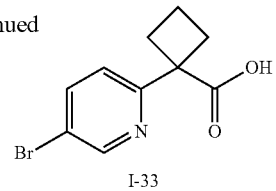

To a solution of I-13 (380 mg, 1.6 mmol) in $H_2O$ (5.0 mL) is added acetic acid (5.0 mL), and $H_2SO_4$ (5.0 mL). The reaction mixture is heated at 85° C. for 3 hours, allowed to cool to room temperature, and partitioned between EtOAc and $H_2O$. The combined organics are washed with brine, dried with $Na_2SO_4$, filtered, and concentrated in vacuo to give the title intermediate I-33 (150 mg).

Synthesis of 4-(5-bromo-pyridin-2-yl)-tetrahydro-pyran-4-carboxylic acid

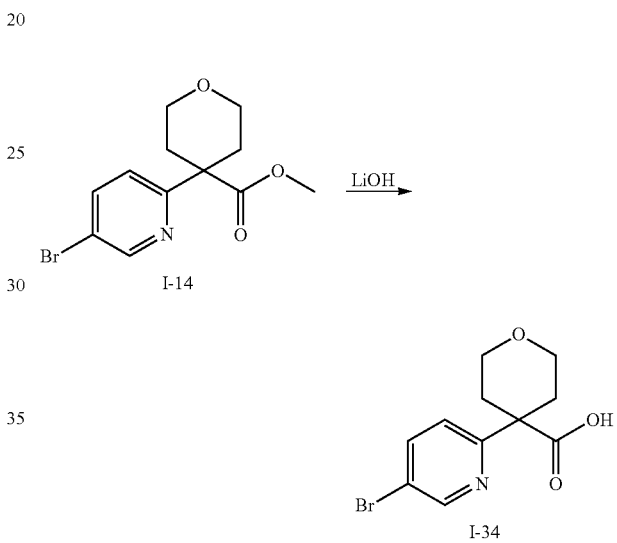

To a solution of I-14 (1.5 g, 5.0 mmol) in THF (2.5 mL) and MeOH (2.5 mL) at room temperature is added LiOH (1.05 g, 25 mmol) in $H_2O$ (10 mL). The reaction mixture is concentrated in vacuo, and partitioned between 1M HCl solution and EtOAc. The combined organics are dried with $Na_2SO_4$, filtered, and concentrated in vacuo to give the title intermediate I-34 (1.4 g).

Synthesis of 2-[4-(5-methoxy-pyridin-3-yl)-phenyl]-2,3-dimethyl-butyric acid

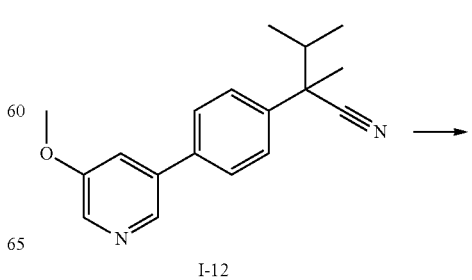

-continued

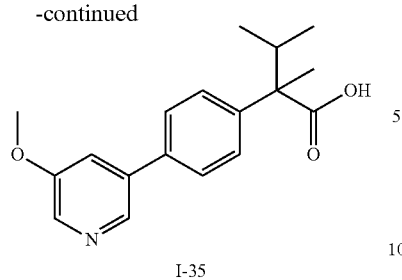

I-35

To a solution of I-12 (1.0 g, 3.6 mmol) in H₂O (10 mL) is added concentrated H₂SO₄ (10.0 mL). The reaction mixture is heated at 85° C. for 16 hours, allowed to cool to room temperature, and partitioned between EtOAc and saturated NaHCO₃ solution. The combined organics are washed with H₂O, filtered, and concentrated in vacuo to give the title intermediate I-35 (901 mg).

Synthesis of 1-{4-[2-(2,5-dimethyl-pyrrol-1-yl)-pyrimidin-5-yl]-phenyl}-cyclobutanecarboxylic acid

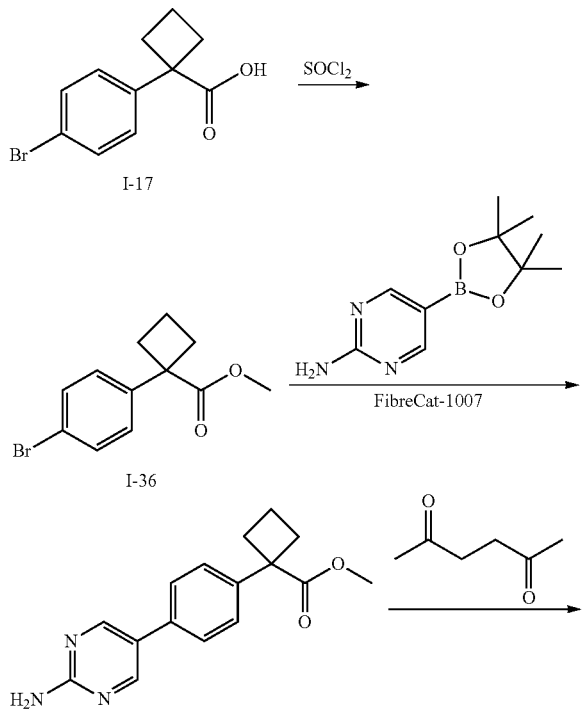

-continued

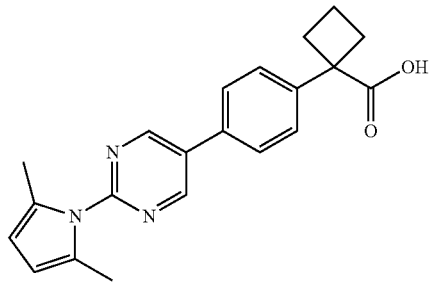

I-39

To MeOH (3.0 mL) at 0° C. is added slowly SOCl₂ (0.5 mL), followed by the addition of I-17 (400 mg, 1.57 mmol). The reaction mixture is heated at 60° C. for 4 hours, allowed to cool to room temperature, and concentrated in vacuo to give the I-36 (415 mg).

To a mixture of 2-aminopyrimidine-5-boronic acid pinacol ester (221 mg, 1.0 mmol), I-36 (200 mg, 0.74 mmol), Pd-FibreCat-1007 (75 mg, 0.045 mmol) in THF (2.0 mL) at room temperature is added 2M Na₂CO₃ solution (0.75 mL). The mixture is heated in the microwave at 120° C. for 30 minutes, allowed to cool to room temperature, and partitioned between EtOAc and H₂O. The combined organics are washed with brine, filtered, and concentrated in vacuo. The residue is purified by flash chromatography (SiO₂, 0-100% EtOAc in heptane) to give I-37 (75 mg).

A mixture of I-37 (42 mg, 0.15 mmol), 2,5-hexanedione (82 µL, 0.7 mmol), p-TsOH (3 mg) in toluene (15 mL) is heated at 140° C. for 5 hours with a Dean-Stark condenser. The reaction mixture is allowed to cool to room temperature, and concentrated in vacuo. The residue is purified by flash chromatography (SiO₂, 0-100% EtOAc in heptane) to give I-38 (47 mg).

To a solution of I-38 (340 mg, 0.94 mmol) in THF (3.0 mL) at room temperature is added a solution of LiOH (72 mg, 3.0 mmol) in H₂O (1.0 mL). The reaction mixture is heated at 60° C. for 24 hours, allowed to cool to room temperature, acidified with 6M HCl solution, and partitioned between EtOAc and H₂O. The combined organics are washed with brine, dried with Na₂SO₄, filtered, and concentrated in vacuo to give the title intermediate I-39 (322 mg).

Synthesis of Amine Intermediates

Synthesis of 5-phenoxy-pyridin-2-ylamine

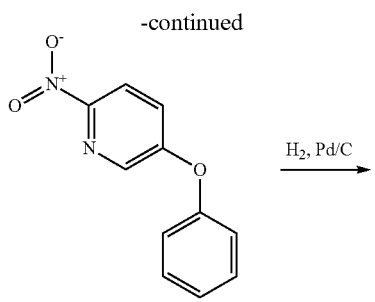

I-40

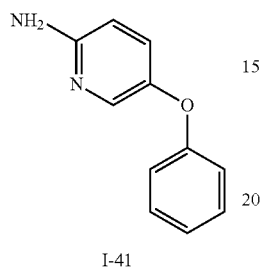

I-41

To a solution of 5-bromo-2-nitropyridine R-9 (1.0 g, 5.76 mmol) in DMF (10.0 mL) at room temperature is added $Cs_2CO_3$ (2.5 g, 7.67 mmol). The reaction mixture is stirred at room temperature for 15 minutes, followed by the addition of phenol (1.0 g, 10.62 mmol). The reaction mixture is stirred at room temperature for 72 hours, and partitioned between EtOAc and $H_2O$. The combined organics are washed with $H_2O$, dried with $Na_2SO_4$, filtered, and concentrated in vacuo. The residue is purified by flash chromatography ($SiO_2$, 0-45% EtOAc in heptane) to give I-40 (664 mg).

A reaction mixture of I-40 (664 mg, 3.07 mmol), 10% Pd/C (120 mg) in EtOH (25 mL) at room temperature under $H_2$ is stirred for 16 hours. The reaction mixture is filtered through celite, and concentrated in vacuo to give the title intermediate I-41 (530 mg).

Synthesis of 5'-methoxy-[3,3']bipyridinyl-6-ylamine

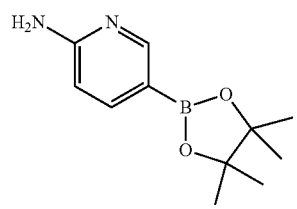

R-10

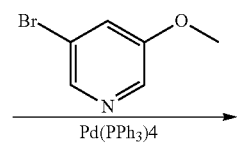

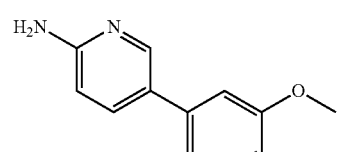

I-42

To a mixture of 2-aminopyridine-5-boronic acid pinacol ester R-10 (150 mg, 0.68 mmol), 3-bromo-5-methoxypyridine (141 mg, 0.75 mmol), tetrakis(triphenylphosphine)palladium(0) (8 mg, 0.007 mmol) in DMF (25 mL) at room temperature is added 2M $Na_2CO_3$ solution (1.0 mL). The mixture is heated in the microwave at 110° C. for 1 hour, allowed to cool to room temperature, and partitioned between EtOAc and $H_2O$. The combined organics are washed with brine, dried with $Na_2SO_4$, filtered, and concentrated in vacuo. The residue is purified by flash chromatography ($SiO_2$, 0-3% 2M $NH_3$ in MeOH in $CH_2Cl_2$) to give the title intermediate I-42 (95 mg).

The following intermediates were synthesized in similar fashion from the appropriate reagents:

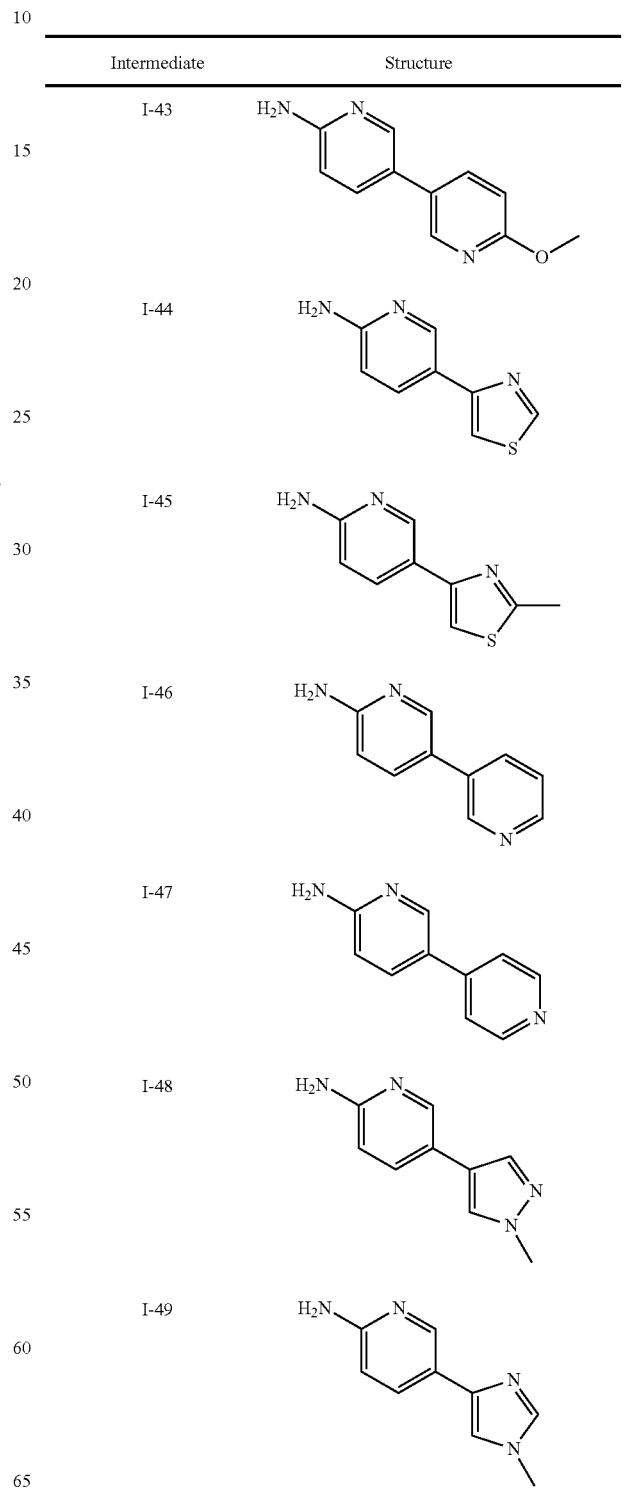

| Intermediate | Structure |
| --- | --- |
| I-43 | 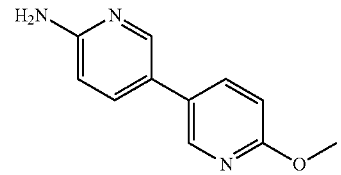 |
| I-44 | 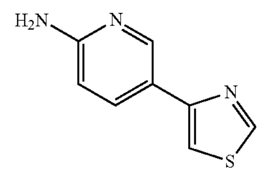 [SMILES: Nc1ccc(-c2cscn2)cn1] |
| I-45 | 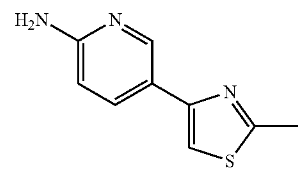 |
| I-46 | 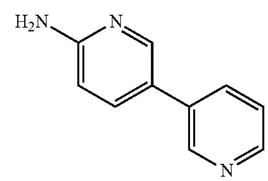 [SMILES: Nc1ccc(-c2cccnc2)cn1] |
| I-47 | 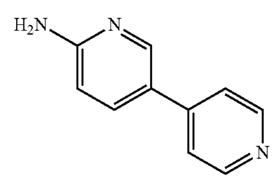 [SMILES: Nc1ccc(-c2ccncc2)cn1] |
| I-48 | 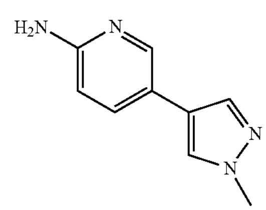 |
| I-49 | 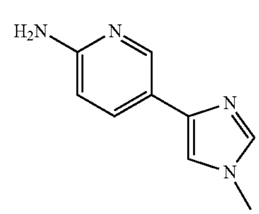 |

| Intermediate | Structure |
|---|---|
| I-50 | 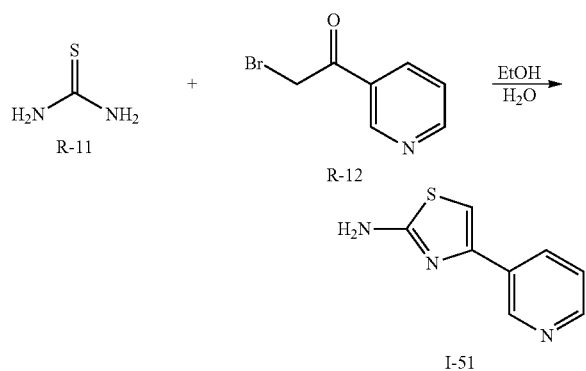 |

Synthesis of 4-pyridin-3-yl-thiazol-2-ylamine

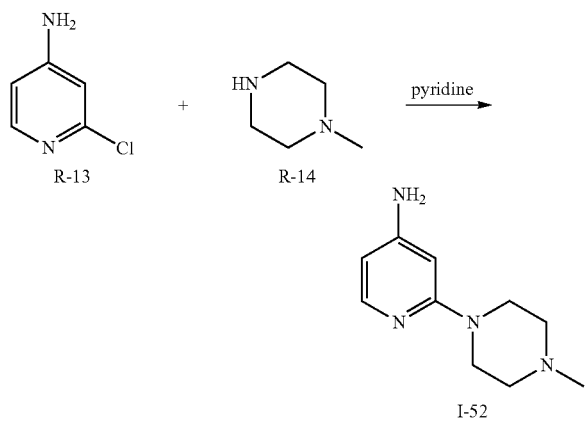

To a solution of 3-(bromoacetyl)pyridine hydrobromide R-12 (920 mg, 3.27 mmol) in EtOH (10.0 mL) and H$_2$O (2.0 mL) at room temperature is added thiourea R-11 (250 mg, 3.27 mmol). The reaction mixture is heated at 80° C. for 2 hours, allowed to room temperature, and taken to pH8 with NH$_4$OH. The mixture is cooled to 0° C., and filtered to give the title intermediate I-51 (536 mg).

Synthesis of 2-(4-methyl-piperazin-1-yl)-pyridin-4-ylamine

A solution of R-13 (26.7 g, 179 mmol), R-14 (20 mL, 179 mmol) in pyridine (42 mL) is heated in the microwave at 220° C. for 30 minutes. The reaction mixture is allowed to cool to room temperature, and concentrated in vacuo. The residue is purified by flash chromatography (SiO$_2$, 0-2.5% 2M NH$_3$ in MeOH in CH$_2$Cl$_2$) to give the title intermediate I-52 (27.3 g).

Synthesis of 5-methyl-4,5,6,7-tetrahydro-thiazolo[5,4-c]pyridin-2-ylamine

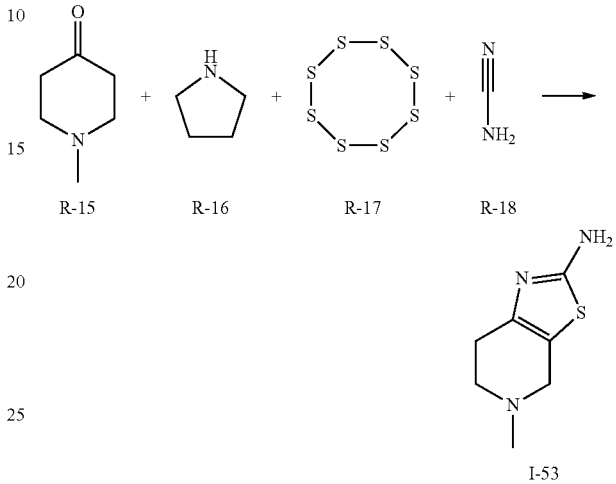

To a solution of R-15 (30 mL g, 244 mmol) in cyclohexane (200 mL) at room temperature is added R-16 (20 mL, 240 mmol), a catalytic amount of p-TsOH. The reaction mixture is refluxed with a Dean-Stark condenser for 5 hours, allowed to cool to room temperature, and concentrated in vacuo. The residue is dissolved in MeOH (50 mL) followed by the addition of R-17 (7.77 g, 30 mmol), and cooled to 0° C. To the reaction mixture is added R-18 (10.2 g, 243 mmol) in portions, and stirred for 2 hours. The reaction mixture is allowed to warm to room temperature, filtered, washed with MeOH and Et$_2$O to give title intermediate I-53 (20 g).

Synthesis of 2-butyl-quinolin-6-ylamine

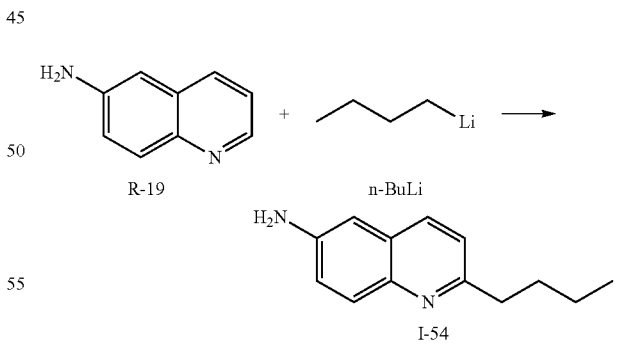

To a solution of R-19 (1.0 g, 6.9 mmol) in THF (10.0 mL) at −30° C. is added n-BuLi (1.6M in hexanes, 33.6 mL, 21.0 mmol). The reaction mixture is stirred at −30° C. for 2 hours, followed by the dropwise addition of acetone (3 mL). The reaction mixture is allowed to warm to room temperature, and partitioned between EtOAc and H$_2$O. The combined organics are washed with saturated NH$_4$Cl solution, dried with Na$_2$SO$_4$, filtered, and concentrated in vacuo. The residue is purified by flash chromatography (SiO$_2$, 10-70% EtOAc in heptane) to give title intermediate I-54 (950 mg).

Synthesis of 3-(2-methyl-thiazol-4-yl)-phenylamine

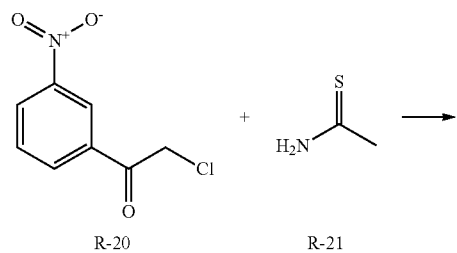

R-20    R-21

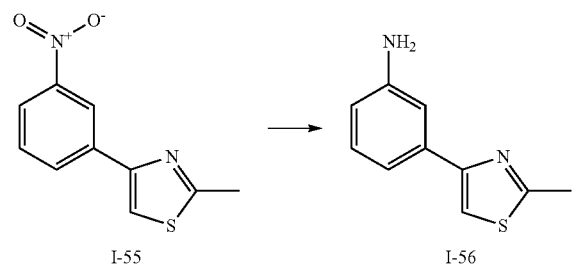

I-55    I-56

To a solution of R-20 (2.0 g, 10.0 mmol) in EtOH (50.0 mL) at room temperature is added R-21 (750 mg, 10.0 mmol). The solid formed is filtered, and rinsed with cold EtOH to give I-55 (2.9 g).

To a solution of I-55 (800 mg, 3.6 mmol) in MeOH (10 mL) at 70° C. is added ammonium formate (2.27 g, 36 mmol) in H$_2$O (5 mL), and Zn (300 mg). The reaction mixture is stirred at 70° C. for 15 minutes, allowed to cool to room temperature, and partitioned between EtOAc and H$_2$O. The combined organics are dried with Na$_2$SO$_4$, filtered, and concentrated in vacuo. The residue is purified by flash chromatography (SiO$_2$, 0-45% EtOAc in heptane) to give title intermediate I-56 (664 mg).

Synthesis of 4-(pyridin-2-ylmethoxy)-phenylamine

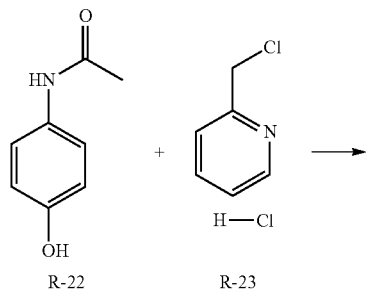

R-22    R-23

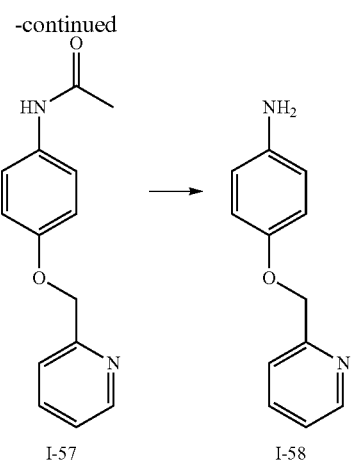

I-57    I-58

To a mixture of R-22 (7.5 g, 50.0 mmol), R-23 (8.2 g, 50 mmol) in DMF (50 mL) at room temperature is added K$_2$CO$_3$ (20.7 g, 150 mmol). The reaction mixture is stirred at room temperature for 72 hours, triturated with ice-H$_2$O, and the resulting solid is filtered to give I-57 (8.8 g).

A mixture of I-57 (8.8 g) in EtOH (50 mL) and 12M NaOH solution (12 mL) is heated at 90° C. for 16 hours. The reaction mixture is allowed to cool to room temperature, concentrated in vacuo, and partitioned between EtOAc and H$_2$O. The combined organics are dried with Na$_2$SO$_4$, filtered, and concentrated in vacuo to give title intermediate I-58 (6.5 g).

Synthesis of Activated Acid Intermediates

Synthesis of 1-(4-bromo-phenyl)-cyclobutanecarboxylic acid 1,2,3-triazolo[4,5-b]pyridin-3-yl ester

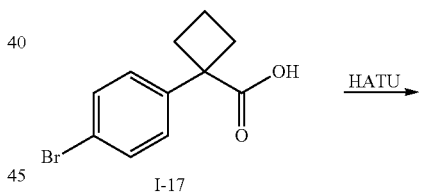

I-17

I-59

To a solution of I-17 (2.74 g, 11.0 mmol), O-(7-azabenzotriazol-1-yl)-N,N,N',N'-tetramethyluronium hexafluorophosphate (4.5 g, 12.0 mmol) in DMF (25 mL) at room temperature is added DIPEA (2.3 mL, 13 mmol). The mixture is stirred at room temperature for 30 minutes, and partitioned between EtOAc and H$_2$O. The combined organics are dried with Na$_2$SO$_4$, filtered, and concentrated in vacuo. The residue is purified by flash chromatography (SiO$_2$, 0-60% EtOAc in heptane) to give the title intermediate I-59 (2.75 g).

The following intermediates were synthesized in similar fashion from the appropriate reagents:

| Intermediate | Structure |
|---|---|
| I-60 | 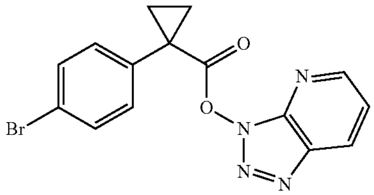 [SMILES: O=C(On1nnc2cccnc21)C1(c2ccc(Br)cc2)CC1] |
| I-61 | 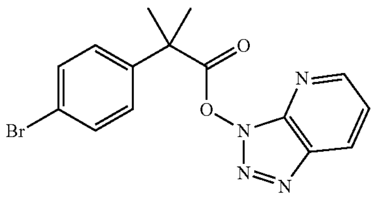 [SMILES: CC(C)(C(=O)On1nnc2cccnc21)c1ccc(Br)cc1] |
| I-62 | 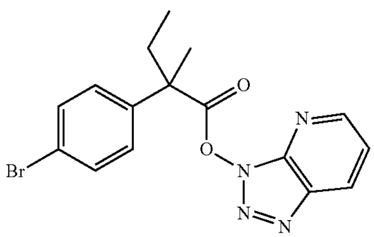 [SMILES: CCC(C)(C(=O)On1nnc2cccnc21)c1ccc(Br)cc1] |
| I-63 | 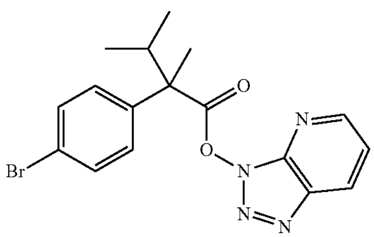 [SMILES: CC(C)C(C)(C(=O)On1nnc2cccnc21)c1ccc(Br)cc1] |
| I-64 | 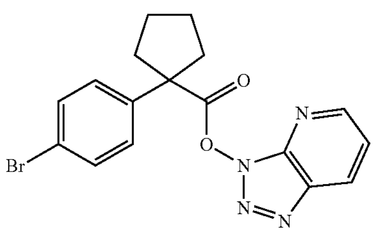 [SMILES: O=C(On1nnc2cccnc21)C1(c2ccc(Br)cc2)CCCC1] |
| I-65 | 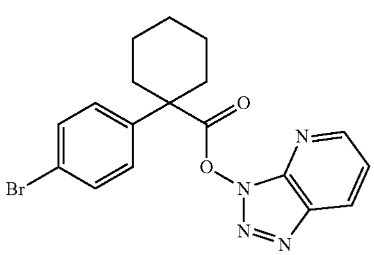 [SMILES: O=C(On1nnc2cccnc21)C1(c2ccc(Br)cc2)CCCCC1] |
| I-66 | 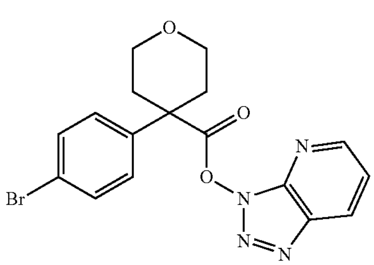 [SMILES: O=C(On1nnc2cccnc21)C1(c2ccc(Br)cc2)CCOCC1] |
-continued
| Intermediate | Structure |
|---|---|
| I-67 | 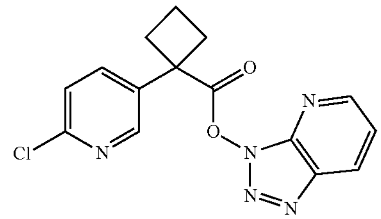 [SMILES: O=C(On1nnc2cccnc21)C1(c2ccc(Cl)nc2)CCC1] |
| I-68 | 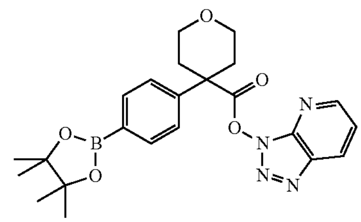 [SMILES: CC1(C)OB(c2ccc(C3(C(=O)On4nnc5cccnc54)CCOCC3)cc2)OC1(C)C] |
| I-69 | 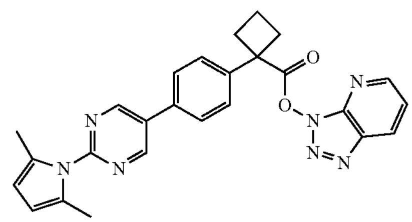 [SMILES: Cc1ccc(C)n1-c1ncc(-c2ccc(C3(C(=O)On4nnc5cccnc54)CCC3)cc2)cn1] |
| I-71 | 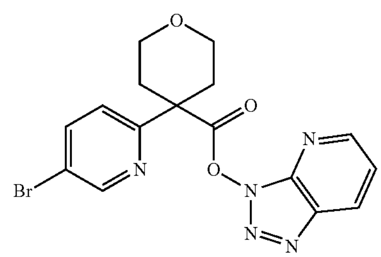 [SMILES: O=C(On1nnc2cccnc21)C1(c2ccc(Br)cn2)CCOCC1] |
Synthesis of
1-(4-bromo-phenyl)-cyclobutanecarbonyl chloride
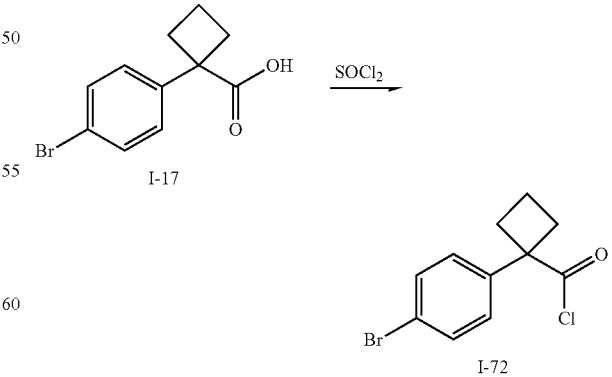
To a solution of I-17 (400 mg, 1.57 mmol), in CH$_2$Cl$_2$ (3 mL) at room temperature is added thionyl chloride (1.7 mL, 14.3 mmol). The mixture is heated at 50° C. for 16 h, allowed to cool to room temperature, and concentrated in vacuo to give the title intermediate I-72 (430 mg).

The following intermediates were synthesized in similar fashion from the appropriate reagents:

| Intermediate | Structure |
| --- | --- |
| I-73 | 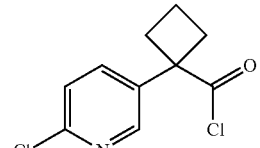 |
| I-74 | 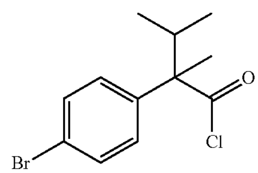 |
| I-75 | 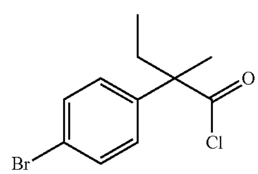 |
| I-76 | 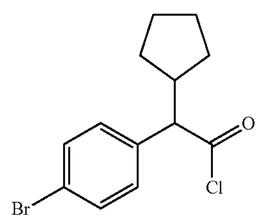 [SMILES: O=C(Cl)C(c1ccc(Br)cc1)C1CCCC1] |
| I-77 | 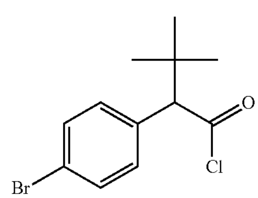 |
| I-78 | 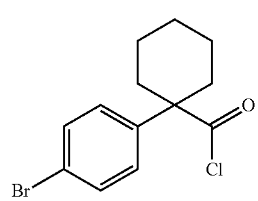 |
| I-79 | 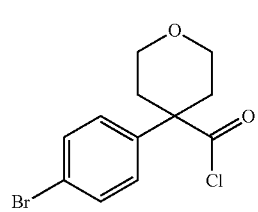 |
| I-80 | 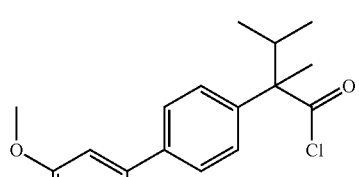 |
| I-81 | |

Synthesis of Final Compounds

Method 1

Synthesis of 1-[4-(2-aminopyrimidin-5-yl)phenyl]-N-(pyridin-4-yl)cyclobutanecarboxamide (Example 177)

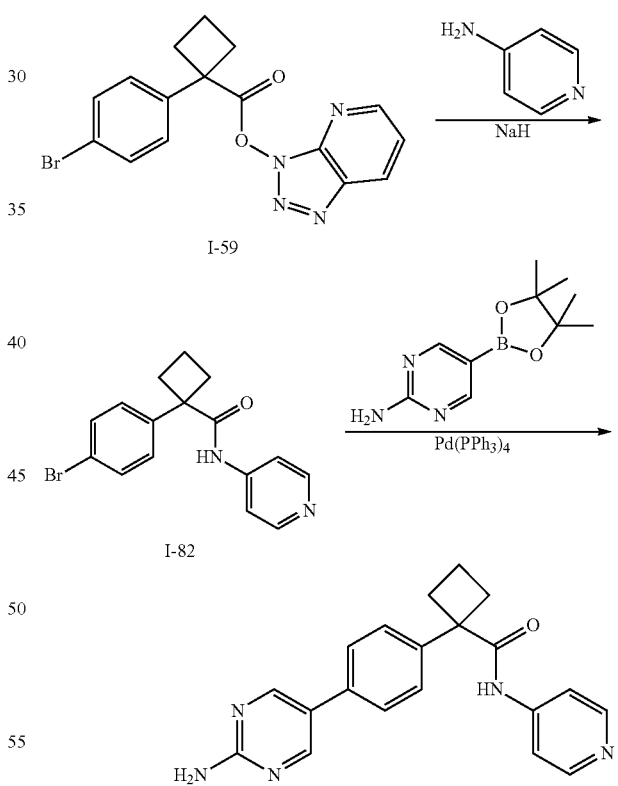

To a solution of 4-aminopyridine (75 mg, 0.80 mmol) in THF (5.0 mL) at room temperature is added NaH (60% in mineral oil, 40 mg, 1.0 mmol). The reaction mixture is stirred at room temperature for 15 minutes followed by the addition of I-59 (200 mg, 0.54 mmol). The reaction mixture is heated at 80° C. for 2 hours, allowed to cool to room temperature, and partitioned between EtOAc and H₂O. The combined organics are washed with H₂O, dried with Na₂SO₄, filtered, and concentrated in vacuo to give the I-82 (170 mg).

To a mixture of 2-aminopyrimidine-5-boronic acid pinacol ester (85 mg, 0.38 mmol), I-82 (85 mg, 0.26 mmol), tetrakis(triphenylphosphine)palladium(0) (30 mg, 0.026 mmol) in DMF (2.5 mL) at room temperature is added 2M $Na_2CO_3$ solution (2.5 mL). The mixture is stirred at 100° C. for 2 hours, allowed to cool to room temperature, and partitioned between EtOAc and $H_2O$. The combined organics are washed with $H_2O$, dried with $Na_2SO_4$, filtered, and concentrated in vacuo. The residue is purified by flash chromatography ($SiO_2$, 0-10% MeOH in $CH_2Cl_2$) to give the title compound 177 (60 mg).

The following final compounds were synthesized in similar fashion from the appropriate reagents and intermediates:
173-174, 180, 183-191, 194-196, 198-205, 209-217, 222, 225, 236, 240-241, 249

134-135 (conditions as above except for part 2 where mixture is heated in microwave at 110° C. for 1 hour)

110 (conditions as above except acid chloride I-72 was used in the $1^{st}$ step as the activated acid)

219 (conditions as above except acid chloride I-80 was used in the $1^{st}$ step as the activated acid)

Method 2

Synthesis of 1-[4-(2-aminopyrimidin-5-yl)phenyl]-N-(pyridin-4-yl)cyclopentanecarboxamide (Example 230)

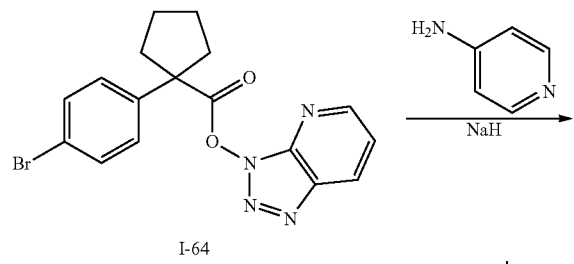

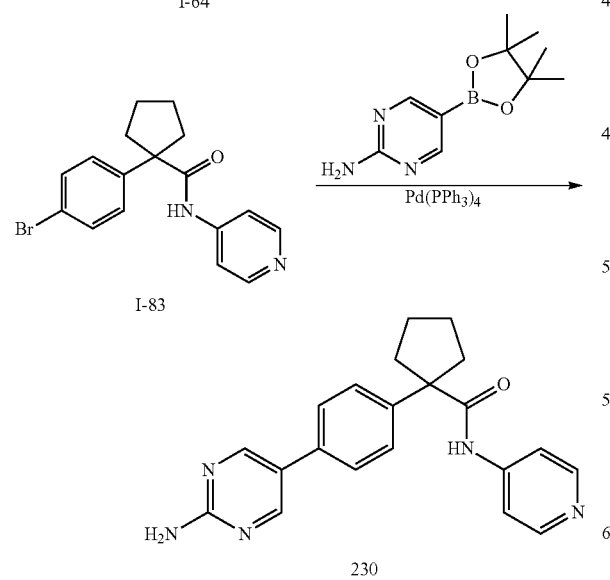

To a solution of 4-aminopyridine (26 mg, 0.28 mmol) in THF (5.0 mL) at room temperature is added NaH (60% dispersion in mineral oil, 12 mg, 0.5 mmol). The reaction mixture is stirred at room temperature for 15 minutes, followed by the addition of I-64 (200 mg, 0.54 mmol). The reaction mixture is heated in the microwave at 120° C. for 60 minutes, allowed to cool to room temperature, and partitioned between EtOAc and $H_2O$. The combined organics are washed with $H_2O$, dried with $Na_2SO_4$, filtered, and concentrated in vacuo to give the I-83 (89 mg).

To a mixture of 2-aminopyrimidine-5-boronic acid pinacol ester (62 mg, 0.28 mmol), I-83 (89 mg, 0.26 mmol), tetrakis(triphenylphosphine)palladium(0) (35 mg, 0.03 mmol) in THF (2.5 mL) at room temperature is added 2M $Na_2CO_3$ solution (2.0 mL). The mixture is stirred at 100° C. for 1 hour, allowed to cool to room temperature, and partitioned between EtOAc and $H_2O$. The combined organics are washed with $H_2O$, dried with $Na_2SO_4$, filtered, and concentrated in vacuo. The residue is purified by flash chromatography ($SiO_2$, 0-10% MeOH in $CH_2Cl_2$) to give the title compound 230 (13 mg).

The following final compounds were synthesized in similar fashion from the appropriate reagents and intermediates:
154, 165-168, 206, 208, 218, 223-224, 228-229, 237-239, 245-246

156, 162, 163 (conditions as above except thermal conditions were used for the $1^{st}$ step)

90-92, 98-99, 247-248 (conditions as above except acid chloride was used in the $1^{st}$ step as the activated acid)

231 (conditions as above except acid chloride was used in the $1^{st}$ step as the activated acid and under thermal not microwave conditions)

116-121, 123-126, 133 (conditions as above except acid chloride was used in the $1^{st}$ step as the activated acid and the reaction was heated under thermal conditions at 55 deg ° C.)

147-151 (conditions as above except BEMP, not NaH, was used for the first step)

Method 3

Synthesis of 1-[4-(2-aminopyrimidin-5-yl)phenyl]-N-(2-hydroxypyridin-4-yl)cyclobutanecarboxamide (Example 220)

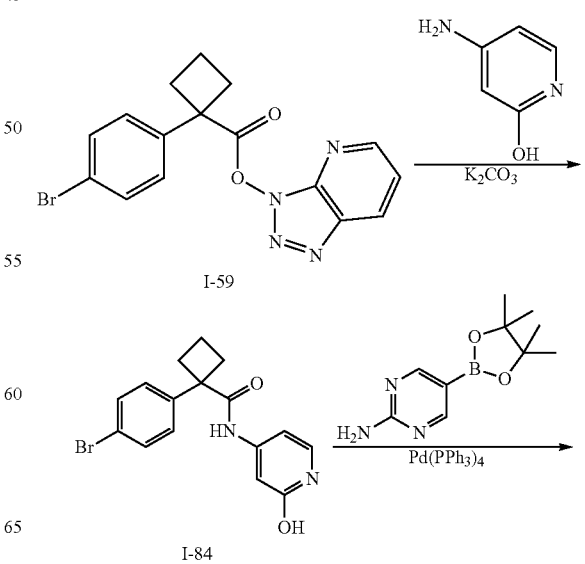

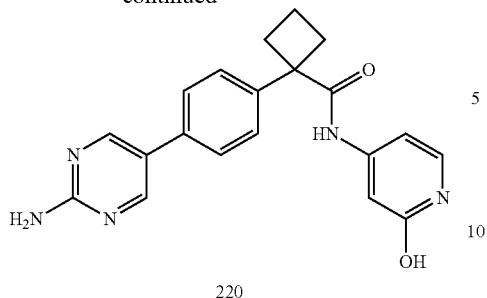

220

To a solution of 4-amino-pyridin-2-ol (50 mg, 0.45 mmol) in THF (5.0 mL) at room temperature is added K$_2$CO$_3$ (100 mg, 0.72 mmol). The reaction mixture is stirred at room temperature for 15 minutes, followed by the addition of I-59 (100 mg, 0.27 mmol). The reaction mixture is heated at 60° C. for 2 hours, allowed to cool to room temperature, and partitioned between EtOAc and H$_2$O. The combined organics are washed with H$_2$O, dried with Na$_2$SO$_4$, filtered, and concentrated in vacuo to give the I-84 (90 mg).

To a mixture of 2-aminopyrimidine-5-boronic acid pinacol ester (90 mg, 0.41 mmol), I-84 (93 mg, 0.27 mmol), tetrakis (triphenylphosphine)palladium(0) (30 mg, 0.026 mmol) in DMF (2.5 mL) at room temperature is added 2M Na$_2$CO$_3$ solution (2.5 mL). The mixture is stirred at 100° C. for 2 hours, allowed to cool to room temperature, and partitioned between EtOAc and H$_2$O. The combined organics are washed with H$_2$O, dried with Na$_2$SO$_4$, filtered, and concentrated in vacuo. The residue is purified by flash chromatography (SiO$_2$, 0-10% MeOH in CH$_2$Cl$_2$) to give the title compound 220 (2 mg).

The following final compound(s) were synthesized in similar fashion from the appropriate reagents and intermediates:
221

Method 4

Synthesis of 2-[4-(2-aminopyrimidin-5-yl)phenyl]-2,3-dimethyl-N-(pyridin-4-yl)butanamide (Example 169)

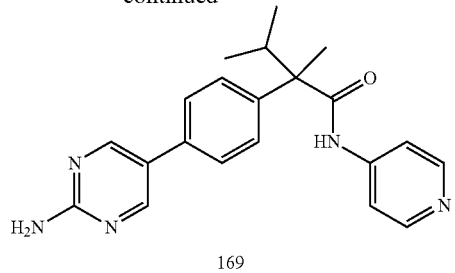

169

To a solution of 4-aminopyridine (24 mg, 0.25 mmol), and 1-63 (78 mg, 0.20 mmol) in THF (2.0 mL) at room temperature was added 2-tert-butylimino-2-diethylamino-1,3-dimethylperhydro-1,3,2-diazaphosphorine on polymer support (~2.2 mmol/g loading, 225 mg, 0.45 mmol). The reaction mixture is heated in the microwave at 120° C. for 1 hour, allowed to cool to room temperature, filtered, and concentrated in vacuo to give the I-85 (70 mg).

To a mixture of 2-aminopyrimidine-5-boronic acid pinacol ester (50 mg, 0.23 mmol), I-85 (70 mg, 0.20 mmol), bis (triphenylphosphine)palladium(II)dichloride (12 mg, 0.01 mmol) in DMF (2.0 mL) at room temperature is added 2M Na$_2$CO$_3$ solution (1.0 mL). The mixture is heated in the microwave at 120° C. for 30 minutes, allowed to cool to room temperature, and partitioned between EtOAc and H$_2$O. The combined organics are washed with brine, filtered, and concentrated in vacuo. The residue is purified by preparative HPLC (CH$_3$CN in water containing 0.1% formic acid) to give the title compound 169 (72 mg).

The following final compounds were synthesized in similar fashion from the appropriate reagents and intermediates:
122, 127, 136, 138-146, 155, 158, 160-161, 169, 232-235, 242-244, 251-253, 255
87-89, 94-95, 97, 250, 254 (conditions as above except Pd-FibreCat-1007 was used as the palladium catalyst for step 2)
94 (conditions as above except only step 2 was required, starting from 103. Pd-FibreCat-1007 was used as the palladium catalyst)

Method 5

Synthesis of 4-[4-(2-aminopyrimidin-5-yl)phenyl]-N-(4-tert-butylphenyl)tetrahydro-2H-pyran-4-carboxamide (Example 17)

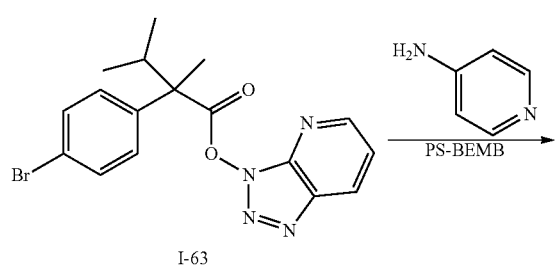

I-63

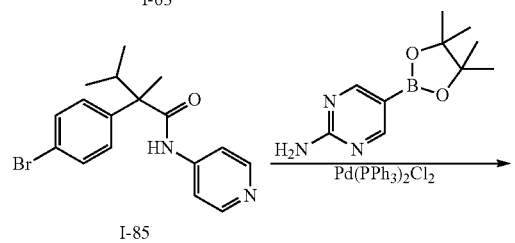

I-85

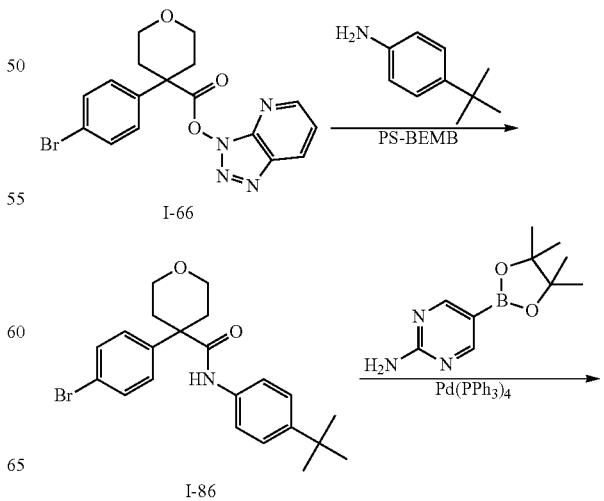

I-66

I-86

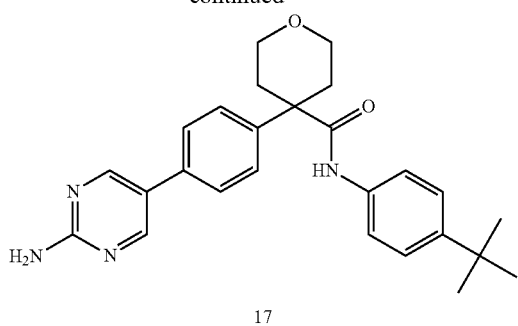

17

To a solution of 4-tert-butylamine (28 mg, 0.18 mmol), and I-66 (50 mg, 0.12 mmol) in 1,2-dichloroethane (1.5 mL) at room temperature is added 2-tert-butylimino-2-diethylamino-1,3-dimethylperhydro-1,3,2-diazaphosphorine on polymer support (~2.2 mmol/g loading, 135 mg, 0.30 mmol). The reaction mixture is heated in the microwave at 130° C. for 1 hour, allowed to cool to room temperature, filtered, and concentrated in vacuo to give the I-86 (51 mg).

To a mixture of 2-aminopyrimidine-5-boronic acid pinacol ester (33 mg, 0.14 mmol), I-86 (51 mg, 0.12 mmol), tetrakis (triphenylphosphine)palladium(0) (29 mg, 0.025 mmol) in THF (1.5 mL) at room temperature is added 2M $Na_2CO_3$ solution (1.0 mL). The mixture is stirred at 100° C. for 2 hours, allowed to cool to room temperature, and partitioned between 1,2-dichloroethane and $H_2O$. The combined organics are washed with $H_2O$, filtered, and concentrated in vacuo. The residue is purified by preparative HPLC ($CH_3CN$ in water containing 0.1% formic acid) to give the title compound 17 (14 mg).

The following final compound(s) were synthesized in similar fashion from the appropriate reagents and intermediates: I-86

Method 6

Synthesis of 4-[6-(2-aminopyrimidin-5-yl)pyridin-3-yl]-N-(5'-methoxy-3,3'-bipyridin-6-yl)tetrahydro-2H-pyran-4-carboxamide(Example 132)

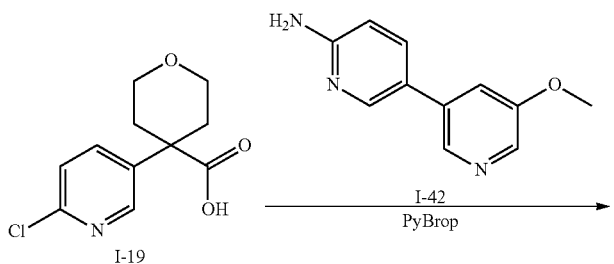

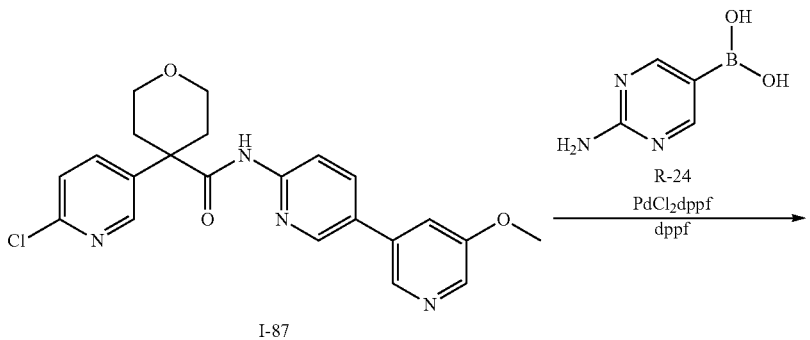

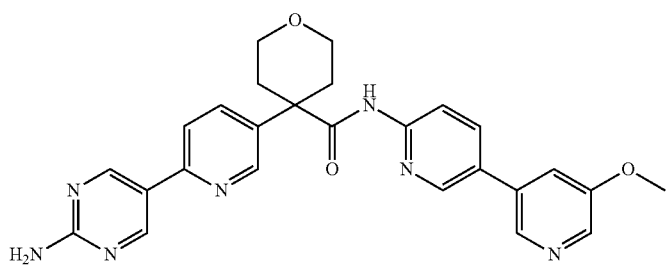

132

To a mixture of I-19 (50 mg, 0.21 mmol), I-42 (42 mg, 0.21 mmol), Et$_3$N (72 µL) in CH$_2$Cl$_2$ (1.0 mL) at room temperature is added PyBrop (108 mg, 0.21 mmol). The reaction mixture is stirred at room temperature for 24 hours, and partitioned between CH$_2$Cl$_2$ and H$_2$O. The combined organics are washed with saturated NaHCO$_3$ solution, dried with Na$_2$SO$_4$, filtered, and concentrated in vacuo. The residue is purified by flash chromatography (SiO$_2$, 0-10% MeOH in CH$_2$Cl$_2$) to give I-87 (18 mg).

To a mixture of 1-87 (59 mg, 0.14 mmol), R-24 (23 mg, 0.17 mmol), PdCl$_2$dppf (5 mg, 0.07 mmol), dppf (4 mg, 0.07 mmol) in EtOH (0.4 mL) and toluene (0.1 mL) at room temperature is added 2M Na$_2$CO$_3$ solution (0.2 mL). The mixture is refluxed for 16 hours, allowed to cool to room temperature, and partitioned between CH$_2$Cl$_2$ and H$_2$O. The combined organics are washed with saturated NaHCO$_3$ solution, dried with Na$_2$SO$_4$, filtered, and concentrated in vacuo. The residue is purified by flash chromatography (SiO$_2$, 0-10% MeOH in CH$_2$Cl$_2$) to give title compound 132 (15 mg).

The following final compounds were synthesized in similar fashion from the appropriate reagents and intermediates: 129-131
128 (conditions as above except I-71 was used in the first step and PyBrop was not used)

Method 7

Synthesis of 2-(4-{6-[(2-hydroxyethyl)amino]pyridin-3-yl}phenyl)-2,3-dimethyl-N-(pyridin-4-yl)butanamide (Example 226) and 2-{4-[6-(dimethylamino)pyridin-3-yl]phenyl}-2,3-dimethyl-N-(pyridin-4-yl)butanamide (Example 227)

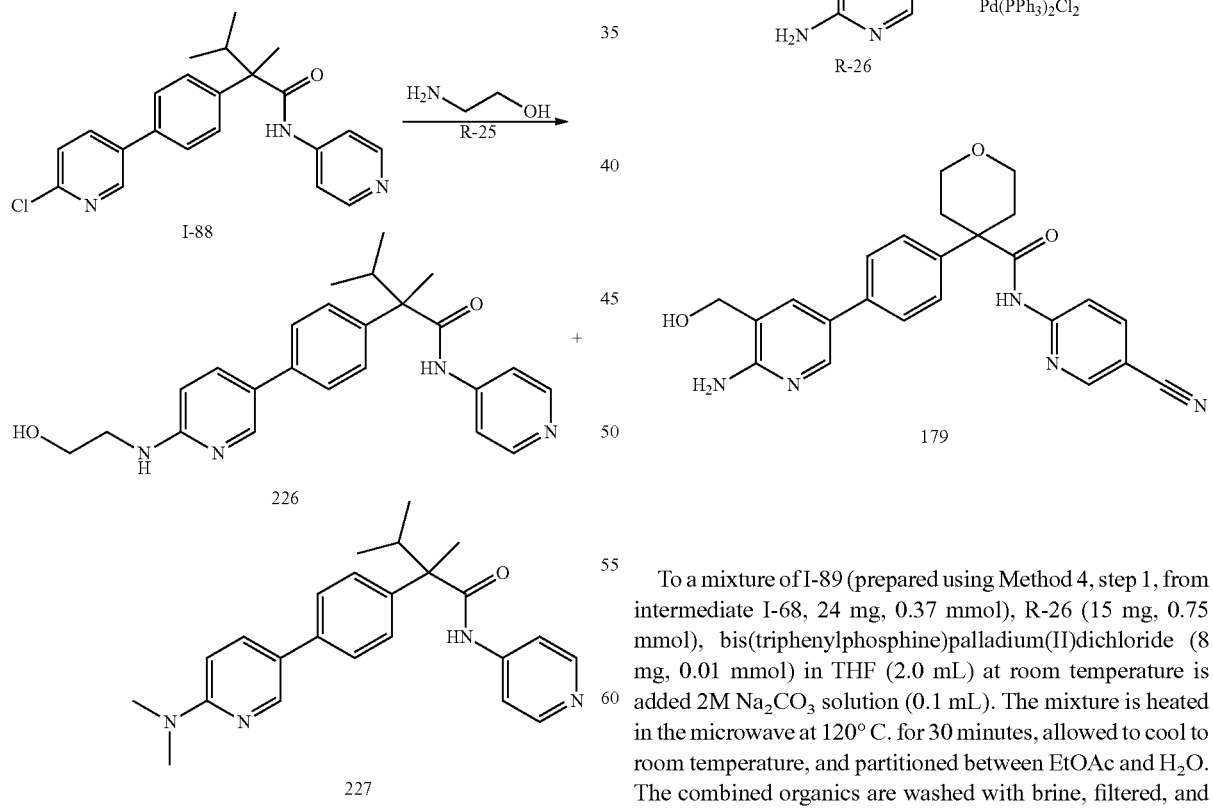

A solution of 1-88 (prepared using Method 4, step 1, 40 mg, 0.105 mmol), and R-25 (200 µL, 3.31 mmol) in DMF (2.0 mL) was heated at 200° C. in the microwave for 2.5 hours. The reaction mixture is allowed to cool to room temperature, filtered, and purified by preparative HPLC (CH$_3$CN in water containing 0.1% formic acid) to give the title compounds 226 (4 mg) and 227 (18 mg).

Method 8

Synthesis of 4-{4-[6-amino-5-(hydroxymethyl)pyridin-3-yl]phenyl}-N-(5-cyanopyridin-2-yl)tetrahydro-2H-pyran-4-carboxamide (Example 179)

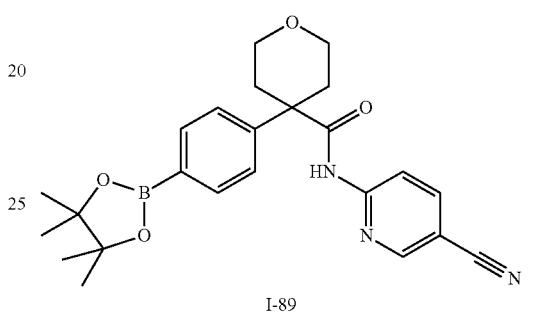

I-89

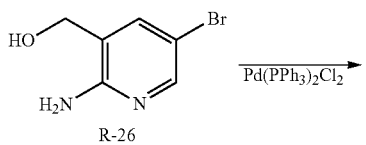

R-26

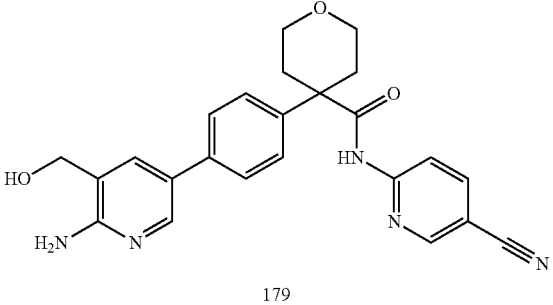

179

To a mixture of I-89 (prepared using Method 4, step 1, from intermediate I-68, 24 mg, 0.37 mmol), R-26 (15 mg, 0.75 mmol), bis(triphenylphosphine)palladium(II)dichloride (8 mg, 0.01 mmol) in THF (2.0 mL) at room temperature is added 2M Na$_2$CO$_3$ solution (0.1 mL). The mixture is heated in the microwave at 120° C. for 30 minutes, allowed to cool to room temperature, and partitioned between EtOAc and H$_2$O. The combined organics are washed with brine, filtered, and concentrated in vacuo. The residue is purified by flash chromatography (SiO$_2$, 0-100% EtOAc in heptane) to give the title compound 179 (3.5 mg).

Method 9

Synthesis of 4-[4-(2-aminopyrimidin-5-yl)phenyl]-N-[5-(3-methyl-1,2,4-oxadiazol-5-yl)pyridin-2-yl]tetrahydro-2H-pyran-4-carboxamide (Example 178)

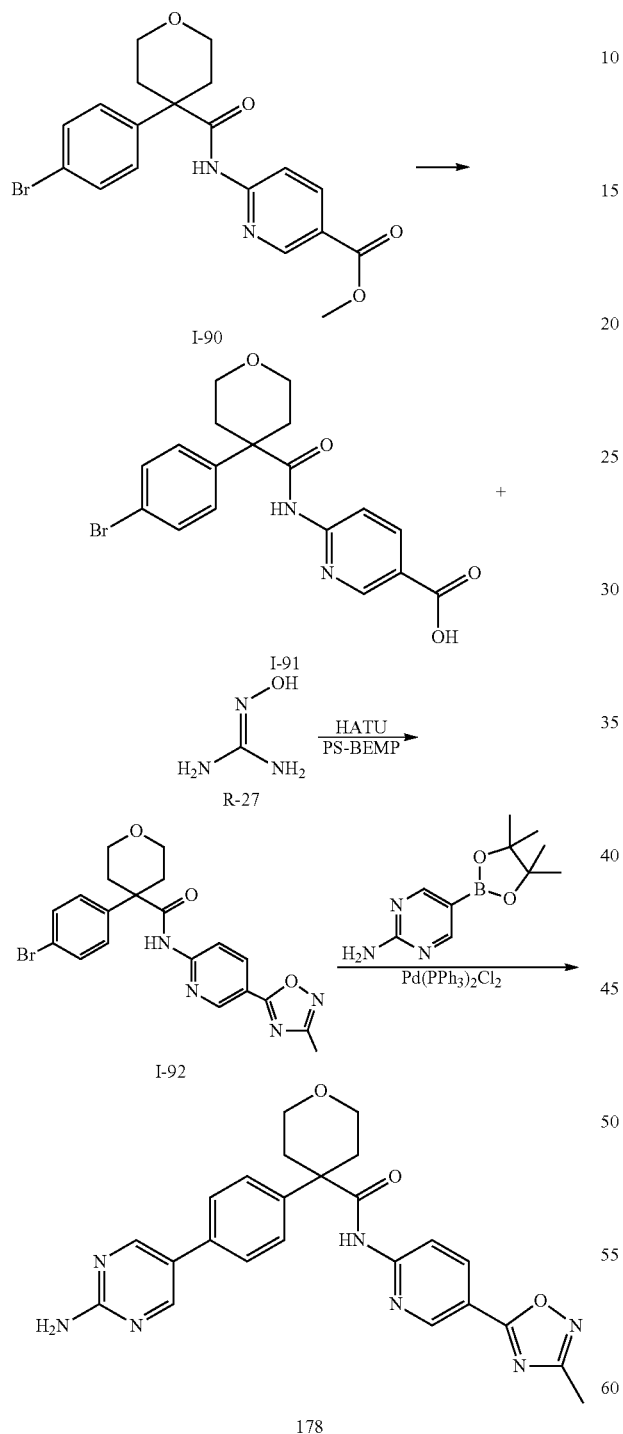

A mixture of I-90 (prepared using Method 2, step 1, 240 mg, 0.37 mmol), Amberlyst A-26 (OH) (1.8g g, 2.5 mmol) in MeOH (10 mL) is stirred at room temperature for 16 hours. The reaction mixture is filtered, and the resin is washed with CH₂Cl₂-MeOH, 20% formic acid in MeOH, and 1M HCl solution. The combined eluents are concentrated in vacuo to give I-91 (184 mg).

To a solution of I-91 (90 mg, 0.22 mmol), O-(7-azabenzotriazol-1-yl)-N,N,N',N'-tetramethyluronium hexafluorophosphate (95 mg, 0.25 mmol) in THF (25 mL) at room temperature is added DIPEA (75 μL, 0.43 mmol) and R-27 (25 mg, 0.34 mmol). The mixture is stirred at room temperature for 30 minutes, followed by the addition of 2-tert-butylimino-2-diethylamino-1,3-dimethylperhydro-1,3,2-diazaphosphorine on polymer support (~2.2 mmol/g loading, 200 mg, 0.40 mmol), and heated at 120° C. in the microwave for 40 minutes. The reaction mixture is allowed to cool to room temperature, filtered, and concentrated in vacuo to give 1-92 (90 mg).

The final step to prepare the title compound 178 from I-92 can be prepared according to Method 4, step 2.

The following final compound(s) were synthesized in similar fashion from the appropriate reagents and intermediates: 100

Method 10

Synthesis of 4-[4-(2-aminopyrimidin-5-yl)phenyl]-N-[5-(2-hydroxypropan-2-yl)pyridin-2-yl]tetrahydro-2H-pyran-4-carboxamide (Example 159)

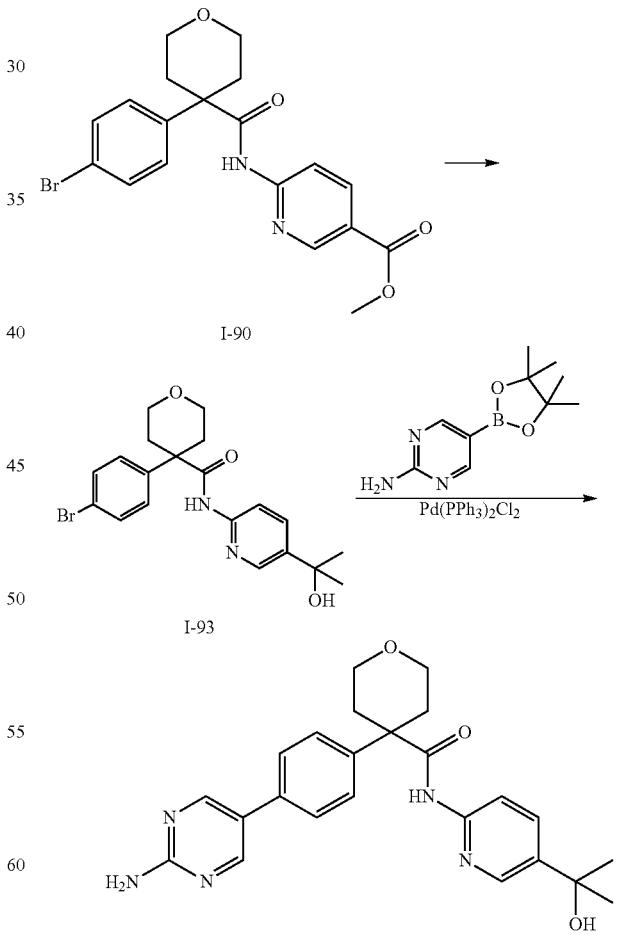

To a solution of I-90 (as used in Method 9, 20 mg, 0.048 mmol), in THF (2.0 mL) at −78° C. is added MeMgCl (3.0 M in THF, 0.35 mL, 0.1 mmol). The reaction mixture is stirred at −78° C. for 30 minutes, and allowed to warm to room temperature slowly. The reaction mixture partitioned between EtOAc and saturated NH₄Cl solution. The combined organics are washed with brine, and concentrated in vacuo to give I-93 (20 mg).

The final step to prepare the title compound 159 from I-93 can be prepared according to Method 4, step 2.

Method 11

Synthesis of 6-[({4-[4-(2-aminopyrimidin-5-yl)phenyl]tetrahydro-2H-pyran-4-yl}carbonyl)amino]pyridine-3-carboxylic acid (Example 157)

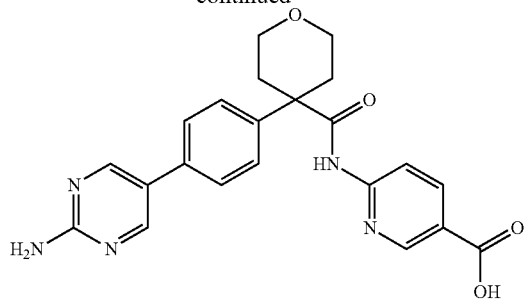

157

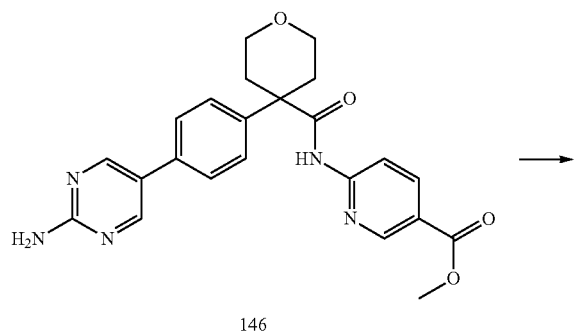

146

A mixture of 146 (20 mg, 0.046 mmol), Amberlyst A-26 (OH) (350 mg, 0.47 mmol) in MeOH (1 mL) is stirred at room temperature for 16 hours. The reaction mixture is filtered, and the resin is washed with 20% formic acid in MeOH. The combined eluents are concentrated in vacuo to give the title compound 157 (17 mg).

The following final compounds were synthesized in similar fashion from the appropriate reagents and intermediates:
96 (prepared from 95) and purified by preparative HPLC (CH₃CN in water containing 0.1% formic acid)
101 (prepared from 97) and purified by preparative HPLC (CH₃CN in water containing 0.1% formic acid)

Method 12

Synthesis of 6-[({1-[4-(2-aminopyrimidin-5-yl)phenyl]cyclobutyl}carbonyl)amino]-N-carbamimidoylpyridine-3-carboxamide (Example 108)

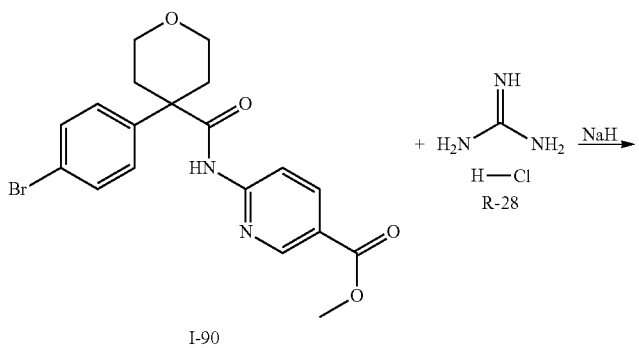

I-90

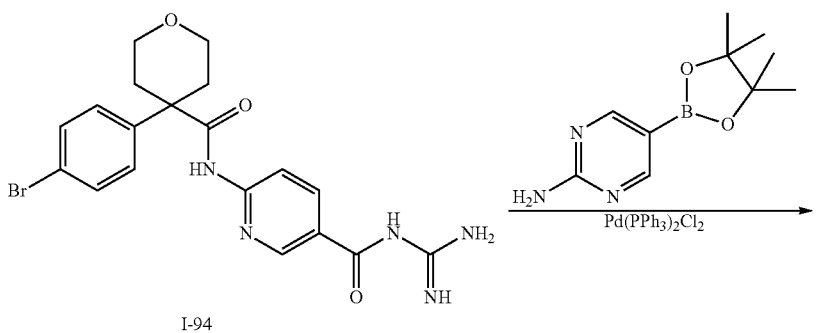

I-94

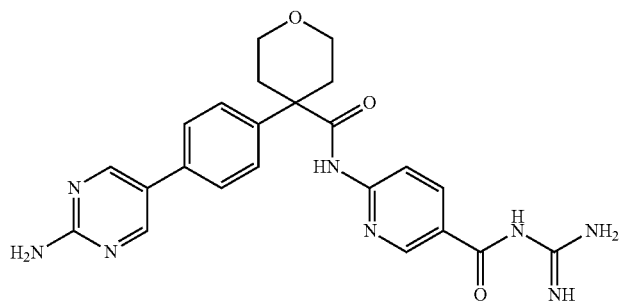

108

To a solution of R-28 (176 mg, 1.85 mmol) in NMP (10 mL) at room temperature is added NaH (60% dispersion in mineral oil, 42 mg, 1.83 mmol). The reaction mixture is stirred for 30 minutes, followed by the addition of 1-90 (97 mg, 0.025 mmol) in NMP (1 mL). The reaction mixture is heated at 75° C. for 4 hours. The reaction mixture is allowed to cool to room temperature, and partitioned between EtOAc and $H_2O$. The combined organics are washed with brine, and concentrated in vacuo. The residue is purified by flash chromatography ($SiO_2$, 0-10% 2M $NH_3$ in MeOH in $CH_2Cl_2$) to give I-94 (52 mg).

The final step to prepare the title compound 108 from I-94 can be prepared according to Method 4, step 2.

Method 13

Synthesis of 1-[4-(2-aminopyrimidin-5-yl)phenyl]-N-[5-(1-methyl-1H-1,2,4-triazol-5-yl)pyridin-2-yl]cyclobutanecarboxamide (Example 103)

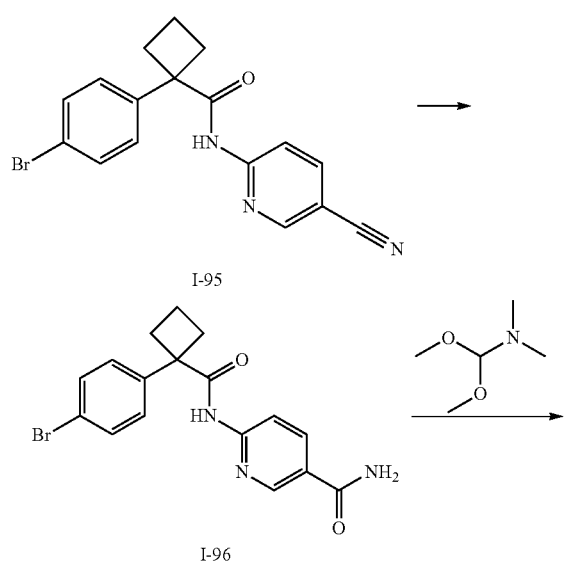

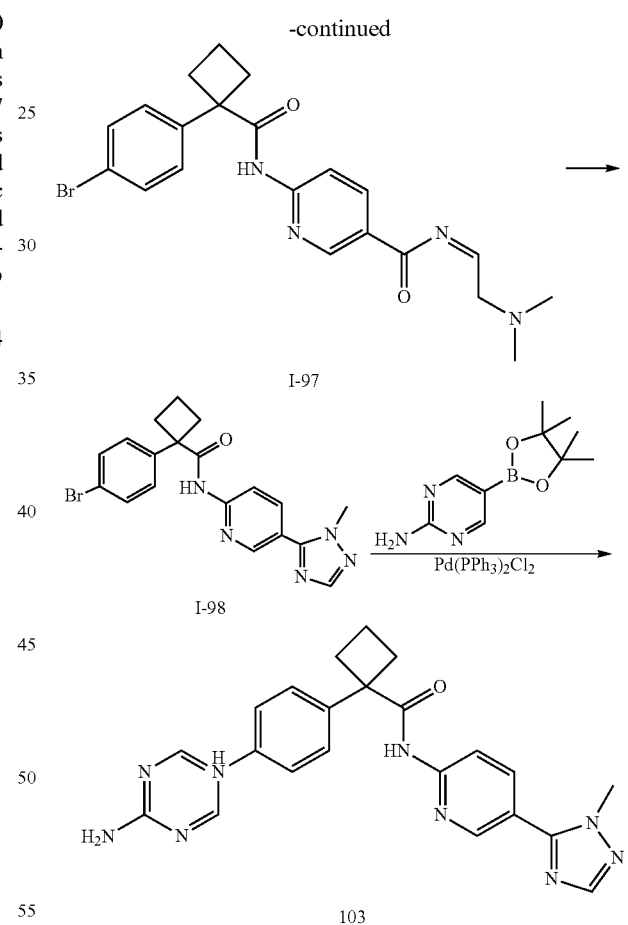

A mixture of I-95 (prepared using Method 2, step 1, 100 mg, 0.28 mmol), $H_2SO_4$ (15 drops) in TFA (1.0 mL) is stirred at room temperature for 16 hours. The reaction mixture is concentrated in vacuo, and the reaction mixture partitioned between EtOAc and $H_2O$. The combined organics are washed with saturated $NaHCO_3$ solution, dried with $Na_2SO_4$, filtered, and concentrated in vacuo to give the I-96 (118 mg).

A mixture of I-96 (118 mg) in N,N'-dimethylformamide dimethyl acetal (1.0 mL) is heated at 110° C. for 1 hour. The reaction mixture is allowed to cool to room temperature, and concentrated in vacuo to give the I-97 (139 mg).

To a solution of I-97 (66 mg, 0.15 mmol) in acetic acid (2.0 mL) at room temperature is added methylhydrazine (0.53 mL, 10 mmol). The reaction mixture is stirred for 1 hour, concentrated in vacuo, and the reaction mixture partitioned between EtOAc and H₂O. The combined organics are washed with saturated NaHCO₃ solution, dried with Na₂SO₄, filtered, and concentrated in vacuo. The residue is purified by flash chromatography (SiO₂, 0-100% EtOAc in heptane) to give I-98 (21 mg).

The final step to prepare the title compound 103 from I-98 can be prepared according to Method 4, step 2.

The following final compounds(s) were synthesized in similar fashion from the appropriate reagents and intermediates:
102

Method 14

—Synthesis of 6-[({1-[4-(2-aminopyrimidin-5-yl) phenyl]cyclobutyl}carbonyl)amino]-N-(methylsulfonyl)pyridine-3-carboxamide (Example 105)

To a solution of I-99 (prepared using Method 2, step 1, 100 mg, 0.26 mmol) in THF (1.0 mL) at room temperature is added a solution of LiOH (24 mg, 1.0 mmol) in H₂O (0.5 mL). The reaction mixture is stirred at room temperature for 16 hours, and partitioned between EtOAc and H₂O. The combined aqueous layers are acidified with 6M HCl solution to form a white solid which is filtered to give I-100 (70 mg).

To a solution of I-100 (70 mg, 0.19 mmol) in THF (1.0 mL) at room temperature is added 1,1'-carbonyldiimidazole (68 mg, 0.42 mmol). The mixture is stirred at room temperature for 30 minutes, heated at 55° C. for 30 minutes, and allowed to cool to room temperature. To the reaction mixture is added R-29 (44 mg, 0.46 mmol), and DBU (75 μL, 0.48 mmol), stirred at room temperature for 16 hours, and partitioned between EtOAc and H₂O. The combined organics are dried with Na₂SO₄, and concentrated in vacuo to give I-101 (70 mg).

The final step to prepare the title compound 105 from I-101 can be prepared according to Method 4, step 2, with FibreCat-1007 as the palladium catalyst.

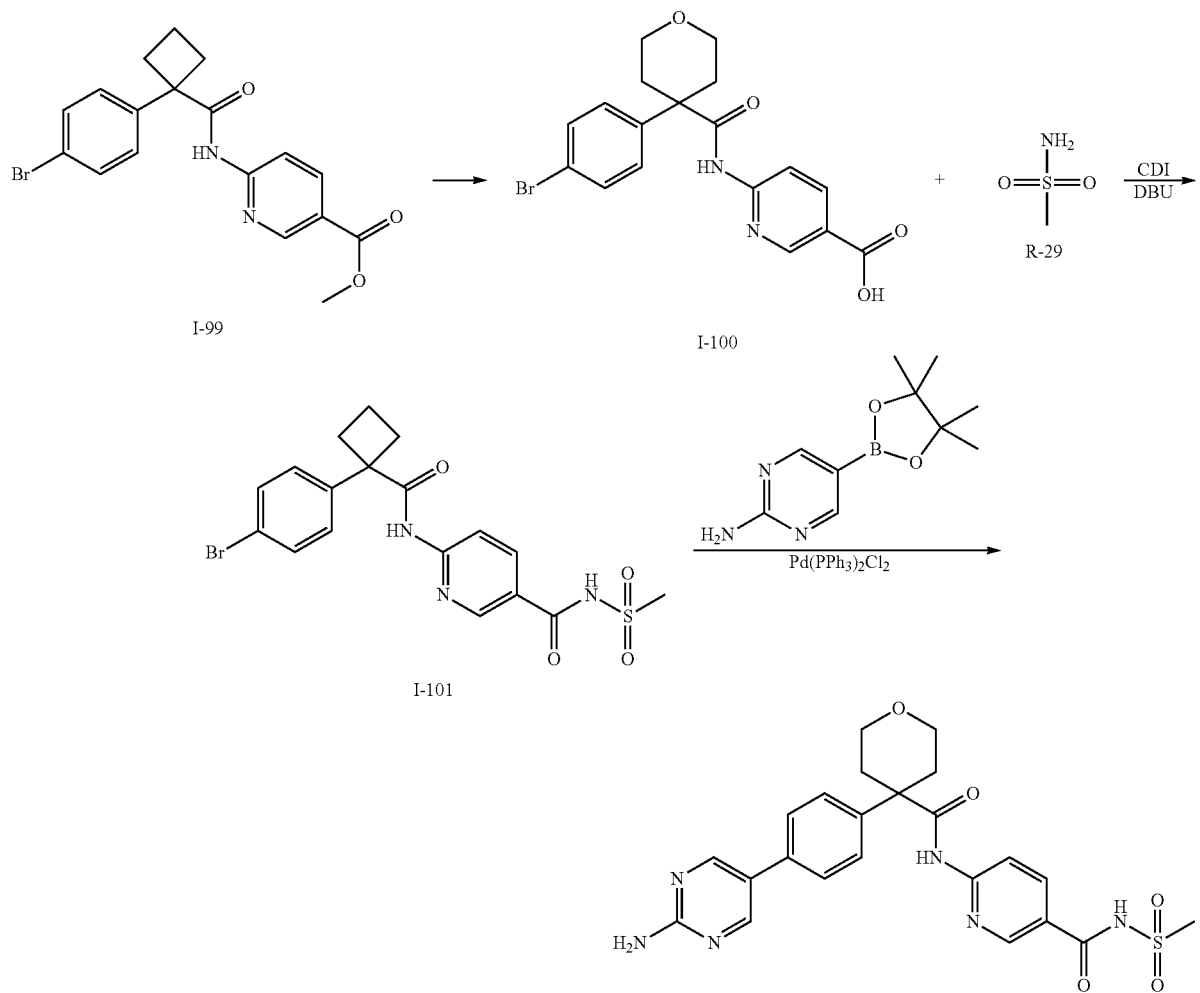

Method 15

Synthesis of 1-[5-(2-aminopyrimidin-5-yl)pyridin-2-yl]-N-[5-(1-methyl-1H-pyrazol-4-yl)pyridin-2-yl]cyclobutanecarboxamide (Example 109)

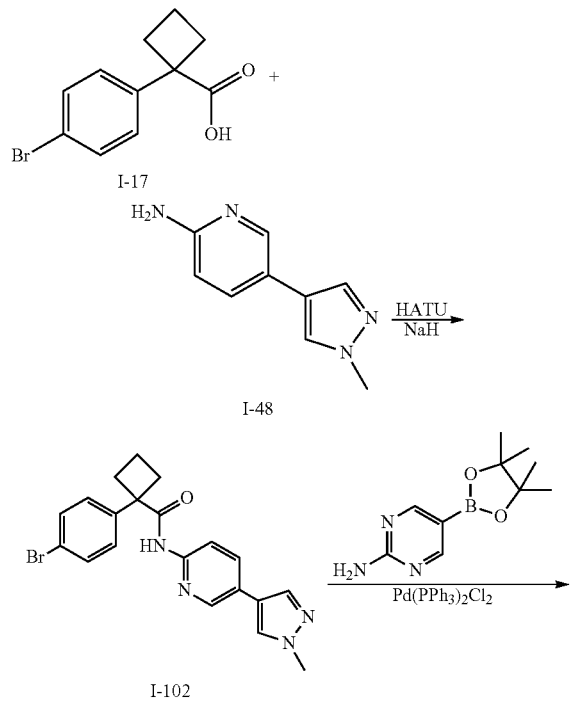

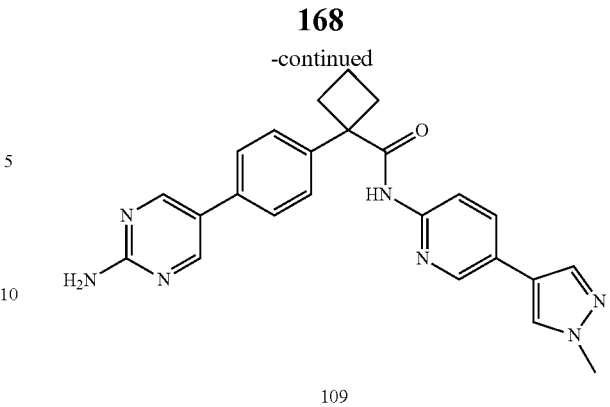

109

To a solution of I-17 (45 mg, 0.176 mmol), O-(7-azabenzotriazol-1-yl)-N,N,N',N'-tetramethyluronium hexafluorophosphate (67 mg, 0.18 mmol) in DMF (1.0 mL) at room temperature is added 4-methylmorpholine (25 μL, 0.22 mmol), and the reaction mixture is stirred at room temperature for 30 minutes. To a solution of I-48 (50 mg, 0.29 mmol) in THF (1.0 mL) at room temperature is added NaH (60% dispersion in mineral oil, 7 mg, 0.3 mmol), and the reaction mixture is stirred at room temperature for 15 minutes. The two reaction mixtures are combined and heated at 55° C. for 1 hour. The reaction mixture is allowed to cool to room temperature, and concentrated in vacuo. The residue is purified by flash chromatography ($SiO_2$, 0-10% MeOH in $CH_2Cl_2$) to give the I-102 (10 mg).

The final step to prepare the title compound 109 from I-102 can be prepared according to Method 4, step 2, with FibreCat-1007 as the palladium catalyst.

The following final compound(s) were synthesized in similar fashion from the appropriate reagents and intermediates 107

Method 16

Synthesis of 1-[4-(2-aminopyrimidin-5-yl)phenyl]-N-[5-(1-methyl-1H-pyrazol-5-yl)pyridin-2-yl]cyclobutanecarboxamide (Example 106)

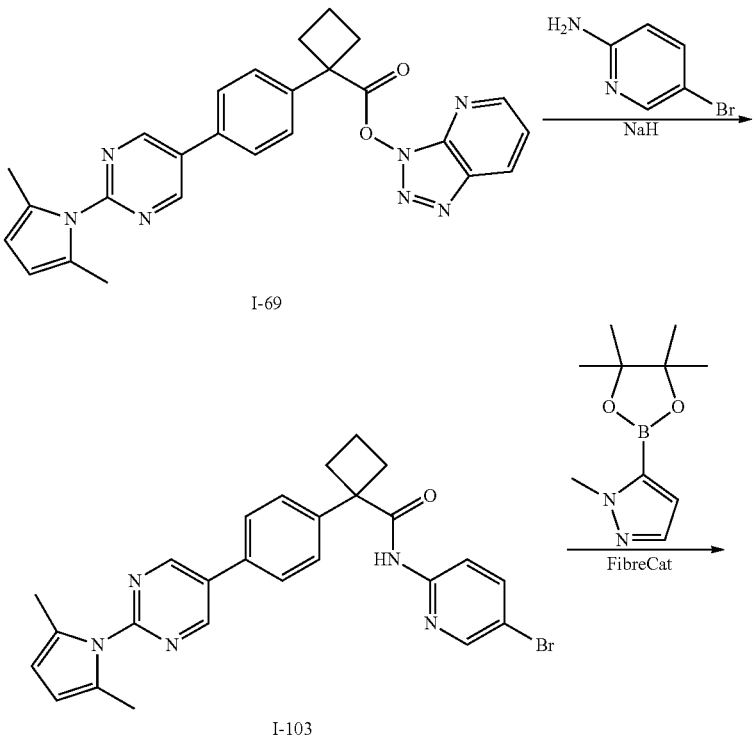

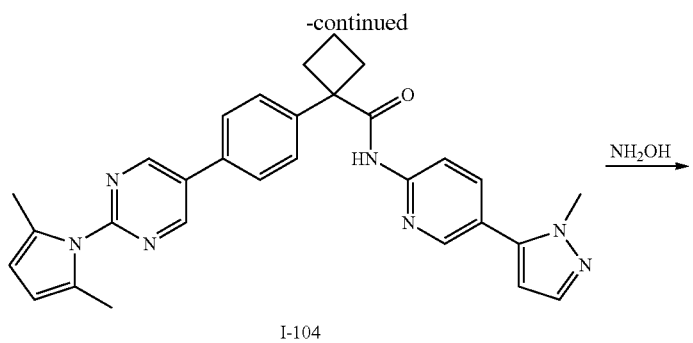

I-104

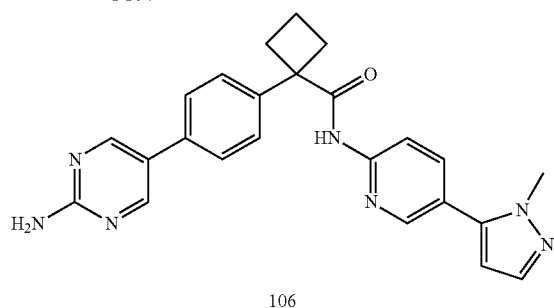

106

The first step to prepare I-103 from I-69 can be prepared according to Method 1, step 1. The second step to prepare I-104 from I-103 can be prepared according to Method 4, step 2, with FibreCat-1007 as the palladium catalyst.

To a solution of I-104 (35 mg, 0.069 mmol) in EtOH (2.0 mL) and dioxane (1.0 mL) is added NH$_2$OH.HCl (48 mg, 0.7 mmol) in H$_2$O (0.5 mL), and Et$_3$N (10 μL, 0.07 mmol). The reaction mixture is heated at 90° C. for 24 hours, allowed to cool to room temperature, and partitioned between EtOAc and saturated NaHCO$_3$ solution. The combined organics are washed with brine, dried with Na$_2$SO$_4$, filtered, and concentrated in vacuo. The residue is purified by preparative HPLC (CH$_3$CN in water containing 0.1% formic acid) to give the title compound 106 (10 mg).

The following final compound(s) were synthesized in similar fashion from the appropriate reagents and intermediates: 104

Method 17

Synthesis of 4-[4-(2,3-dihydro-1H-pyrrolo[2,3-b]pyridin-5-yl)phenyl]-N-[5-(2-methyl-1,3-thiazol-4-yl)pyridin-2-yl]tetrahydro-2H-pyran-4-carboxamide (Example 153)

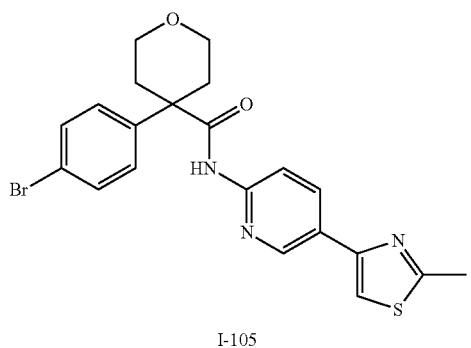

I-105

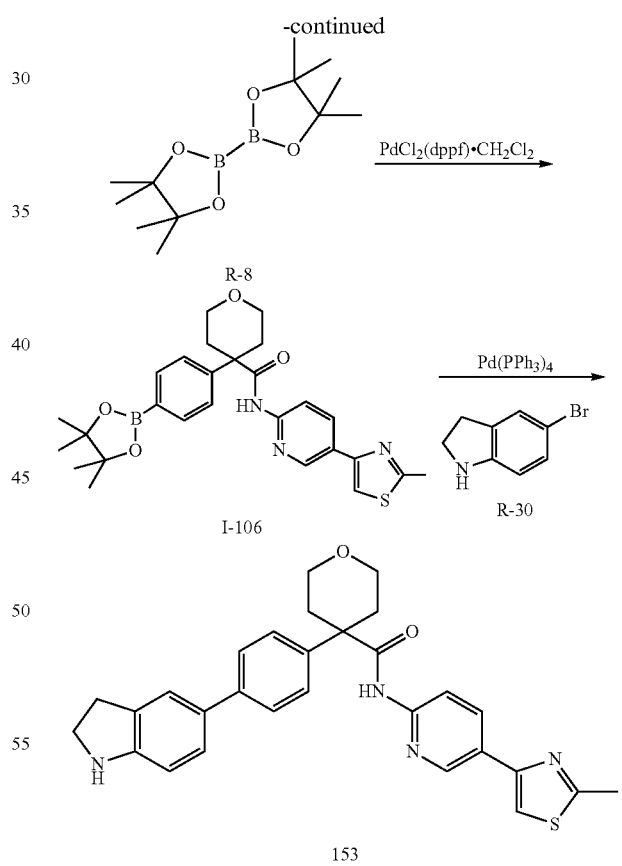

To a solution of I-105 (prepared using Method 1, step 1, 143 mg, 0.31 mmol), KOAc (128 mg, 1.3 mmol), PdCl$_2$(dppf).CH$_2$Cl$_2$ (27 mg, 0.04 mmol) in dioxane (5.0 mL) at room temperature is added R-8 (95 mg, 0.38 mmol). The reaction mixture is heated at 100° C. in a sealed tube for 4 hours. The reaction mixture is allowed to cool to room temperature, and partitioned between EtOAc and H$_2$O. The combined organics are washed with brine, dried with Na$_2$SO$_4$, filtered, and concentrated in vacuo. The residue is purified by flash chromatography (SiO$_2$, 30-70% EtOAc in heptane) to give I-106 (120 mg).

To a solution of I-106 (60 mg, 0.12 mmol) in THF (3.0 mL), is added R-30 (20 mg, 0.1 mmol), 20% Na$_2$CO$_3$ solution (2.0 mL), and Pd(PPh$_3$)$_4$. The reaction mixture is heated at 100° C. for 60 minutes, allowed to cool to room temperature, and partitioned between EtOAc and H$_2$O. The combine organics are dried with Na$_2$SO$_4$, filtered, and concentrated in vacuo. The residue is purified by flash chromatography (SiO$_2$, 0-10% MeOH in EtOAc) to give the title compound 153 (25 mg).

The following final compounds were synthesized in similar fashion from the appropriate reagents and intermediates:

152

170, 171, 175 (conditions as above except bistricylcohexylphosphinepalladium(II)chloride was used as the palladium catalyst for step 2)

Method 18

Synthesis of 4-(4-{2-[(2-methoxyethyl)amino]pyrimidin-5-yl}phenyl)-N-[5-(2-methyl-1,3-thiazol-4-yl)pyridin-2-yl]tetrahydro-2H-pyran-4-carboxamide (Example 207)

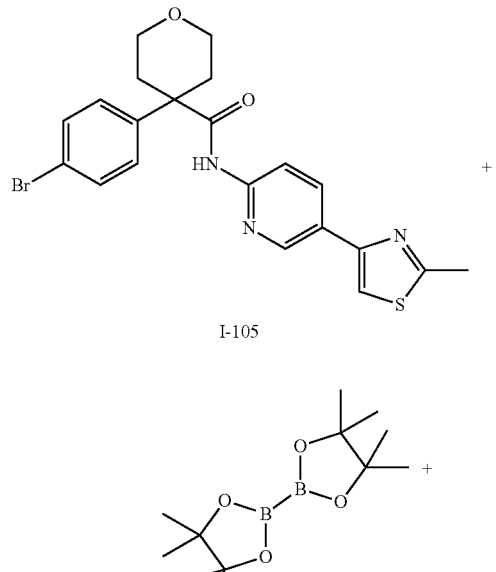

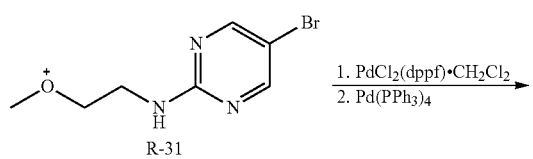

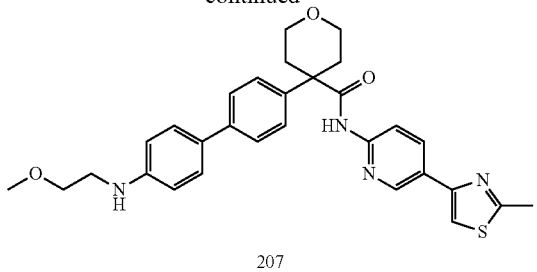

To a solution of I-105 (75 mg, 0.16 mmol), KOAc (157 mg, 1.6 mmol), PdCl$_2$(dppf).CH$_2$Cl$_2$ (33 mg, 0.04 mmol) in dioxane (2.0 mL) at room temperature is added R-8 (115 mg, 0.46 mmol). The reaction mixture is heated at 100° C. in a sealed tube for 16 hours. The reaction mixture is allowed to cool to room temperature, followed by the addition R-31 (88 mg, 0.38 mmol) in THF (2.0 mL), 20% Na$_2$CO$_3$ solution (2.0 mL), and Pd(PPh$_3$)$_4$ (23 mg, 0.20 mmol). The reaction mixture is heated in the microwave at 120° C. for 60 minutes, allowed to cool to room temperature, and partitioned between EtOAc and H$_2$O. The combined organics are washed with H$_2$O, dried with Na$_2$SO$_4$, filtered, and concentrated in vacuo. The residue is purified by flash chromatography (SiO$_2$, 0-10% MeOH in EtOAc) to give the title compound 207 (36 mg).

The following final compounds were synthesized in similar fashion from the appropriate reagents and intermediates:

164, 181-182, 192-193, 197

Method 19

—Synthesis of 4-{4-[6-amino-5-(hydroxymethyl)pyridin-3-yl]phenyl}-N-[5-(2-methyl-1,3-thiazol-4-yl)pyridin-2-yl]tetrahydro-2H-pyran-4-carboxamide (Example 176)

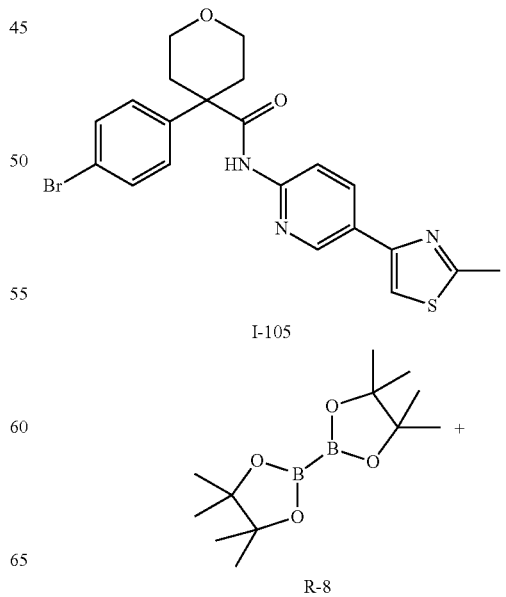

173
-continued

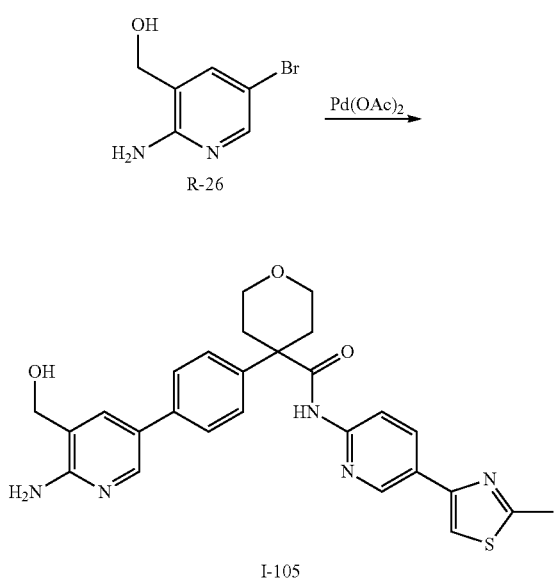

To a solution of I-105 (125 mg, 0.27 mmol) in dioxane (5.0 mL) is added R-8 (380 mg, 1.50 mmol), Pd(OAc)₂ (10 mg, 0.045 mmol), 2-(dicyclohexylphosphino)biphenyl (36 mg, 0.10 mmol) at room temperature. The reaction mixture is heated at 80° C. for 1 hour, and allowed to cool to room temperature. To the reaction mixture is added Ba(OH)₂ (257 mg, 1.5 mmol), R-26 (102 mg, 0.50 mmol), and H₂O (0.5 mL). The reaction mixture is heated at 120° C. for 4 hours, allowed to cool to room temperature, and partitioned between EtOAc and H₂O. The combined organics are washed with H₂O, dried with Na₂SO₄, filtered, and concentrated in vacuo. The residue is purified by flash chromatography (SiO₂, 0-10% MeOH in EtOAc) to give the title compound 176 (35 mg).

174

Method 20

—Synthesis of N-(2-butylquinolin-6-yl)-2-[4-(5-methoxypyridin-3-yl)phenyl]-2,3-dimethylbutanamide (Example 115)

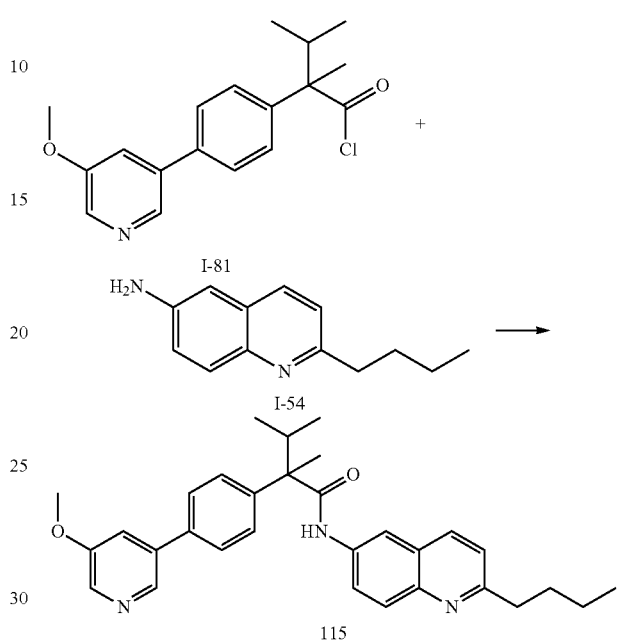

To a solution of I-54 (950 mg, 0.5 mmol) in DMA (2.0 mL) is added DIPEA (116 mg, 0.9 mmol), and I-81 (150 mg, 0.47 mmol). The reaction mixture is heated at 90° C. for 4 hours, allowed to cool to room temperature, and partitioned between EtOAc and H₂O. The combined organics are washed with H₂O, dried with Na₂SO₄, filtered, and concentrated in vacuo. The residue is purified by flash chromatography (SiO₂, 0-20% EtOAc in heptane) to give the title compound 115 (84 mg).

The following final compounds were synthesized in similar fashion from the appropriate reagents and intermediates: 111-114

Table of final compounds

| Example | Structure | Method | Retention Time (min) | m/z | LC-MS Method |
|---|---|---|---|---|---|
| 1 | 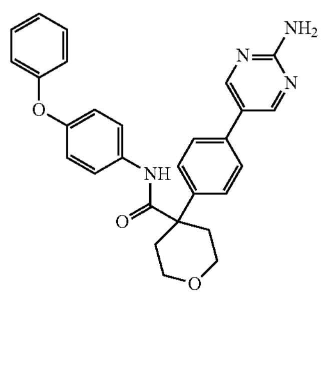 [SMILES: Nc1ncc(-c2ccc(C3(C(=O)Nc4ccc(Oc5ccccc5)cc4)CCOCC3)cc2)cn1] | 5 | 2.48 | 467 | A |

-continued

Table of final compounds

| Example | Structure | Method | Retention Time (min) | m/z | LC-MS Method |
|---|---|---|---|---|---|
| 2 | 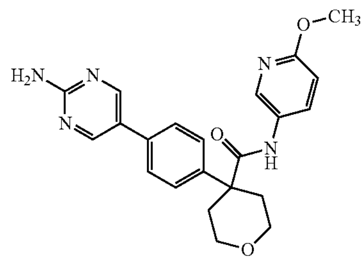 [SMILES: COc1ccc(NC(=O)C2(c3ccc(-c4cnc(N)nc4)cc3)CCOCC2)cn1] | 5 | 1.58 | 406 | A |
| 3 | 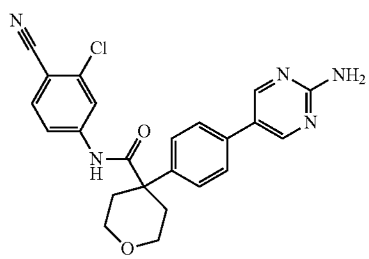 [SMILES: N#Cc1ccc(NC(=O)C2(c3ccc(-c4cnc(N)nc4)cc3)CCOCC2)cc1Cl] | 5 | 2.16 | 434 | A |
| 4 | 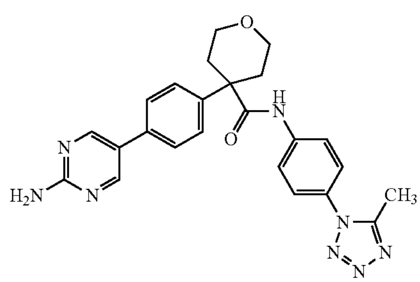 [SMILES: Cc1nnnn1-c1ccc(NC(=O)C2(c3ccc(-c4cnc(N)nc4)cc3)CCOCC2)cc1] | 5 | 1.65 | 457 | A |
| 5 | 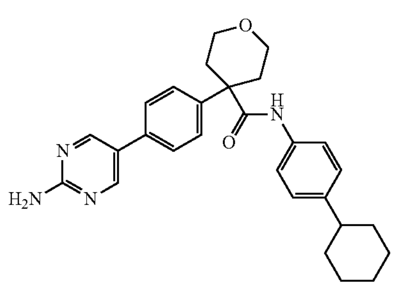 [SMILES: Nc1ncc(-c2ccc(C3(C(=O)Nc4ccc(C5CCCCC5)cc4)CCOCC3)cc2)cn1] | 5 | 1.12 | 457 | C |
| 6 | 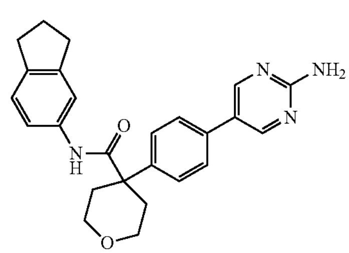 [SMILES: Nc1ncc(-c2ccc(C3(C(=O)Nc4ccc5c(c4)CCC5)CCOCC3)cc2)cn1] | 5 | 0.9 | 413 (ES−) | C |

-continued

Table of final compounds

| Example | Structure | Method | Retention Time (min) | m/z | LC-MS Method |
|---|---|---|---|---|---|
| 7 | 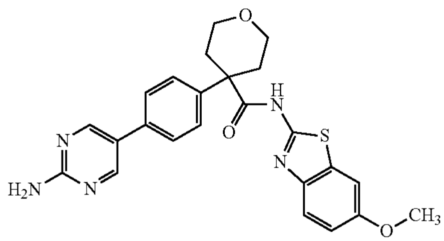 [SMILES: COc1ccc2nc(NC(=O)C3(c4ccc(-c5cnc(N)nc5)cc4)CCOCC3)sc2c1] | 5 | 0.87 | 462 | C |
| 8 | 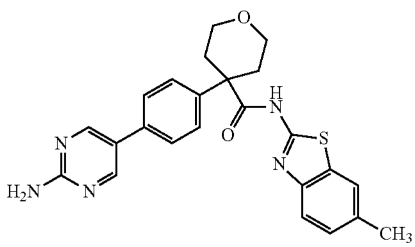 [SMILES: Cc1ccc2nc(NC(=O)C3(c4ccc(-c5cnc(N)nc5)cc4)CCOCC3)sc2c1] | 5 | 0.95 | 446 | C |
| 9 | 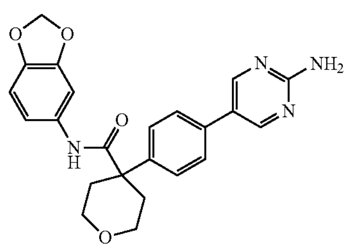 [SMILES: Nc1ncc(-c2ccc(C3(C(=O)Nc4ccc5c(c4)OCO5)CCOCC3)cc2)cn1] | 5 | 0.72 | 417 (ES−) | C |
| 10 | 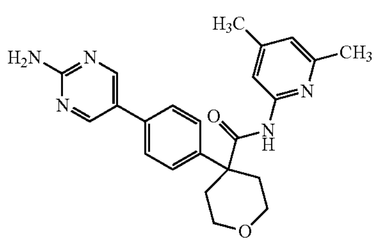 [SMILES: Cc1cc(C)nc(NC(=O)C2(c3ccc(-c4cnc(N)nc4)cc3)CCOCC2)c1] | 5 | 0.73 | 404 | C |
| 11 | 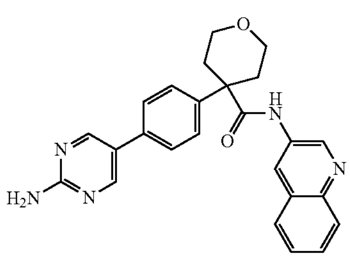 [SMILES: Nc1ncc(-c2ccc(C3(C(=O)Nc4cnc5ccccc5c4)CCOCC3)cc2)cn1] | 5 | 0.73 | 426 | C |
| 12 | 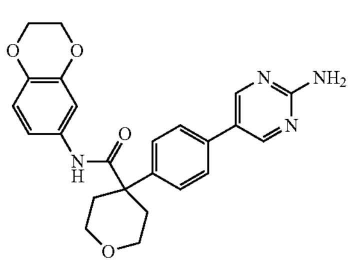 [SMILES: Nc1ncc(-c2ccc(C3(C(=O)Nc4ccc5c(c4)OCCO5)CCOCC3)cc2)cn1] | 5 | 0.72 | 431 (ES−) | C |

-continued
Table of final compounds
| Example | Structure | Method | Retention Time (min) | m/z | LC-MS Method |
|---|---|---|---|---|---|
| 13 | 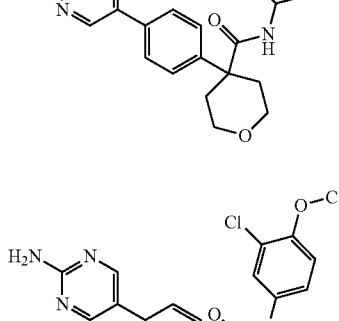 | 5 | 0.98 | 443/445 | C |
| 14 | 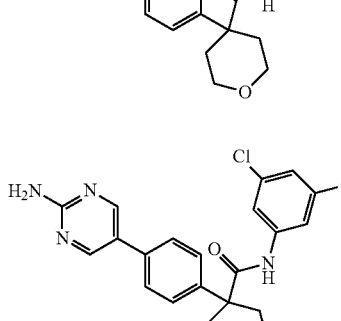 | 5 | 0.82 | 439 | C |
| 15 | 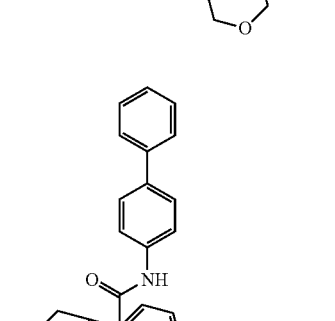 | 5 | 1.02 | 443/445 | C |
| 16 | 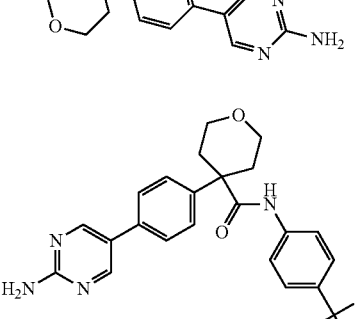 | 5 | 0.98 | 451 | C |
| 17 | 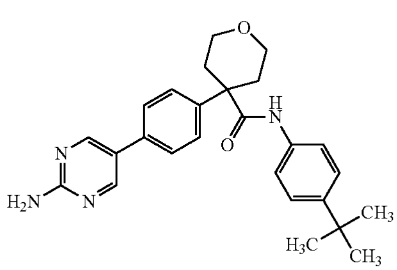 [SMILES: CC(C)(C)c1ccc(NC(=O)C2(c3ccc(-c4cnc(N)nc4)cc3)CCOCC2)cc1] | 5 | 1.01 | 429 (ES−) | C |

-continued

Table of final compounds

| Example | Structure | Method | Retention Time (min) | m/z | LC-MS Method |
|---|---|---|---|---|---|
| 18 | 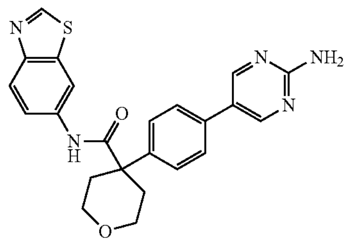 [SMILES: Nc1ncc(-c2ccc(C3(C(=O)Nc4ccc5ncsc5c4)CCOCC3)cc2)cn1] | 5 | 0.7 | 432 | C |
| 19 | 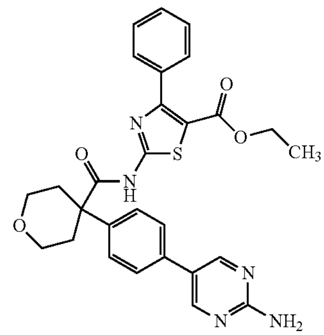 [SMILES: CCOC(=O)c1sc(NC(=O)C2(c3ccc(-c4cnc(N)nc4)cc3)CCOCC2)nc1-c1ccccc1] | 5 | 1.02 | 530 | C |
| 20 | 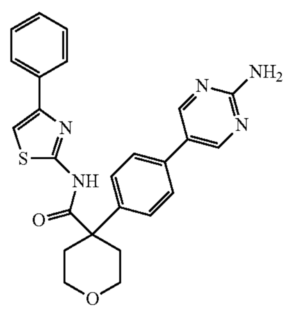 [SMILES: Nc1ncc(-c2ccc(C3(C(=O)Nc4nc(-c5ccccc5)cs4)CCOCC3)cc2)cn1] | 5 | 0.95 | 458 | C |
| 21 | 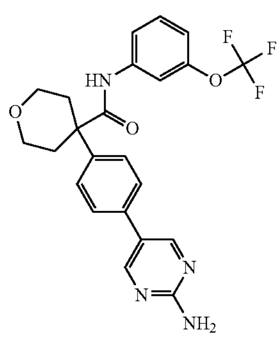 [SMILES: Nc1ncc(-c2ccc(C3(C(=O)Nc4cccc(OC(F)(F)F)c4)CCOCC3)cc2)cn1] | 5 | 0.96 | 457 (ES−) | C |
| 22 | 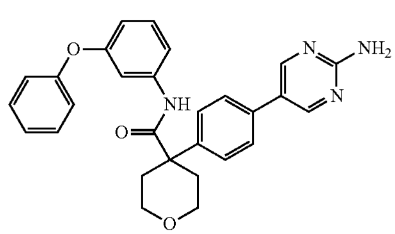 [SMILES: Nc1ncc(-c2ccc(C3(C(=O)Nc4cccc(Oc5ccccc5)c4)CCOCC3)cc2)cn1] | 5 | 0.98 | 467 | C |

183
184
-continued
Table of final compounds
| Example | Structure | Method | Retention Time (min) | m/z | LC-MS Method |
|---|---|---|---|---|---|
| 23 | 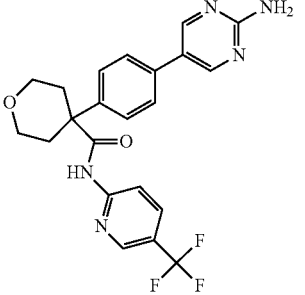 [SMILES: Nc1ncc(-c2ccc(C3(C(=O)Nc4ccc(C(F)(F)F)cn4)CCOCC3)cc2)cn1] | 5 | 0.9 | 442 (ES−) | C |
| 24 | 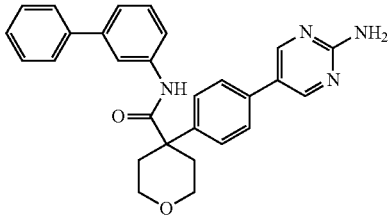 [SMILES: Nc1ncc(-c2ccc(C3(C(=O)Nc4cccc(-c5ccccc5)c4)CCOCC3)cc2)cn1] | 5 | 0.98 | 451 | C |
| 25 | 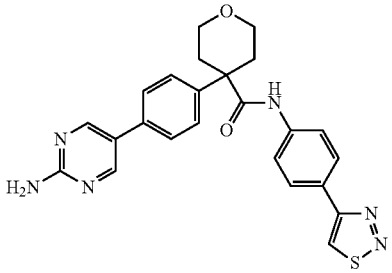 [SMILES: Nc1ncc(-c2ccc(C3(C(=O)Nc4ccc(-c5csnn5)cc4)CCOCC3)cc2)cn1] | 5 | 0.78 | 459 | C |
| 26 | 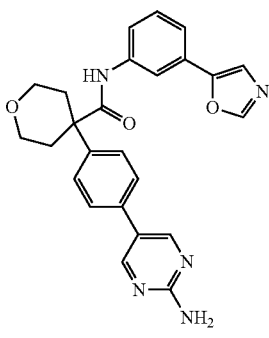 [SMILES: Nc1ncc(-c2ccc(C3(C(=O)Nc4cccc(-c5cnco5)c4)CCOCC3)cc2)cn1] | 5 | 0.74 | 442 | C |
| 27 | 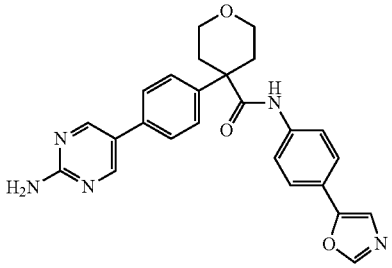 [SMILES: Nc1ncc(-c2ccc(C3(C(=O)Nc4ccc(-c5cnco5)cc4)CCOCC3)cc2)cn1] | 5 | 0.73 | 442 | C |

-continued

Table of final compounds

| Example | Structure | Method | Retention Time (min) | m/z | LC-MS Method |
|---|---|---|---|---|---|
| 28 | 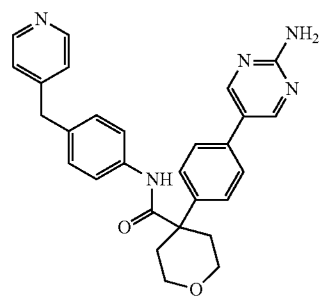 [SMILES: Nc1ncc(-c2ccc(C3(C(=O)Nc4ccc(Cc5ccncc5)cc4)CCOCC3)cc2)cn1] | 5 | 0.55 | 466 | C |
| 29 | 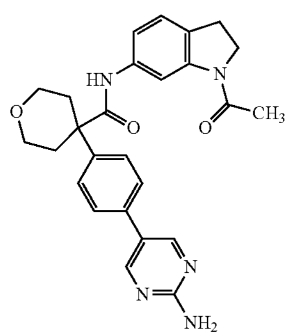 [SMILES: CC(=O)N1CCc2ccc(NC(=O)C3(c4ccc(-c5cnc(N)nc5)cc4)CCOCC3)cc21] | 5 | 0.69 | 458 | C |
| 30 | 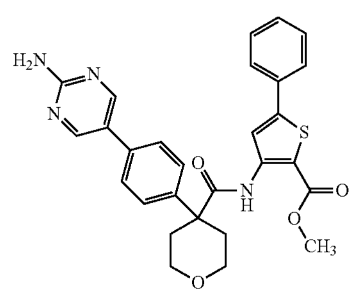 [SMILES: COC(=O)c1sc(-c2ccccc2)cc1NC(=O)C1(c2ccc(-c3cnc(N)nc3)cc2)CCOCC1] | 5 | 1.15 | 515 | C |
| 31 | 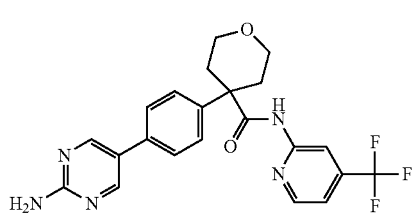 [SMILES: Nc1ncc(-c2ccc(C3(C(=O)Nc4cc(C(F)(F)F)ccn4)CCOCC3)cc2)cn1] | 5 | 0.9 | 442 (ES−) | C |
| 32 | 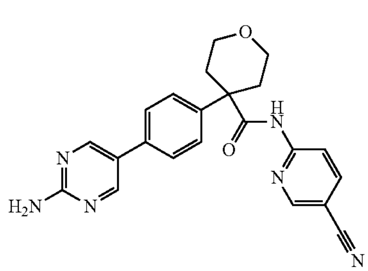 [SMILES: N#Cc1ccc(NC(=O)C2(c3ccc(-c4cnc(N)nc4)cc3)CCOCC2)nc1] | 5 | 0.72 | 401 | C |

-continued

Table of final compounds

| Example | Structure | Method | Retention Time (min) | m/z | LC-MS Method |
|---|---|---|---|---|---|
| 33 | 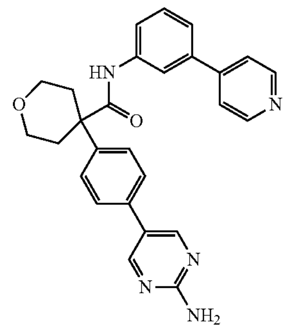 [SMILES: Nc1ncc(-c2ccc(C3(C(=O)Nc4cccc(-c5ccncc5)c4)CCOCC3)cc2)cn1] | 5 | 0.57 | 452 | C |
| 34 | 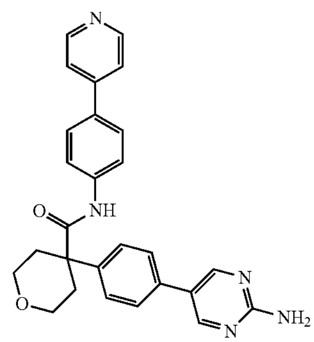 [SMILES: Nc1ncc(-c2ccc(C3(C(=O)Nc4ccc(-c5ccncc5)cc4)CCOCC3)cc2)cn1] | 5 | 0.55 | 452 | C |
| 35 | 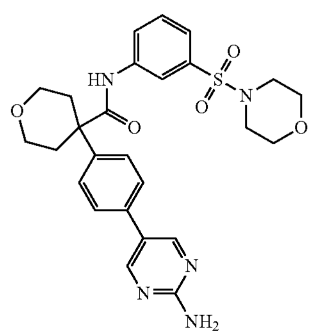 [SMILES: Nc1ncc(-c2ccc(C3(C(=O)Nc4cccc(S(=O)(=O)N5CCOCC5)c4)CCOCC3)cc2)cn1] | 5 | 0.75 | 524 | C |
| 36 | 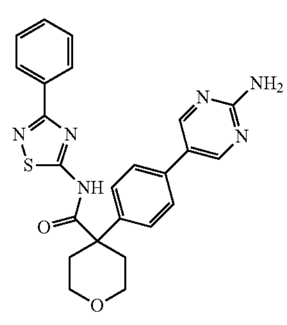 [SMILES: Nc1ncc(-c2ccc(C3(C(=O)Nc4nc(-c5ccccc5)ns4)CCOCC3)cc2)cn1] | 5 | 0.95 | 459 | C |

-continued

Table of final compounds

| Example | Structure | Method | Retention Time (min) | m/z | LC-MS Method |
|---|---|---|---|---|---|
| 37 | 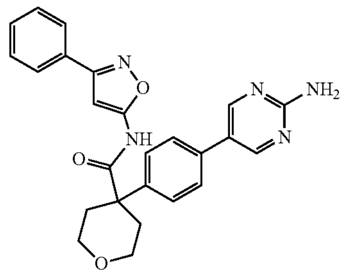 [SMILES: Nc1ncc(-c2ccc(C3(C(=O)Nc4cc(-c5ccccc5)no4)CCOCC3)cc2)cn1] | 5 | 0.89 | 440 (ES−) | C |
| 38 | 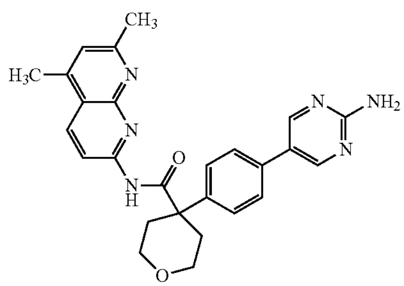 [SMILES: Cc1cc(C)c2ccc(NC(=O)C3(c4ccc(-c5cnc(N)nc5)cc4)CCOCC3)nc2n1] | 5 | 0.52 | 455 | C |
| 39 | 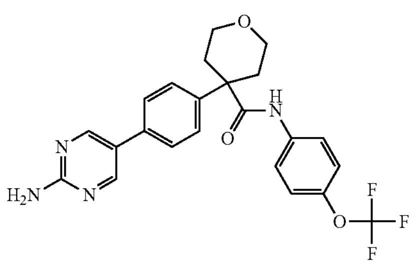 [SMILES: Nc1ncc(-c2ccc(C3(C(=O)Nc4ccc(OC(F)(F)F)cc4)CCOCC3)cc2)cn1] | 5 | 0.9 | 457 (ES−) | C |
| 40 | 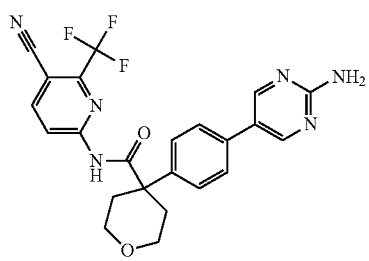 [SMILES: N#Cc1ccc(NC(=O)C2(c3ccc(-c4cnc(N)nc4)cc3)CCOCC2)nc1C(F)(F)F] | 5 | 0.87 | 466 (ES−) | C |
| 41 | 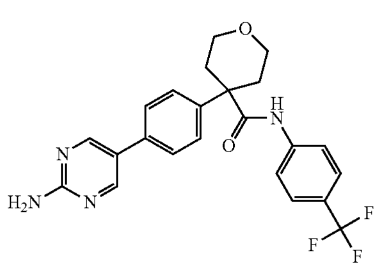 [SMILES: Nc1ncc(-c2ccc(C3(C(=O)Nc4ccc(C(F)(F)F)cc4)CCOCC3)cc2)cn1] | 5 | 0.89 | 441 (ES−) | C |

-continued

Table of final compounds

| Example | Structure | Method | Retention Time (min) | m/z | LC-MS Method |
|---|---|---|---|---|---|
| 42 | 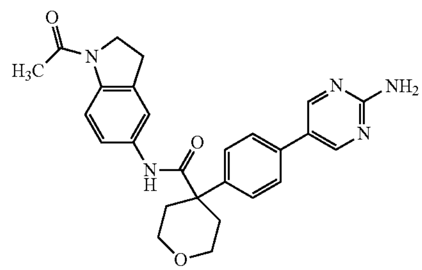 [SMILES: CC(=O)N1CCc2cc(NC(=O)C3(c4ccc(-c5cnc(N)nc5)cc4)CCOCC3)ccc21] | 5 | 0.6 | 458 | C |
| 43 | 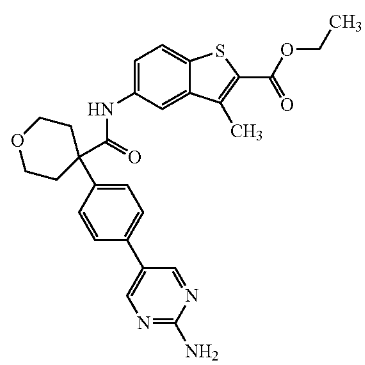 [SMILES: CCOC(=O)c1sc2ccc(NC(=O)C3(c4ccc(-c5cnc(N)nc5)cc4)CCOCC3)cc2c1C] | 5 | 0.96 | 516 | C |
| 44 | 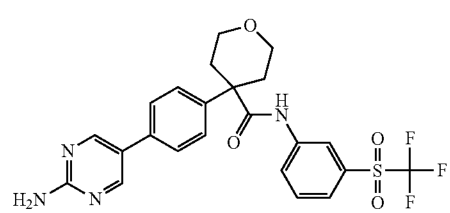 [SMILES: Nc1ncc(-c2ccc(C3(C(=O)Nc4cccc(S(=O)(=O)C(F)(F)F)c4)CCOCC3)cc2)cn1] | 5 | 0.89 | 505 (ES−) | C |
| 45 | 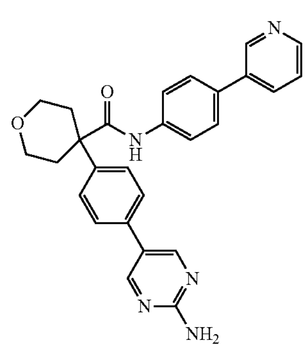 [SMILES: Nc1ncc(-c2ccc(C3(C(=O)Nc4ccc(-c5cccnc5)cc4)CCOCC3)cc2)cn1] | 5 | 0.52 | 452 | C |
| 46 | 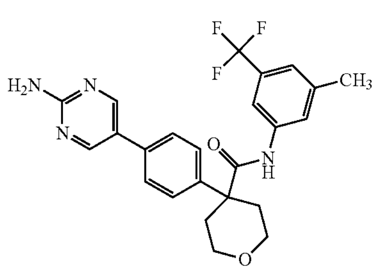 [SMILES: Cc1cc(NC(=O)C2(c3ccc(-c4cnc(N)nc4)cc3)CCOCC2)cc(C(F)(F)F)c1] | 5 | 0.94 | 457 | C |

-continued

Table of final compounds

| Example | Structure | Method | Retention Time (min) | m/z | LC-MS Method |
|---|---|---|---|---|---|
| 47 | 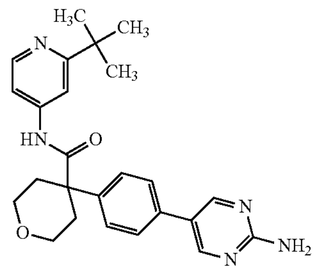 [SMILES: CC(C)(C)c1cc(NC(=O)C2(c3ccc(-c4cnc(N)nc4)cc3)CCOCC2)ccn1] | 5 | 0.54 | 432 | C |
| 48 | 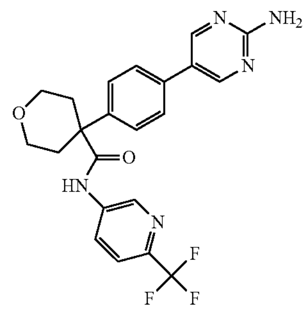 [SMILES: Nc1ncc(-c2ccc(C3(C(=O)Nc4ccc(C(F)(F)F)nc4)CCOCC3)cc2)cn1] | 5 | 0.78 | 444 | C |
| 49 | 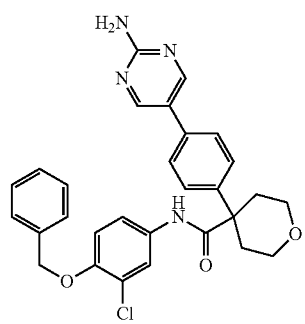 [SMILES: Nc1ncc(-c2ccc(C3(C(=O)Nc4ccc(OCc5ccccc5)c(Cl)c4)CCOCC3)cc2)cn1] | 5 | 0.99 | 515 | C |
| 50 | 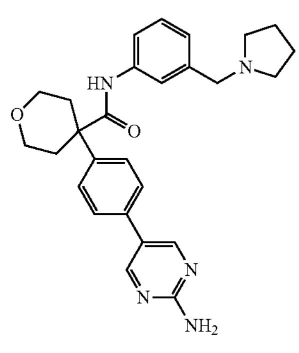 [SMILES: Nc1ncc(-c2ccc(C3(C(=O)Nc4cccc(CN5CCCC5)c4)CCOCC3)cc2)cn1] | 5 | 0.45 | 458 | C |
| 51 | 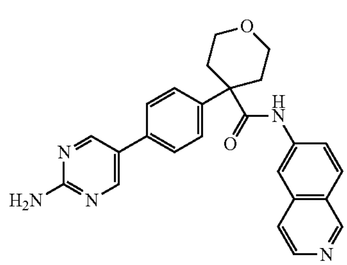 [SMILES: Nc1ncc(-c2ccc(C3(C(=O)Nc4ccc5cnccc5c4)CCOCC3)cc2)cn1] | 5 | 0.46 | 426 | C |

-continued

Table of final compounds

| Example | Structure | Method | Retention Time (min) | m/z | LC-MS Method |
|---|---|---|---|---|---|
| 52 | 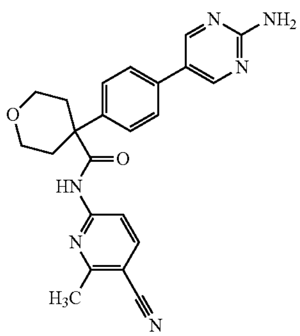 [SMILES: Cc1nc(NC(=O)C2(c3ccc(-c4cnc(N)nc4)cc3)CCOCC2)ccc1C#N] | 5 | 0.72 | 415 | C |
| 53 | 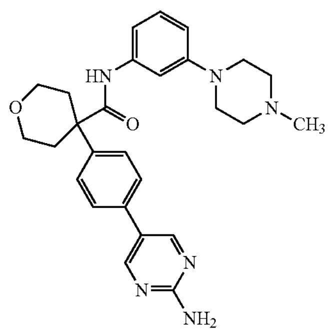 [SMILES: CN1CCN(c2cccc(NC(=O)C3(c4ccc(-c5cnc(N)nc5)cc4)CCOCC3)c2)CC1] | 5 | 0.45 | 473 | C |
| 54 | 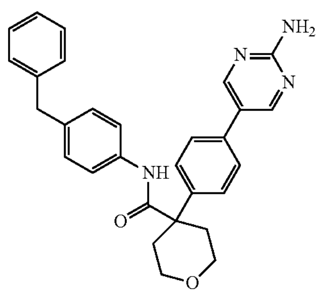 [SMILES: Nc1ncc(-c2ccc(C3(C(=O)Nc4ccc(Cc5ccccc5)cc4)CCOCC3)cc2)cn1] | 5 | 0.96 | 465 | C |
| 55 | 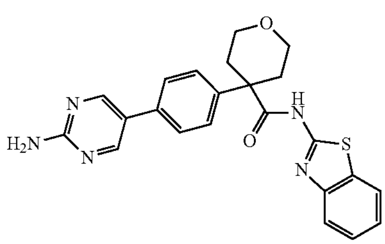 [SMILES: Nc1ncc(-c2ccc(C3(C(=O)Nc4nc5ccccc5s4)CCOCC3)cc2)cn1] | 5 | 0.82 | 432 | C |
| 56 | 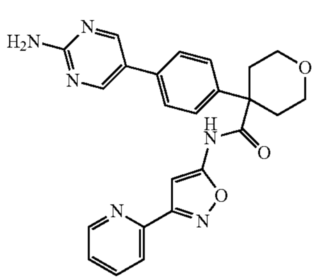 [SMILES: Nc1ncc(-c2ccc(C3(C(=O)Nc4cc(-c5ccccn5)no4)CCOCC3)cc2)cn1] | 5 | 0.66 | 443 | C |

-continued

Table of final compounds

| Example | Structure | Method | Retention Time (min) | m/z | LC-MS Method |
|---|---|---|---|---|---|
| 57 | 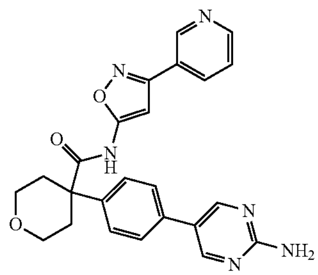 [SMILES: Nc1ncc(-c2ccc(C3(C(=O)Nc4cc(-c5cccnc5)no4)CCOCC3)cc2)cn1] | 5 | 0.59 | 443 | C |
| 58 | 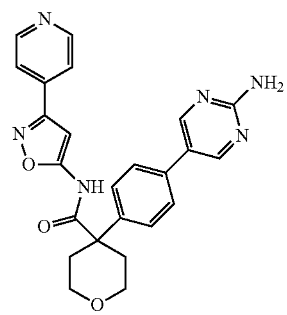 [SMILES: Nc1ncc(-c2ccc(C3(C(=O)Nc4cc(-c5ccncc5)no4)CCOCC3)cc2)cn1] | 5 | 0.54 | 443 | C |
| 59 | 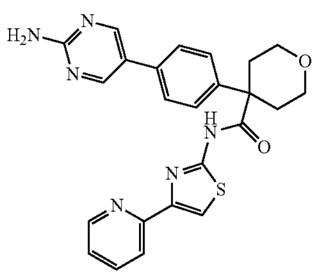 [SMILES: Nc1ncc(-c2ccc(C3(C(=O)Nc4nc(-c5ccccn5)cs4)CCOCC3)cc2)cn1] | 5 | 0.57 | 459 | C |
| 60 | 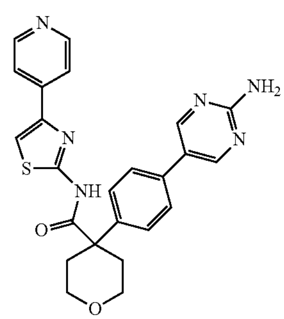 [SMILES: Nc1ncc(-c2ccc(C3(C(=O)Nc4nc(-c5ccncc5)cs4)CCOCC3)cc2)cn1] | 5 | 0.49 | 459 | C |
| 61 | 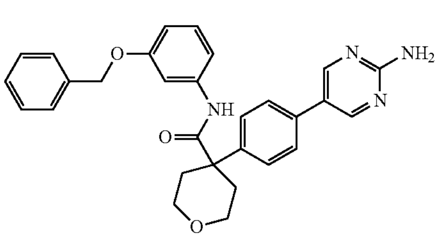 [SMILES: Nc1ncc(-c2ccc(C3(C(=O)Nc4cccc(OCc5ccccc5)c4)CCOCC3)cc2)cn1] | 5 | 0.93 | 481 | C |

-continued

Table of final compounds

| Example | Structure | Method | Retention Time (min) | m/z | LC-MS Method |
|---|---|---|---|---|---|
| 62 | 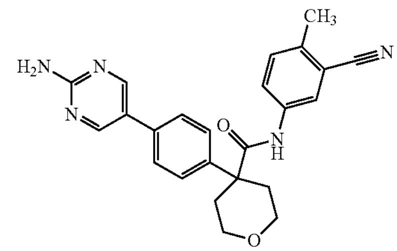 [SMILES: Cc1ccc(NC(=O)C2(c3ccc(-c4cnc(N)nc4)cc3)CCOCC2)cc1C#N] | 5 | 0.74 | 414 | C |
| 63 | 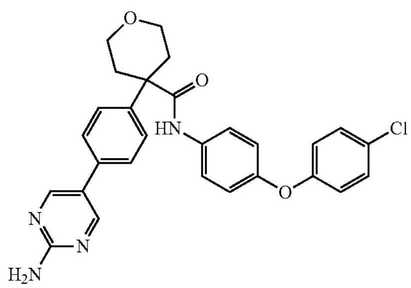 [SMILES: Nc1ncc(-c2ccc(C3(C(=O)Nc4ccc(Oc5ccc(Cl)cc5)cc4)CCOCC3)cc2)cn1] | 5 | 1.02 | 501 | C |
| 64 | 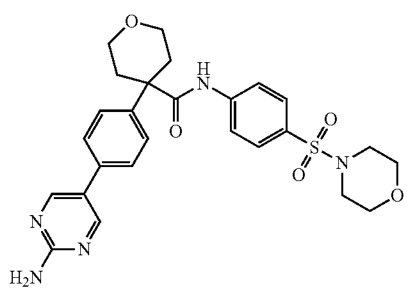 [SMILES: Nc1ncc(-c2ccc(C3(C(=O)Nc4ccc(S(=O)(=O)N5CCOCC5)cc4)CCOCC3)cc2)cn1] | 5 | 0.69 | 524 | C |
| 65 | 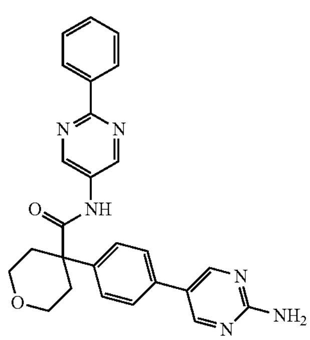 [SMILES: Nc1ncc(-c2ccc(C3(C(=O)Nc4cnc(-c5ccccc5)nc4)CCOCC3)cc2)cn1] | 5 | 0.81 | 453 | C |
| 66 | 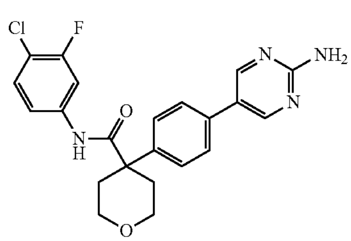 [SMILES: Nc1ncc(-c2ccc(C3(C(=O)Nc4ccc(Cl)c(F)c4)CCOCC3)cc2)cn1] | 5 | 0.86 | 427 | C |

-continued
Table of final compounds
| Example | Structure | Method | Retention Time (min) | m/z | LC-MS Method |
|---|---|---|---|---|---|
| 67 | 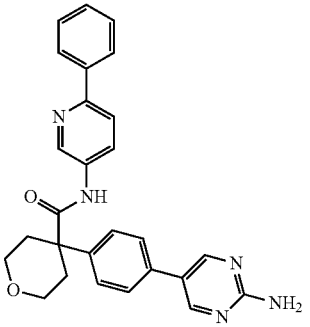 [SMILES: Nc1ncc(-c2ccc(C3(C(=O)Nc4ccc(-c5ccccc5)nc4)CCOCC3)cc2)cn1] | 5 | 0.77 | 452 | C |
| 68 | 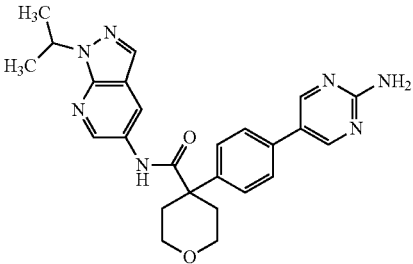 [SMILES: CC(C)n1ncc2cc(NC(=O)C3(c4ccc(-c5cnc(N)nc5)cc4)CCOCC3)cnc21] | 5 | 0.7 | 458 | C |
| 69 | 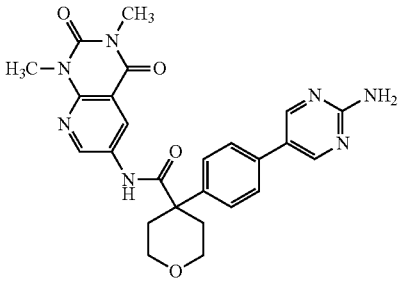 [SMILES: Cn1c(=O)c2cc(NC(=O)C3(c4ccc(-c5cnc(N)nc5)cc4)CCOCC3)cnc2n(C)c1=O] | 5 | 0.62 | 488 | C |
| 70 | 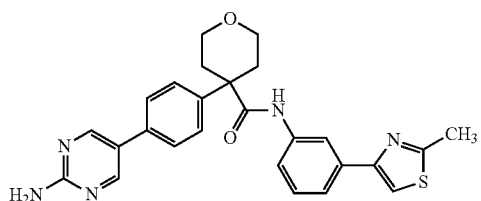 | 5 | 0.79 | 472 | C |
| 71 | 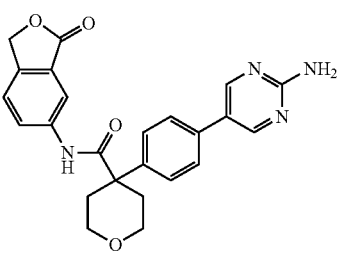 [SMILES: Nc1ncc(-c2ccc(C3(C(=O)Nc4ccc5c(c4)C(=O)OC5)CCOCC3)cc2)cn1] | 5 | 0.56 | 429 (ES−) | C |

-continued
Table of final compounds
| Example | Structure | Method | Retention Time (min) | m/z | LC-MS Method |
|---|---|---|---|---|---|
| 72 | 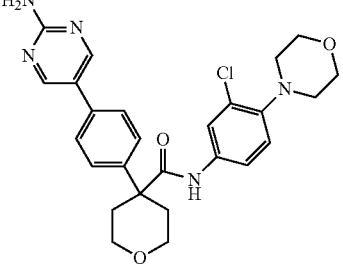 | 5 | 0.76 | 494 | C |
| 73 | 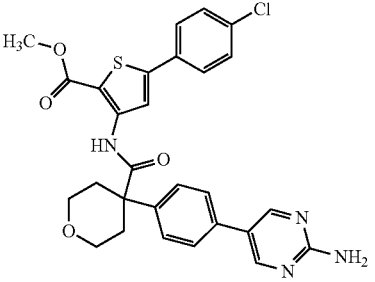 [SMILES: COC(=O)c1sc(-c2ccc(Cl)cc2)cc1NC(=O)C1(c2ccc(-c3cnc(N)nc3)cc2)CCOCC1] | 5 | 1.2 | 549 | C |
| 74 | 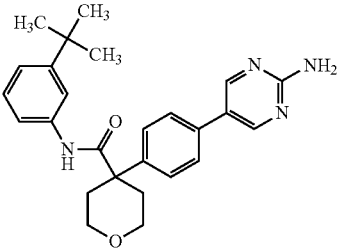 [SMILES: CC(C)(C)c1cccc(NC(=O)C2(c3ccc(-c4cnc(N)nc4)cc3)CCOCC2)c1] | 5 | 0.93 | 431 | C |
| 75 | 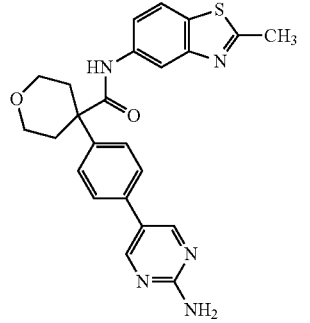 [SMILES: Cc1nc2cc(NC(=O)C3(c4ccc(-c5cnc(N)nc5)cc4)CCOCC3)ccc2s1] | 5 | 0.66 | 446 | C |
| 76 | 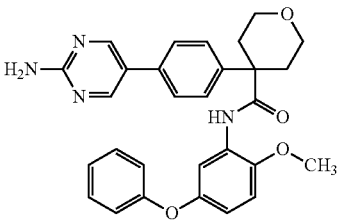 [SMILES: COc1ccc(Oc2ccccc2)cc1NC(=O)C1(c2ccc(-c3cnc(N)nc3)cc2)CCOCC1] | 5 | 0.96 | 497 | C |

-continued
Table of final compounds
| Example | Structure | Method | Retention Time (min) | m/z | LC-MS Method |
|---|---|---|---|---|---|
| 77 | 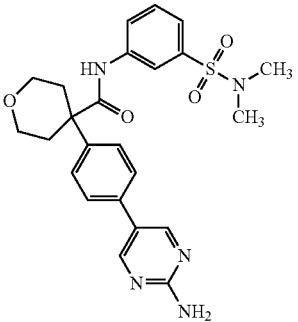 [SMILES: CN(C)S(=O)(=O)c1cccc(NC(=O)C2(c3ccc(-c4cnc(N)nc4)cc3)CCOCC2)c1] | 5 | 0.67 | 482 | C |
| 78 | 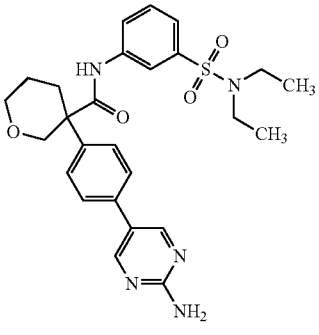 [SMILES: CCN(CC)S(=O)(=O)c1cccc(NC(=O)C2(c3ccc(-c4cnc(N)nc4)cc3)CCCOC2)c1] | 5 | 0.78 | 510 | C |
| 79 | 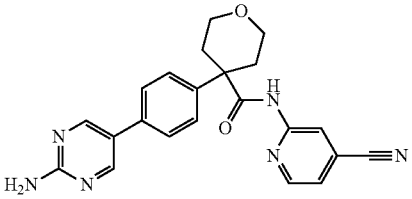 [SMILES: N#Cc1ccnc(NC(=O)C2(c3ccc(-c4cnc(N)nc4)cc3)CCOCC2)c1] | 5 | 0.64 | 399 (ES−) | C |
| 80 | 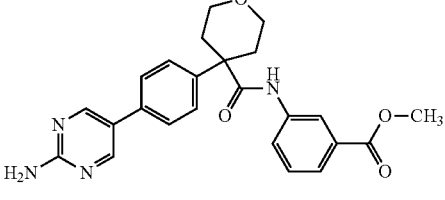 | 5 | 0.69 | 433 | C |
| 81 | 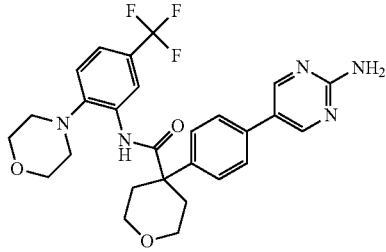 [SMILES: Nc1ncc(-c2ccc(C3(C(=O)Nc4cc(C(F)(F)F)ccc4N4CCOCC4)CCOCC3)cc2)cn1] | 5 | 0.93 | 528 | C |

-continued

Table of final compounds

| Example | Structure | Method | Retention Time (min) | m/z | LC-MS Method |
|---|---|---|---|---|---|
| 82 | 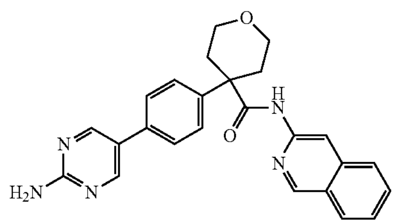 [SMILES: Nc1ncc(-c2ccc(C3(C(=O)Nc4cc5ccccc5cn4)CCOCC3)cc2)cn1] | 5 | 0.76 | 426 | C |
| 83 | 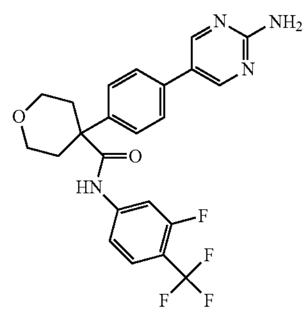 [SMILES: Nc1ncc(-c2ccc(C3(C(=O)Nc4ccc(C(F)(F)F)c(F)c4)CCOCC3)cc2)cn1] | 5 | 0.91 | 459 (ES−) | C |
| 84 | 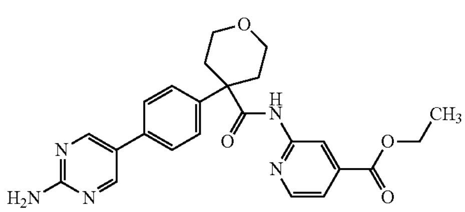 [SMILES: CCOC(=O)c1ccnc(NC(=O)C2(c3ccc(-c4cnc(N)nc4)cc3)CCOCC2)c1] | 5 | 0.74 | 448 | C |
| 85 | 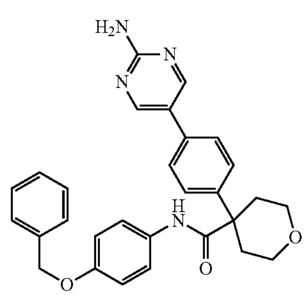 [SMILES: Nc1ncc(-c2ccc(C3(C(=O)Nc4ccc(OCc5ccccc5)cc4)CCOCC3)cc2)cn1] | 5 | 0.88 | 481 | C |
| 86 | 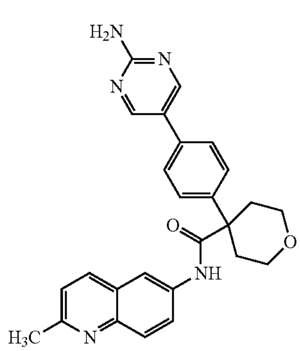 [SMILES: Cc1ccc2cc(NC(=O)C3(c4ccc(-c5cnc(N)nc5)cc4)CCOCC3)ccc2n1] | 5 | 0.42 | 440 | C |

-continued

Table of final compounds

| Example | Structure | Method | Retention Time (min) | m/z | LC-MS Method |
|---|---|---|---|---|---|
| 87 | 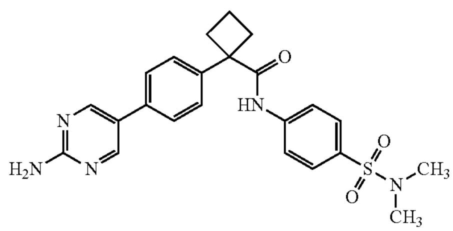 [SMILES: CN(C)S(=O)(=O)c1ccc(NC(=O)C2(c3ccc(-c4cnc(N)nc4)cc3)CCC2)cc1] | 4 | 2.21 | 452 | A |
| 88 | 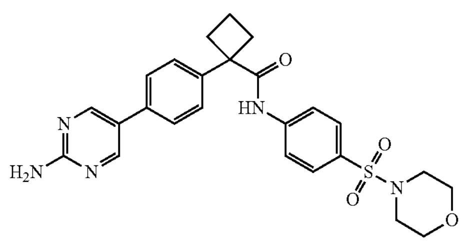 [SMILES: Nc1ncc(-c2ccc(C3(C(=O)Nc4ccc(S(=O)(=O)N5CCOCC5)cc4)CCC3)cc2)cn1] | 4 | 2.17 | 494 | A |
| 89 | 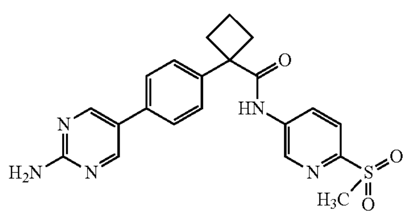 [SMILES: CS(=O)(=O)c1ccc(NC(=O)C2(c3ccc(-c4cnc(N)nc4)cc3)CCC2)cn1] | 4 | 1.79 | 424 | A |
| 90 | 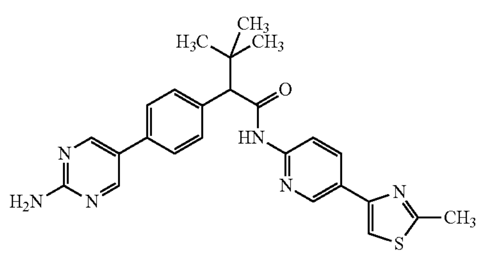 [SMILES: Cc1nc(-c2ccc(NC(=O)C(c3ccc(-c4cnc(N)nc4)cc3)C(C)(C)C)nc2)cs1] | 2 | 1.69 | 459 | D |
| 91 | 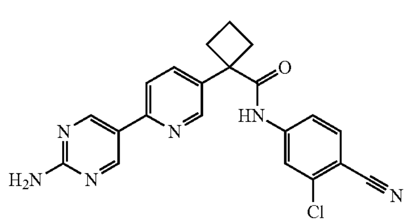 [SMILES: N#Cc1ccc(NC(=O)C2(c3ccc(-c4cnc(N)nc4)nc3)CCC2)cc1Cl] | 2 | 1.49 | 405 | D |
| 92 | 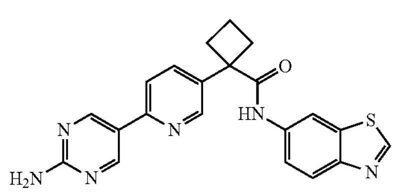 [SMILES: Nc1ncc(-c2ccc(C3(C(=O)Nc4ccc5ncsc5c4)CCC3)cn2)cn1] | 2 | 1.25 | 403 | D |

-continued

Table of final compounds

| Example | Structure | Method | Retention Time (min) | m/z | LC-MS Method |
|---|---|---|---|---|---|
| 93 | 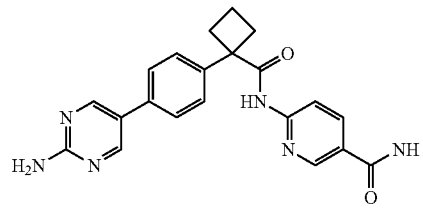 [SMILES: NC(=O)c1ccc(NC(=O)C2(c3ccc(-c4cnc(N)nc4)cc3)CCC2)nc1] | | 1.65 | 389 | A |
| 94 | 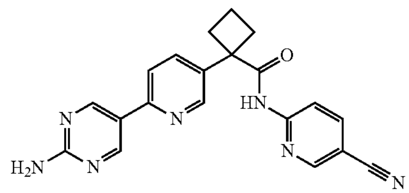 [SMILES: N#Cc1ccc(NC(=O)C2(c3ccc(-c4cnc(N)nc4)nc3)CCC2)nc1] | 4 | 1.88 | 372 | A |
| 95 | 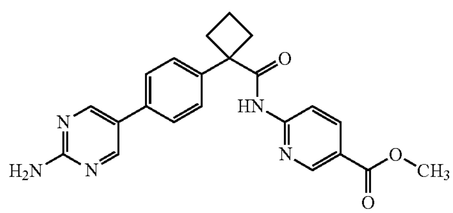 [SMILES: COC(=O)c1ccc(NC(=O)C2(c3ccc(-c4cnc(N)nc4)cc3)CCC2)nc1] | 4 | 1.24 | 404 | A |
| 96 | 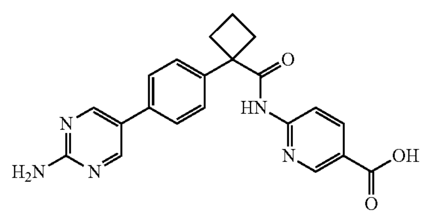 | 11 | 1.88 | 390 | A |
| 97 | 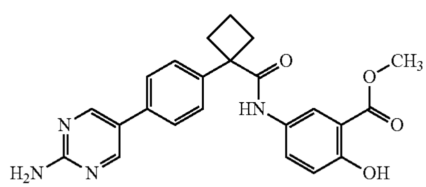 [SMILES: COC(=O)c1cc(NC(=O)C2(c3ccc(-c4cnc(N)nc4)cc3)CCC2)ccc1O] | 4 | 2.3 | 419 | A |
| 98 | 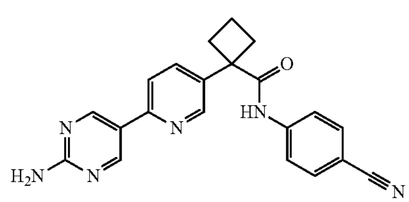 [SMILES: N#Cc1ccc(NC(=O)C2(c3ccc(-c4cnc(N)nc4)nc3)CCC2)cc1] | 2 | 1.35 | 371 | D |
| 99 | 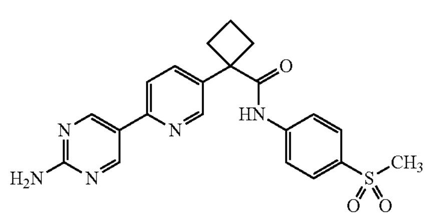 [SMILES: CS(=O)(=O)c1ccc(NC(=O)C2(c3ccc(-c4cnc(N)nc4)nc3)CCC2)cc1] | 2 | 1.21 | 424 | D |

-continued

Table of final compounds

| Example | Structure | Method | Retention Time (min) | m/z | LC-MS Method |
|---|---|---|---|---|---|
| 100 | 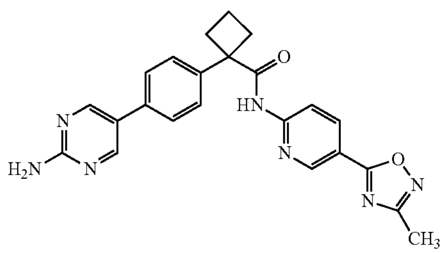 [SMILES: Cc1noc(-c2ccc(NC(=O)C3(c4ccc(-c5cnc(N)nc5)cc4)CCC3)nc2)n1] | 9 | 2.34 | 428 | A |
| 101 | 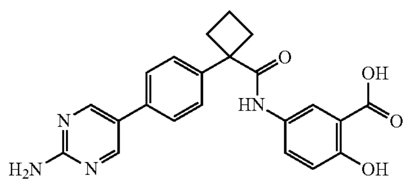 [SMILES: Nc1ncc(-c2ccc(C3(C(=O)Nc4ccc(O)c(C(=O)O)c4)CCC3)cc2)cn1] | 11 | 1.74 | 405 | A |
| 102 | 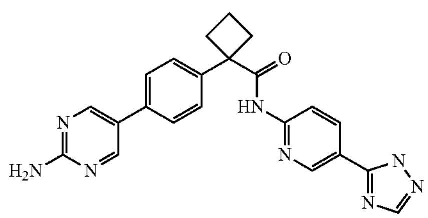 [SMILES: Nc1ncc(-c2ccc(C3(C(=O)Nc4ccc(-c5ncn[nH]5)cn4)CCC3)cc2)cn1] | | 1.67 | 413 | A |
| 103 | 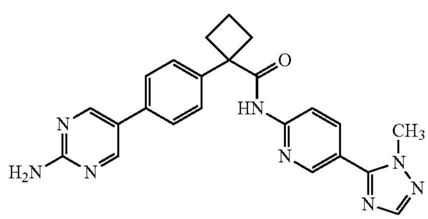 [SMILES: Cn1ncnc1-c1ccc(NC(=O)C2(c3ccc(-c4cnc(N)nc4)cc3)CCC2)nc1] | 103 | 1.81 | 427 | A |
| 104 | 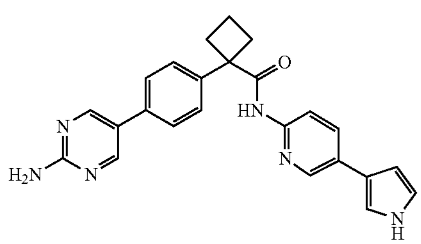 [SMILES: Nc1ncc(-c2ccc(C3(C(=O)Nc4ccc(-c5cc[nH]c5)cn4)CCC3)cc2)cn1] | 16 | 1.84 | 412 | A |
| 105 | 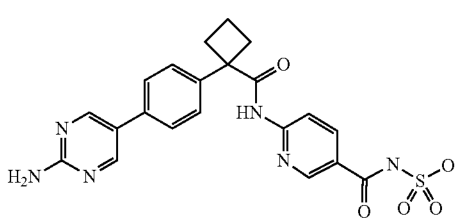 [SMILES: Nc1ncc(-c2ccc(C3(C(=O)Nc4ccc(C(=O)NS(=O)(=O)O)cn4)CCC3)cc2)cn1] | 14 | 1.81 | 467 | A |

-continued

Table of final compounds

| Example | Structure | Method | Retention Time (min) | m/z | LC-MS Method |
|---|---|---|---|---|---|
| 106 | 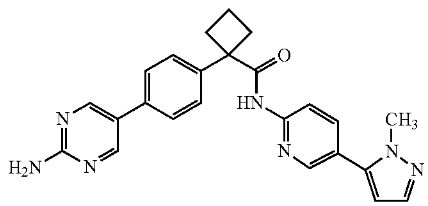 [SMILES: Cn1nccc1-c1ccc(NC(=O)C2(c3ccc(-c4cnc(N)nc4)cc3)CCC2)nc1] | 16 | 1.57 | 426 | E |
| 107 | 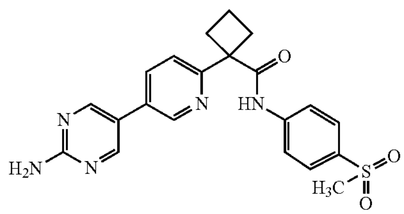 [SMILES: CS(=O)(=O)c1ccc(NC(=O)C2(c3ccc(-c4cnc(N)nc4)cn3)CCC2)cc1] | 15 | 1.67 | 424 | A |
| 108 | 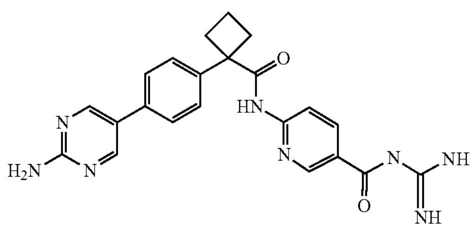 [SMILES: N=C(N)NC(=O)c1ccc(NC(=O)C2(c3ccc(-c4cnc(N)nc4)cc3)CCC2)nc1] | 12 | 1.43 | 431 | A |
| 109 | 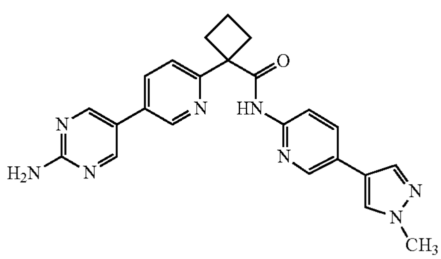 [SMILES: Cn1cc(-c2ccc(NC(=O)C3(c4ccc(-c5cnc(N)nc5)cn4)CCC3)nc2)cn1] | 15 | 1.8 | 427 | A |
| 110 | 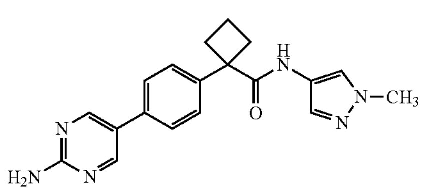 [SMILES: Cn1cc(NC(=O)C2(c3ccc(-c4cnc(N)nc4)cc3)CCC2)cn1] | 1 | 1.17 | 349 | D |
| 111 | 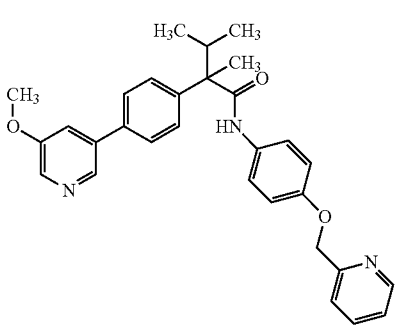 [SMILES: COc1cncc(-c2ccc(C(C)(C(=O)Nc3ccc(OCc4ccccn4)cc3)C(C)C)cc2)c1] | 20 | 1.81 | 482 | D |

-continued

Table of final compounds

| Example | Structure | Method | Retention Time (min) | m/z | LC-MS Method |
|---|---|---|---|---|---|
| 112 | 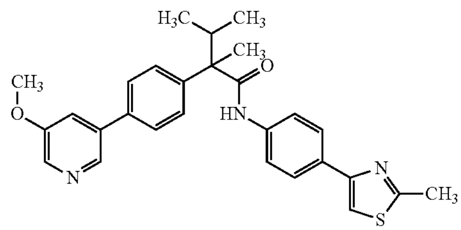 [SMILES: COc1cncc(-c2ccc(C(C)(C(=O)Nc3ccc(-c4csc(C)n4)cc3)C(C)C)cc2)c1] | 20 | 1.76 | 472 | D |
| 113 | 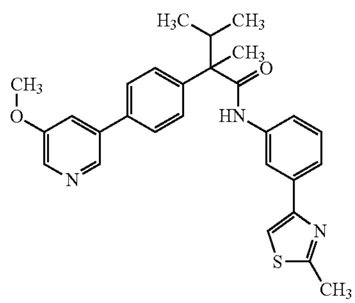 [SMILES: COc1cncc(-c2ccc(C(C)(C(=O)Nc3cccc(-c4csc(C)n4)c3)C(C)C)cc2)c1] | 20 | 2.02 | 472 | D |
| 114 | 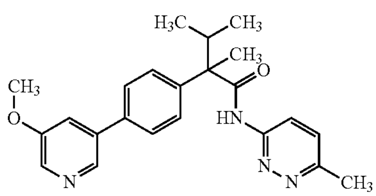 [SMILES: COc1cncc(-c2ccc(C(C)(C(=O)Nc3ccc(C)nn3)C(C)C)cc2)c1] | 20 | 1.42 | 391 | D |
| 115 | 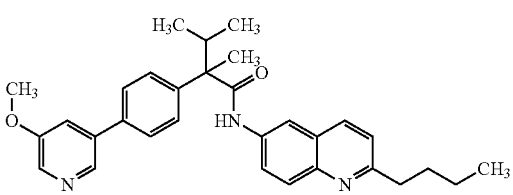 [SMILES: CCCCc1ccc2cc(NC(=O)C(C)(c3ccc(-c4cncc(OC)c4)cc3)C(C)C)ccc2n1] | 20 | 1.49 | 482 | D |
| 116 | 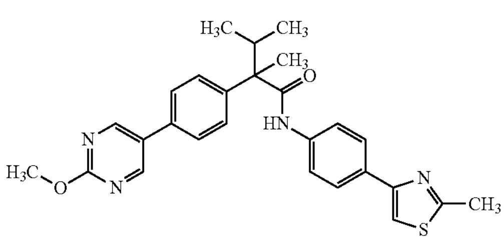 | 2 | 2.02 | 473 | D |
| 117 | 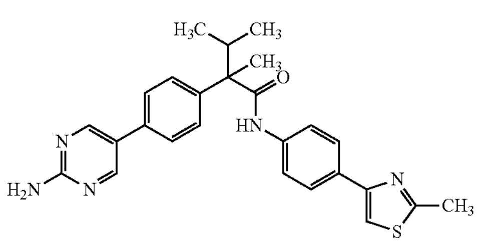 | 2 | 1.66 | 458 | D |

-continued

Table of final compounds

| Example | Structure | Method | Retention Time (min) | m/z | LC-MS Method |
|---|---|---|---|---|---|
| 118 | 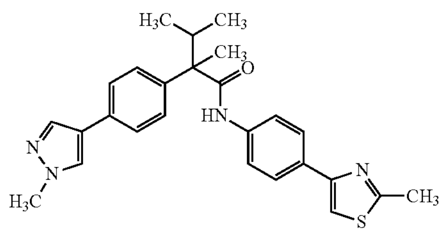 [SMILES: Cc1nc(-c2ccc(NC(=O)C(C)(c3ccc(-c4cnn(C)c4)cc3)C(C)C)cc2)cs1] | 2 | 1.79 | 445 | D |
| 119 | 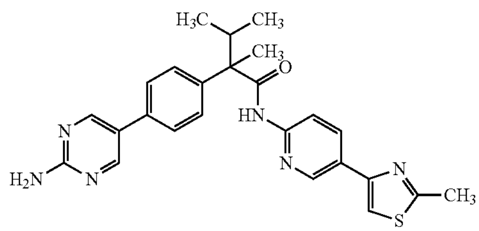 [SMILES: Cc1nc(-c2ccc(NC(=O)C(C)(c3ccc(-c4cnc(N)nc4)cc3)C(C)C)nc2)cs1] | 2 | 1.66 | 459 | D |
| 120 | 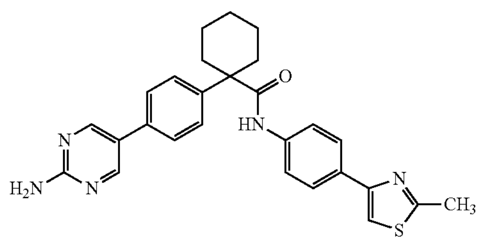 [SMILES: Cc1nc(-c2ccc(NC(=O)C3(c4ccc(-c5cnc(N)nc5)cc4)CCCCC3)cc2)cs1] | 2 | 1.74 | 470 | D |
| 121 | 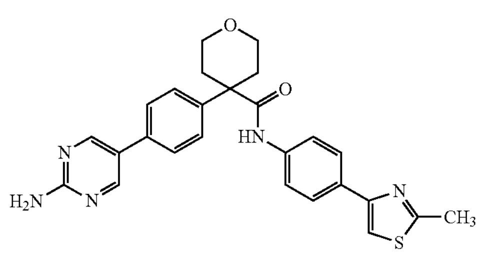 [SMILES: Cc1nc(-c2ccc(NC(=O)C3(c4ccc(-c5cnc(N)nc5)cc4)CCOCC3)cc2)cs1] | 2 | 1.45 | 472 | D |
| 122 | 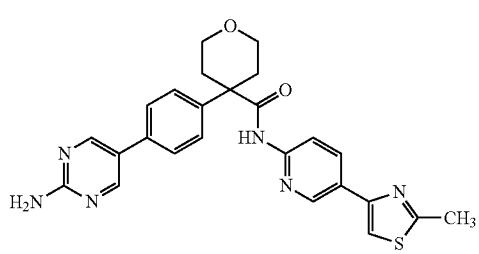 [SMILES: Cc1nc(-c2ccc(NC(=O)C3(c4ccc(-c5cnc(N)nc5)cc4)CCOCC3)nc2)cs1] | 4 | 2.42 | 473 | A |
| 123 | 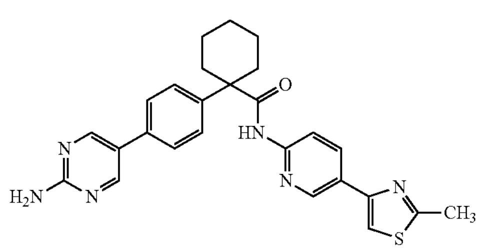 [SMILES: Cc1nc(-c2ccc(NC(=O)C3(c4ccc(-c5cnc(N)nc5)cc4)CCCCC3)nc2)cs1] | 2 | 1.73 | 471 | D |

-continued

Table of final compounds

| Example | Structure | Method | Retention Time (min) | m/z | LC-MS Method |
|---|---|---|---|---|---|
| 124 | 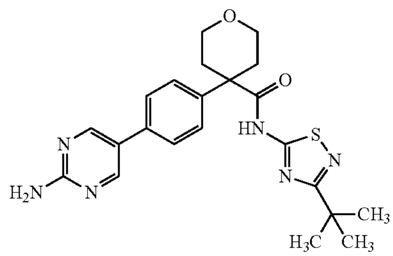 [SMILES: CC(C)(C)c1nsc(NC(=O)C2(c3ccc(-c4cnc(N)nc4)cc3)CCOCC2)n1] | 2 | 1.57 | 439 | D |
| 125 | 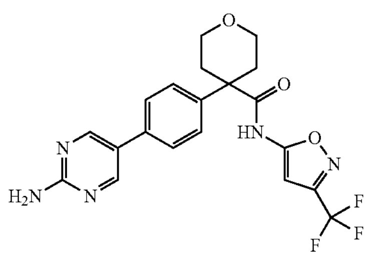 [SMILES: Nc1ncc(-c2ccc(C3(C(=O)Nc4cc(C(F)(F)F)no4)CCOCC3)cc2)cn1] | 2 | 1.53 | 434 | D |
| 126 | 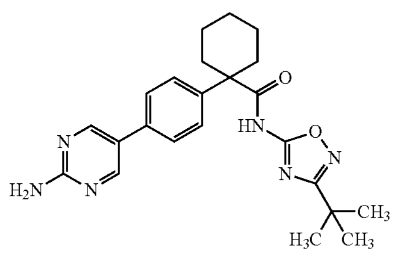 [SMILES: CC(C)(C)c1noc(NC(=O)C2(c3ccc(-c4cnc(N)nc4)cc3)CCCCC2)n1] | 2 | 1.64 | 421 | D |
| 127 | 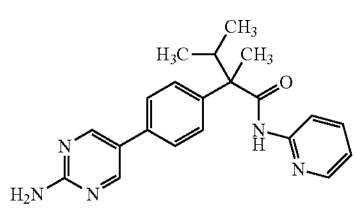 [SMILES: CC(C)C(C)(C(=O)Nc1ccccn1)c1ccc(-c2cnc(N)nc2)cc1] | 4 | 2.45 | 362 | A |
| 128 | 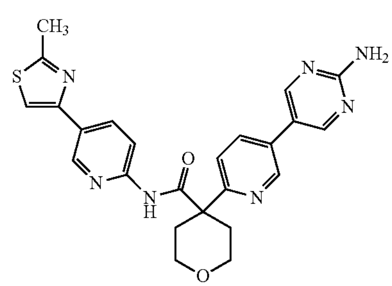 [SMILES: Cc1nc(-c2ccc(NC(=O)C3(c4ccc(-c5cnc(N)nc5)cn4)CCOCC3)nc2)cs1] | 6 | 3.5 | 474 | G |
| 129 | 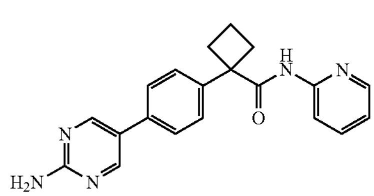 [SMILES: Nc1ncc(-c2ccc(C3(C(=O)Nc4ccccn4)CCC3)cc2)cn1] | 6 | 3.34 | 346 | G |

-continued
Table of final compounds
| Example | Structure | Method | Retention Time (min) | m/z | LC-MS Method |
|---|---|---|---|---|---|
| 130 | 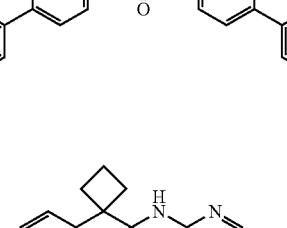 | 6 | 3.56 | 453 | G |
| 131 | 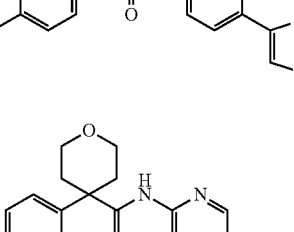 | 6 | 4.01 | 443 | G |
| 132 | 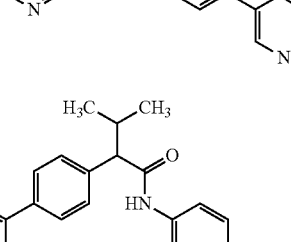 | 6 | 3.04 | 484 | G |
| 133 | 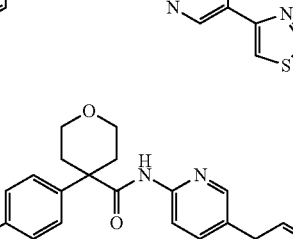 | 2 | 1.62 | 445 | D |
| 134 | 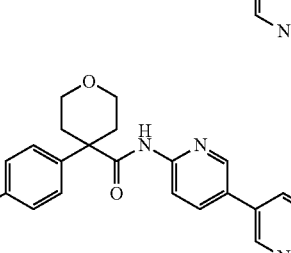 | 1 | 1.44 | 483 | D |
| 135 | 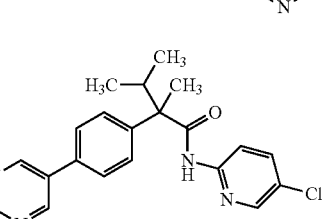 | 1 | 1.25 | 483 | D |
| 136 | 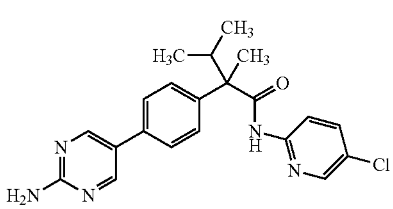 [SMILES: CC(C)C(C)(C(=O)Nc1ccc(Cl)cn1)c1ccc(-c2cnc(N)nc2)cc1] | 4 | 2.97 | 396 | A |

-continued

Table of final compounds

| Example | Structure | Method | Retention Time (min) | m/z | LC-MS Method |
|---|---|---|---|---|---|
| 138 | 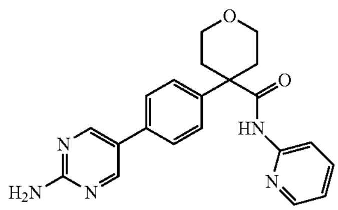 [SMILES: Nc1ncc(-c2ccc(C3(C(=O)Nc4ccccn4)CCOCC3)cc2)cn1] | 4 | 1.84 | 376 | A |
| 139 | 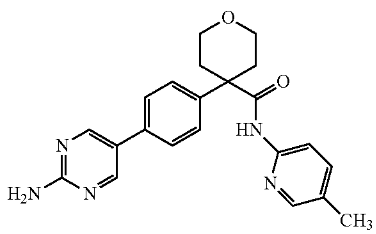 [SMILES: Cc1ccc(NC(=O)C2(c3ccc(-c4cnc(N)nc4)cc3)CCOCC2)nc1] | 4 | 2.01 | 390 | A |
| 140 | 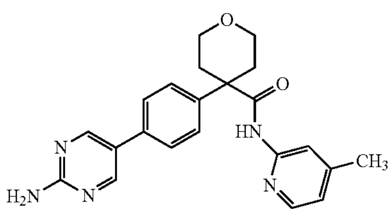 [SMILES: Cc1ccnc(NC(=O)C2(c3ccc(-c4cnc(N)nc4)cc3)CCOCC2)c1] | 4 | 1.92 | 390 | A |
| 141 | 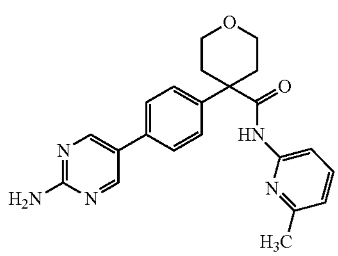 [SMILES: Cc1cccc(NC(=O)C2(c3ccc(-c4cnc(N)nc4)cc3)CCOCC2)n1] | 4 | 2.04 | 390 | F |
| 142 | 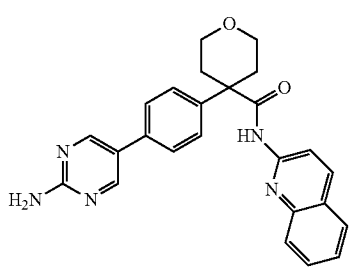 [SMILES: Nc1ncc(-c2ccc(C3(C(=O)Nc4ccc5ccccc5n4)CCOCC3)cc2)cn1] | 4 | 1.54 | 426 | E |
| 143 | 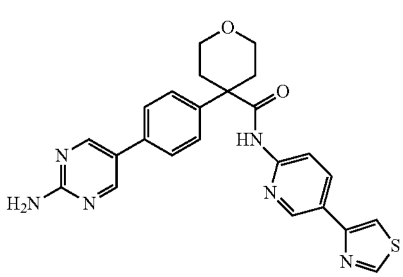 [SMILES: Nc1ncc(-c2ccc(C3(C(=O)Nc4ccc(-c5cscn5)cn4)CCOCC3)cc2)cn1] | 4 | 2.22 | 459 | F |

-continued

Table of final compounds

| Example | Structure | Method | Retention Time (min) | m/z | LC-MS Method |
|---|---|---|---|---|---|
| 144 | 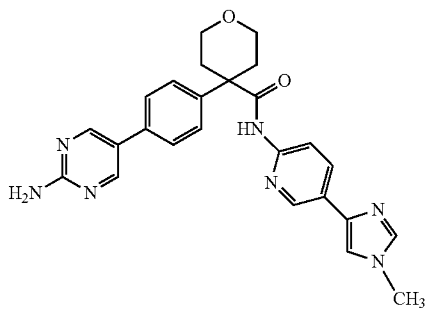 [SMILES: Cn1cnc(-c2ccc(NC(=O)C3(c4ccc(-c5cnc(N)nc5)cc4)CCOCC3)nc2)c1] | 4 | 1.33 | 456 | F |
| 145 | 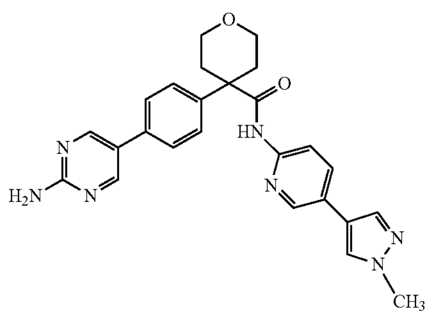 [SMILES: Cn1cc(-c2ccc(NC(=O)C3(c4ccc(-c5cnc(N)nc5)cc4)CCOCC3)nc2)cn1] | 4 | 1.96 | 456 | F |
| 146 | 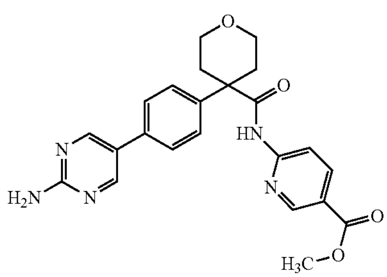 [SMILES: COC(=O)c1ccc(NC(=O)C2(c3ccc(-c4cnc(N)nc4)cc3)CCOCC2)nc1] | 4 | 1.35 | 434 | E |
| 147 | 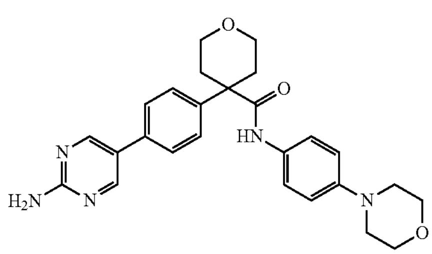 [SMILES: Nc1ncc(-c2ccc(C3(C(=O)Nc4ccc(N5CCOCC5)cc4)CCOCC3)cc2)cn1] | 2 | 1.35 | 460 | D |
| 148 | 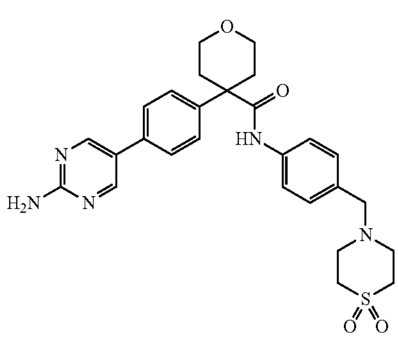 [SMILES: Nc1ncc(-c2ccc(C3(C(=O)Nc4ccc(CN5CCS(=O)(=O)CC5)cc4)CCOCC3)cc2)cn1] | 2 | 1.22 | 522 | D |

-continued

Table of final compounds

| Example | Structure | Method | Retention Time (min) | m/z | LC-MS Method |
|---|---|---|---|---|---|
| 149 | 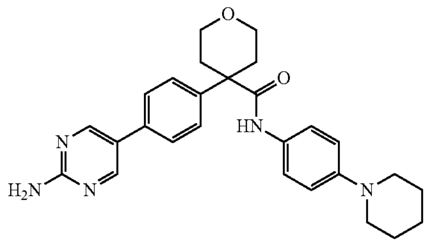 [SMILES: Nc1ncc(-c2ccc(C3(C(=O)Nc4ccc(N5CCCCC5)cc4)CCOCC3)cc2)cn1] | 2 | 1.14 | 458 | D |
| 150 | 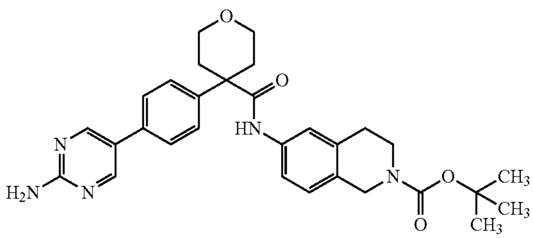 [SMILES: CC(C)(C)OC(=O)N1CCc2cc(NC(=O)C3(c4ccc(-c5cnc(N)nc5)cc4)CCOCC3)ccc2C1] | 2 | 1.57 | 530 | D |
| 151 | 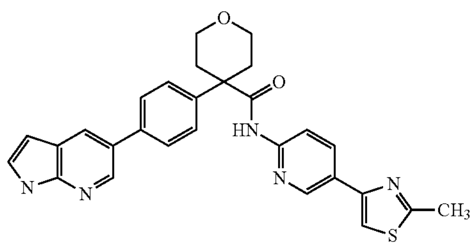 [SMILES: Cc1nc(-c2ccc(NC(=O)C3(c4ccc(-c5cnc6[nH]ccc6c5)cc4)CCOCC3)nc2)cs1] | 2 | 1.56 | 496 | D |
| 152 | 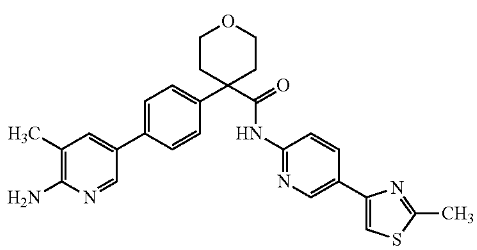 | 17 | 1.28 | 486 | D |
| 153 | 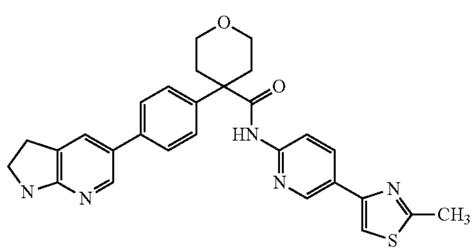 [SMILES: Cc1nc(-c2ccc(NC(=O)C3(c4ccc(-c5cnc6c(c5)CCN6)cc4)CCOCC3)nc2)cs1] | 17 | 1.26 | 498 | D |
| 154 | 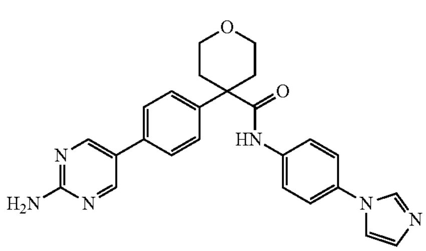 [SMILES: Nc1ncc(-c2ccc(C3(C(=O)Nc4ccc(-n5ccnc5)cc4)CCOCC3)cc2)cn1] | 2 | 1.17 | 441 | D |

-continued

Table of final compounds

| Example | Structure | Method | Retention Time (min) | m/z | LC-MS Method |
|---|---|---|---|---|---|
| 155 | 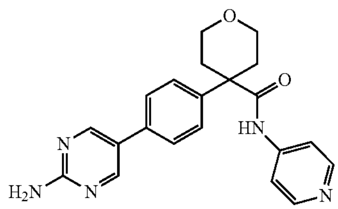 [SMILES: Nc1ncc(-c2ccc(C3(C(=O)Nc4ccncc4)CCOCC3)cc2)cn1] | 4 | 1.47 | 376 | A |
| 156 | 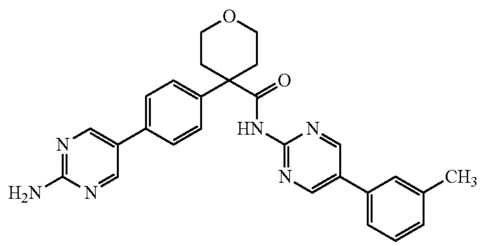 [SMILES: Cc1cccc(-c2cnc(NC(=O)C3(c4ccc(-c5cnc(N)nc5)cc4)CCOCC3)nc2)c1] | 2 | 1.45 | 467 | D |
| 157 | 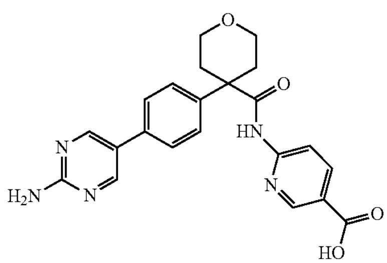 [SMILES: Nc1ncc(-c2ccc(C3(C(=O)Nc4ccc(C(=O)O)cn4)CCOCC3)cc2)cn1] | 11 | 1.8 | 420 | A |
| 158 | 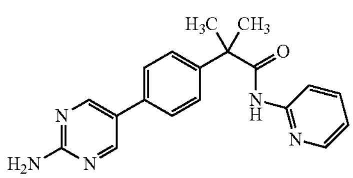 [SMILES: CC(C)(C(=O)Nc1ccccn1)c1ccc(-c2cnc(N)nc2)cc1] | 4 | 2.02 | 334 | A |
| 159 | 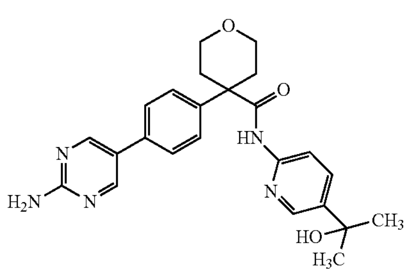 [SMILES: CC(C)(O)c1ccc(NC(=O)C2(c3ccc(-c4cnc(N)nc4)cc3)CCOCC2)nc1] | 10 | 1.86 | 434 | A |
| 160 | 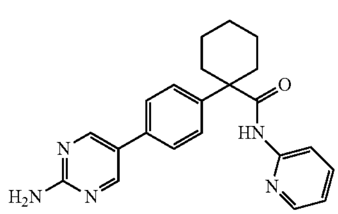 [SMILES: Nc1ncc(-c2ccc(C3(C(=O)Nc4ccccn4)CCCCC3)cc2)cn1] | 4 | 2.59 | 374 | A |

-continued

Table of final compounds

| Example | Structure | Method | Retention Time (min) | m/z | LC-MS Method |
|---|---|---|---|---|---|
| 161 | 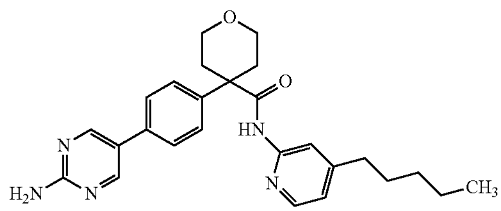 [SMILES: CCCCCc1ccnc(NC(=O)C2(c3ccc(-c4cnc(N)nc4)cc3)CCOCC2)c1] | 4 | 2.86 | 446 | A |
| 162 | 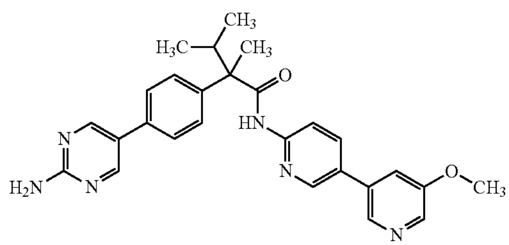 [SMILES: COc1cncc(-c2ccc(NC(=O)C(C)(c3ccc(-c4cnc(N)nc4)cc3)C(C)C)nc2)c1] | 2 | 1.65 | 469 | D |
| 163 | 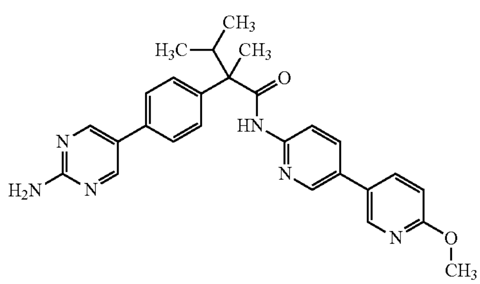 [SMILES: COc1ccc(-c2ccc(NC(=O)C(C)(c3ccc(-c4cnc(N)nc4)cc3)C(C)C)nc2)cn1] | 2 | 1.91 | 469 | D |
| 164 | 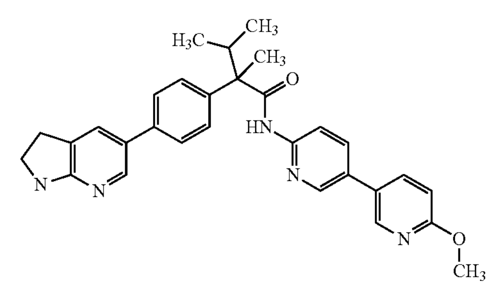 [SMILES: COc1ccc(-c2ccc(NC(=O)C(C)(c3ccc(-c4cnc5c(c4)CCN5)cc3)C(C)C)nc2)cn1] | 18 | 1.64 | 494 | D |
| 165 | 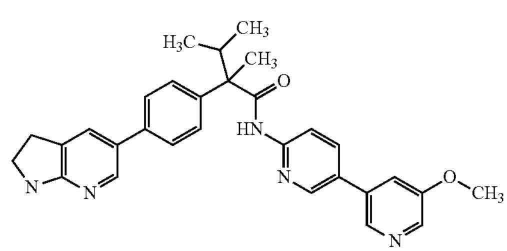 [SMILES: COc1cncc(-c2ccc(NC(=O)C(C)(c3ccc(-c4cnc5c(c4)CCN5)cc3)C(C)C)nc2)c1] | 2 | 1.47 | 494 | D |

-continued

Table of final compounds

| Example | Structure | Method | Retention Time (min) | m/z | LC-MS Method |
|---|---|---|---|---|---|
| 166 | 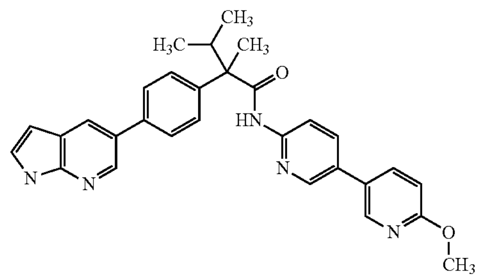 [SMILES: COc1ccc(-c2ccc(NC(=O)C(C)(c3ccc(-c4cnc5[nH]ccc5c4)cc3)C(C)C)nc2)cn1] | 2 | 1.87 | 492 | D |
| 167 | 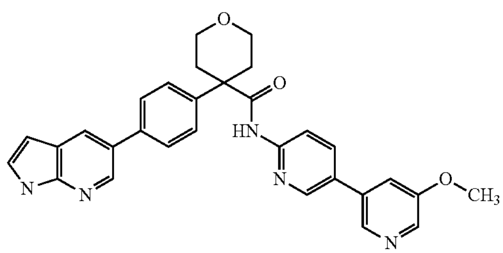 [SMILES: COc1cncc(-c2ccc(NC(=O)C3(c4ccc(-c5cnc6[nH]ccc6c5)cc4)CCOCC3)nc2)c1] | 2 | 1.56 | 506 | D |
| 168 | 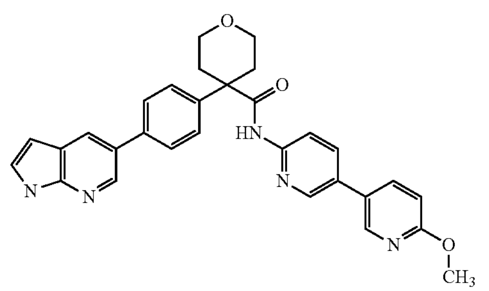 [SMILES: COc1ccc(-c2ccc(NC(=O)C3(c4ccc(-c5cnc6[nH]ccc6c5)cc4)CCOCC3)nc2)cn1] | 2 | 1.69 | 506 | D |
| 169 | 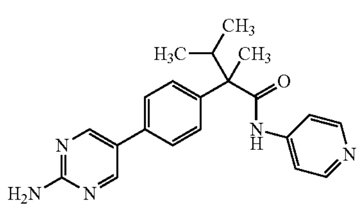 [SMILES: CC(C)C(C)(C(=O)Nc1ccncc1)c1ccc(-c2cnc(N)nc2)cc1] | 4 | 2.03 | 362 | A |
| 170 | 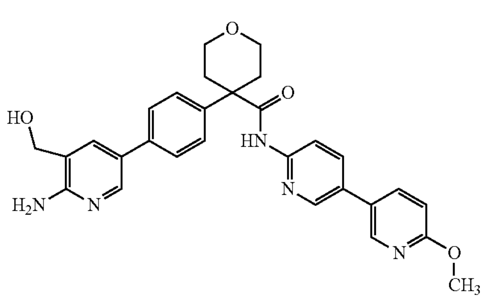 [SMILES: COc1ccc(-c2ccc(NC(=O)C3(c4ccc(-c5cnc(N)c(CO)c5)cc4)CCOCC3)nc2)cn1] | 17 | 1.37 | 510 (ES−) | D |

-continued

Table of final compounds

| Example | Structure | Method | Retention Time (min) | m/z | LC-MS Method |
|---------|-----------|--------|----------------------|-----|--------------|
| 171 | 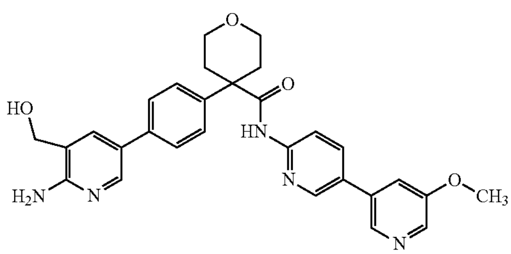 [SMILES: COc1cncc(-c2ccc(NC(=O)C3(c4ccc(-c5cnc(N)c(CO)c5)cc4)CCOCC3)nc2)c1] | 17 | 1.18 | 512 | D |
| 173 | 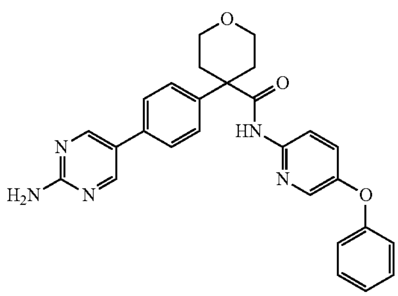 [SMILES: Nc1ncc(-c2ccc(C3(C(=O)Nc4ccc(Oc5ccccc5)cn4)CCOCC3)cc2)cn1] | 1 | 1.35 | 468 | B |
| 174 | 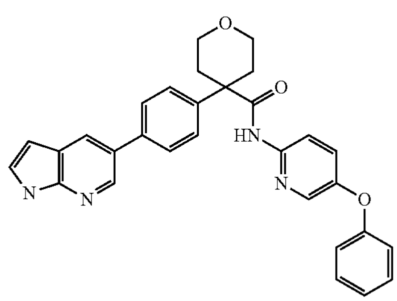 [SMILES: O=C(Nc1ccc(Oc2ccccc2)cn1)C1(c2ccc(-c3cnc4[nH]ccc4c3)cc2)CCOCC1] | 1 | 1.47 | 491 | B |
| 175 | 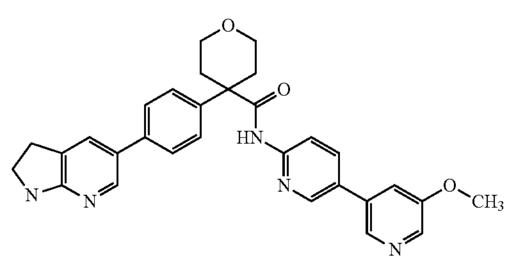 [SMILES: COc1cncc(-c2ccc(NC(=O)C3(c4ccc(-c5cnc6c(c5)CCN6)cc4)CCOCC3)nc2)c1] | 17 | 1.19 | 508 | D |
| 176 | 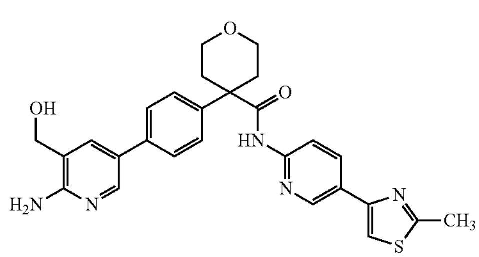 [SMILES: Cc1nc(-c2ccc(NC(=O)C3(c4ccc(-c5cnc(N)c(CO)c5)cc4)CCOCC3)nc2)cs1] | 19 | 1.16 | 500 (ES−) | D |

Table of final compounds

| Example | Structure | Method | Retention Time (min) | m/z | LC-MS Method |
|---|---|---|---|---|---|
| 177 | 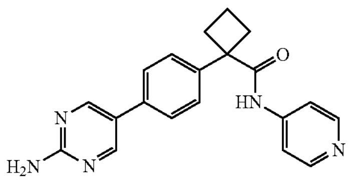 [SMILES: Nc1ncc(-c2ccc(C3(C(=O)Nc4ccncc4)CCC3)cc2)cn1] | 1 | 1.02 | 346 | B |
| 178 | 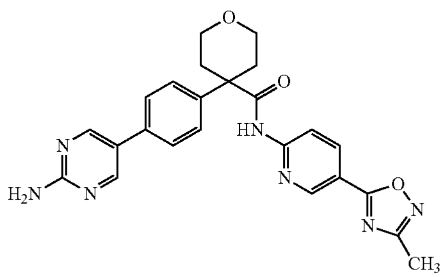 [SMILES: Cc1noc(-c2ccc(NC(=O)C3(c4ccc(-c5cnc(N)nc5)cc4)CCOCC3)nc2)n1] | 9 | 2.4 | 458 | A |
| 179 | 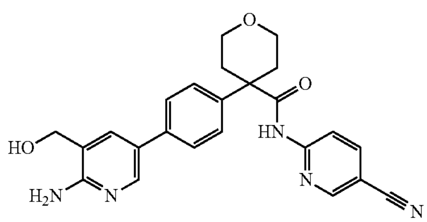 [SMILES: N#Cc1ccc(NC(=O)C2(c3ccc(-c4cnc(N)c(CO)c4)cc3)CCOCC2)nc1] | 8 | 1.89 | 430 | A |
| 180 | 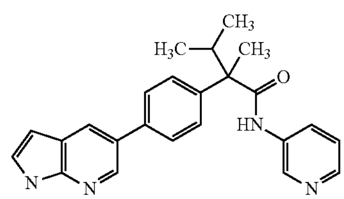 [SMILES: CC(C)C(C)(C(=O)Nc1cccnc1)c1ccc(-c2cnc3[nH]ccc3c2)cc1] | 1 | 1.28 | 385 | B |
| 181 | 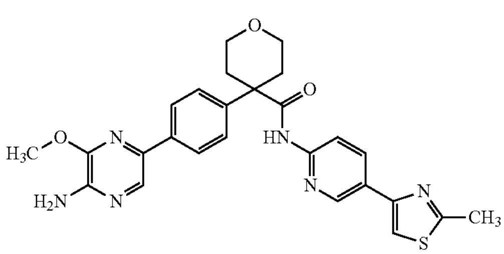 | 18 | 1.72 | 501 (ES−) | D |
| 182 | 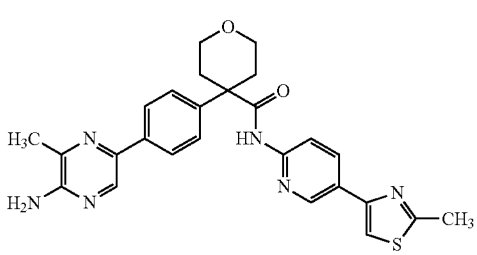 | 18 | 1.66 | 485 (ES−) | D |

-continued

Table of final compounds

| Example | Structure | Method | Retention Time (min) | m/z | LC-MS Method |
|---|---|---|---|---|---|
| 183 | 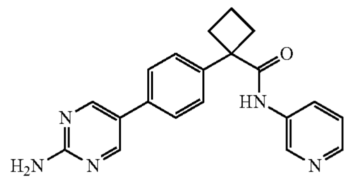 [SMILES: Nc1ncc(-c2ccc(C3(C(=O)Nc4cccnc4)CCC3)cc2)cn1] | 1 | 1.05 | 346 | B |
| 184 | 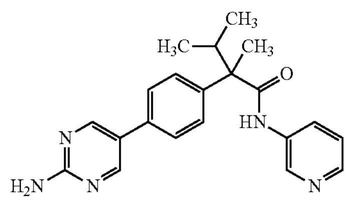 [SMILES: CC(C)C(C)(C(=O)Nc1cccnc1)c1ccc(-c2cnc(N)nc2)cc1] | 1 | 1.14 | 362 | B |
| 185 | 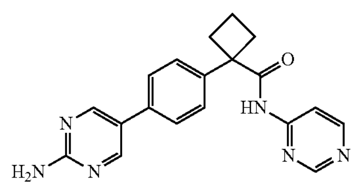 | 1 | 1.22 | 347 | B |
| 186 | 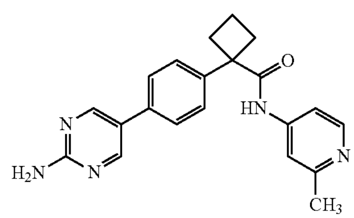 [SMILES: Cc1cc(NC(=O)C2(c3ccc(-c4cnc(N)nc4)cc3)CCC2)ccn1] | 1 | 1.14 | 360 | D |
| 187 | 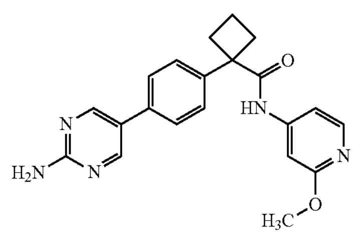 [SMILES: COc1cc(NC(=O)C2(c3ccc(-c4cnc(N)nc4)cc3)CCC2)ccn1] | 1 | 1.3 | 376 | D |
| 188 | 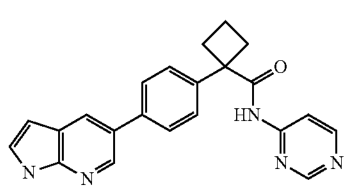 [SMILES: O=C(Nc1ccncn1)C1(c2ccc(-c3cnc4[nH]ccc4c3)cc2)CCC1] | 1 | 1.33 | 370 | B |
| 189 | 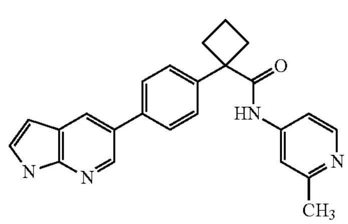 [SMILES: Cc1cc(NC(=O)C2(c3ccc(-c4cnc5[nH]ccc5c4)cc3)CCC2)ccn1] | 1 | 1.16 | 383 | B |

-continued

Table of final compounds

| Example | Structure | Method | Retention Time (min) | m/z | LC-MS Method |
|---------|-----------|--------|----------------------|-----|--------------|
| 190 | 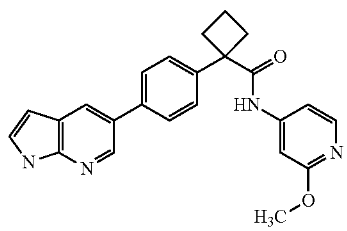 [SMILES: COc1cc(NC(=O)C2(c3ccc(-c4cnc5[nH]ccc5c4)cc3)CCC2)ccn1] | 1 | 1.35 | 399 | V: 2 min ESI+/− Medium Polar |
| 191 | 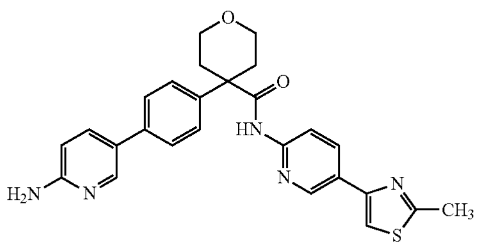 [SMILES: Cc1nc(-c2ccc(NC(=O)C3(c4ccc(-c5ccc(N)nc5)cc4)CCOCC3)nc2)cs1] | 1 | 1.41 | 470 (ES−) | D |
| 192 | 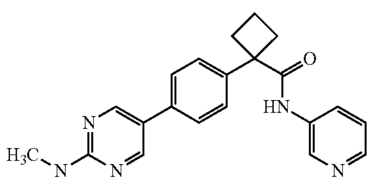 [SMILES: CNc1ncc(-c2ccc(C3(C(=O)Nc4cccnc4)CCC3)cc2)cn1] | 18 | 1.34 | 358 (ES−) | D |
| 193 | 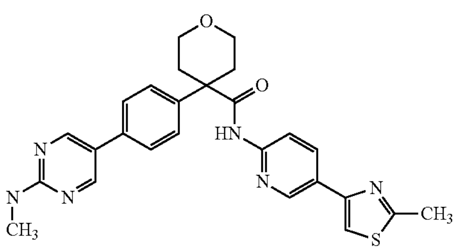 [SMILES: CNc1ncc(-c2ccc(C3(C(=O)Nc4ccc(-c5csc(C)n5)cn4)CCOCC3)cc2)cn1] | 18 | 1.69 | 485 (ES−) | D |
| 194 | 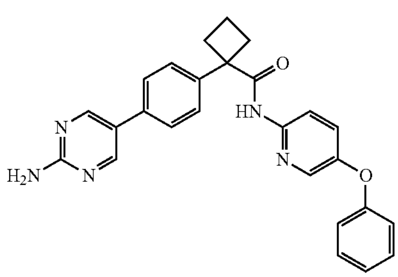 [SMILES: Nc1ncc(-c2ccc(C3(C(=O)Nc4ccc(Oc5ccccc5)cn4)CCC3)cc2)cn1] | 1 | 1.54 | 438 | B |
| 195 | 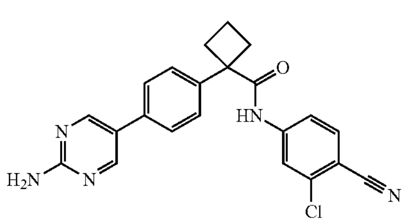 [SMILES: N#Cc1ccc(NC(=O)C2(c3ccc(-c4cnc(N)nc4)cc3)CCC2)cc1Cl] | 1 | 1.43 | 404 | B |

-continued

Table of final compounds

| Example | Structure | Method | Retention Time (min) | m/z | LC-MS Method |
|---|---|---|---|---|---|
| 196 | 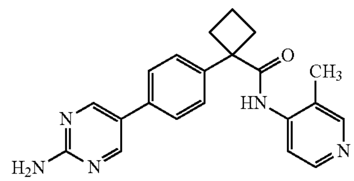 | 1 | 1.09 | 360 | B |
| 197 | 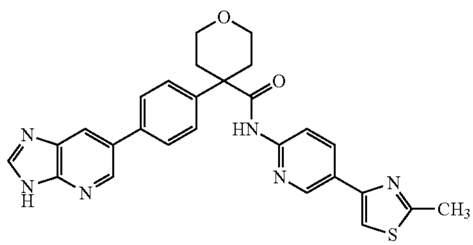 [SMILES: Cc1nc(-c2ccc(NC(=O)C3(c4ccc(-c5cnc6[nH]cnc6c5)cc4)CCOCC3)nc2)cs1] | 18 | 1.53 | 495 | D |
| 198 | 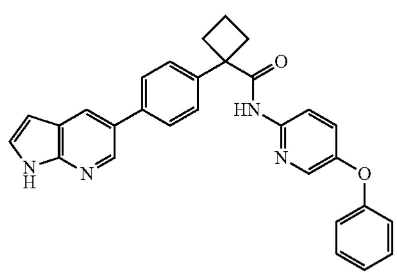 [SMILES: O=C(Nc1ccc(Oc2ccccc2)cn1)C1(c2ccc(-c3cnc4[nH]ccc4c3)cc2)CCC1] | 1 | 1.83 | 461 | D |
| 199 | 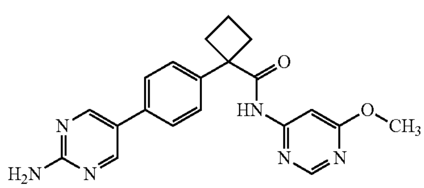 [SMILES: COc1cc(NC(=O)C2(c3ccc(-c4cnc(N)nc4)cc3)CCC2)ncn1] | 1 | 1.44 | 377 | D |
| 200 | 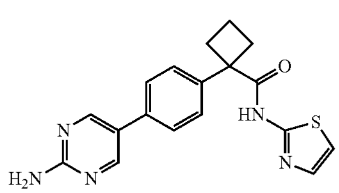 [SMILES: Nc1ncc(-c2ccc(C3(C(=O)Nc4nccs4)CCC3)cc2)cn1] | 1 | 1.15 | 352 | B |
| 201 | 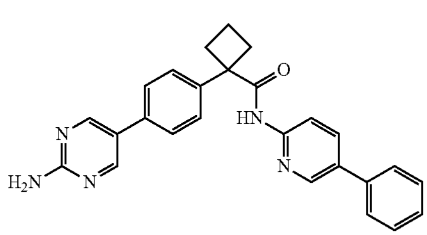 [SMILES: Nc1ncc(-c2ccc(C3(C(=O)Nc4ccc(-c5ccccc5)cn4)CCC3)cc2)cn1] | 1 | 1.41 | 422 | B |

-continued

Table of final compounds

| Example | Structure | Method | Retention Time (min) | m/z | LC-MS Method |
|---|---|---|---|---|---|
| 202 | 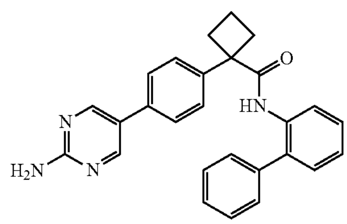 [SMILES: Nc1ncc(-c2ccc(C3(C(=O)Nc4ccccc4-c4ccccc4)CCC3)cc2)cn1] | 1 | 1.69 | 421 | D |
| 203 | 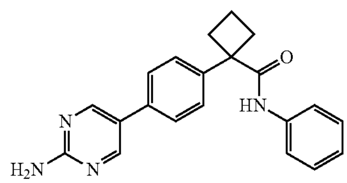 | 1 | 1.25 | 345 | B |
| 204 | 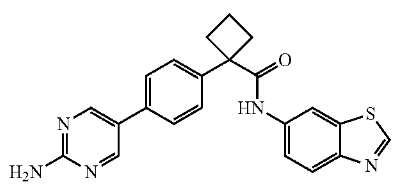 [SMILES: Nc1ncc(-c2ccc(C3(C(=O)Nc4ccc5ncsc5c4)CCC3)cc2)cn1] | 1 | 1.21 | 402 | B |
| 205 | 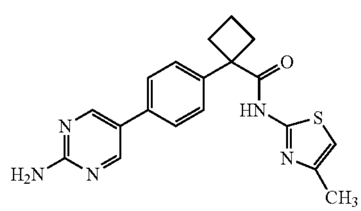 | 1 | 1.22 | 366 | B |
| 206 | 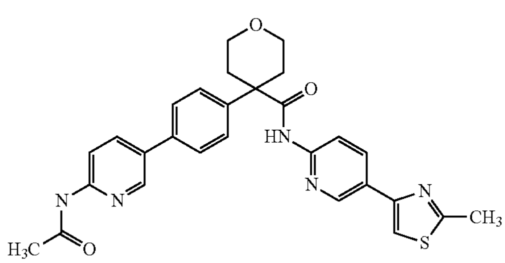 [SMILES: CC(=O)Nc1ccc(-c2ccc(C3(C(=O)Nc4ccc(-c5csc(C)n5)cn4)CCOCC3)cc2)cn1] | 2 | 1.53 | 514 | D |
| 207 | 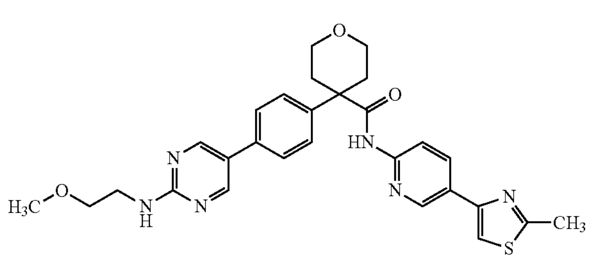 | 18 | 1.57 | 531 | D |

-continued

Table of final compounds

| Example | Structure | Method | Retention Time (min) | m/z | LC-MS Method |
|---------|-----------|--------|----------------------|-----|--------------|
| 208 | 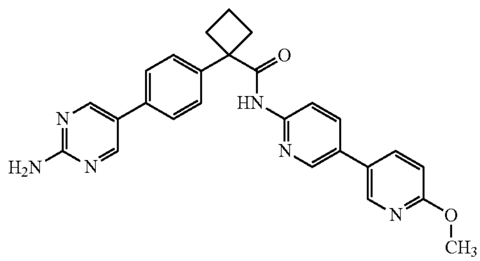 [SMILES: COc1ccc(-c2ccc(NC(=O)C3(c4ccc(-c5cnc(N)nc5)cc4)CCC3)nc2)cn1] | 2 | 1.65 | 453 | D |
| 209 | 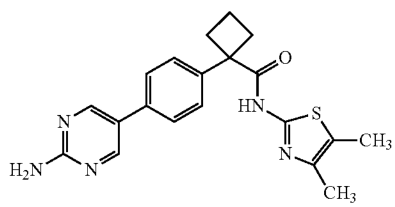 [SMILES: Cc1nc(NC(=O)C2(c3ccc(-c4cnc(N)nc4)cc3)CCC2)sc1C] | 1 | 1.28 | 380 | B |
| 210 | 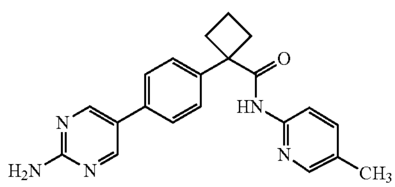 | 1 | 1.17 | 360 | B |
| 211 | 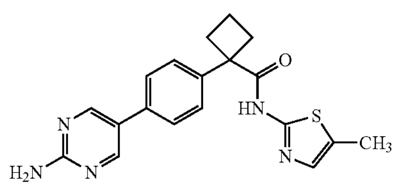 [SMILES: Cc1cnc(NC(=O)C2(c3ccc(-c4cnc(N)nc4)cc3)CCC2)s1] | 1 | 1.23 | 366 | B |
| 212 | 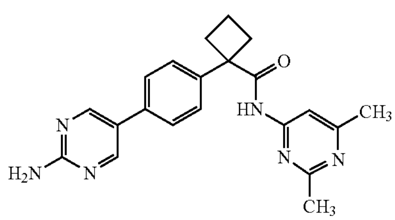 [SMILES: Cc1cc(NC(=O)C2(c3ccc(-c4cnc(N)nc4)cc3)CCC2)nc(C)n1] | 1 | 1.12 | 375 | B |
| 213 | 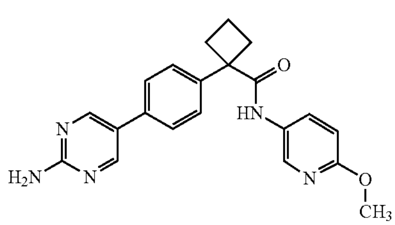 [SMILES: COc1ccc(NC(=O)C2(c3ccc(-c4cnc(N)nc4)cc3)CCC2)cn1] | 1 | 1.36 | 376 | D |
| 214 | 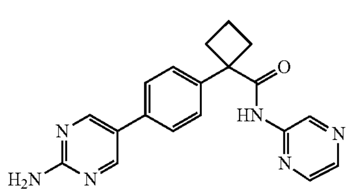 [SMILES: Nc1ncc(-c2ccc(C3(C(=O)Nc4cnccn4)CCC3)cc2)cn1] | 1 | 1.32 | 347 | D |

-continued

Table of final compounds

| Example | Structure | Method | Retention Time (min) | m/z | LC-MS Method |
|---|---|---|---|---|---|
| 215 | 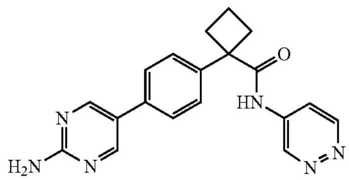 [SMILES: Nc1ncc(-c2ccc(C3(C(=O)Nc4ccnnc4)CCC3)cc2)cn1] | 1 | 1.22 | 347 | D |
| 216 | 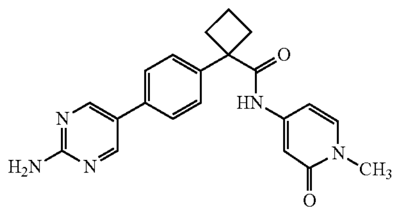 [SMILES: Cn1ccc(NC(=O)C2(c3ccc(-c4cnc(N)nc4)cc3)CCC2)cc1=O] | 1 | 1.2 | 376 | D |
| 217 | 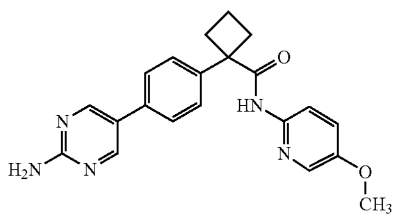 | 1 | 1.41 | 376 | D |
| 218 | 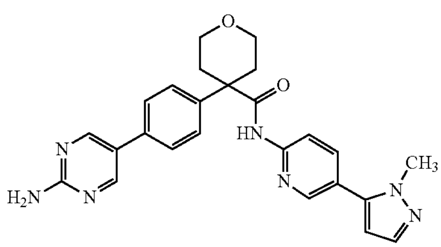 [SMILES: Cn1nccc1-c1ccc(NC(=O)C2(c3ccc(-c4cnc(N)nc4)cc3)CCOCC2)nc1] | 2 | 1.37 | 456 | D |
| 219 | 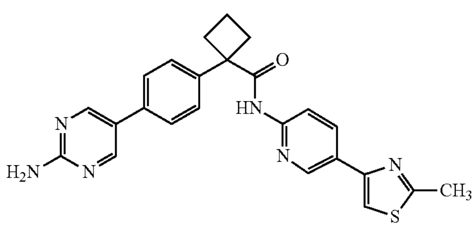 [SMILES: Cc1nc(-c2ccc(NC(=O)C3(c4ccc(-c5cnc(N)nc5)cc4)CCC3)nc2)cs1] | 1 | 1.47 | 444 | D |
| 220 | 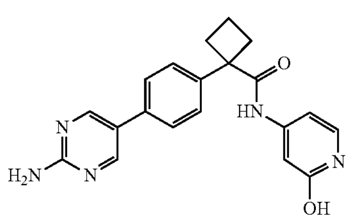 [SMILES: Nc1ncc(-c2ccc(C3(C(=O)Nc4ccnc(O)c4)CCC3)cc2)cn1] | 3 | 0.94 | 362 | B |
| 221 | 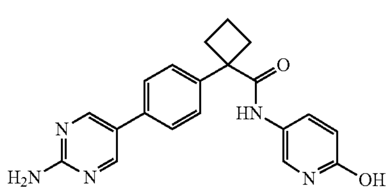 | 3 | 0.92 | 362 | B |

-continued

Table of final compounds

| Example | Structure | Method | Retention Time (min) | m/z | LC-MS Method |
|---|---|---|---|---|---|
| 222 | 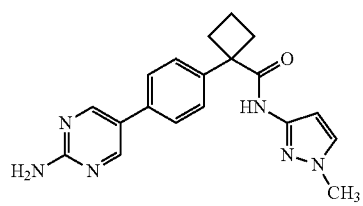 | 1 | 1.01 | 349 | B |
| 223 | 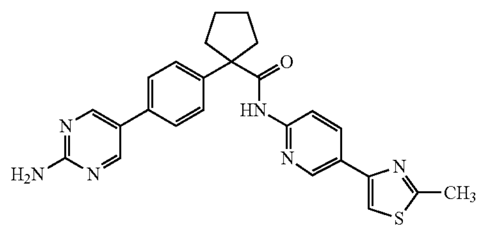 [SMILES: Cc1nc(-c2ccc(NC(=O)C3(c4ccc(-c5cnc(N)nc5)cc4)CCCC3)nc2)cs1] | 2 | 1.68 | 457 | D |
| 224 | 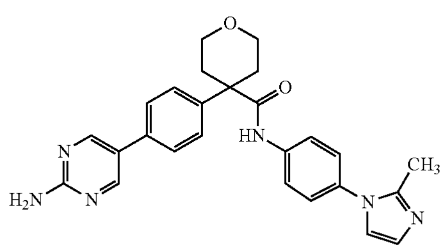 [SMILES: Cc1nccn1-c1ccc(NC(=O)C2(c3ccc(-c4cnc(N)nc4)cc3)CCOCC2)cc1] | 2 | 1.05 | 455 | D |
| 225 | 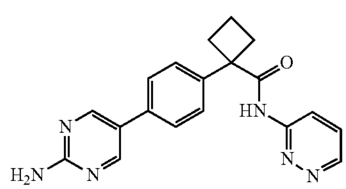 [SMILES: Nc1ncc(-c2ccc(C3(C(=O)Nc4cccnn4)CCC3)cc2)cn1] | 1 | 1.02 | 347 | B |
| 226 | 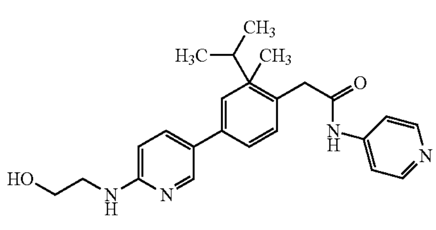 | 7 | 1.32 | 405 | A |
| 227 | 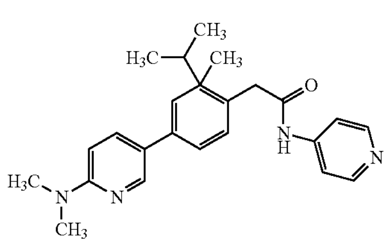 | 7 | 1.47 | 389 | A |

-continued

Table of final compounds

| Example | Structure | Method | Retention Time (min) | m/z | LC-MS Method |
|---|---|---|---|---|---|
| 228 | 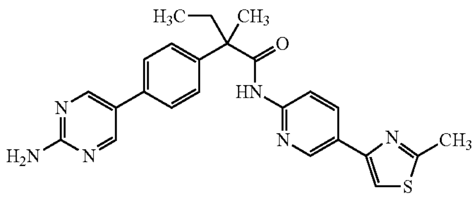 [SMILES: CCC(C)(C(=O)Nc1ccc(-c2csc(C)n2)cn1)c1ccc(-c2cnc(N)nc2)cc1] | 2 | 1.64 | 445 | D |
| 229 | 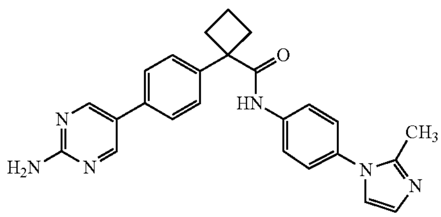 [SMILES: Cc1nccn1-c1ccc(NC(=O)C2(c3ccc(-c4cnc(N)nc4)cc3)CCC2)cc1] | 2 | 1.21 | 425 | D |
| 230 | 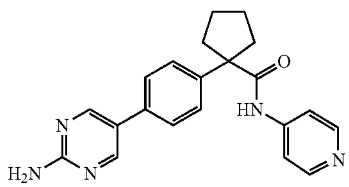 [SMILES: Nc1ncc(-c2ccc(C3(C(=O)Nc4ccncc4)CCCC3)cc2)cn1] | 2 | 1.07 | 360 | D |
| 231 | 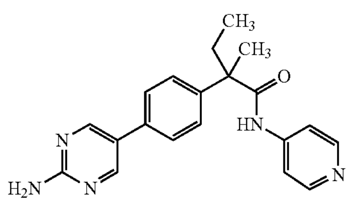 [SMILES: CCC(C)(C(=O)Nc1ccncc1)c1ccc(-c2cnc(N)nc2)cc1] | 2 | 1.12 | 348 | D |
| 232 | 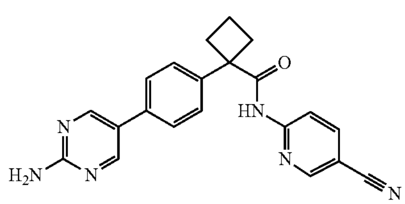 [SMILES: N#Cc1ccc(NC(=O)C2(c3ccc(-c4cnc(N)nc4)cc3)CCC2)nc1] | 4 | 2.24 | 371 | A |
| 233 | 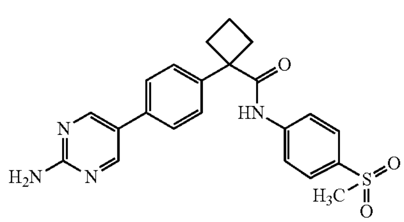 | 4 | 2.04 | 423 | A |
| 234 | 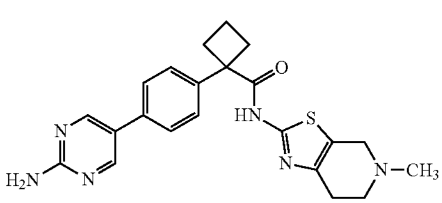 [SMILES: CN1CCc2nc(NC(=O)C3(c4ccc(-c5cnc(N)nc5)cc4)CCC3)sc2C1] | 4 | 1.46 | 421 | A |

-continued

| | | | Retention | | |
|---|---|---|---|---|---|
| Example | Structure | Method | Time (min) | m/z | LC-MS Method |
| 235 | | 4 | 2.41 | 431 | A |
| 236 | | 1 | 1.13 | 371 | B |
| 237 | | 2 | 1.66 | 418 | D |
| 238 | | 2 | 1.28 | 423 | D |
| 239 | | 2 | 1.36 | 423 | D |
| 240 | | 1 | 1.01 | 389 | B |

Table of final compounds

-continued

Table of final compounds

| Example | Structure | Method | Retention Time (min) | m/z | LC-MS Method |
|---|---|---|---|---|---|
| 241 | 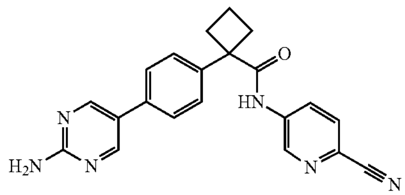 [SMILES: N#Cc1ccc(NC(=O)C2(c3ccc(-c4cnc(N)nc4)cc3)CCC2)cn1] | 1 | 1.13 | 371 | B |
| 242 | 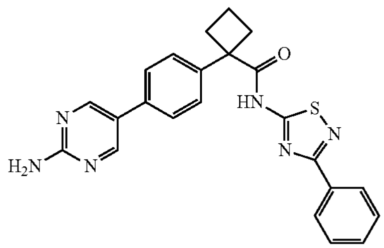 [SMILES: Nc1ncc(-c2ccc(C3(C(=O)Nc4nc(-c5ccccc5)ns4)CCC3)cc2)cn1] | 4 | 2.81 | 429 | A |
| 243 | 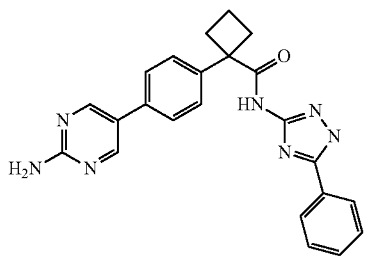 [SMILES: Nc1ncc(-c2ccc(C3(C(=O)Nc4n[nH]c(-c5ccccc5)n4)CCC3)cc2)cn1] | 4 | 2.6 | 412 | A |
| 244 | 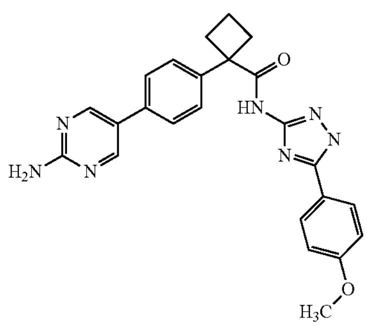 [SMILES: COc1ccc(-c2nc(NC(=O)C3(c4ccc(-c5cnc(N)nc5)cc4)CCC3)n[nH]2)cc1] | 4 | 2.6 | 442 | A |
| 245 | 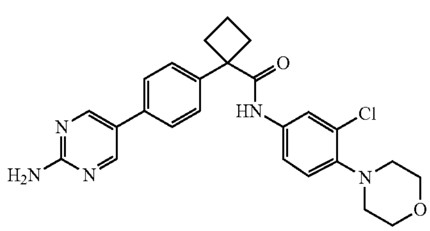 [SMILES: Nc1ncc(-c2ccc(C3(C(=O)Nc4ccc(N5CCOCC5)c(Cl)c4)CCC3)cc2)cn1] | 2 | 1.58 | 464 | D |
| 246 | 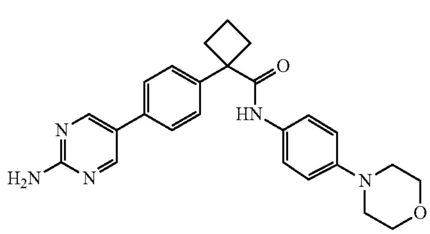 [SMILES: Nc1ncc(-c2ccc(C3(C(=O)Nc4ccc(N5CCOCC5)cc4)CCC3)cc2)cn1] | 2 | 1.33 | 430 | D |

-continued

Table of final compounds

| Example | Structure | Method | Retention Time (min) | m/z | LC-MS Method |
|---|---|---|---|---|---|
| 247 | 2-aminopyrimidin-5-yl–phenyl–CH(cyclopentyl)–C(O)NH–pyridin-4-yl | 2 | 1.08 | 374 | D |
| 248 | 2-aminopyrimidin-5-yl–phenyl–CH(cyclopentyl)–C(O)NH–[5-(2-methylthiazol-4-yl)pyridin-2-yl] | 2 | 1.69 | 471 | D |
| 249 | 2-aminopyrimidin-5-yl–phenyl–C(cyclobutyl)–C(O)NH–(6-methylpyridin-3-yl) | 1 | 0.88 | 360 | B |
| 250 | 2-aminopyrimidin-5-yl–phenyl–C(cyclobutyl)–C(O)NH–(4-cyanophenyl) | 4 | 2.31 | 370 | A |
| 251 | 2-aminopyrimidin-5-yl–phenyl–C(cyclopropyl)–C(O)NH–[5-(2-methylthiazol-4-yl)pyridin-2-yl] | 4 | 2.35 | 429 | A |
| 252 | 2-aminopyrimidin-5-yl–phenyl–C(cyclobutyl)–C(O)NH–[2-(4-methylpiperazin-1-yl)pyridin-4-yl] | 4 | 1.35 | 444 | A |

-continued

Table of final compounds

| Example | Structure | Method | Retention Time (min) | m/z | LC-MS Method |
|---|---|---|---|---|---|
| 253 | 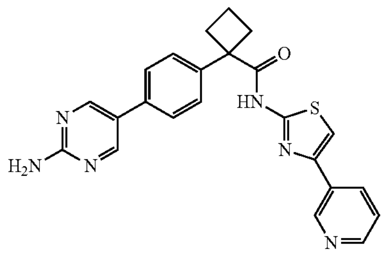 [SMILES: Nc1ncc(-c2ccc(C3(C(=O)Nc4nc(-c5cccnc5)cs4)CCC3)cc2)cn1] | 4 | 1.94 | 429 | A |
| 254 | 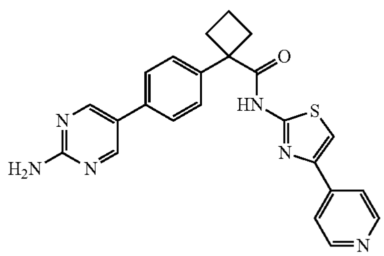 [SMILES: Nc1ncc(-c2ccc(C3(C(=O)Nc4nc(-c5ccncc5)cs4)CCC3)cc2)cn1] | 4 | 1.8 | 429 | A |
| 255 | 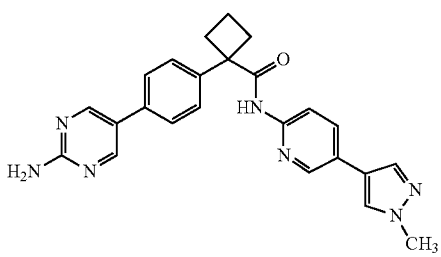 [SMILES: Cn1cc(-c2ccc(NC(=O)C3(c4ccc(-c5cnc(N)nc5)cc4)CCC3)nc2)cn1] | 4 | 1.11 | 426 | B |

| LC-MS Method A | |
|---|---|
| Column | Agilent SB-C18 1.81 μm, 3 × 50 mm Ambient temperature |
| Mobile phase | A = Formic acid (aq) 0.1% B = Formic acid (acetonitrile) 0.1% |
| Flow rate | 1.5 ml/min |
| Injection volume | 3 μl |
| Detector | 220 and 254 nm (nominal) |

| Gradient | Time (mins) | % B |
|---|---|---|
| | 0 | 5 |
| | 3.8 | 90 |
| | 4.5 | 100 |

| LC-MS Method B | |
|---|---|
| Column | Agilent SB-C18 1.8 μm, 3 × 50 mm column Ambient temperature |
| Mobile phase | A = Formic acid (aq) 0.1% B = Formic acid (acetonitrile) 0.1% |
| Flow rate | 1.5 ml/min |
| Injection volume | 3 μl |
| Detector | 220 and 254 nm (nominal) |

-continued

| LC-MS Method B | | |
|---|---|---|
| Gradient | Time (mins) | % B |
| | 0 | 12 |
| | 0.25 | 30 |
| | 0.3 | 40 |
| | 1.19 | 95 |
| | 1.75 | 100 |

| LC-MS Method C | |
|---|---|
| Column | Waters BEH C18 1.7 μm, 2.1 × 50 mm Ambient temperature |
| Mobile phase | A = Formic acid (aq) 0.05% B = Formic acid (acetonitrile) 0.05% |
| Flow rate | 0.8 ml/min |
| Injection volume | 1 μl |
| Detector | 254 nm (nominal) |

| Gradient | Time (mins) | % B |
|---|---|---|
| | 0 | 10 |
| | 1.19 | 95 |
| | 1.7 | 95 |

| LC-MS Method D | |
|---|---|
| Column | Agilent Zorbax C18 SB<br>3.5 μm, 4.6 × 30 mm<br>Ambient temperature |
| Mobile phase | A = Formic acid (aq) 0.1%<br>B = Formic acid (acetonitrile) 0.1% |
| Flow rate | 2.5 ml/min |
| Injection volume | 7 μl |
| Detector | 200-600 nm (nominal) |
| Gradient | Time (mins) | % B |
| --- | --- | --- |
| | 0 | 5 |
| | 1.7 | 95 |
| | 2 | 95 |
| | 2.1 | 5 |
| | 2.3 | 5 |

| LC-MS Method E | |
|---|---|
| Column | Waters BEH C18<br>1.7 μm, 2.1 × 50 mm<br>Ambient temperature |
| Mobile phase | A = Formic acid (aq) 0.05%<br>B = Formic acid (acetonitrile) 0.05% |
| Flow rate | 0.8 ml/min |
| Injection volume | 1 μl |
| Detector | 254 nm (nominal) |
| Gradient | Time (mins) | % B |
| --- | --- | --- |
| | 0 | 10 |
| | 4.5 | 95 |
| | 4.58 | 95 |

| LC-MS Method F | |
|---|---|
| Column | Waters BEH C18<br>1.7 μm, 2.1 × 50 mm<br>Ambient temperature |
| Mobile phase | A = Formic acid (aq) 0.05%<br>B = Formic acid (acetonitrile) 0.05% |
| Flow rate | 0.6 ml/min |
| Injection volume | 1 μl |
| Detector | 254 nm (nominal) |
| Gradient | Time (mins) | % B |
| --- | --- | --- |
| | 0 | 5 |
| | 4.45 | 100 |
| | 5 | 100 |

| LC-MS Method G | |
|---|---|
| Column | Waters Atlantis dC18 100 ×<br>2.1 mm, 3 μm column<br>40° C. |
| Mobile phase | A - 0.1% Formic acid (water)<br>B - 0.1% Formic acid (acetonitrile) |
| Flow rate | 0.6 ml/min |
| Injection volume | 3 μl |
| Detector | 215 nm (nominal) |
| Gradient | Time (mins) | % B |
| --- | --- | --- |
| | 0 | 5 |
| | 5 | 100 |
| | 5.4 | 100 |
| | 5.42 | 5 |

Assessment of Biological Properties

1. Binding Assay

Compounds are assessed for the ability to bind to FLAP in a binding assay that measures compound-specific displacement of an iodinated ($^{125}$I) FLAP inhibitor via a Scintillation Proximity Assay format (adapted from S. Charleson et al., Mol. Pharmacol., 1992, 41, 873-879).

Cell pellets produced from sf9 insect cells expressing recombinant human FLAP protein are resuspended in buffer A [15 mM Tris-HCl (pH 7.5), 2 mM MgCl$_2$, 0.3 mM EDTA, 1 mM PMSF]. The cells are lysed with a Dounce homogenizer and the material is centrifuged at 10,000×g for 10 minutes. The supernatant is then collected and centrifuged at 100,000×g for 60 minutes. To prepare membrane protein for an assay, an aliquot of the 100,000×g pellet is resuspended in 1 ml of buffer A, Dounce homogenized, and finally subjected to polytron mixing (30 seconds). Membrane protein (25 μl, 5 μg) is mixed with WGA SPA beads (Amersham) and stirred for 1 h. To an assay plate (Perkin Elmer FlexiPlate) is added 25 μl of test compound prepared in Binding buffer [100 mM Tris (pH 7.5), 140 mM NaCl, 5% glycerol, 2 mM EDTA, 0.5 mM TCEP, 0.05% Tween 20], 25 μl of [$^{125}$I]L-691,831 (an iodinated analog of MK-591, Charleson et al. Mol. Pharmacol., 41, 873-879, 1992) and finally 50 μl of the bead/protein mixture. (final concentrations: beads, 200 μg/well; protein, 5μg/well; [$^{125}$I] probe, 0 08 nM/well(17 nCi/well). The plates are shaken for 2 h before reading on a Microbeta plate reader. Non-specific binding is determined by the addition of 10 μM cold L-691,831 compound.

2. Whole Blood Assay

Compounds are additionally tested in a human whole blood assay to determine their ability to inhibit the synthesis of LTB$_4$ in a cellular system. Compounds are combined with heparinized human whole blood and incubated for 15 minutes at 37° C. Calcimycin (20 μM final, prepared in phosphate-buffered saline, pH 7.4) is then added and the mixture is incubated for another 30 minutes at 37° C. The samples are centrifuged for 5 min at low speed (1500×g) and the plasma layer is removed. Plasma LTB$_4$ concentrations are then measured using an antibody-based homogenous time-resolved fluorescence method (CisBio, Bedford, Mass.).

In general, the preferred potency range (IC$_{50}$) of compounds in the above assay is between 0.1 nM to 10 μM, the more preferred potency range is 0.1 nM to 1 μM, and the most preferred potency range is 0.1 nM to 100 nM.

Method of Use

The compounds of the invention are effective inhibitors of 5-lipoxygenase activating protein (FLAP) and thus inhibit leukotriene production. Therefore, in one embodiment of the invention, there is provided methods of treating leukotriene-mediated disorders using compounds of the invention. In another embodiment, there is provided methods of treating cardiovascular, inflammatory, allergic, pulmonary and fibrotic diseases, renal diseases and cancer using compounds of the invention.

Without wishing to be bound by theory, by inhibiting the activity of FLAP, the compounds of the invention block the production of LTs resulting from the oxidation of arachidonic acid by 5-LO and subsequent metabolism. Thus, the inhibition of FLAP activity is an attractive means for preventing and treating a variety of diseases mediated by LTs. These include:

Cardiovascular diseases including atherosclerosis, myocardial infarction, stroke, aortic aneurysm, sickle cell crisis, ischemia-reperfusion injury, pulmonary arterial hypertension and sepsis;

Allergic diseases including asthma, allergic rhinitis, rhinosinusitis, atopic dermatitis and urticaria;

Fibrotic diseases including airway remodeling in asthma, idiopathic pulmonary fibrosis, scleroderma, asbestosis;

Pulmonary syndromes including adult respiratory distress syndrome, viral bronchiolitis, obstructive sleep apnea, chronic obstructive pulmonary disease, cystic fibrosis, and bronchopulmonary dysplasia;

Inflammatory diseases including rheumatoid arthritis, osteoarthritis, gout, lomerulonephritis, interstitial cystitis, psoriasis, inflammatory bowel disease systemic lupus erythematosus, transplant rejection, multiple sclerosis, inflammatory pain, inflammatory and allergic ocular diseases;

Cancer including solid tumors, leukemias and lymphomas; and

Renal diseases such as glomerulonephritis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:

1. A compound of formula (I),

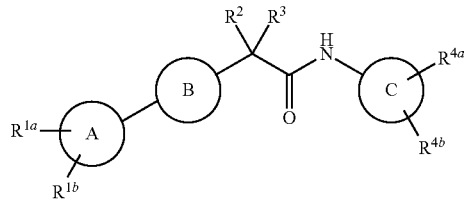

or a pharmaceutically acceptable salt thereof, wherein:

A is selected from pyrazolyl, imidazolyl, pyrrolyl, thienyl, thiazolyl, triazolyl, pyridinyl, pyrimidinyl, pyrazinyl, pyridazinyl, indolyl, pyrrolopyridinyl, dihydropyrrolopyridinyl, imidazopyridinyl, pyrazolopyridinyl and quinolinyl;

B is selected from phenyl, pyridinyl, pyrimidinyl, pyrazinyl and pyridazinyl;

C is pyridinyl;

$R^{1a}$ and $R^{1b}$ are each independently selected from —H, $C_{1-6}$ alkyl, $C_{1-3}$ alkoxyl, —$C_{1-3}$ alkyl —OH, hydroxy, —C(O)—$C_{1-3}$ alkyl and —$NR^5R^6$;

$R^2$ and $R^3$ together with the carbon atom to which they are attached form a cyclopropyl, cyclobutyl, cyclopentyl, cyclohexyl, tetrahydrofuranyl or a tetrahydropyranyl ring;

$R^{4a}$ and $R^{4b}$ are each independently selected from —H, $C_{1-3}$ alkyl, $C_{1-3}$ alkoxyl, -$C_{1-3}$ alkyl—OH, phenyl, —O—phenyl, thiazolyl, oxazolyl, isoxazolyl, furanyl, thienyl, pyrrolyl, thiadiazolyl, tetrazolyl, pyridinyl, pyrimidinyl, pyridazinyl, pyrazinyl, cyclopropyl, cyclopbutyl, cyclopenyl, cyclohexyl, pyrrolidinyl, tetrahydrothienyl, piperidinyl, piperazinyl, morpholinyl, —$C_{1-3}$ alkyl-phenyl, —$C_{1-3}$ alkyl-pyridinyl, —$C_{1-3}$ alkyl- pyrimidinyl, —$C_{1-3}$ alkyl- pyridazinyl, —$C_{1-3}$ alkyl- pyrazinyl, —$C_{1-3}$ alkyl-heterocyclyl, —O—$C_{1-3}$ alkyl-phenyl, —O—$C_{1-3}$ alkyl-pyridinyl, —O $C_{1-3}$ alkyl, $CF_3$, O—$CF_3$, —COO $R^5$, —C(O) $C_{1-3}$ alkyl —$S(O)_2$—$NR^5R^6$, —$S(O)_2CF_3$, —$S(O)_2C_{1-3}$ alkyl, —C(O) $NR^7R^8$, hydroxy, halogen, and cyano, wherein each group is optionally independently substituted with 1-3 substituents chosen from $C_{1-6}$ alkyl, $C_{1-6}$ alkoxyl, hydroxy and halogen;

R[5] and R[6] are each independently chosen from H, $C_{1-5}$ alkyl, —$C_{1-3}$ alkylhydroxy and $C_{1-3}$ alkyl—O—$C_{1-3}$ alkyl;

or, R[5] and R[6] together with the nitrogen atom to which they are attached form a piperidinyl, morpholinyl or thiomorpholinyl ring;

R[7] and R[8] are each independently chosen from H, $C_{1-6}$ alkyl, —S(O)$_2$C$_{1-3}$ alkyl, and —C(NH)—NH$_2$.

2. A compound of formula (I) according to claim 1, or a pharmaceutically acceptable salt thereof, wherein:

A is selected from pyrazolyl, pyridinyl, pyrimidinyl, pyrazinyl, pyrrolopyridinyl, dihydropyrrolopyridinyl and imidazopyridinyl.

3. A compound of formula (I) according to claim 1, or a pharmaceutically acceptable salt thereof, wherein:

B is selected from phenyl and pyridinyl.

4. A compound of formula (I) according to claim 1, or a pharmaceutically acceptable salt thereof, wherein:

C is pyridinyl.

5. A compound of formula (I) according to claim 1, or a pharmaceutically acceptable salt thereof, wherein:

R[2] and R[3] together with the carbon atom to which they are attached form a cyclopropyl, cyclobutyl, cyclopentyl, cyclohexyl or a tetrahydropyranyl ring.

6. A compound of formula (I) according to claim 1, or a pharmaceutically acceptable salt thereof, wherein:

A is selected from pyrazolyl, pyridinyl, pyrimidinyl, pyrazinyl, pyrrolopyridinyl, dihydropyrrolopyridinyl and imidazopyridinyl;

B is selected from phenyl and pyridinyl;

C is pyridinyl;

R[2] and R[3] together with the carbon atom to which they are attached form a cyclopropyl, cyclobutyl, cyclopentyl, cyclohexyl or a tetrahydropyranyl ring;

R[1a] and R[1b] are each independently selected from —H, $C_{1-6}$ alkyl, methoxy, —CH$_2$—OH, hydroxy, —C(O)—CH$_3$ and —NR[5]R[6];

R[4a] and R[4b] are each independently selected from —H, $C_{1-3}$ alkyl, $C_{1-3}$ alkoxyl, —$C_{1-3}$ alkyl—OH, phenyl, —O—phenyl, thiazolyl, oxazolyl, isoxazolyl, furanyl, thienyl, pyrrolyl, thiadiazolyl, tetrazolyl, pyridinyl, pyrimidinyl, pyridazinyl, pyrazinyl, cyclopropyl, cyclobutyl, cyclopenyl, cyclohexyl, pyrrolidinyl, tetrahydrothienyl, piperidinyl, piperazinyl, morpholinyl, —$C_{1-3}$alkyl-phenyl, —$C_{1-3}$ alkyl-pyridinyl, —$C_{1-3}$ alkyl- pyrimidinyl, —$C_{1-3}$ alkyl- pyridazinyl, —$C_{1-3}$ alkyl-heterocyclyl, —O—$C_{1-3}$ alkyl-phenyl, —O—$C_{1-3}$ alkyl-pyridinyl, —O $C_{1-3}$ alkyl, CF$_3$, O—CF$_3$, —COO R[5], —C(O) $C_{1-3}$ alkyl —S(O)$_2$—NR[5]R[6], —S(O)$_2$CF$_3$, —S(O)$_2$C$_{1-3}$ alkyl, —C(O) NR[7]R[8], hydroxy, halogen, and cyano, wherein each group is optionally independently substituted with 1-3 substituents chosen from $C_{1-6}$ alkyl, $C_{1-6}$ alkoxyl, hydroxy and halogen;

R[5] and R[6] are each independently chosen from H, $C_{1-5}$ alkyl, —$C_{1-3}$ alkylhydroxy and $C_{1-3}$ alkyl—O—$C_{1-3}$ alkyl;

or, R[5] and R[6] together with the nitrogen atom to which they are attached form a piperidinyl, morpholinyl or thiomorpholinyl ring;

R[7] and R[8] are each independently chosen from H, $C_{1-6}$ alkyl, —S(O)$_2$C$_{1-3}$ alkyl, and C(NH)—NH$_2$.

7. A compound of formula (I) according to claim 6, or a pharmaceutically acceptable salt thereof, wherein:

R[2] and R[3] together with the carbon atom to which they are attached form a cyclopropyl, cyclobutyl, cyclopentyl, cyclohexyl or a tetrahydropyranyl ring.

8. A compound of formula (I) according to claim 6, or a pharmaceutically acceptable salt thereof, wherein:

B is phenyl.

9. A compound of formula (I) according to claim 6, or a pharmaceutically acceptable salt thereof, wherein:

B is pyridyl.

10. A compound of formula (I), selected from a group consisting of:

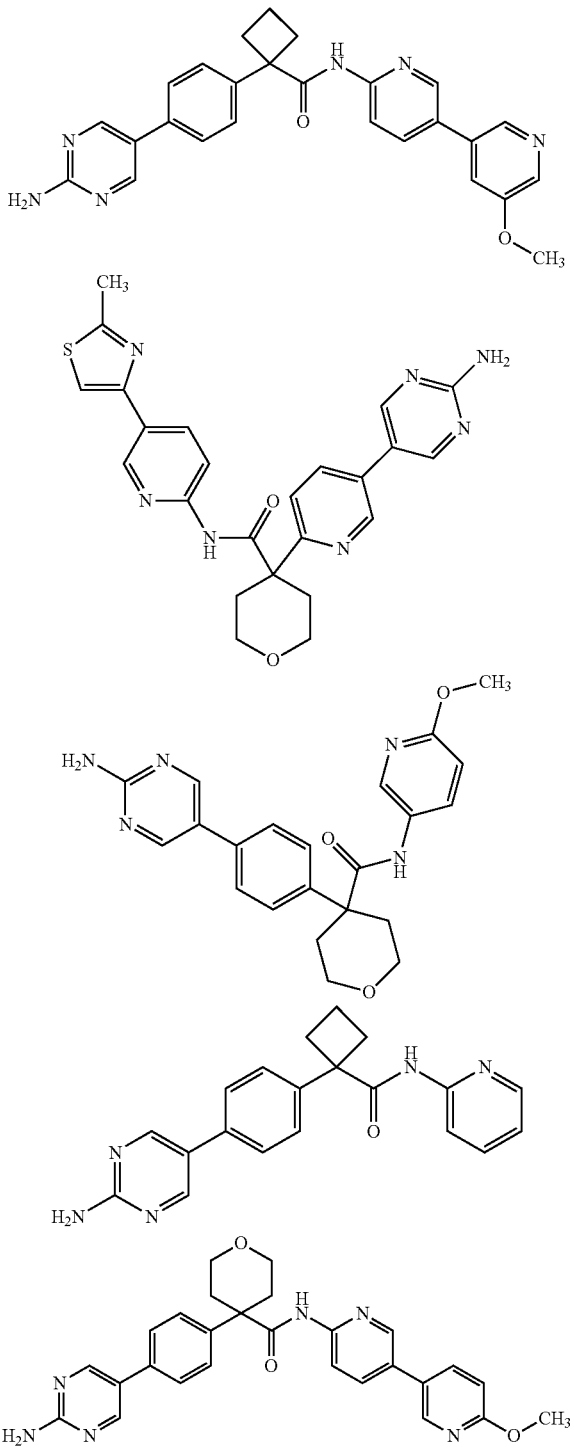

-continued
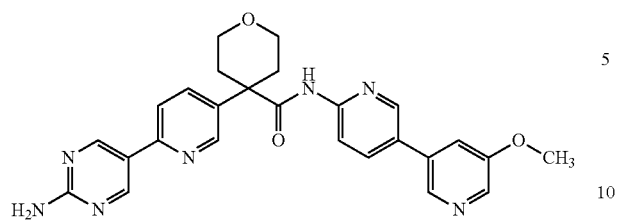
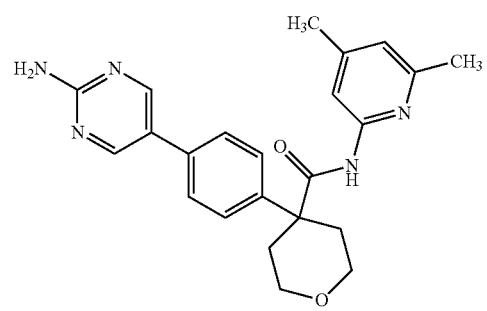
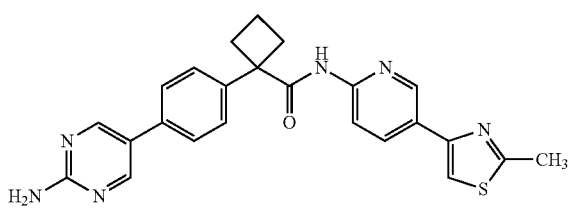
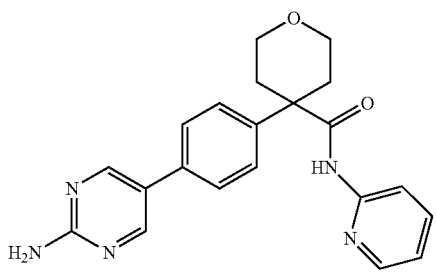
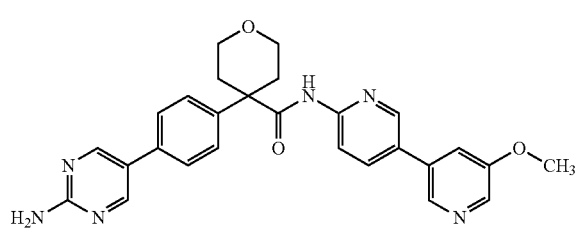
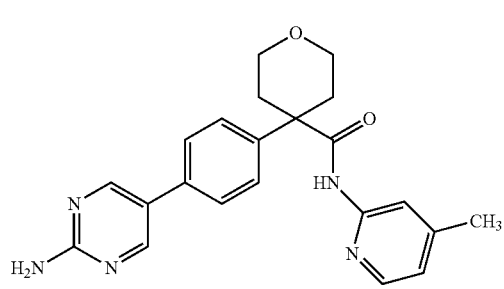
-continued
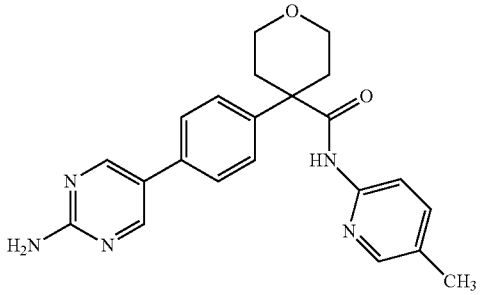
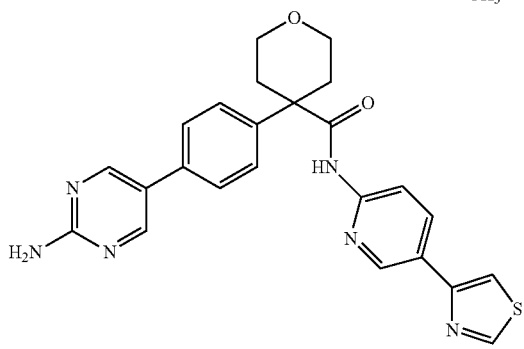
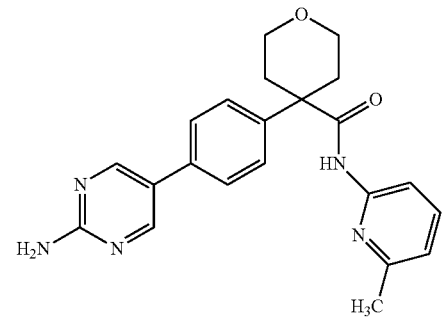
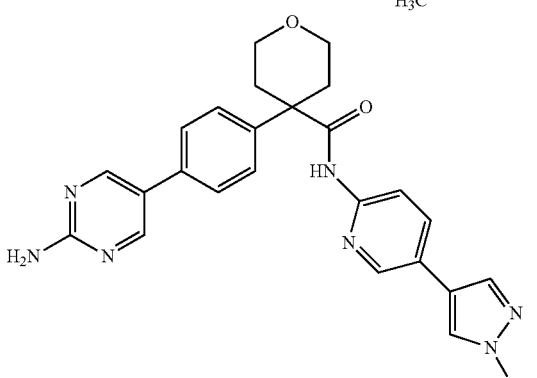
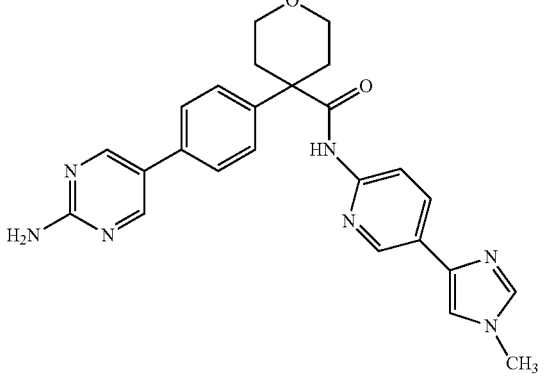

273
-continued
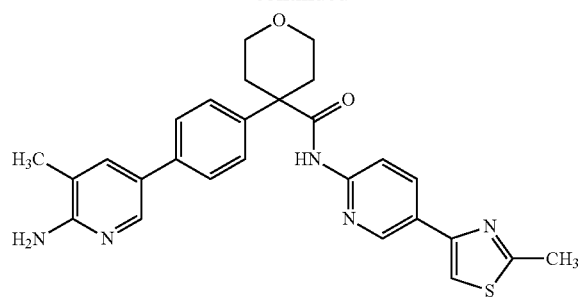
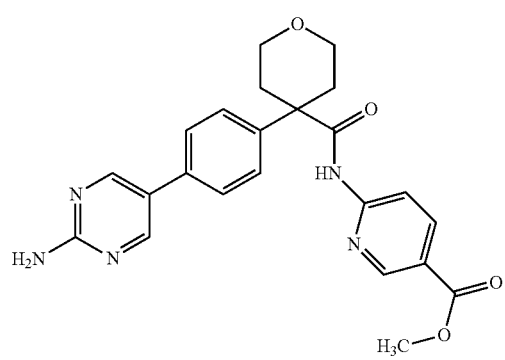
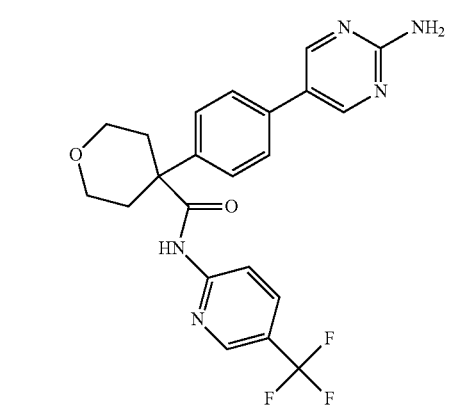
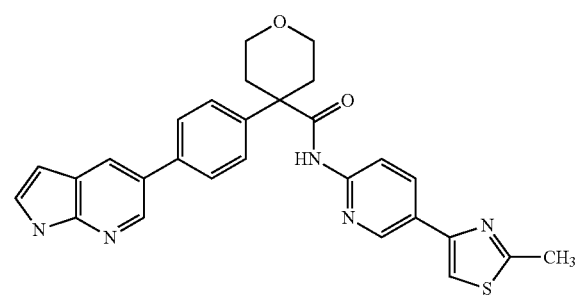
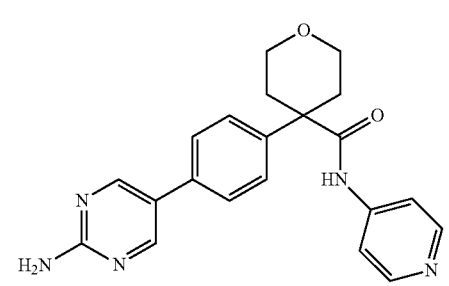
274
-continued
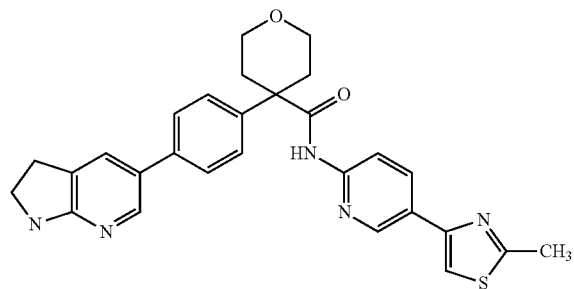
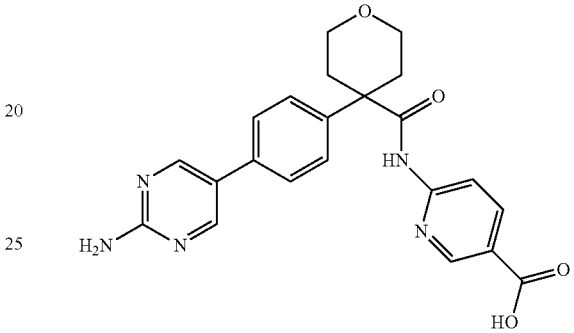
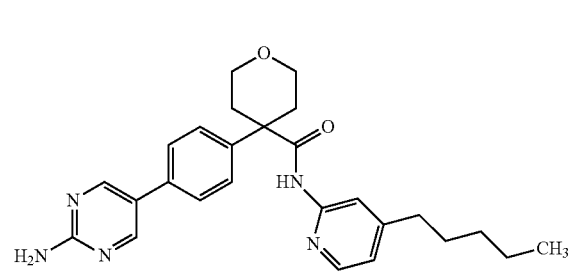
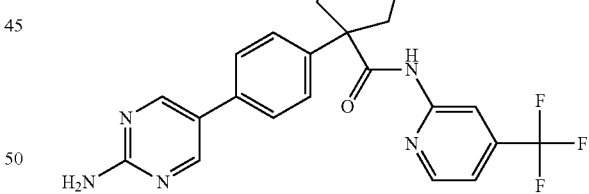
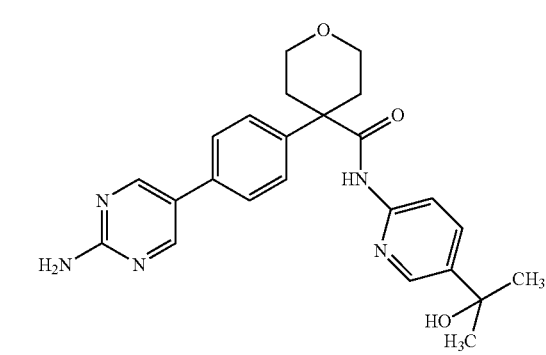

275
-continued
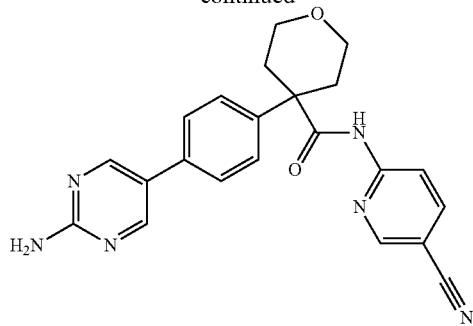
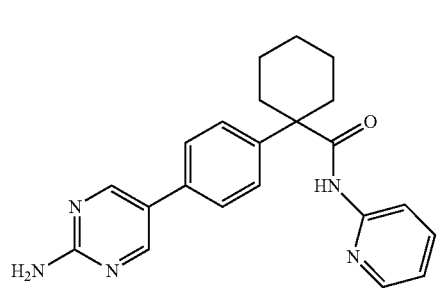
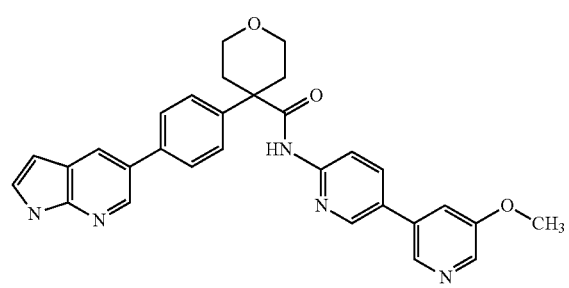
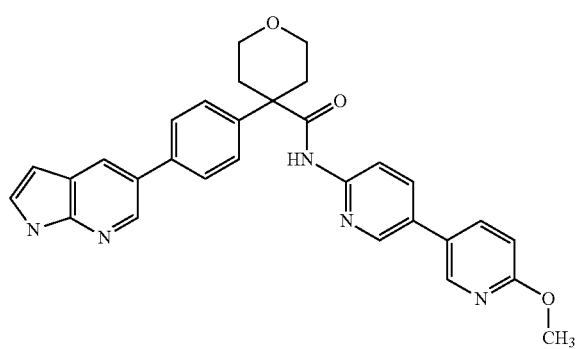
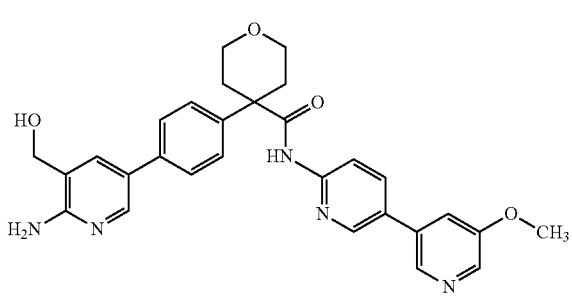
276
-continued
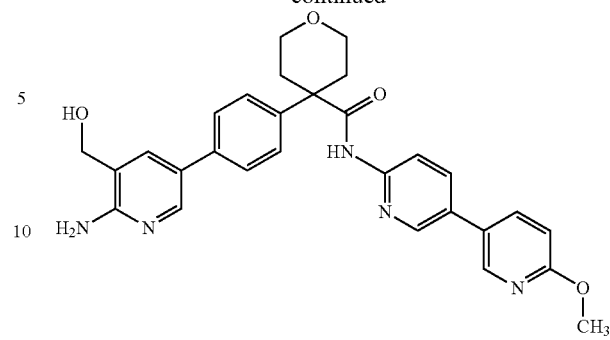
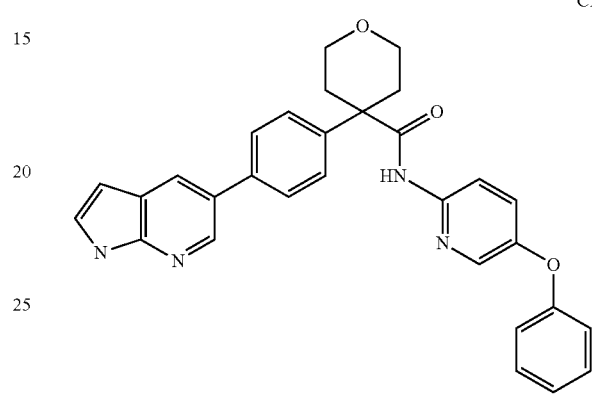
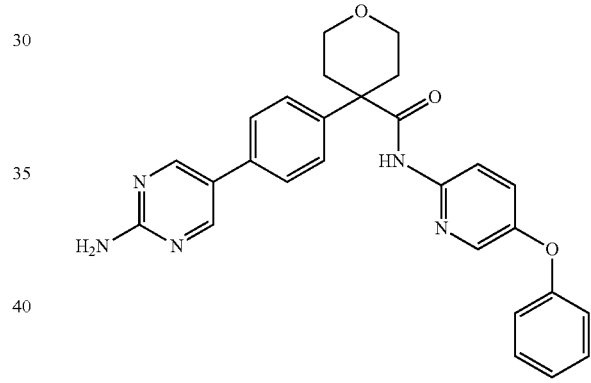
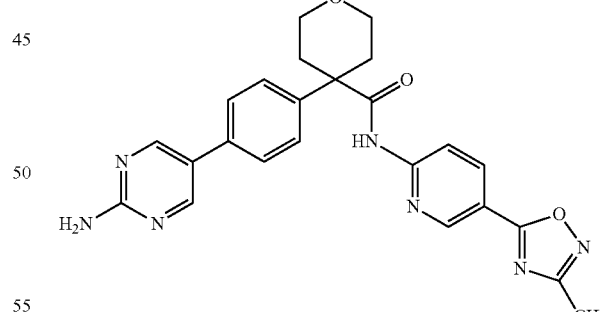
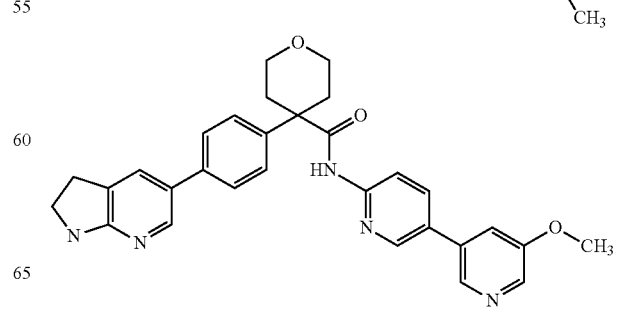

277
-continued
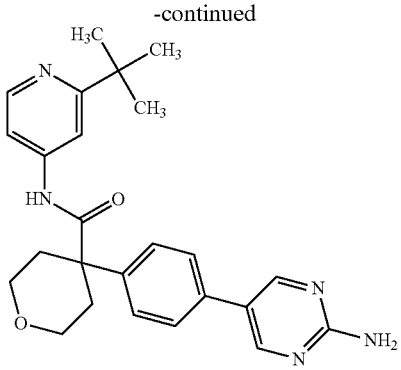
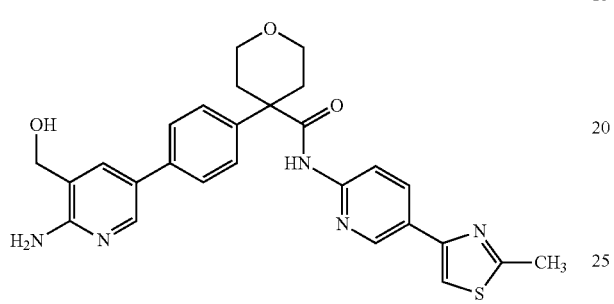
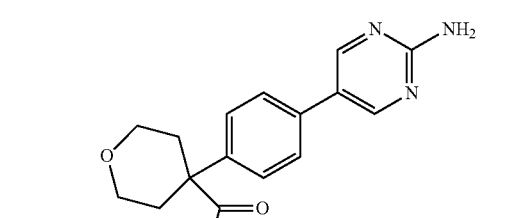
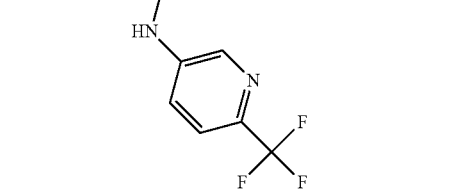
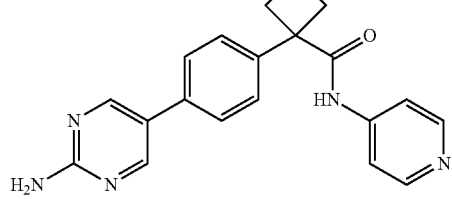
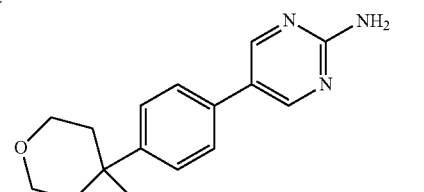
278
-continued
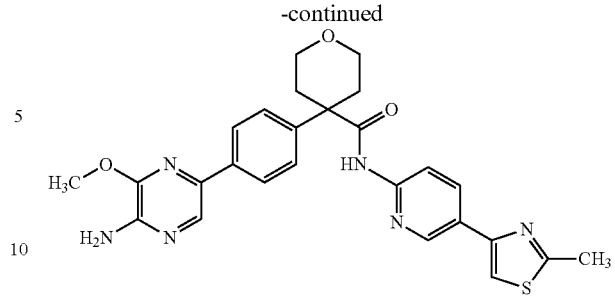
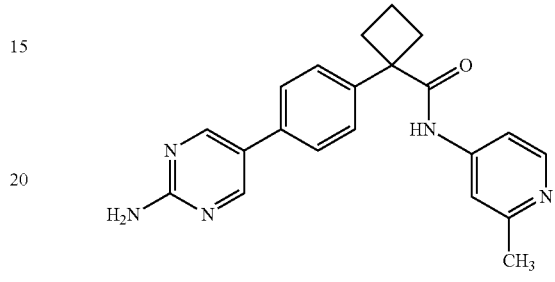
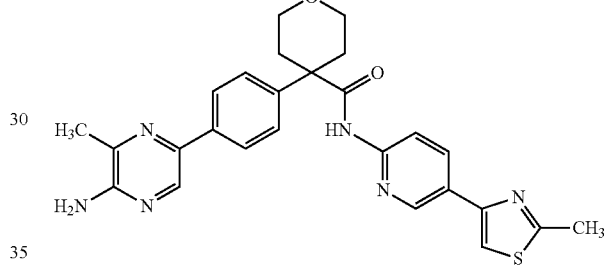
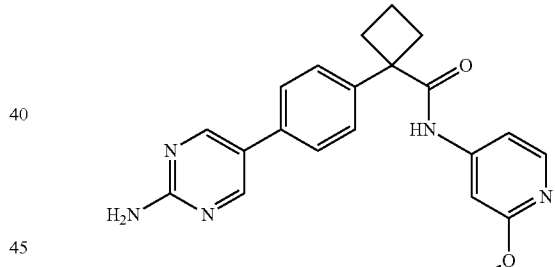
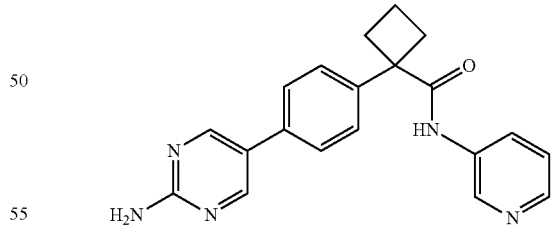
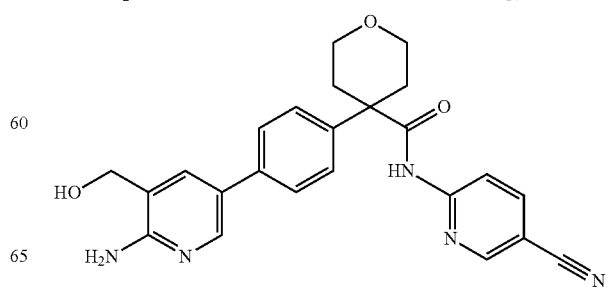

279
-continued
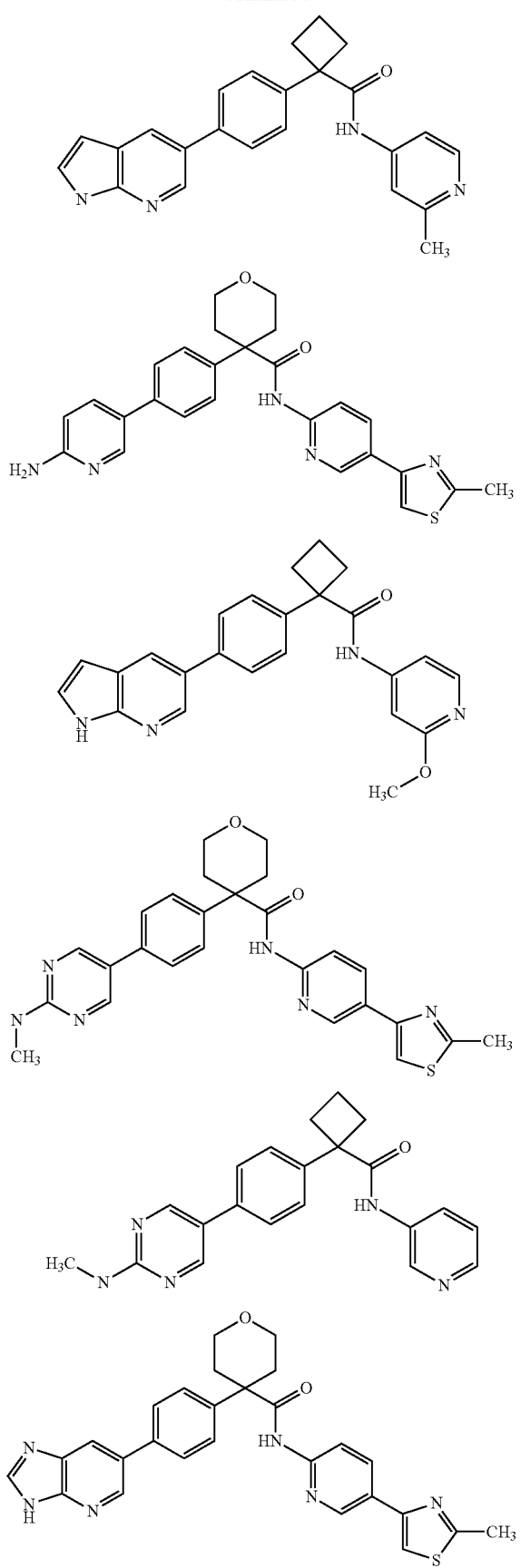
280
-continued
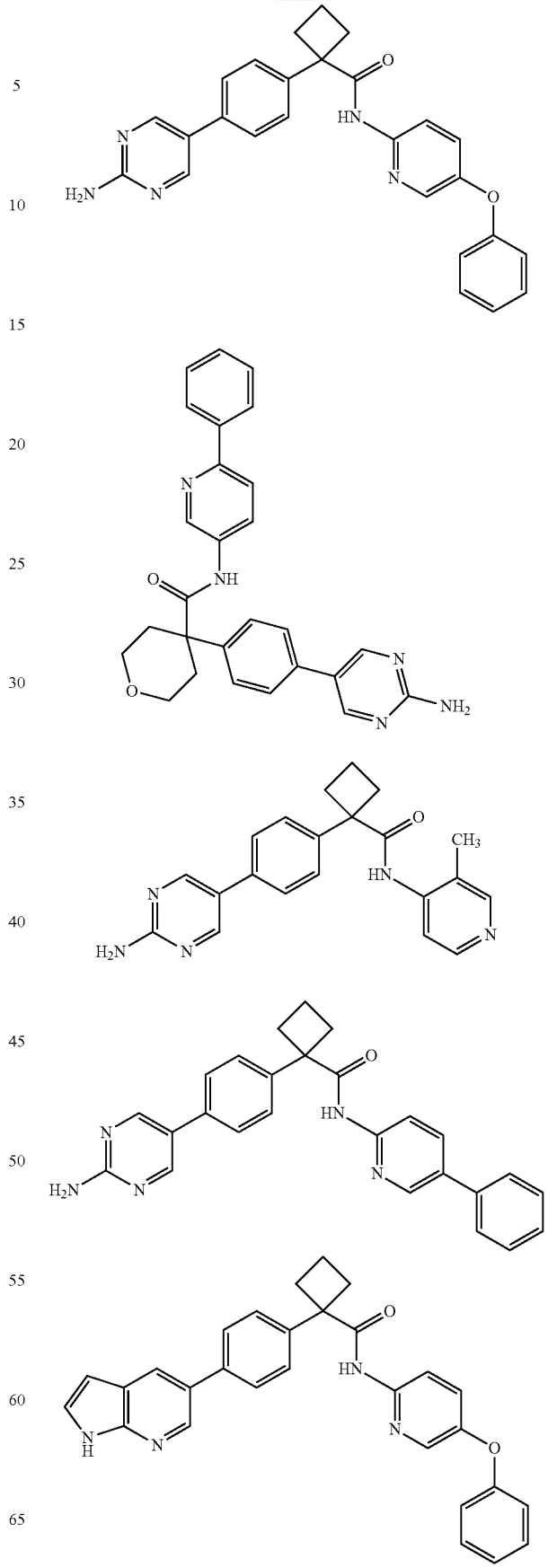

281
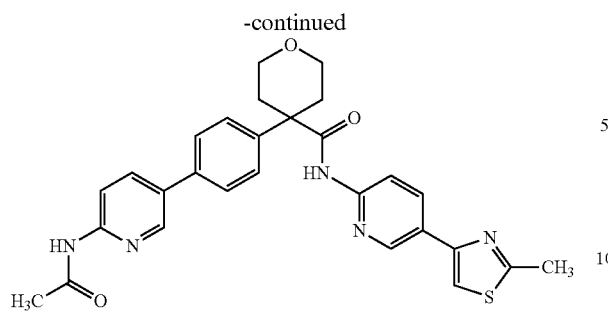
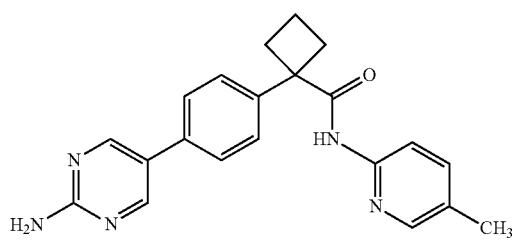
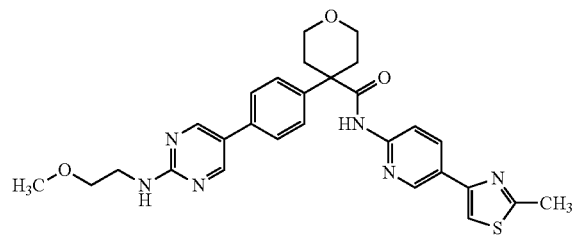
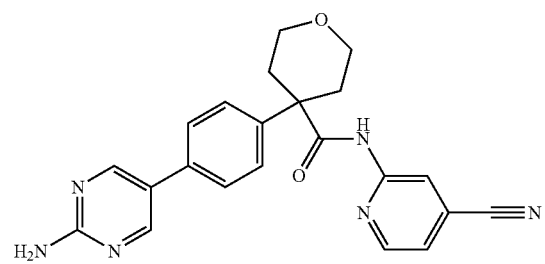
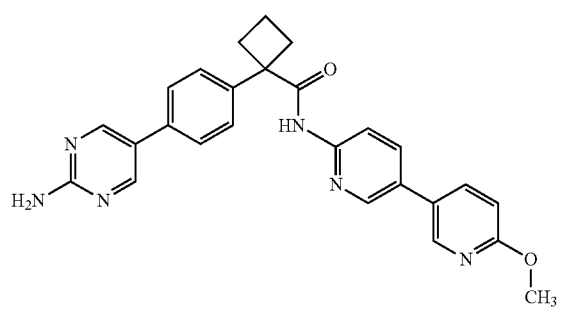
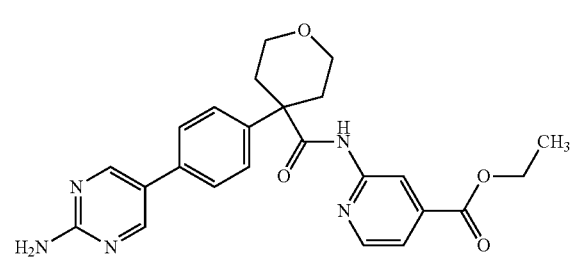
282
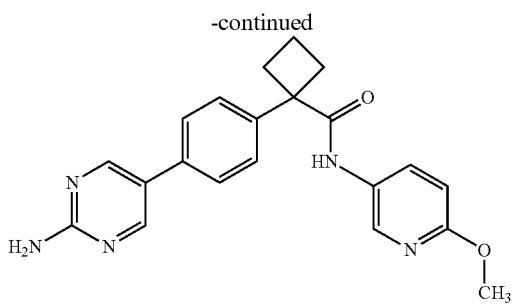
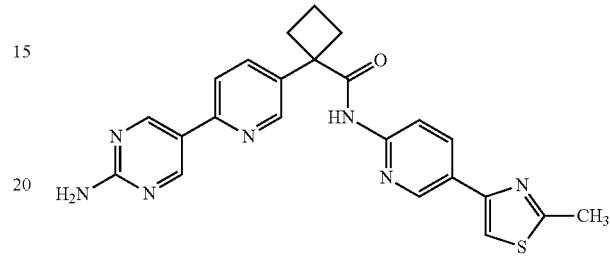
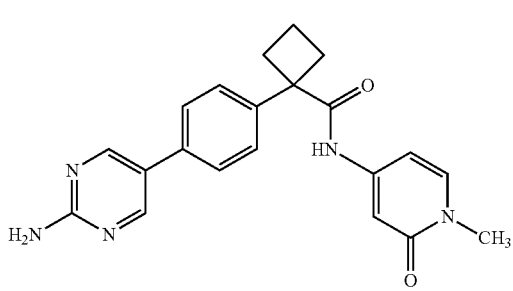
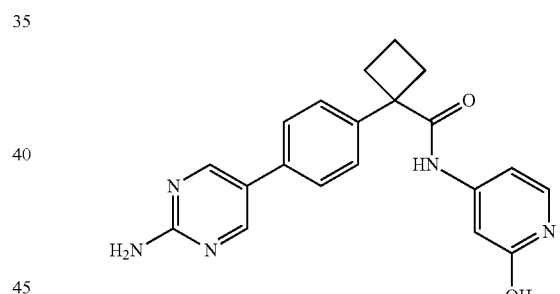
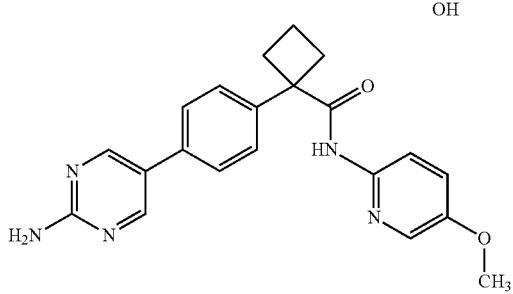
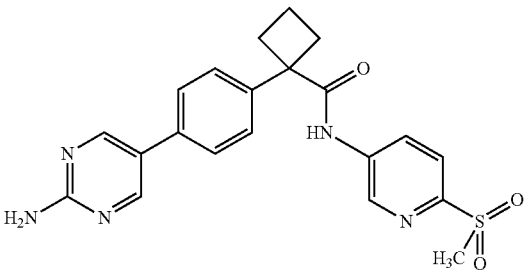

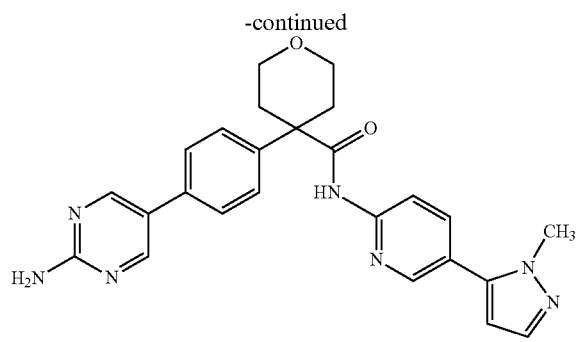
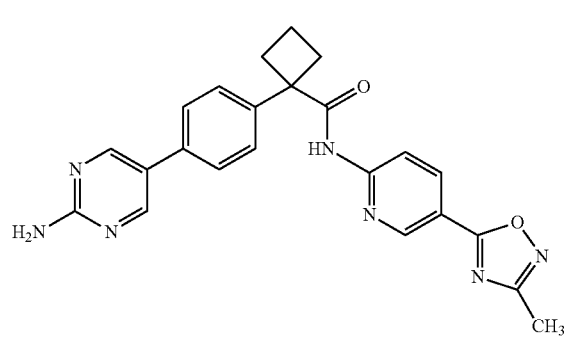
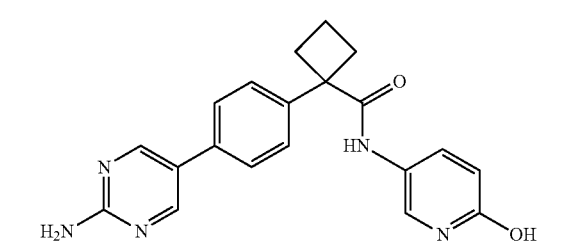
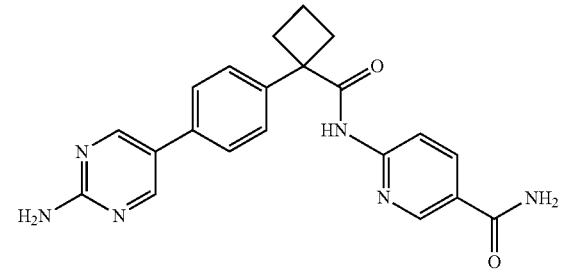
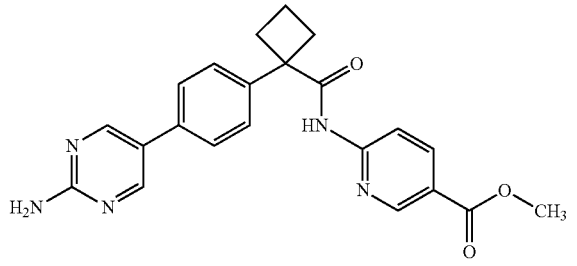
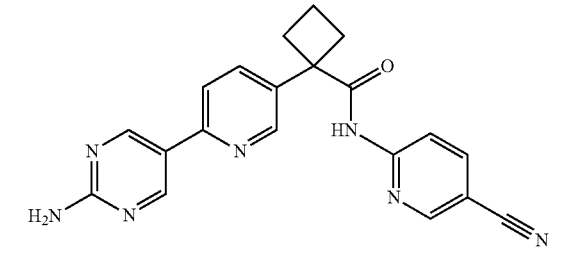
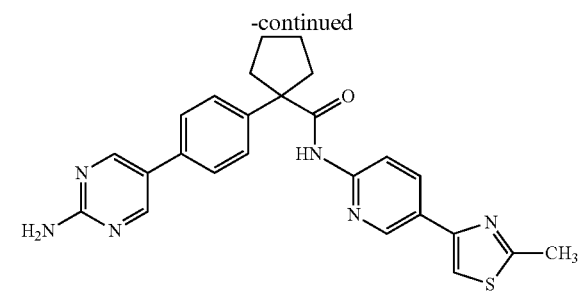
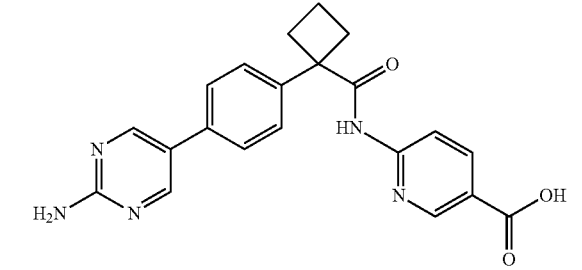
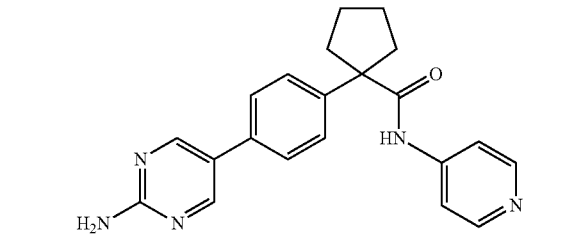
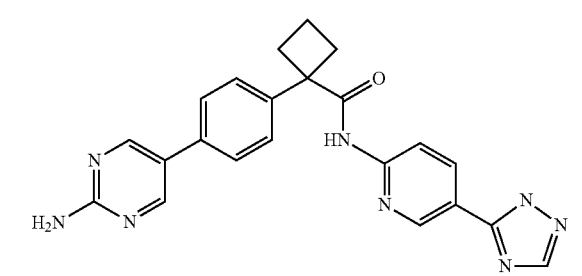
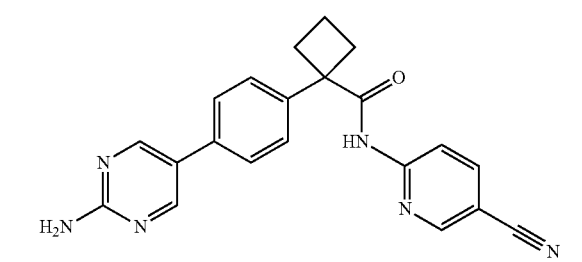
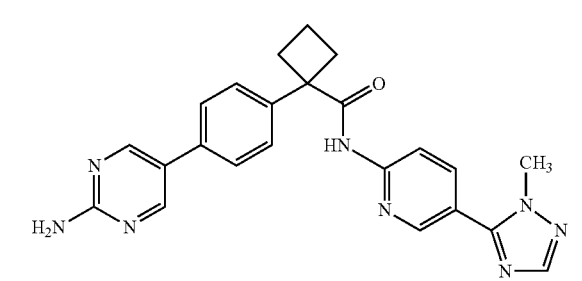

285
-continued
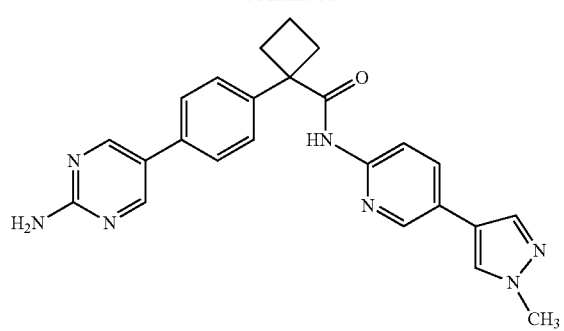
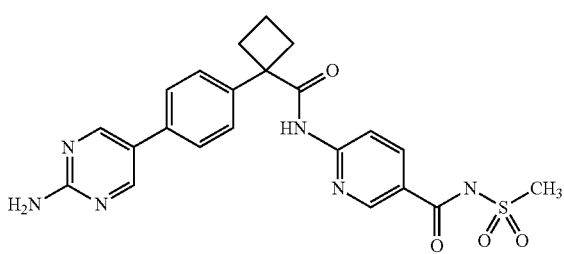
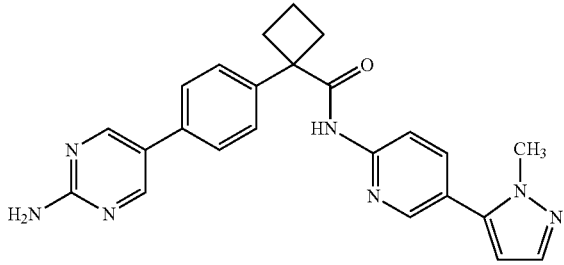
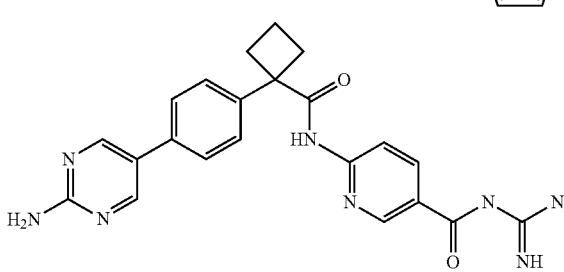
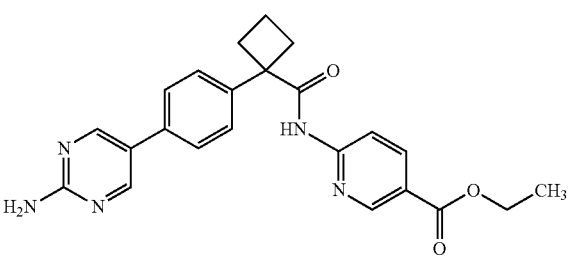
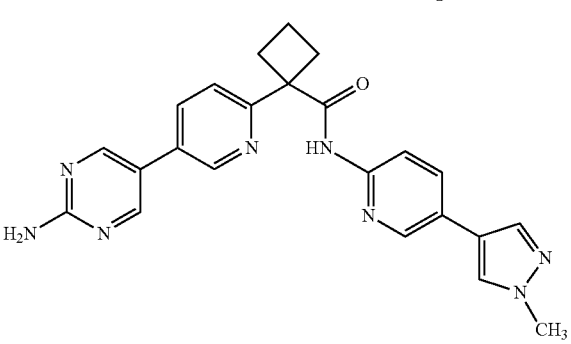
286
-continued
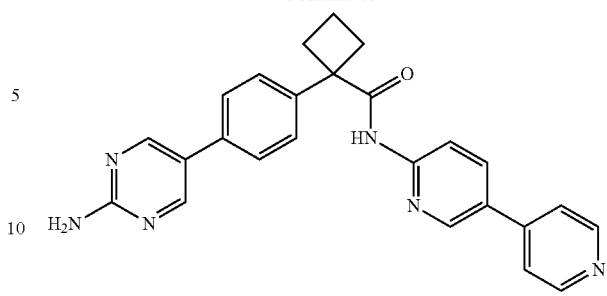
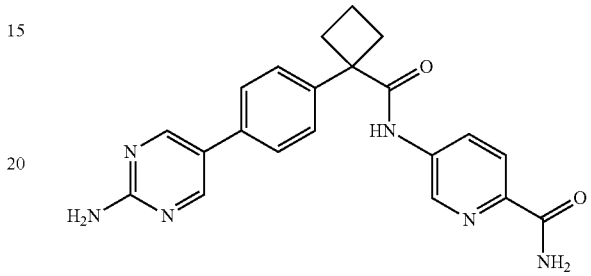
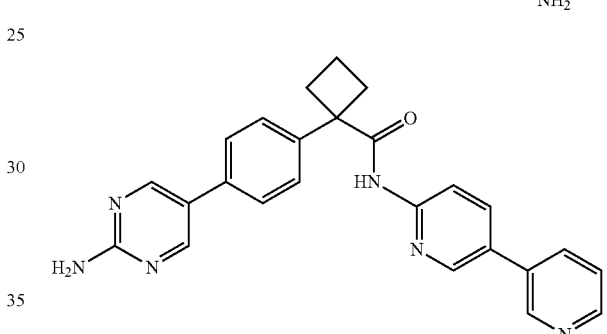
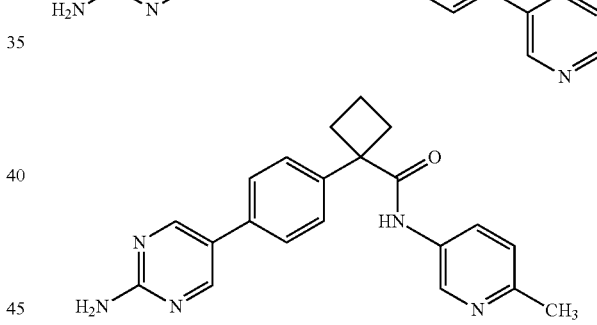
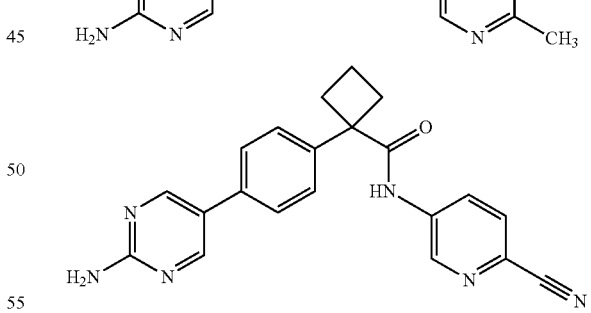
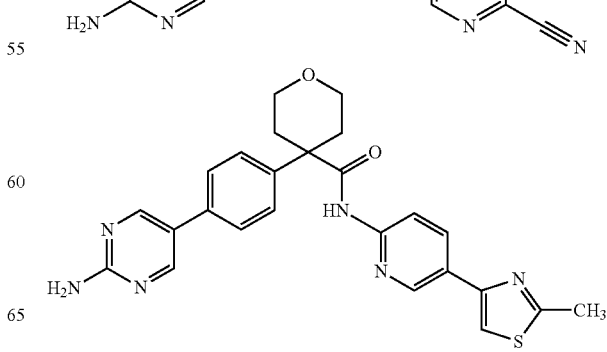

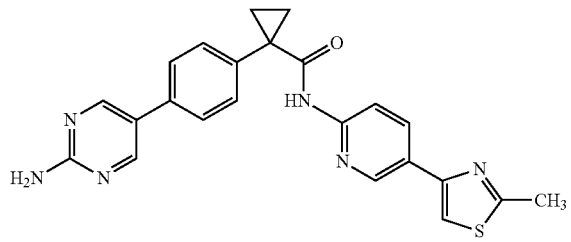
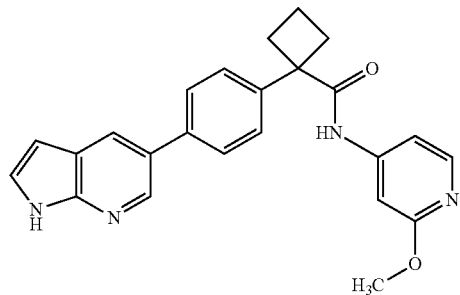
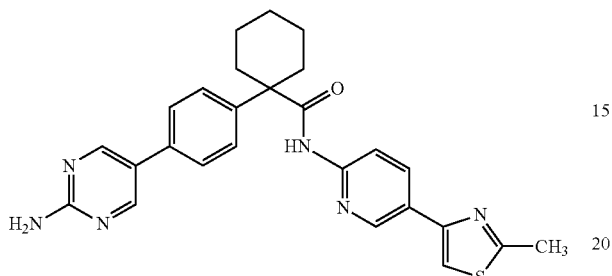
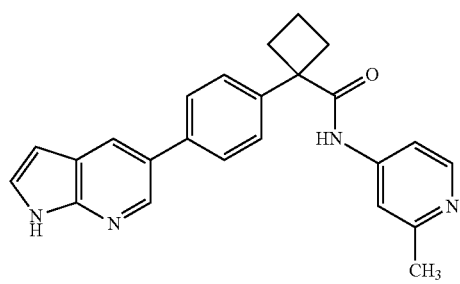
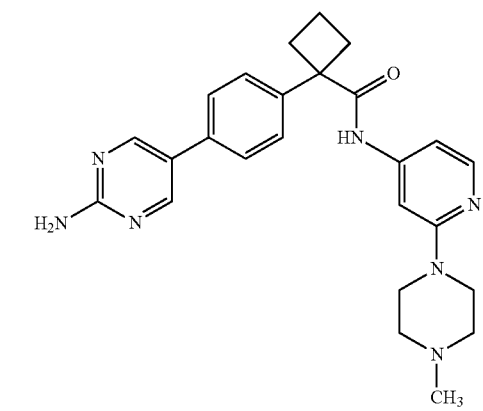
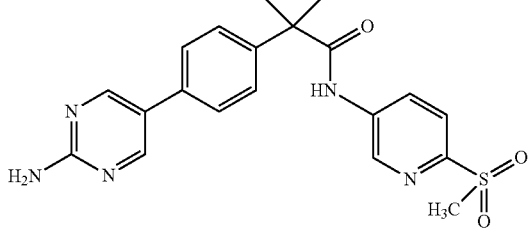
or pharmaceutically acceptable salts thereof.
11. A compound of formula (I) according to claim 10, selected from a group consisting of:
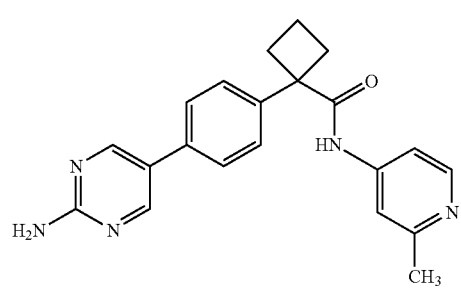
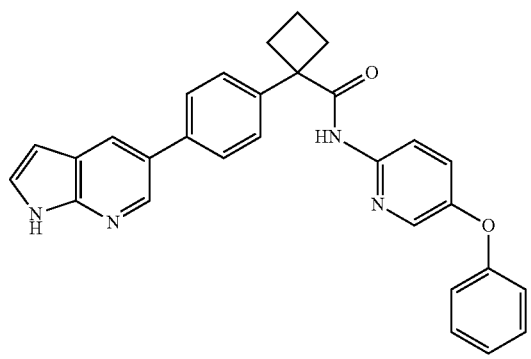
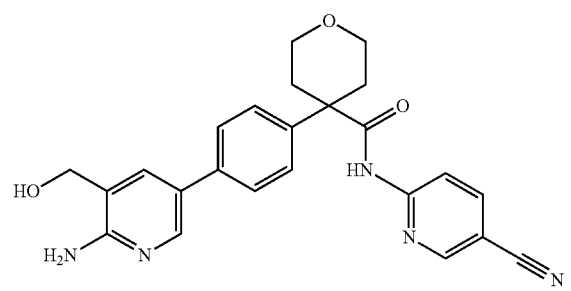
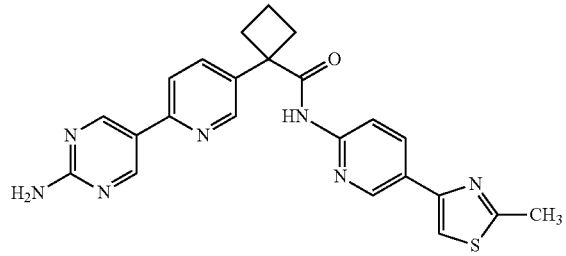

289
-continued
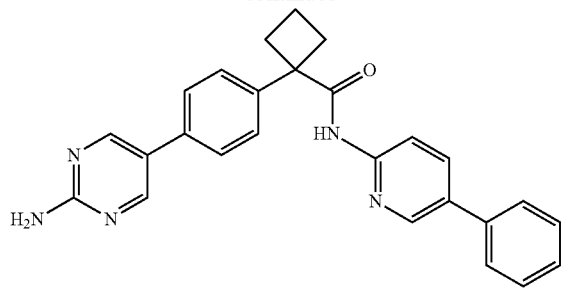
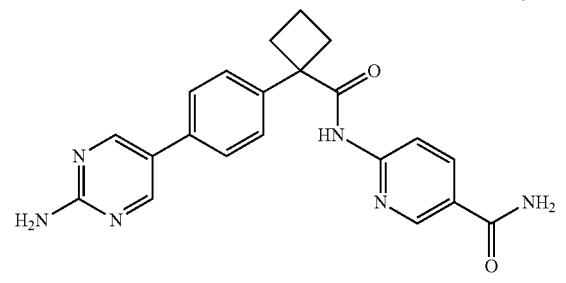
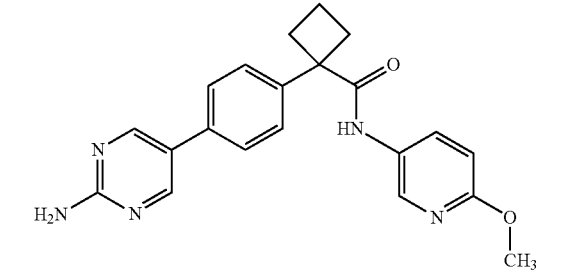
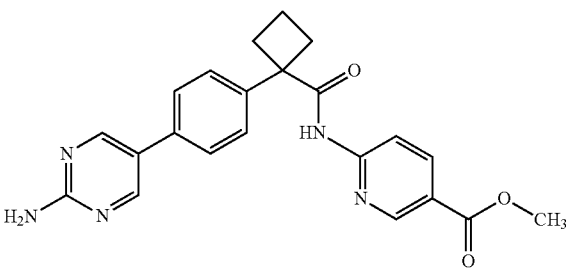
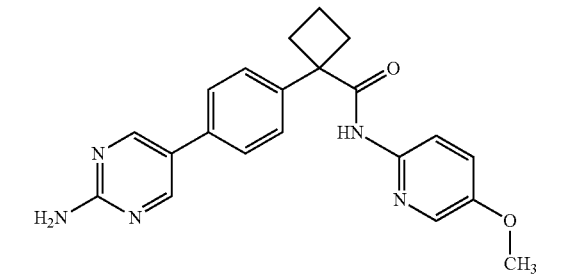
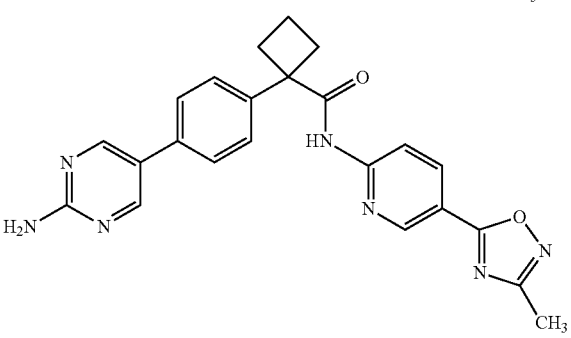
290
-continued
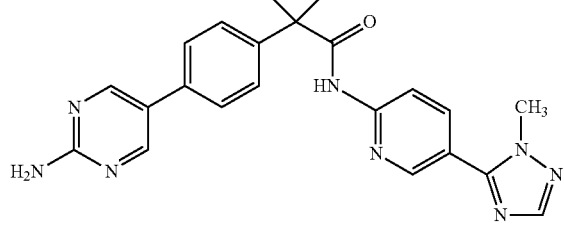
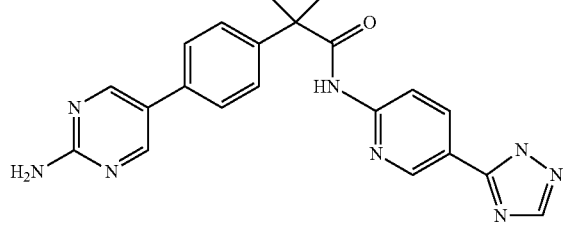
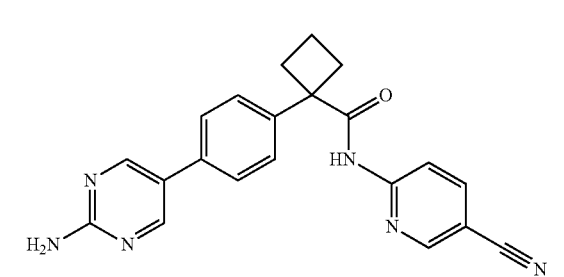
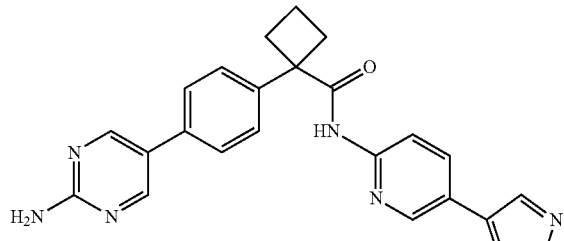
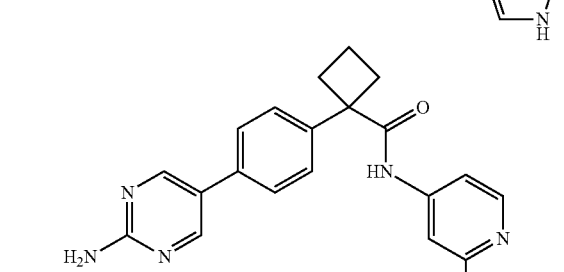
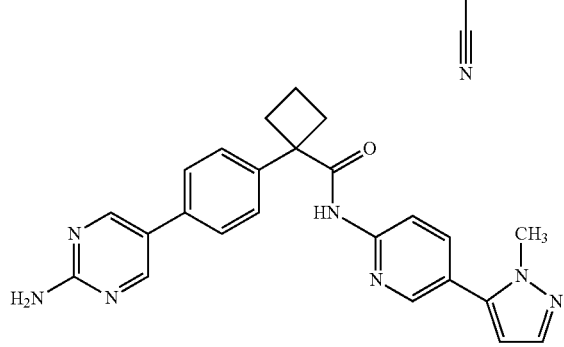

291

-continued

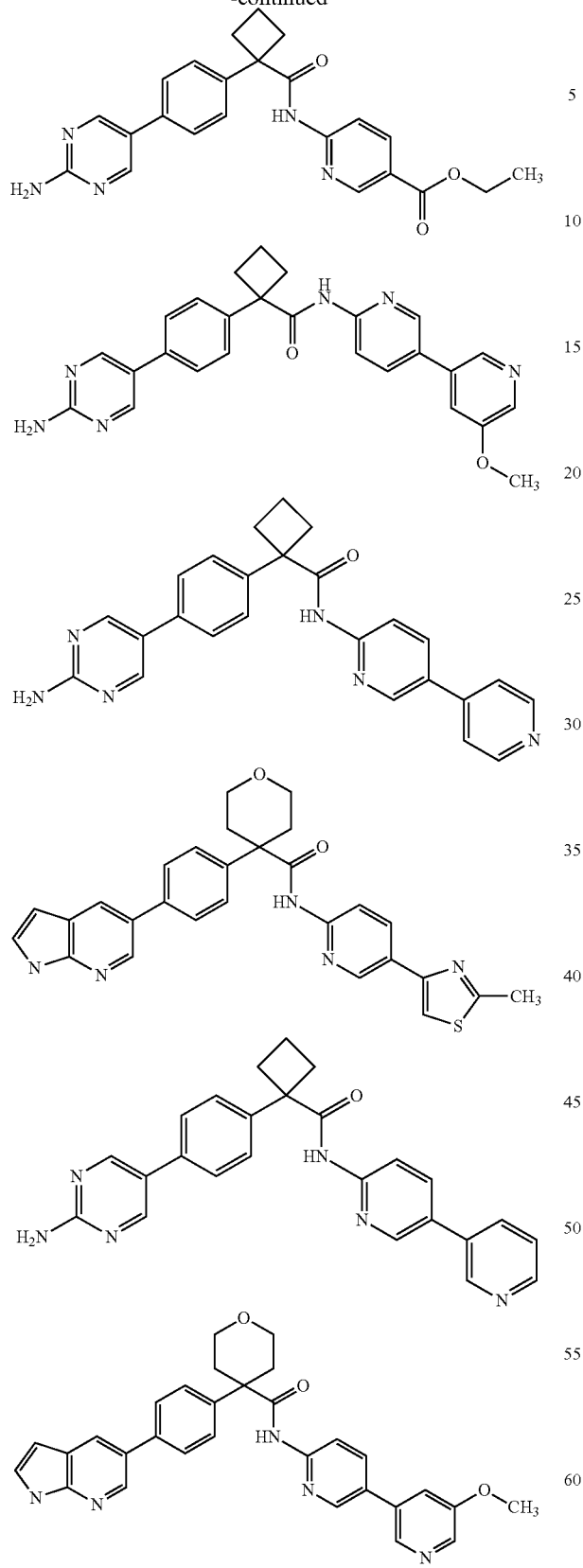

292

-continued

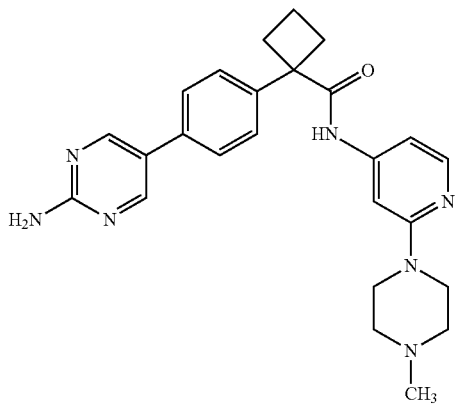

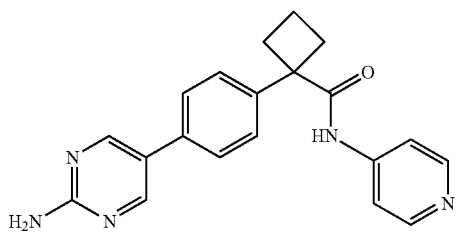

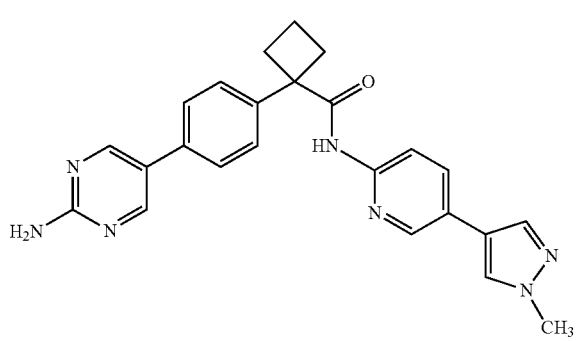

or pharmaceutically acceptable salts thereof.

12. A pharmaceutical composition comprising a compound according to claim 1, or a pharmaceutically acceptable salt thereof, and a pharmaceutically acceptable excipient and/or carrier.

13. A method of treating a leukotriene-mediated disorder comprising administering an effective amount of a compound according to claim 1 or a pharmaceutically acceptable salt thereof, to a patient in need thereof, wherein said leukotriene-mediated disorder is Atherosclerosis.

* * * * *